(12) United States Patent
Blagg et al.

(10) Patent No.: US 10,689,344 B2
(45) Date of Patent: Jun. 23, 2020

(54) BIPHENYLAMIDE DERIVATIVE HSP90 INHIBITORS

(71) Applicant: University of Kansas, Lawrence, KS (US)

(72) Inventors: Brian S. J. Blagg, Lawrence, KS (US); Huiping Zhao, Lawrence, KS (US)

(73) Assignee: UNIVERSITY OF KANSAS, Lawrence, KS (US)

( * ) Notice: Subject to any disclaimer, the term of this patent is extended or adjusted under 35 U.S.C. 154(b) by 382 days.

(21) Appl. No.: 15/034,957

(22) PCT Filed: Nov. 7, 2014

(86) PCT No.: PCT/US2014/064676
§ 371 (c)(1),
(2) Date: May 6, 2016

(87) PCT Pub. No.: WO2015/070091
PCT Pub. Date: May 14, 2015

(65) Prior Publication Data
US 2016/0272584 A1 Sep. 22, 2016

Related U.S. Application Data

(60) Provisional application No. 61/901,230, filed on Nov. 7, 2013.

(51) Int. Cl.
C07D 211/46 (2006.01)
C07D 401/12 (2006.01)
(Continued)

(52) U.S. Cl.
CPC .......... *C07D 211/46* (2013.01); *A61K 31/167* (2013.01); *A61K 31/40* (2013.01);
(Continued)

(58) Field of Classification Search
CPC .. C07D 207/08; C07D 211/22; C07D 401/12; C07D 409/12; C07D 451/06; C07D 487/08
(Continued)

(56) References Cited

U.S. PATENT DOCUMENTS

2001/0007873 A1* 7/2001 Volkmann ............ C07D 401/12
514/329
2004/0229911 A1 11/2004 Saltarelli et al.
(Continued)

FOREIGN PATENT DOCUMENTS

EP         23706     2/1981
GB       2060619     5/1981
(Continued)

OTHER PUBLICATIONS

Federal register, Sep. 2010, pp. 53651-53653.*
(Continued)

*Primary Examiner* — Rita J Desai
(74) *Attorney, Agent, or Firm* — Parker Highlander PLLC

(57) ABSTRACT

Compounds of the formulas are provided: wherein variables $Y_1$-$Y_5$, $X_1$-$X_5$, $A_1$-$A_4$, X, y, $n_1$, $n_2$, and $R_1$-$R_{15}$ are as defined herein. Pharmaceutical compositions of the compounds are also provided. In some aspects, these compounds are useful for the treatment of a disease or disorder, including, for example, a proliferative disease, such as cancer.

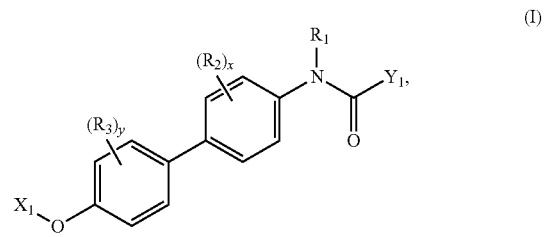

(I)

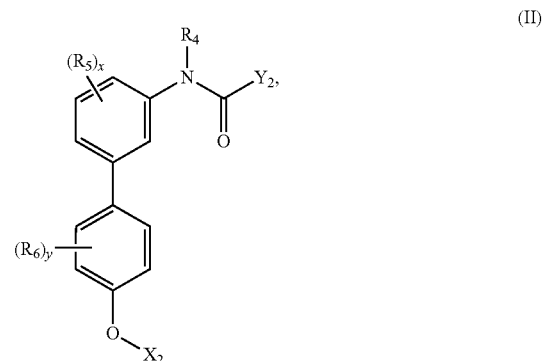

(II)

(III)

(IV)

(Continued)

-continued

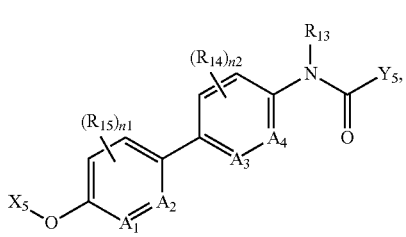

(V)

16 Claims, 3 Drawing Sheets

(51) Int. Cl.
| | |
|---|---|
| C07C 235/56 | (2006.01) |
| C07D 207/08 | (2006.01) |
| C07D 211/22 | (2006.01) |
| C07D 487/08 | (2006.01) |
| C07D 451/06 | (2006.01) |
| A61K 31/167 | (2006.01) |
| A61K 31/40 | (2006.01) |
| A61K 31/445 | (2006.01) |
| A61K 31/4458 | (2006.01) |
| A61K 31/4465 | (2006.01) |
| A61K 31/4535 | (2006.01) |
| A61K 31/454 | (2006.01) |
| A61K 31/4545 | (2006.01) |
| A61K 31/46 | (2006.01) |
| A61K 45/06 | (2006.01) |
| C07D 409/12 | (2006.01) |

(52) U.S. Cl.
CPC ........ *A61K 31/445* (2013.01); *A61K 31/4458* (2013.01); *A61K 31/4465* (2013.01); *A61K 31/454* (2013.01); *A61K 31/4535* (2013.01); *A61K 31/4545* (2013.01); *A61K 31/46* (2013.01); *A61K 45/06* (2013.01); *C07C 235/56* (2013.01); *C07D 207/08* (2013.01); *C07D 211/22* (2013.01); *C07D 401/12* (2013.01); *C07D 409/12* (2013.01); *C07D 451/06* (2013.01); *C07D 487/08* (2013.01)

(58) Field of Classification Search
USPC ...................................................... 546/192
See application file for complete search history.

(56) References Cited

U.S. PATENT DOCUMENTS

| | | |
|---|---|---|
| 2005/0159597 A1 | 7/2005 | Ji et al. |
| 2005/0245531 A1 | 11/2005 | Ji et al. |
| 2008/0146547 A1 | 6/2008 | Araldi et al. |
| 2013/0116227 A1 | 5/2013 | Katayama et al. |

FOREIGN PATENT DOCUMENTS

| | | | | |
|---|---|---|---|---|
| JP | 2009-67729 A | 4/2009 | | |
| WO | WO 2007/017669 | 2/2007 | | |
| WO | WO-2010039238 A1 | * 4/2010 | ............ | C07D 213/30 |
| WO | WO-2010100144 A1 | * 9/2010 | ............ | C07D 277/82 |
| WO | 2010039238 | * 4/2013 | | |

OTHER PUBLICATIONS

Fun-Gang Zhu et al. Role of Heat Shock Protein 90 in Immune Response Stimulation by Bacterial DNA and Synthetic Pligonucleotides (Year: 2001).*

Leah E. Cowen et al Harnessing Hsp90 function as a powerful, broadly effective therapeutic strategy for fungal infectious disease (Year: 2008).*
Huiping Zhao et al 3D-QSAR-assisted Design , Synthesis, and Ebaluation of Novobiocin Analogues (Year: 2012).*
Alison Donnelly et al Novobiocin and additional inhibitors of the Hsp90 C-terminal Nucleotide-binding Pocket. (Year: 2008).*
Burlison et al., "Development of novobiocin analogues that manifest anti-proliferative activity against several cancer cell lines", *J. Org. Chem.*, 73:2130, 2008.
Burlison et al., "Novobiocin: redesigning a DNA gyrase inhibitor for selective inllibition of hsp90", *J. Am. Chem. Soc.*, 128:15529, 2006.
Donnelly et al., "Cytotoxic sugar analogues of an optimized novobiocin scaffold", *Med. Chem. Commun.*, 1:165, 2010.
Donnelly et al, "The design, synthesis, and evaluation of cowl-mirth ring derivatives of the novobiocin scaffold that exhibit antiproliferative activity", *J. Org. Chem.*, 73:8901, 2008.
International Preliminary Report on Patentability issued in International Application No. PCT/US2014/064676, dated May 19, 2016.
International Search Report and Written Opinion issued in International Application No. PCT/US2014/064676, dated Feb. 19, 2015.
Kraiss, et al., "Chemistry of tropan-3-yl ethers. I. Synthesis of tropan-3-yl ethers.," *J. Chem. Soc. B., Phys. Org.*, 11:2145-2149, 1971.
Liu, et al., "Synthesis and SAR studies of biaryloxy-substituted triazoles as antifungal agents,"*Bioorg. Med. Chem. Lett.*, 18(11):3261-3265, 2008.
Nador, et al., "Synthesis and the stereochemistry of tropanyl ethers," *Kemiai Kozlemenyek*, 31(4):351-81, 1969. (Chemical Formulas).
Tian, et al., "Epigallocatechin-3-gallate suppresses the expression of HSP70 and HSP90 and exhibits anti-tumor activity in vitro and in vivo", *BMC Cancer*, 10:276, 2010.
Yu et al., "Hsp90 inhibitors identified from a library of novohiocin analogues", *J. Am. Chem. Soc..*, 127:12778, 2005.
Zhao et al., "3D-QSAR-assisted design, synthesis and evaluation of novobiocin analogues," *ACS Medicinal Chemistry Letters*, 4(1):57-62, 2013.
Zhao et al., "Design, synthesis and biological evaluation of biphenylamide drivatives as Hsp90 C-terminal inhibitors," *European Journal of Medicinal Chemistry*, 89:442-466, 2014.
Zhao et al., "Engineering an antibiotic to fight cancer: optimization of the novobiocin scaffold to produce anti-proliferative agents," *Journal of Medicinal Chemistry*, 54(11):3839-3853, 2011.
Zhao et al., "Identification and initial SAR of silybin: An Hsp90 inhibitor", *Bioorg. Med Chem. Lett.*, 21:2659-2664, 2011.
Zhao et al., "Identification of a new scaffold for Hsp90 C-terminal inhibition," *ACS Medicinal Chemistry Letters*, 5(1):84-88, 2013.
Zhao et al., "Synthesis and evaluation of noviose replacements on novobiocin that manifest antiproliferative activity", *ACS Med. Chem. Lett.*, 1:311, 2010.
Zhao et al., "Triazole containing novobiocin and biphenyl amides as Hsp90 C-terminal inhibitors," *MEDCHEMCOMM*, 5(9):1317-1323, 2014.
Zhao, et al., "3-Arvlcoumarin derivatives manifest anti-proliferative activity through Hsp90 inhibition", *ACS Med. Chem. Lett.*, 3:327-331, 2012.
Office Communication issued in European Application No. 14815479. 2, dated Mar. 14, 2018.
Chen and Flies, "Molecular mechanisms of T cell co-stimulation and co-inhibition," *Nat. Rev. Immunol.*, 13:227-242, 2013.
Odds et al., "Antifungal agents: mechanisms of action," *Trends Microbiol.*, 11(6):272-279, 2003.
Office Communication issued in European Application No. 14815479. 2, dated Dec. 4, 2014.

* cited by examiner

BIPHENYLAMIDE DERIVATIVE HSP90 INHIBITORS

This application is a national phase application under 35 U.S.C. § 371 of International Application No. PCT/US2014/064676, filed Nov. 7, 2014, which claims the benefit of U.S. Provisional Application 61/901,230, filed on Nov. 7, 2013, the entire content of which are incorporated herein by reference.

This invention was made with government support under CA120448 and CA167079 awarded by the National Institutes of Health and National Cancer Institute. The government has certain rights in the invention.

BACKGROUND OF THE INVENTION

I. Field of the Invention

The present invention relates generally to the fields of biology, chemistry, and medicine. More particularly, it concerns compounds, compositions and methods for the treatment and prevention of diseases such as cancer and other proliferative diseases.

II. Description of Related Art

The 90 kDa heat shock protein (Hsp90) is a highly conserved molecular chaperone that plays a pivotal role in the maintenance of protein homeostasis and sustains cell viability during cellular stress (Taipale, et al., 2010). Abnormal expression of Hsp90 has been implicated in a variety of disease states. In cancer, elevated Hsp90 levels are critical for the stabilization and function of oncogenic proteins distributed amongst all six hallmarks of cancer (Hanahan and Weinberg, 2011). Therefore, small molecules that inhibit the Hsp90 folding machinery can simultaneously attack multiple signaling pathways that are essential for cancer cell survival, adaptation, proliferation, and provides a unique opportunity for development of cancer therapeutics (Blagg and Kerr, 2006).

Several small molecules that inhibit the N-terminus Hsp90 function are currently in clinical trials for the treatment of various cancers, demonstrating the viability of this treatment paradigm (Neckers and Workman, 2012). Unfortunately, small molecules that target the Hsp90 N-terminus have been reported to lead to the concomitant heat shock response induced upon administration of such agents. This tends to compromise their efficacy and allows cancer cell survival, which may lead to resistance and metastasis (Whitesell, et al., 2012). Recent studies have demonstrated the existence of a second nucleotide-binding site at the Hsp90 C-terminus and these small molecules have been shown to bind this region and induce a dose-dependent degradation of Hsp90 client proteins in a manner similar to Hsp90 N-terminal inhibitors (Marcu, et al., 2000). In contrast to N-terminal inhibitors, C-terminal inhibitors do not induce the pro-survival heat shock response, and therefore provide an alternative model for Hsp90 modulation (Eskew, et al., 2011; Shelton, et al., 2009; and Conde, et al., 2009). Novobiocin was identified as the first Hsp90 C-terminal inhibitor in 2000; albeit with low efficiency (~700 µM in SKBr3 cells) (Marcu, et al., 2000).

Starting from novobiocin, extensive structural modifications to the coumarin moiety have been performed to elucidate structure-activity relationships and to identify analogues that exhibit increased inhibitory activities (Yu, et al., 2005; Burlison, et al., 2006; Donnelly, et al., 2008; Donnelly, et al., 2010; Zhao and Blagg, 2010; Zhao, et al., 2011; and Burlison, et al., 2008). The construction of the coumarin moiety is not trivial and modification on the coumarin ring is not easily accessible, which makes the discovery of a simple and readily available replacement for coumarin moiety highly desired. The scarcity of scaffolds that bind the Hsp90 C-terminus makes the expansion of chemical space around the Hsp90 C-terminus scaffold highly desirable for the development of new and more potent inhibitors.

SUMMARY OF THE INVENTION

The present disclosure provides novel compounds, including biphenylamine compounds with anti-proliferative properties, pharmaceutical compositions thereof, methods for their manufacture, and methods for their use.

In one aspect of the present disclosure there are provided compounds of the formulas I, II, III, IV, or V, wherein the formulas are further defined as:

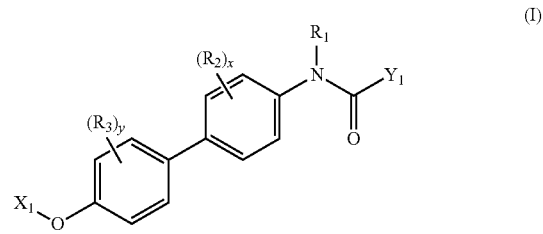

(I)

wherein: $X_1$ is heterocycloalkyl$_{(C \leq 12)}$, -alkanediyl$_{(C \leq 6)}$-heterocycloalkyl$_{(C \leq 12)}$, -alkanediyl$_{(C \leq 6)}$-amino, -alkanediyl$_{(C \leq 6)}$-alkylamino$_{(C \leq 8)}$, -alkanediyl$_{(C \leq 6)}$-dialkylamino$_{(C \leq 12)}$, or a substituted version thereof; $Y_1$ is cycloalkyl$_{(C \leq 18)}$, aryl$_{(C \leq 24)}$, heteroaryl$_{(C \leq 24)}$, -arenediyl$_{(C \leq 18)}$-alkyl$_{(C \leq 8)}$, -arenediyl$_{(C \leq 18)}$-alkenyl$_{(C \leq 8)}$, -arenediyl$_{(C \leq 18)}$-alkoxy$_{(C \leq 8)}$, or a substituted version of any of these groups; $R_1$ is hydrogen, alkyl$_{(C \leq 6)}$, or substituted alkyl$_{(C \leq 6)}$; each $R_2$ and $R_3$ are each independently selected from hydrogen, amino, cyano, halo, hydroxy, mercapto, nitro, sulfato, sulfamido, alkyl$_{(C \leq 12)}$, substituted alkyl$_{(C \leq 12)}$, alkoxy$_{(C \leq 12)}$, substituted alkoxy$_{(C \leq 12)}$, acyl$_{(C \leq 12)}$, substituted acyl$_{(C \leq 12)}$, acyloxy$_{(C \leq 12)}$, substituted acyloxy$_{(C \leq 12)}$, amido$_{(C \leq 12)}$, or substituted amido$_{(C \leq 12)}$; and x and y are each independently selected from 0, 1, 2, 3, or 4;

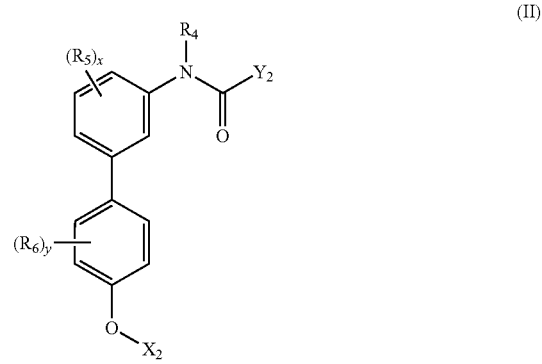

(II)

wherein: $X_2$ is heterocycloalkyl$_{(C \leq 12)}$, -alkanediyl$_{(C \leq 6)}$-heterocycloalkyl$_{(C \leq 12)}$, -alkanediyl$_{(C \leq 6)}$-amino, -alkanediyl$_{(C \leq 6)}$-alkylamino$_{(C \leq 8)}$, -alkanediyl$_{(C \leq 6)}$-dialkylamino$_{(C \leq 12)}$, or a substituted version thereof; $Y_2$ is cycloalkyl$_{(C \leq 18)}$, aryl$_{(C \leq 24)}$, heteroaryl$_{(C \leq 24)}$, -arenediyl$_{(C\leq18)}$-alkyl$_{(C\leq8)}$, -arenediyl$_{(C\leq18)}$-alkenyl$_{(C\leq8)}$, -arenediyl$_{(C\leq18)}$-alkoxy$_{(C\leq8)}$, or a substituted version of any of these groups; $R_4$ is hydrogen, alkyl$_{(C\leq6)}$, or substituted alkyl$_{(C\leq6)}$; each $R_5$ and $R_6$ are each independently selected from hydrogen, amino, cyano, halo, hydroxy, mercapto, nitro, sulfato, sulfamido, alkyl$_{(C\leq12)}$, substituted alkyl$_{(C\leq12)}$, alkoxy$_{(C\leq12)}$, substituted alkoxy$_{(C\leq12)}$, acyl$_{(C\leq12)}$, substituted acyl$_{(C\leq12)}$, acyloxy$_{(C\leq12)}$, substituted acyloxy$_{(C\leq12)}$, amido$_{(C\leq12)}$, or substituted amido$_{(C\leq12)}$; and x and y are each independently selected from 0, 1, 2, 3, or 4;

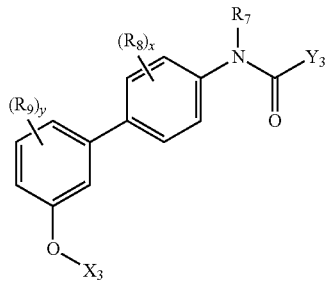

(III)

wherein: $X_3$ is heterocycloalkyl$_{(C\leq12)}$, -alkanediyl$_{(C\leq6)}$-heterocycloalkyl$_{(C\leq12)}$, -alkanediyl$_{(C\leq6)}$-amino, -alkanediyl$_{(C\leq6)}$-alkylamino$_{(C\leq8)}$, -alkanediyl$_{(C\leq6)}$-di-alkylamino$_{(C\leq12)}$, or a substituted version thereof; $Y_3$ is cycloalkyl$_{(C\leq18)}$, aryl$_{(C\leq24)}$, heteroaryl$_{(C\leq24)}$, -arenediyl$_{(C\leq18)}$-alkyl$_{(C\leq8)}$, -arenediyl$_{(C\leq18)}$-alkenyl$_{(C\leq8)}$, -arenediyl$_{(C\leq18)}$-alkoxy$_{(C\leq8)}$, or a substituted version of any of these groups; $R_7$ is hydrogen, alkyl$_{(C\leq6)}$, or substituted alkyl$_{(C\leq6)}$; each $R_8$ and $R_9$ are each independently selected from hydrogen, amino, cyano, halo, hydroxy, mercapto, nitro, sulfato, sulfamido, alkyl$_{(C\leq12)}$, substituted alkyl$_{(C\leq12)}$, alkoxy$_{(C\leq12)}$, substituted alkoxy$_{(C\leq12)}$, acyl$_{(C\leq12)}$, substituted acyl$_{(C\leq12)}$, acyloxy$_{(C\leq12)}$, substituted acyloxy$_{(C\leq12)}$, amido$_{(C\leq12)}$, or substituted amido$_{(C\leq12)}$; and x and y are each independently selected from 0, 1, 2, 3, or 4;

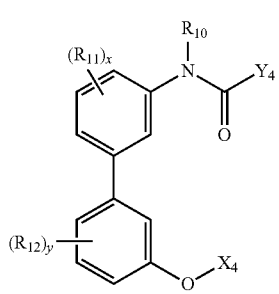

(IV)

wherein: $X_4$ is heterocycloalkyl$_{(C\leq12)}$, -alkanediyl$_{(C\leq6)}$-heterocycloalkyl$_{(C\leq12)}$, -alkanediyl$_{(C\leq6)}$-amino, -alkanediyl$_{(C\leq6)}$-alkylamino$_{(C\leq8)}$, -alkanediyl$_{(C\leq6)}$-di-alkylamino$_{(C\leq12)}$, or a substituted version thereof; $Y_4$ is cycloalkyl$_{(C\leq18)}$, aryl$_{(C\leq24)}$, heteroaryl$_{(C\leq24)}$, -arenediyl$_{(C\leq18)}$-alkyl$_{(C\leq8)}$, -arenediyl$_{(C\leq18)}$-alkenyl$_{(C\leq8)}$, -arenediyl$_{(C\leq18)}$-alkoxy$_{(C\leq8)}$, or a substituted version of any of these groups; $R_{10}$ is hydrogen, alkyl$_{(C\leq6)}$, or substituted alkyl$_{(C\leq6)}$; each $R_{11}$ and $R_{12}$ are each independently selected from hydrogen, amino, cyano, halo, hydroxy, mercapto, nitro, sulfato, sulfamido, alkyl$_{(C\leq12)}$, substituted alkyl$_{(C\leq12)}$, alkoxy$_{(C\leq12)}$, substituted alkoxy$_{(C\leq12)}$, acyl$_{(C\leq12)}$, substituted acyl$_{(C\leq12)}$, acyloxy$_{(C\leq12)}$, substituted acyloxy$_{(C\leq12)}$, amido$_{(C\leq12)}$, or substituted amido$_{(C\leq12)}$; and x and y are each independently selected from 0, 1, 2, 3, or 4; or

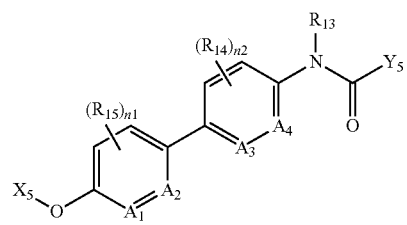

(V)

wherein: $A_1$ and $A_2$ are each independently selected from N or $CR_{15}$ and $A_3$ and $A_4$ are each independently selected from N or $CR_{14}$ provided at least one of $A_1$, $A_2$, $A_3$, and $A_4$ is N; $X_5$ is heterocycloalkyl$_{(C\leq12)}$, -alkanediyl$_{(C\leq6)}$-heterocycloalkyl$_{(C\leq12)}$, -alkanediyl$_{(C\leq6)}$-amino, -alkanediyl$_{(C\leq6)}$-alkylamino$_{(C\leq8)}$, -alkanediyl$_{(C\leq6)}$-dialkylamino$_{(C\leq12)}$, or a substituted version thereof; $Y_5$ is cycloalkyl$_{(C\leq18)}$, aryl$_{(C\leq24)}$, heteroaryl$_{(C\leq24)}$, -arenediyl$_{(C\leq18)}$-alkyl$_{(C\leq8)}$, -arenediyl$_{(C\leq18)}$-alkenyl$_{(C\leq8)}$, -arenediyl$_{(C\leq18)}$-alkoxy$_{(C\leq8)}$, or a substituted version of any of these groups; $R_{13}$ is hydrogen, alkyl$_{(C\leq6)}$, or substituted alkyl$_{(C\leq6)}$; each $R_{14}$ and $R_{15}$ are each independently selected from hydrogen, amino, cyano, halo, hydroxy, mercapto, nitro, sulfato, sulfamido, alkyl$_{(C\leq12)}$, substituted alkyl$_{(C\leq12)}$, alkoxy$_{(C\leq12)}$, substituted alkoxy$_{(C\leq12)}$, acyl$_{(C\leq12)}$, substituted acyl$_{(C\leq12)}$, acyloxy$_{(C\leq12)}$, substituted acyloxy$_{(C\leq12)}$, amido$_{(C\leq12)}$, or substituted amido$_{(C\leq12)}$; and $n_1$ and $n_2$ are each independently 0, 1, or 2; or a pharmaceutically acceptable salt thereof. In some embodiments, the compound is further defined as:

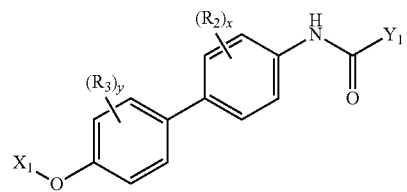

(VI)

wherein: $X_1$ is heterocycloalkyl$_{(C\leq12)}$, -alkanediyl$_{(C\leq6)}$-heterocycloalkyl$_{(C\leq12)}$, -alkanediyl$_{(C\leq6)}$-amino, -alkanediyl$_{(C\leq6)}$-alkylamino$_{(C\leq8)}$, -alkanediyl$_{(C\leq6)}$-di-alkylamino$_{(C\leq12)}$, or a substituted version thereof; $Y_1$ is cycloalkyl$_{(C\leq18)}$, aryl$_{(C\leq24)}$, heteroaryl$_{(C\leq24)}$, -arenediyl$_{(C\leq18)}$-alkyl$_{(C\leq8)}$, -arenediyl$_{(C\leq18)}$-alkenyl$_{(C\leq8)}$, -arenediyl$_{(C\leq18)}$-alkoxy$_{(C\leq8)}$, or a substituted version of any of these groups; each $R_2$ and $R_3$ are each independently selected from hydrogen, amino, cyano, halo, hydroxy, mercapto, nitro, sulfato, sulfamido, alkyl$_{(C\leq12)}$, substituted alkyl$_{(C\leq12)}$, alkoxy$_{(C\leq12)}$, substituted alkoxy$_{(C\leq12)}$, acyl$_{(C\leq12)}$, substituted acyl$_{(C\leq12)}$, acyloxy$_{(C\leq12)}$, substituted acyloxy$_{(C\leq12)}$, amido$_{(C\leq12)}$, or substituted amido$_{(C\leq12)}$; and x and y are each independently selected from 0, 1, 2, 3, or 4; or a pharmaceutically acceptable salt thereof. In some embodiments, the compound is further defined as:

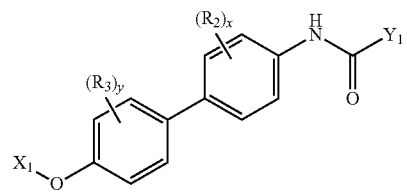

(VI)

wherein: $X_1$ is heterocycloalkyl$_{(C \leq 12)}$ or substituted heterocycloalkyl$_{(C \leq 12)}$; $Y_1$ is cycloalkyl$_{(C \leq 18)}$, aryl$_{(C \leq 24)}$, heteroaryl$_{(C \leq 24)}$, -arenediyl$_{(C \leq 18)}$-alkyl$_{(C \leq 8)}$, -arenediyl$_{(C \leq 18)}$-alkenyl$_{(C \leq 8)}$, -arenediyl$_{(C \leq 18)}$-alkoxy$_{(C \leq 8)}$, or a substituted version of any of these groups; each $R_2$ and $R_3$ are each independently selected from hydrogen, amino, cyano, halo, hydroxy, mercapto, nitro, sulfato, sulfamido, alkyl$_{(C \leq 12)}$, substituted alkyl$_{(C \leq 12)}$, alkoxy$_{(C \leq 12)}$, substituted alkoxy$_{(C \leq 12)}$, acyl$_{(C \leq 12)}$, substituted acyl$_{(C \leq 12)}$, acyloxy$_{(C \leq 12)}$, substituted acyloxy$_{(C \leq 12)}$, amido$_{(C \leq 12)}$, or substituted amido$_{(C \leq 12)}$; and x and y are each independently selected from 1, 2, 3, or 4; or a pharmaceutically acceptable salt thereof. In some embodiments, the compound is further defined as:

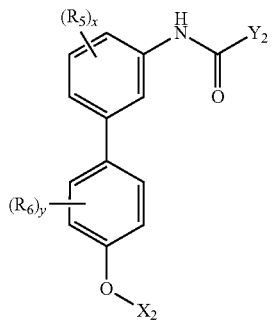

(VII)

wherein: $X_2$ is heterocycloalkyl$_{(C \leq 12)}$, -alkanediyl$_{(C \leq 6)}$-heterocycloalkyl$_{(C \leq 12)}$, -alkanediyl$_{(C \leq 6)}$-amino, -alkanediyl$_{(C \leq 6)}$-alkylamino$_{(C \leq 8)}$, -alkanediyl$_{(C \leq 6)}$-di-alkylamino$_{(C \leq 12)}$, or a substituted version thereof; $Y_2$ is cycloalkyl$_{(C \leq 18)}$, aryl$_{(C \leq 24)}$, heteroaryl$_{(C \leq 24)}$, -arenediyl$_{(C \leq 18)}$-alkyl$_{(C \leq 8)}$, -arenediyl$_{(C \leq 18)}$-alkenyl$_{(C \leq 8)}$, -arenediyl$_{(C \leq 18)}$-alkoxy$_{(C \leq 8)}$, or a substituted version of any of these groups; each $R_5$ and $R_6$ are each independently selected from hydrogen, amino, cyano, halo, hydroxy, mercapto, nitro, sulfato, sulfamido, alkyl$_{(C \leq 12)}$, substituted alkyl$_{(C \leq 12)}$, alkoxy$_{(C \leq 12)}$, substituted alkoxy$_{(C \leq 12)}$, acyl$_{(C \leq 12)}$, substituted acyl$_{(C \leq 12)}$, acyloxy$_{(C \leq 12)}$, substituted acyloxy$_{(C \leq 12)}$, amido$_{(C \leq 12)}$, or substituted amido$_{(C \leq 12)}$; and x and y are each independently selected from 0, 1, 2, 3, or 4; or a pharmaceutically acceptable salt thereof. In some embodiments, the compound is further defined as:

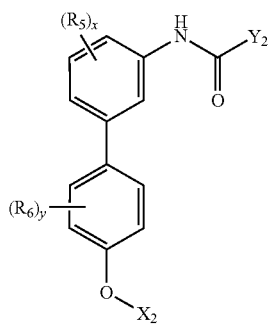

(VII)

wherein: $X_2$ is heterocycloalkyl$_{(C \leq 12)}$ or substituted heterocycloalkyl$_{(C \leq 12)}$; $Y_2$ is cycloalkyl$_{(C \leq 18)}$, aryl$_{(C \leq 24)}$, heteroaryl$_{(C \leq 24)}$, -arenediyl$_{(C \leq 18)}$-alkyl$_{(C \leq 8)}$, -arenediyl$_{(C \leq 18)}$-alkenyl$_{(C \leq 8)}$, -arenediyl$_{(C \leq 18)}$-alkoxy$_{(C \leq 8)}$, or a substituted version of any of these groups; each $R_5$ and $R_6$ are each independently selected from hydrogen, amino, cyano, halo, hydroxy, mercapto, nitro, sulfato, sulfamido, alkyl$_{(C \leq 12)}$, substituted alkyl$_{(C \leq 12)}$, alkoxy$_{(C \leq 12)}$, substituted alkoxy$_{(C \leq 12)}$, acyl$_{(C \leq 12)}$, substituted acyl$_{(C \leq 12)}$, acyloxy$_{(C \leq 12)}$, substituted acyloxy$_{(C \leq 12)}$, amido$_{(C \leq 12)}$, or substituted amido$_{(C \leq 12)}$; and x and y are each independently selected from 1, 2, 3, or 4; or a pharmaceutically acceptable salt thereof. In other embodiments, the compound is further defined as:

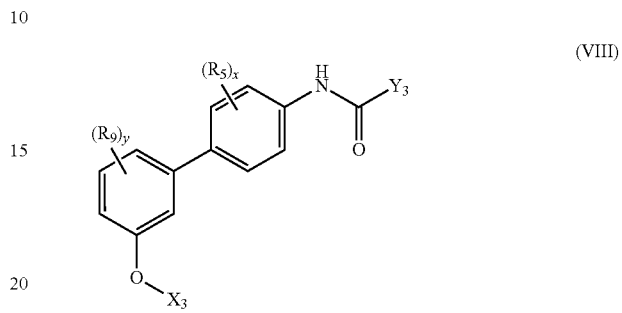

(VIII)

wherein: $X_3$ is heterocycloalkyl$_{(C \leq 12)}$, -alkanediyl$_{(C \leq 6)}$-heterocycloalkyl$_{(C \leq 12)}$, -alkanediyl$_{(C \leq 6)}$-amino, -alkanediyl$_{(C \leq 6)}$-alkylamino$_{(C \leq 8)}$, -alkanediyl$_{(C \leq 6)}$-di-alkylamino$_{(C \leq 12)}$, or a substituted version thereof; $Y_3$ is cycloalkyl$_{(C \leq 18)}$, aryl$_{(C \leq 24)}$, heteroaryl$_{(C \leq 24)}$, -arenediyl$_{(C \leq 18)}$-alkyl$_{(C \leq 8)}$, -arenediyl$_{(C \leq 18)}$-alkenyl$_{(C \leq 8)}$, -arenediyl$_{(C \leq 18)}$-alkoxy$_{(C \leq 8)}$, or a substituted version of any of these groups; each $R_8$ and $R_9$ are each independently selected from hydrogen, amino, cyano, halo, hydroxy, mercapto, nitro, sulfato, sulfamido, alkyl$_{(C \leq 12)}$, substituted alkyl$_{(C \leq 12)}$, alkoxy$_{(C \leq 12)}$, substituted alkoxy$_{(C \leq 12)}$, acyl$_{(C \leq 12)}$, substituted acyl$_{(C \leq 12)}$, acyloxy$_{(C \leq 12)}$, substituted acyloxy$_{(C \leq 12)}$, amido$_{(C \leq 12)}$, or substituted amido$_{(C \leq 12)}$; and x and y are each independently selected from 0, 1, 2, 3, or 4; or a pharmaceutically acceptable salt thereof. In some embodiments, the compound is further defined as:

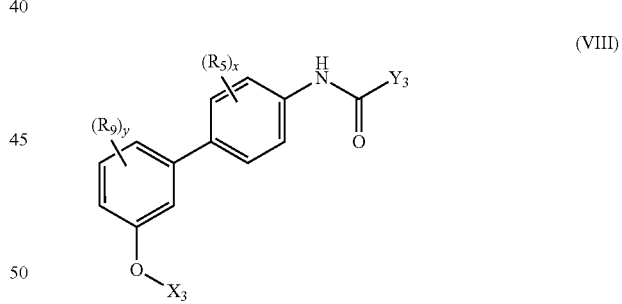

(VIII)

wherein: $X_3$ is heterocycloalkyl$_{(C \leq 12)}$ or substituted heterocycloalkyl$_{(C \leq 12)}$; $Y_3$ is cycloalkyl$_{(C \leq 18)}$, aryl$_{(C \leq 24)}$, heteroaryl$_{(C \leq 24)}$, -arenediyl$_{(C \leq 18)}$-alkyl$_{(C \leq 8)}$, -arenediyl$_{(C \leq 18)}$-alkenyl$_{(C \leq 8)}$, -arenediyl$_{(C \leq 18)}$-alkoxy$_{(C \leq 8)}$, or a substituted version of any of these groups; each $R_8$ and $R_9$ are each independently selected from hydrogen, amino, cyano, halo, hydroxy, mercapto, nitro, sulfato, sulfamido, alkyl$_{(C \leq 12)}$, substituted alkyl$_{(C \leq 12)}$, alkoxy$_{(C \leq 12)}$, substituted alkoxy$_{(C \leq 12)}$, acyl$_{(C \leq 12)}$, substituted acyl$_{(C \leq 12)}$, acyloxy$_{(C \leq 12)}$, substituted acyloxy$_{(C \leq 12)}$, amido$_{(C \leq 12)}$, or substituted amido$_{(C \leq 12)}$; and x and y are each independently selected from 1, 2, 3, or 4; or a pharmaceutically acceptable salt thereof. In other embodiments, the compound is further defined as:

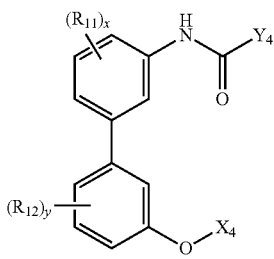

wherein: $X_4$ is heterocycloalkyl$_{(C\leq12)}$, -alkanediyl$_{(C\leq6)}$-heterocycloalkyl$_{(C\leq12)}$, -alkanediyl$_{(C\leq6)}$-amino, -alkanediyl$_{(C\leq6)}$-alkylamino$_{(C\leq8)}$, -alkanediyl$_{(C\leq6)}$-di-alkylamino$_{(C\leq12)}$, or a substituted version thereof; $Y_4$ is cycloalkyl$_{(C\leq18)}$, aryl$_{(C\leq24)}$, heteroaryl$_{(C\leq24)}$, -arenediyl$_{(C\leq18)}$-alkyl$_{(C\leq8)}$, -arenediyl$_{(C\leq18)}$-alkenyl$_{(C\leq8)}$, -arenediyl$_{(C\leq18)}$-alkoxy$_{(C\leq8)}$, or a substituted version of any of these groups; each $R_{11}$ and $R_{12}$ are each independently selected from hydrogen, amino, cyano, halo, hydroxy, mercapto, nitro, sulfato, sulfamido, alkyl$_{(C\leq12)}$, substituted alkyl$_{(C\leq12)}$, alkoxy$_{(C\leq12)}$, substituted alkoxy$_{(C\leq12)}$, acyl$_{(C\leq12)}$, substituted acyl$_{(C\leq12)}$, acyloxy$_{(C\leq12)}$, substituted acyloxy$_{(C\leq12)}$, amido$_{(C\leq12)}$, or substituted amido$_{(C\leq12)}$; and x and y are each independently selected from 0, 1, 2, 3, or 4; or a pharmaceutically acceptable salt thereof. In some embodiments, the compound is further defined as:

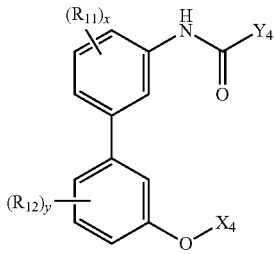

wherein: $X_4$ is heterocycloalkyl$_{(C\leq12)}$ or substituted heterocycloalkyl$_{(C\leq12)}$; $Y_4$ is cycloalkyl$_{(C\leq18)}$, aryl$_{(C\leq24)}$, heteroaryl$_{(C\leq24)}$, -arenediyl$_{(C\leq18)}$-alkyl$_{(C\leq8)}$, -arenediyl$_{(C\leq18)}$-alkenyl$_{(C\leq8)}$, -arenediyl$_{(C\leq18)}$-alkoxy$_{(C\leq8)}$, or a substituted version of any of these groups; each $R_{11}$ and $R_{12}$ are each independently selected from hydrogen, amino, cyano, halo, hydroxy, mercapto, nitro, sulfato, sulfamido, alkyl$_{(C\leq12)}$, substituted alkyl$_{(C\leq12)}$, alkoxy$_{(C\leq12)}$, substituted alkoxy$_{(C\leq12)}$, acyl$_{(C\leq12)}$, substituted acyl$_{(C\leq12)}$, acyloxy$_{(C\leq12)}$, substituted acyloxy$_{(C\leq12)}$, amido$_{(C\leq12)}$, or substituted amido$_{(C\leq12)}$; and x and y are each independently selected from 1, 2, 3, or 4; or a pharmaceutically acceptable salt thereof. In other embodiments, the compound is further defined as:

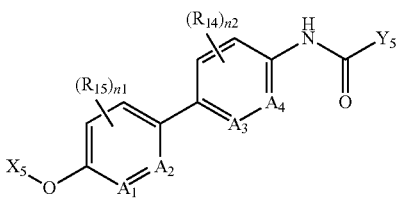

wherein: $A_1$ and $A_2$ are each independently selected from N or $CR_{15}$ and $A_3$ and $A_4$ are each independently selected from N or $CR_{14}$ provided at least one of $A_1$, $A_2$, $A_3$, and $A_4$ is N; $X_5$ is heterocycloalkyl$_{(C\leq12)}$, -alkanediyl$_{(C\leq6)}$-heterocycloalkyl$_{(C\leq12)}$, -alkanediyl$_{(C\leq6)}$-amino, -alkanediyl$_{(C\leq6)}$-alkylamino$_{(C\leq8)}$, -alkanediyl$_{(C\leq6)}$-dialkylamino$_{(C\leq12)}$, or a substituted version thereof; $Y_5$ is cycloalkyl$_{(C\leq18)}$, aryl$_{(C\leq24)}$, heteroaryl$_{(C\leq24)}$, -arenediyl$_{(C\leq18)}$-alkyl$_{(C\leq8)}$, -arenediyl$_{(C\leq18)}$-alkenyl$_{(C\leq8)}$, -arenediyl$_{(C\leq18)}$-alkoxy$_{(C\leq8)}$, or a substituted version of any of these groups; each $R_{14}$ and $R_{15}$ are each independently selected from hydrogen, amino, cyano, halo, hydroxy, mercapto, nitro, sulfato, sulfamido, alkyl$_{(C\leq12)}$, substituted alkyl$_{(C\leq12)}$, alkoxy$_{(C\leq12)}$, substituted alkoxy$_{(C\leq12)}$, acyl$_{(C\leq12)}$, substituted acyl$_{(C\leq12)}$, acyloxy$_{(C\leq12)}$, substituted acyloxy$_{(C\leq12)}$, amido$_{(C\leq12)}$, or substituted amido$_{(C\leq12)}$; and $n_1$ are each independently 0, 1, or 2; or a pharmaceutically acceptable salt thereof. In some embodiments, the compound is further defined as:

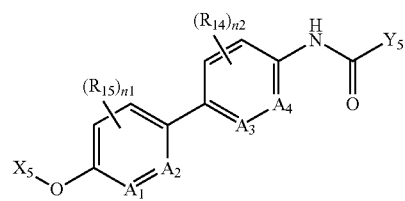

wherein: $A_1$ and $A_2$ are each independently selected from N or $CR_{15}$ and $A_3$ and $A_4$ are each independently selected from N or $CR_{14}$ provided at least one of $A_1$, $A_2$, $A_3$, and $A_4$ is N; $X_5$ is heterocycloalkyl$_{(C\leq12)}$ or substituted heterocycloalkyl$_{(C\leq12)}$; $Y_5$ is cycloalkyl$_{(C\leq18)}$, aryl$_{(C\leq24)}$, heteroaryl$_{(C\leq24)}$, -arenediyl$_{(C\leq18)}$-alkyl$_{(C\leq8)}$, -arenediyl$_{(C\leq18)}$-alkenyl$_{(C\leq8)}$, -arenediyl$_{(C\leq18)}$-alkoxy$_{(C\leq8)}$, or a substituted version of any of these groups; each $R_{14}$ and $R_{15}$ are each independently selected from hydrogen, amino, cyano, halo, hydroxy, mercapto, nitro, sulfato, sulfamido, alkyl$_{(C\leq12)}$, substituted alkyl$_{(C\leq12)}$, alkoxy$_{(C\leq12)}$, substituted alkoxy$_{(C\leq12)}$, acyl$_{(C\leq12)}$, substituted acyl$_{(C\leq12)}$, acyloxy$_{(C\leq12)}$, substituted acyloxy$_{(C\leq12)}$, amido$_{(C\leq12)}$, or substituted amido$_{(C\leq12)}$; and $n_1$ are each independently 0, 1, or 2; or a pharmaceutically acceptable salt thereof. In other embodiments, the compound is further defined as:

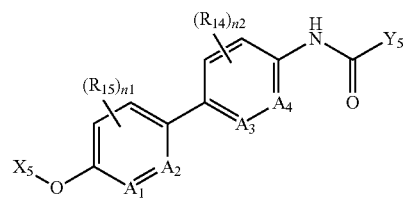

wherein: $A_1$ and $A_2$ are each independently selected from N or $CR_{15}$ and $A_3$ and $A_4$ are each independently selected from N or $CR_{14}$ provided at least one of $A_1$, $A_2$, $A_3$, and $A_4$ is N; $X_5$ is heterocycloalkyl$_{(C\leq12)}$ or substituted heterocycloalkyl$_{(C\leq12)}$; $Y_5$ is aryl$_{(C\leq24)}$ or substituted aryl$_{(C\leq24)}$; each $R_{14}$ and $R_{15}$ are each independently selected from hydrogen, amino, cyano, halo, hydroxy, mercapto, nitro, sulfato, sulfamido, alkyl$_{(C\leq12)}$, substituted alkyl$_{(C\leq12)}$, alkoxy$_{(C\leq12)}$, substituted alkoxy$_{(C\leq12)}$, acyl$_{(C\leq12)}$, substituted acyl$_{(C\leq12)}$, acyloxy$_{(C\leq12)}$, substituted acyloxy$_{(C\leq12)}$, amido$_{(C\leq12)}$, or substituted amido$_{(C≤12)}$; and n$_1$ and n$_2$ are each independently 0, 1, or 2; or a pharmaceutically acceptable salt thereof. In some embodiments, the compound is further defined as:

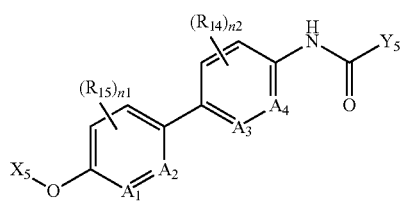
(X)

wherein: A$_1$ and A$_2$ are each independently selected from N or CR$_{15}$ and A$_3$ and A$_4$ are each independently selected from N or CR$_{14}$ provided at least one of A$_1$, A$_2$, A$_3$, and A$_4$ is N; X$_5$ is heterocycloalkyl$_{(C≤12)}$ or substituted heterocycloalkyl$_{(C≤12)}$; Y$_5$ is aryl$_{(C≤24)}$ or substituted aryl$_{(C≤24)}$; each R$_{14}$ and R$_{15}$ are each independently selected from hydrogen, amino, cyano, halo, hydroxy, mercapto, nitro, sulfato, sulfamido, alkyl$_{(C≤12)}$, substituted alkyl$_{(C≤12)}$, alkoxy$_{(C≤12)}$, substituted alkoxy$_{(C≤12)}$, acyl$_{(C≤12)}$, substituted acyl$_{(C≤12)}$, acyloxy$_{(C≤12)}$, substituted acyloxy$_{(C≤12)}$, amido$_{(C≤12)}$, or substituted amido$_{(C≤12)}$; and n$_1$ are each independently 1 or 2; or a pharmaceutically acceptable salt thereof. In some embodiments, the compound is further defined by formula I. In other embodiments, the compound is further defined by formula II. In other embodiments, the compound is further defined by formula III. In other embodiments, the compound is further defined by formula IV. In other embodiments, the compound is further defined by formula V. In some embodiments, X$_1$ is heterocycloalkoxy$_{(C≤12)}$ or heterocycloalkoxy$_{(C≤12)}$. In some embodiments, X$_1$ is heterocycloalkoxy$_{(C≤12)}$. In some embodiments, X$_1$ is

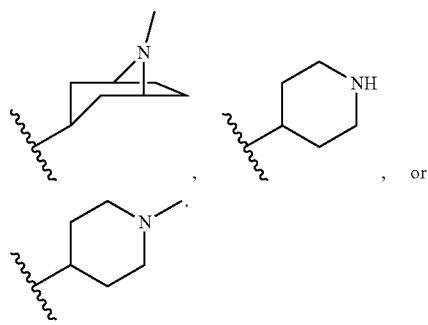

In some embodiments, X$_1$ is

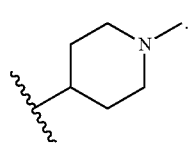

In other embodiments, X$_1$ is -alkanediyl$_{(C≤8)}$-heterocycloalkyl$_{(C≤12)}$ or substituted -alkanediyl$_{(C≤8)}$-heterocycloalkyl$_{(C≤12)}$. In some embodiments, X$_1$ is -alkanediyl$_{(C≤8)}$-heterocycloalkyl$_{(C≤8)}$. In some embodiments, X$_1$ is —CH$_2$CH$_2$-heterocycloalkyl$_{(C≤8)}$. In some embodiments, X$_1$ is

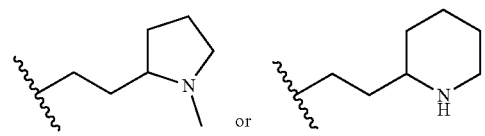

In other embodiments, X$_1$ is -alkanediyl$_{(C≤8)}$-dialkylamino$_{(C≤12)}$ or substituted -alkanediyl$_{(C≤8)}$-dialkylamino$_{(C≤12)}$. In some embodiments, X$_1$ is -alkanediyl$_{(C≤8)}$-dialkylamino$_{(C≤8)}$. In some embodiments, X$_1$ is —CH$_2$CH$_2$-dialkylamino$_{(C≤8)}$ or —CH$_2$CH$_2$CH$_2$-dialkylamino$_{(C≤8)}$. In some embodiments, X$_1$ is

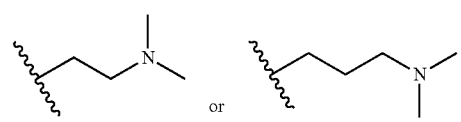

In some embodiments, Y$_1$ is aryl$_{(C≤18)}$ or substituted aryl$_{(C≤18)}$. In some embodiments, Y$_1$ is aryl$_{(C≤18)}$. In some embodiments, Y$_1$ is phenyl, 4-methylphenyl, 3-methylphenyl, 4-t-butylphenyl, naphthyl, or biphenyl. In some embodiments, Y$_1$ is substituted aryl$_{(C≤18)}$. In some embodiments, Y$_1$ is 3-methoxyphenyl, 4-methoxyphenyl, 4-acetoxyphenyl, 2-chlorophenyl, 3-chlorophenyl, 4-chlorophenyl, 4-bromophenyl, 3,4-dichlorophenyl, 2,4-dichlorophenyl, 3,5-dichlorophenyl, 3-iodo-4-methylphenyl, 3-bromo-4-methylphenyl, 3-chloro-4-methylphenyl, 4-iodophenyl, or 3-methyl-4-chlorophenyl. In some embodiments, Y$_1$ is substituted biphenyl$_{(C≤18)}$. In some embodiments, Y$_1$ is:

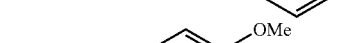
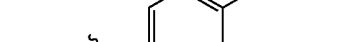
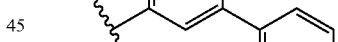
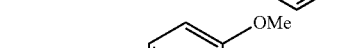
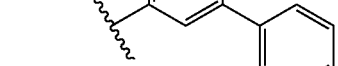
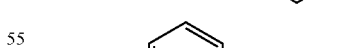
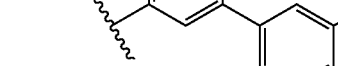
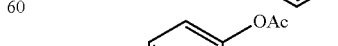
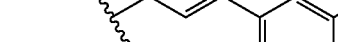

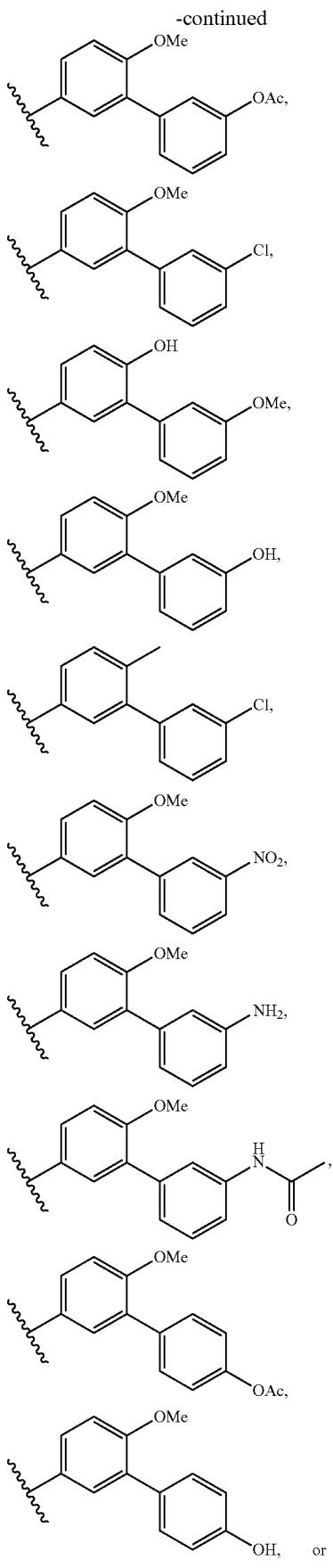

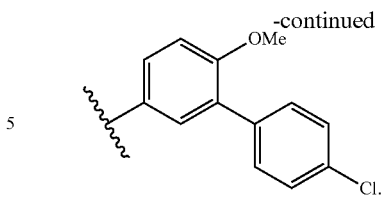

In other embodiments, $Y_1$ is heteroaryl$_{(C \leq 18)}$ or substituted heteroaryl$_{(C \leq 18)}$. In some embodiments, $Y_1$ is heteroaryl$_{(C \leq 18)}$. In some embodiments, $Y_1$ is 2-quinolyl, 6-quinolyl, 2-indolyl, or 2-benzo[b]thiophenyl. In other embodiments, $Y_1$ is -arenediyl$_{(C \leq 12)}$-alkenyl$_{(C \leq 8)}$ or substituted -arenediyl$_{(C \leq 12)}$-alkenyl$_{(C \leq 8)}$. In some embodiments, $Y_1$ is -arenediyl$_{(C \leq 12)}$-CH$_2$CH(CH$_3$)$_2$ or substituted -arenediyl$_{(C \leq 12)}$-CH$_2$CH(CH$_3$)$_2$. In some embodiments, $Y_1$ is —C$_6$H$_4$—CH$_2$CH(CH$_3$)$_2$. In some embodiments, $Y_1$ is

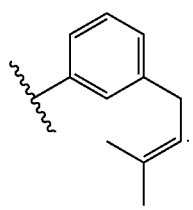

In some embodiments, $Y_1$ is —C$_6$H$_3$(OH)—CH$_2$CH(CH$_3$)$_2$ or —C$_6$H$_3$(OAc)—CH$_2$CH(CH$_3$)$_2$. In some embodiments, $Y_1$ is

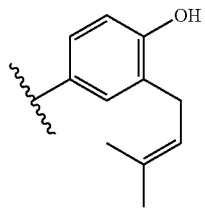 or 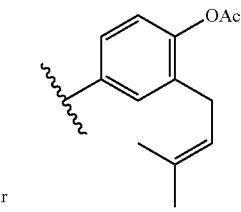.

In other embodiments, $Y_1$ is -arenediyl$_{(C \leq 15)}$-alkoxy$_{(C \leq 8)}$ or substituted -arenediyl$_{(C \leq 15)}$-alkoxy$_{(C \leq 8)}$. In some embodiments, $Y_1$ is -arenediyl$_{(C \leq 15)}$-OCH$_2$CH$_2$CH$_3$ or substituted -arenediyl$_{(C \leq 15)}$-OCH$_2$CH$_2$CH$_3$. In some embodiments, $Y_1$ is

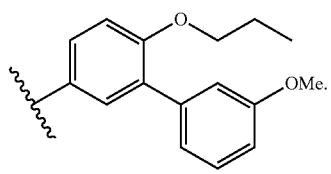 [SMILES: *c1ccc(OCCC)c(-c2cccc(OC)c2)c1]

In some embodiments, x is 1 or 2. In some embodiments, x is 1. In other embodiments, x is 2. In some embodiments, $R_2$ is amino. In other embodiments, $R_2$ is cyano. In other embodiments, $R_2$ is nitro. In other embodiments, $R_2$ is halo. In some embodiments, $R_2$ is chloro. In other embodiments, $R_2$ is amido$_{(C \leq 12)}$ or substituted amido$_{(C \leq 12)}$. In some embodiments, $R_2$ is amido$_{(C \leq 12)}$. In some embodiments, $R_2$ is —NHAc. In some embodiments, $R_2$ is alkyl$_{(C \leq 12)}$ or substituted alkyl$_{(C \leq 12)}$. In some embodiments, $R_2$ is alkyl$_{(C \leq 12)}$. In some embodiments, R$_2$ is methyl. In other embodiments, R$_2$ is alkoxy$_{(C \leq 12)}$ or substituted alkoxy$_{(C \leq 12)}$. In some embodiments, R$_2$ is alkoxy$_{(C \leq 12)}$. In some embodiments, R$_2$ is methoxy. In some embodiments, y is 1 or 2. In some embodiments, y is 1. In other embodiments, y is 2. In some embodiments, R$_3$ is amino. In other embodiments, R$_3$ is cyano. In other embodiments, R$_3$ is nitro. In other embodiments, R$_3$ is halo. In some embodiments, R$_3$ is chloro. In other embodiments, R$_3$ is amido$_{(C \leq 12)}$ or substituted amido$_{(C \leq 12)}$. In some embodiments, R$_3$ is amido$_{(C \leq 12)}$. In some embodiments, R$_3$ is —NHAc. In other embodiments, R$_3$ is alkyl$_{(C \leq 12)}$ or substituted alkyl$_{(C \leq 12)}$. In some embodiments, R$_3$ is alkyl$_{(C \leq 12)}$. In some embodiments, R$_3$ is methyl. In other embodiments, R$_3$ is alkoxy$_{(C \leq 12)}$ or substituted alkoxy$_{(C \leq 12)}$. In some embodiments, R$_3$ is alkoxy$_{(C \leq 12)}$. In some embodiments, R$_3$ is methoxy. In some embodiments, X$_2$ is heterocycloalkoxy$_{(C \leq 12)}$ or heterocycloalkoxy$_{(C \leq 12)}$. In some embodiments, X$_2$ is heterocycloalkoxy$_{(C \leq 12)}$. In some embodiments, X$_2$ is

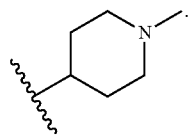 [SMILES: *C1CCN(C)CC1]

In some embodiments, Y$_2$ is aryl$_{(C \leq 18)}$ or substituted aryl$_{(C \leq 18)}$. In some embodiments, Y$_2$ is aryl$_{(C \leq 18)}$. In some embodiments, Y$_2$ is 4-t-butylphenyl. In other embodiments, Y$_2$ is substituted aryl$_{(C \leq 18)}$. In some embodiments, Y$_2$ is 4-methoxyphenyl or 4-chlorophenyl. In other embodiments, Y$_2$ is substituted biphenyl$_{(C \leq 18)}$. In some embodiments, Y$_2$ is

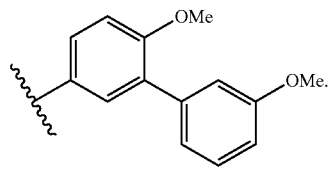 [SMILES: *c1ccc(OC)c(-c2cccc(OC)c2)c1]

In other embodiments, Y$_2$ is -arenediyl$_{(C \leq 12)}$-alkenyl$_{(C \leq 8)}$ or substituted -arenediyl$_{(C \leq 12)}$-alkenyl$_{(C \leq 8)}$. In some embodiments, Y$_2$ is -arenediyl$_{(C \leq 12)}$-CH$_2$CH(CH$_3$)$_2$ or substituted -arenediyl$_{(C \leq 12)}$—CH$_2$CH(CH$_3$)$_2$. In some embodiments, Y$_2$ is —C$_6$H$_3$(OAc)—CH$_2$CH(CH$_3$)$_2$. In some embodiments, Y$_2$ is

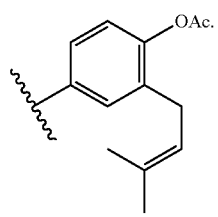 [SMILES: *c1ccc(OC(C)=O)c(CC=C(C)C)c1]

In some embodiments, X$_3$ is heterocycloalkoxy$_{(C \leq 12)}$ or heterocycloalkoxy$_{(C \leq 12)}$. In some embodiments, X$_3$ is heterocycloalkoxy$_{(C \leq 12)}$. In some embodiments, X$_3$ is

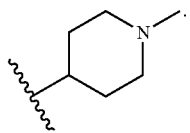 [SMILES: *C1CCN(C)CC1]

In some embodiments, Y$_3$ is aryl$_{(C \leq 18)}$ or substituted aryl$_{(C \leq 18)}$. In some embodiments, Y$_3$ is aryl$_{(C \leq 18)}$. In some embodiments, Y$_3$ is 4-t-butylphenyl. In other embodiments, Y$_3$ is substituted aryl$_{(C \leq 18)}$. In some embodiments, Y$_3$ is 4-methoxyphenyl or 4-chlorophenyl. In other embodiments, Y$_3$ is substituted biphenyl$_{(C \leq 18)}$. In some embodiments, Y$_3$ is

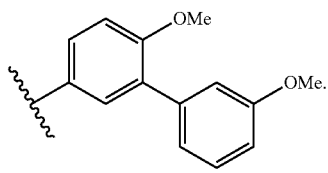 [SMILES: *c1ccc(OC)c(-c2cccc(OC)c2)c1]

In other embodiments, Y$_3$ is -arenediyl$_{(C \leq 12)}$-alkenyl$_{(C \leq 8)}$ or substituted -arenediyl$_{(C \leq 12)}$-alkenyl$_{(C \leq 8)}$. In some embodiments, Y$_3$ is -arenediyl$_{(C \leq 12)}$-CH$_2$CH(CH$_3$)$_2$ or substituted -arenediyl$_{(C \leq 12)}$—CH$_2$CH(CH$_3$)$_2$. In some embodiments, Y$_3$ is —C$_6$H$_3$(OAc)—CH$_2$CH(CH$_3$)$_2$. In some embodiments, Y$_3$ is

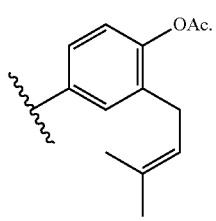 [SMILES: *c1ccc(OC(C)=O)c(CC=C(C)C)c1]

In some embodiments, X$_4$ is heterocycloalkoxy$_{(C \leq 12)}$ or heterocycloalkoxy$_{(C \leq 12)}$. In some embodiments, X$_4$ is heterocycloalkoxy$_{(C \leq 12)}$. In some embodiments, X$_4$ is

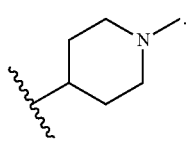 [SMILES: *C1CCN(C)CC1]

In some embodiments, Y$_4$ is aryl$_{(C \leq 18)}$ or substituted aryl$_{(C \leq 18)}$. In some embodiments, Y$_4$ is aryl$_{(C \leq 18)}$. In some embodiments, Y$_4$ is 4-t-butylphenyl. In other embodiments, Y$_4$ is substituted aryl$_{(C \leq 18)}$. In some embodiments, Y$_4$ is 4-methoxyphenyl or 4-chlorophenyl. In other embodiments, Y$_4$ is substituted biphenyl$_{(C \leq 18)}$. In some embodiments, Y$_4$ is

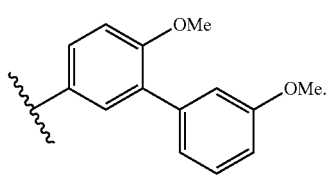 [SMILES: *c1ccc(OC)c(-c2cccc(OC)c2)c1]

In other embodiments, $Y_4$ is -arenediyl$_{(C \leq 12)}$-alkenyl$_{(C \leq 8)}$ or substituted -arenediyl$_{(C \leq 12)}$-alkenyl$_{(C \leq 8)}$. In some embodiments, $Y_4$ is -arenediyl$_{(C \leq 12)}$-CH$_2$CH(CH$_3$)$_2$ or substituted -arenediyl$_{(C \leq 12)}$—CH$_2$CH(CH$_3$)$_2$. In some embodiments, $Y_4$ is —C$_6$H$_3$(OAc)—CH$_2$CH(CH$_3$)$_2$. In some embodiments, $Y_4$ is

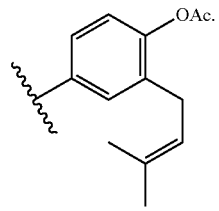 [SMILES: *c1ccc(OC(C)=O)c(CC=C(C)C)c1]

In some embodiments, $X_5$ is heterocycloalkoxy$_{(C \leq 12)}$ or heterocycloalkoxy$_{(C \leq 12)}$. In some embodiments, $X_5$ is heterocycloalkoxy$_{(C \leq 12)}$. In some embodiments, $X_5$ is

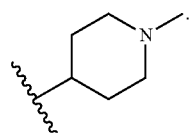

In some embodiments, $Y_5$ is aryl$_{(C \leq 18)}$ or substituted aryl$_{(C \leq 18)}$. In some embodiments, $Y_5$ is substituted aryl$_{(C \leq 18)}$. In some embodiments, $Y_5$ is substituted biphenyl$_{(C \leq 18)}$. In some embodiments, $Y_5$ is

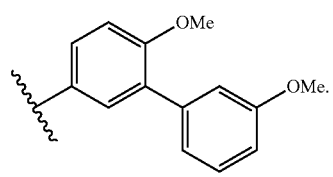 [SMILES: *c1ccc(OC)c(-c2cccc(OC)c2)c1]

In some embodiments, the compound is further defined as:

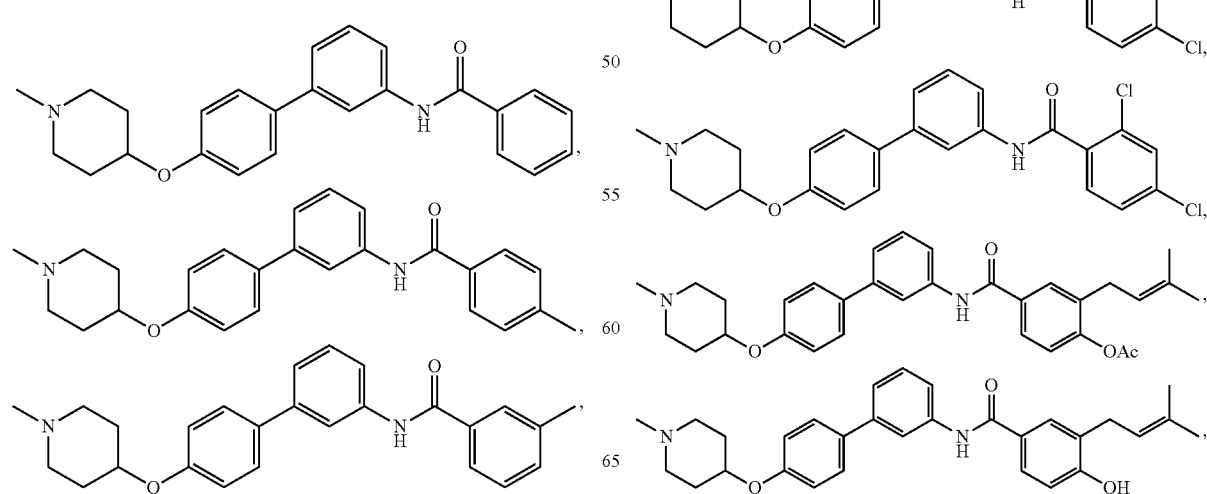

-continued

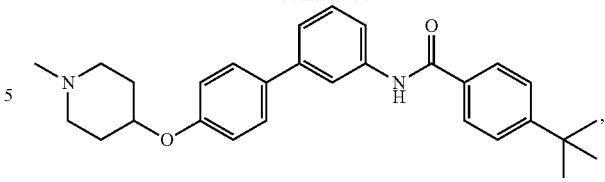
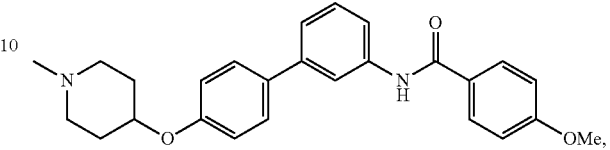
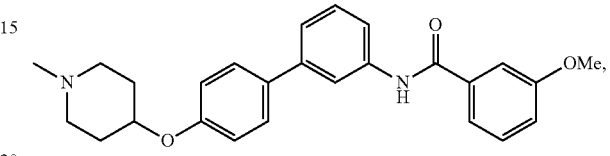
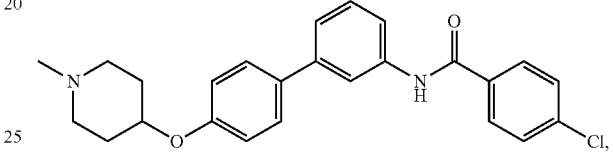
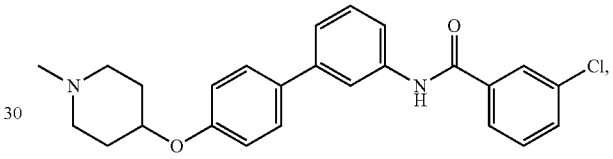
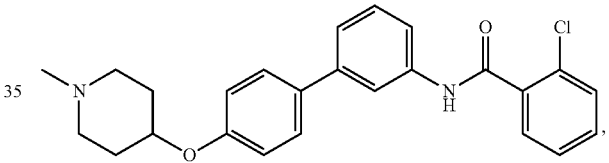
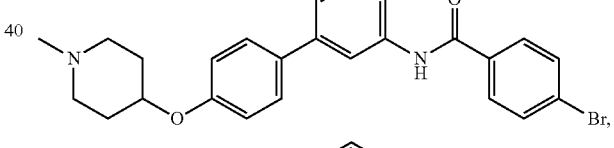
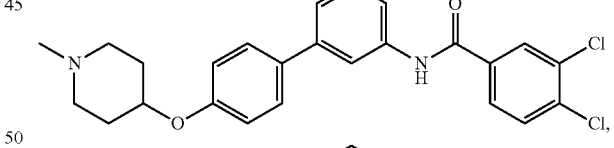
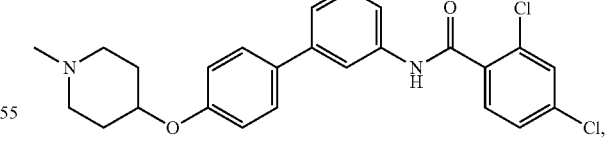
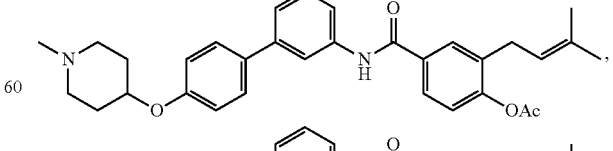
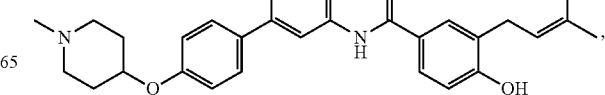

17
-continued
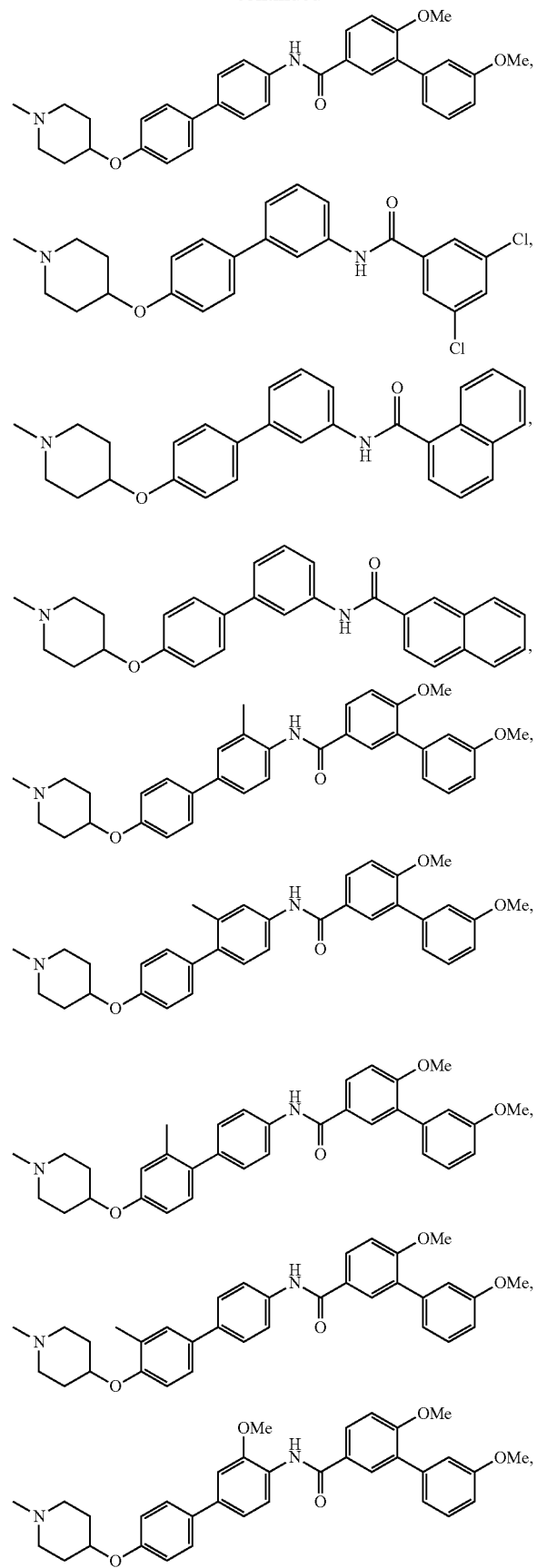
18
-continued
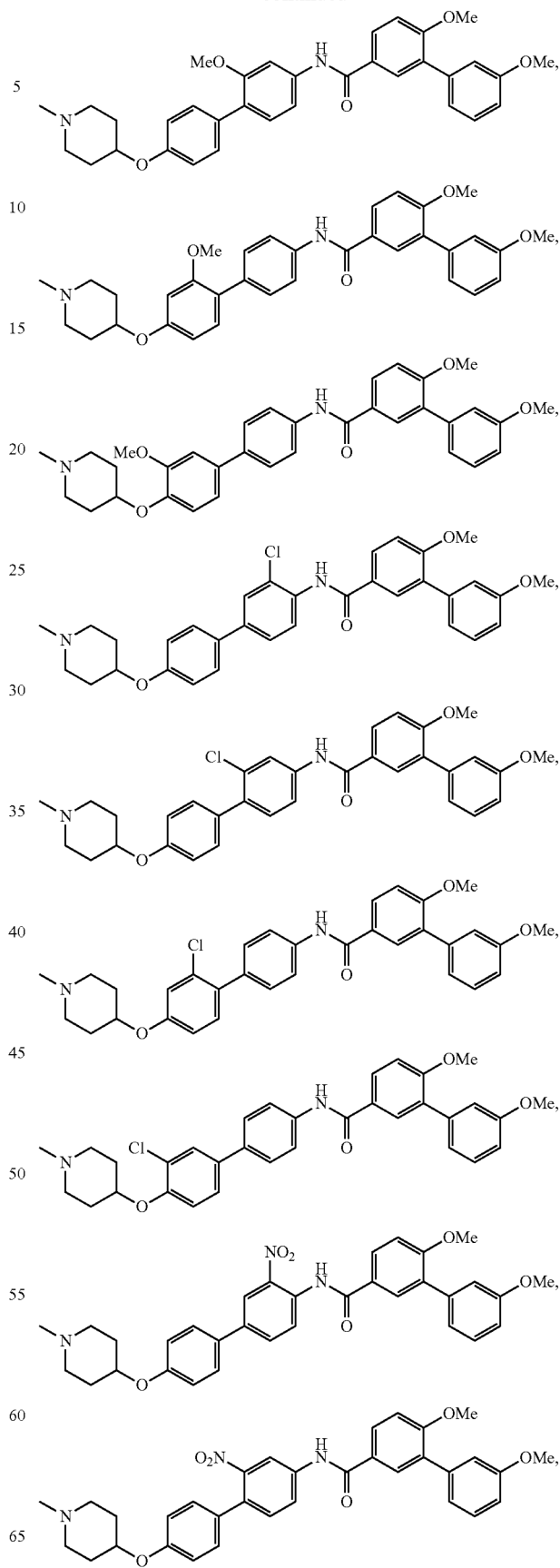

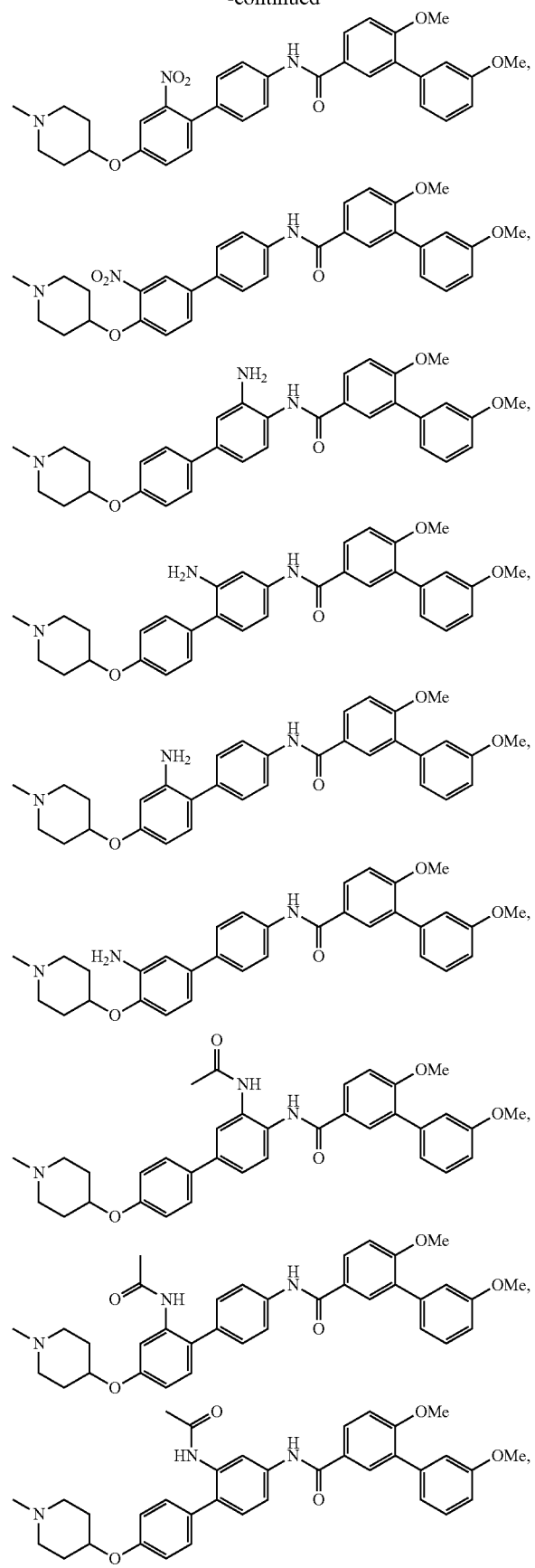
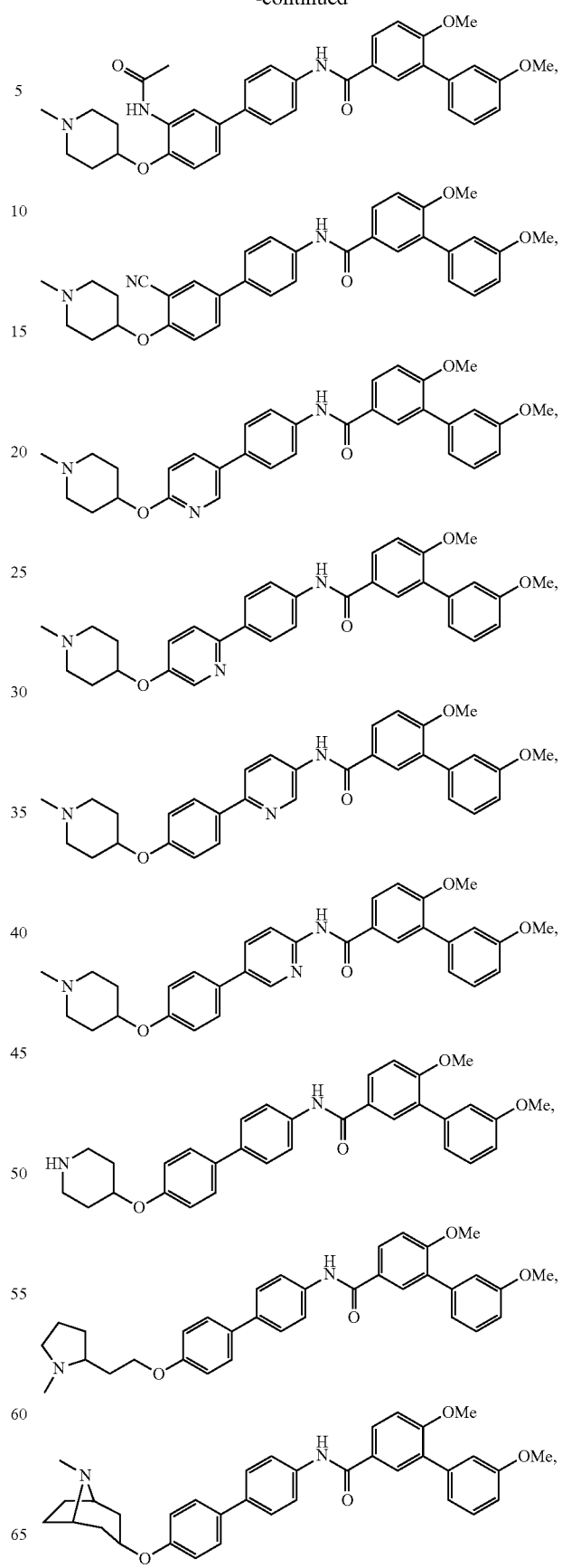

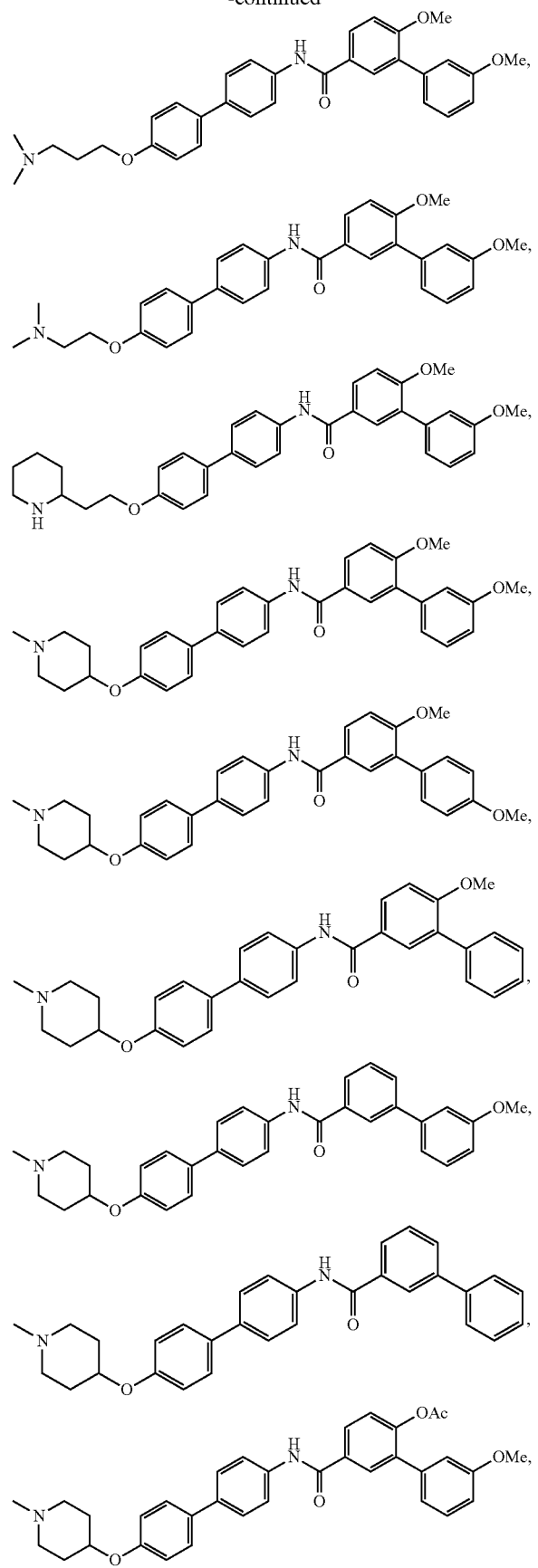
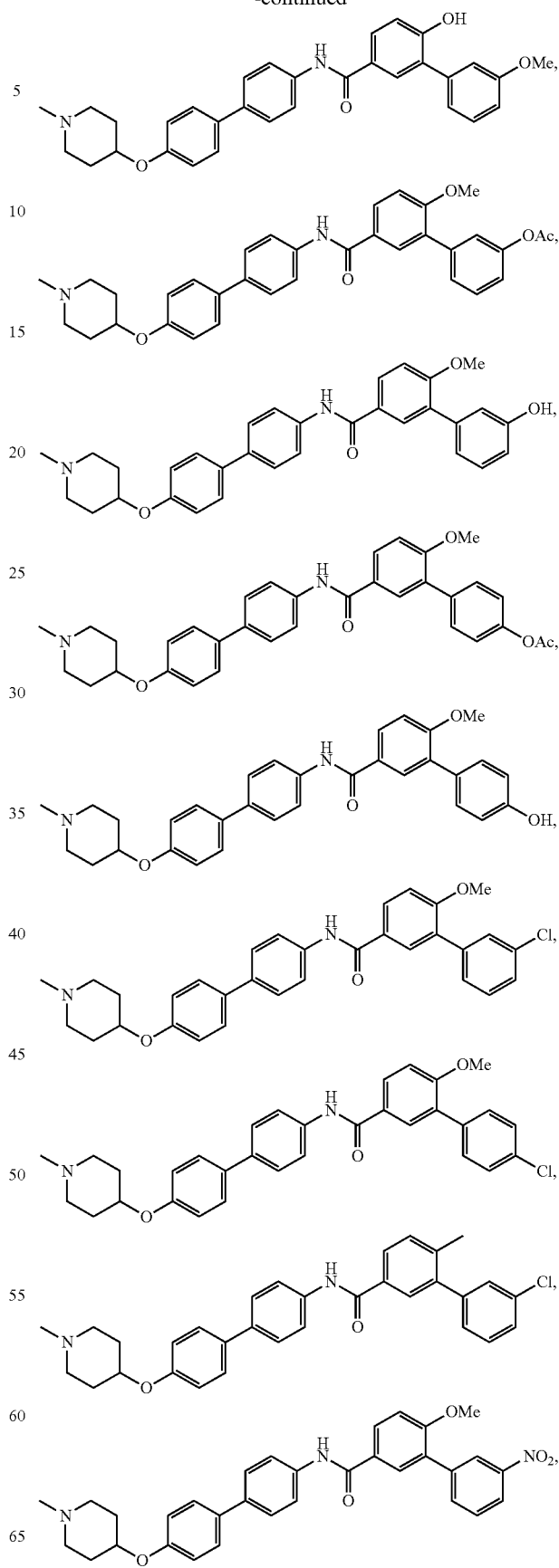

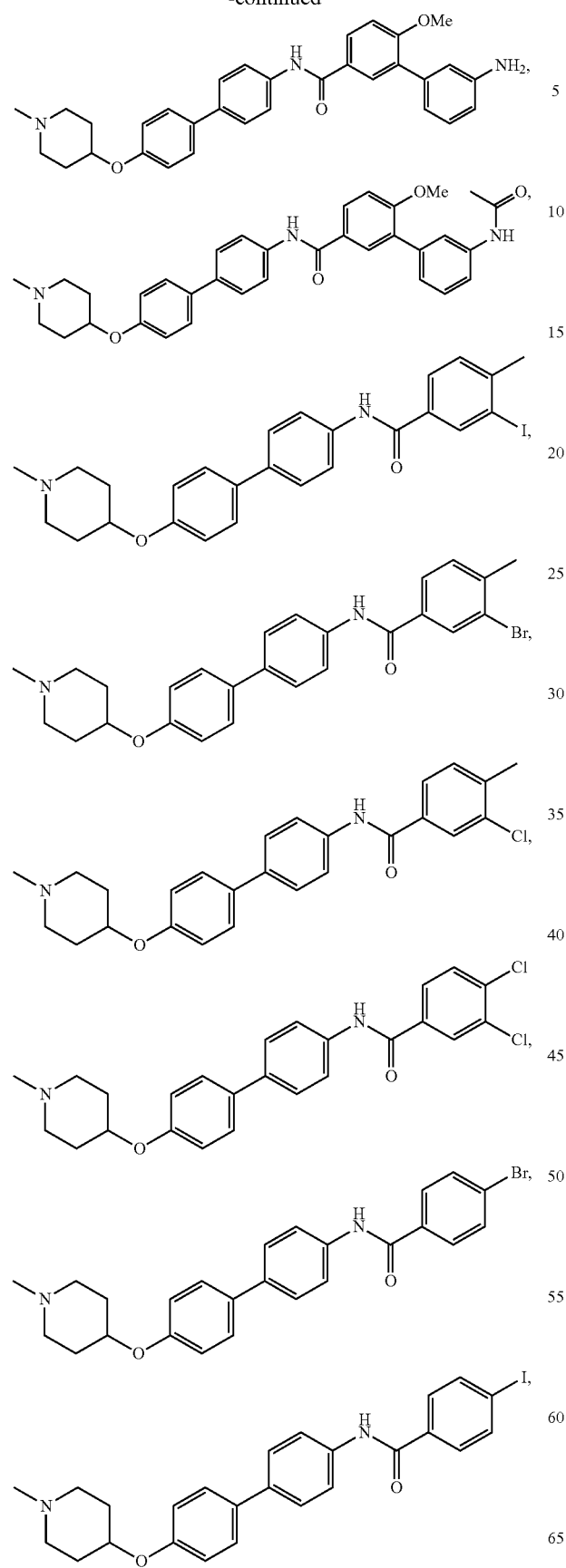
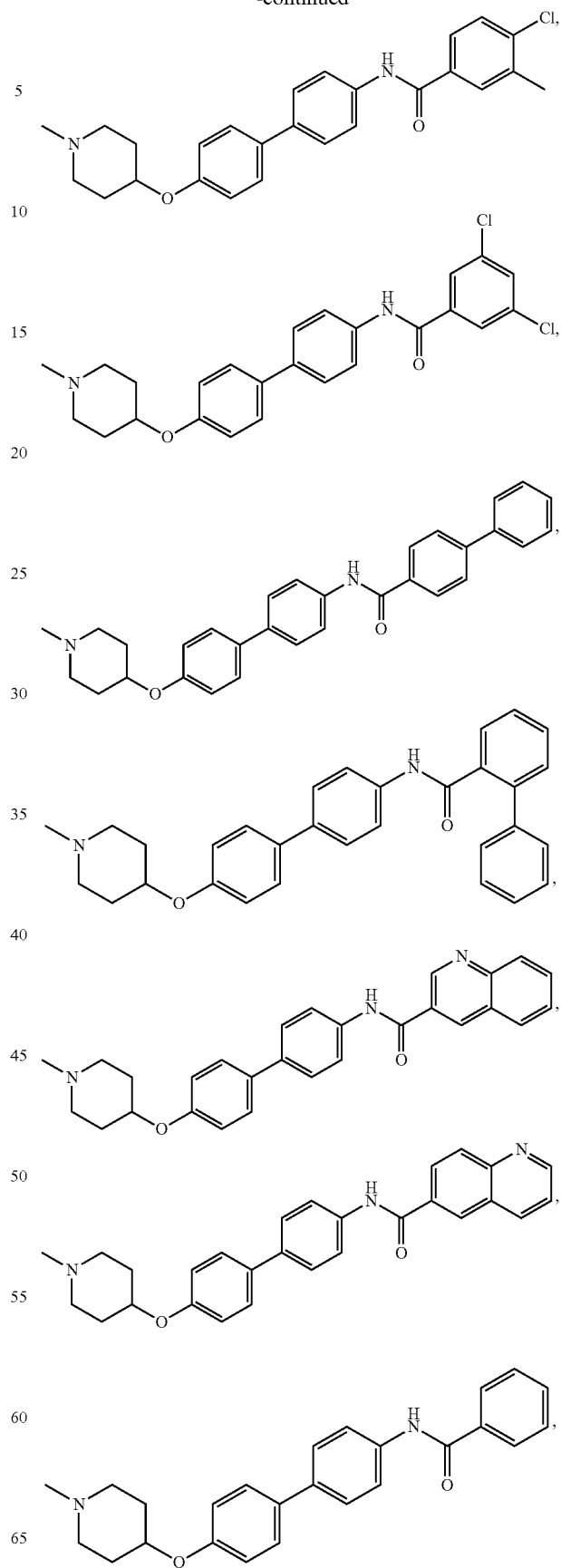

-continued
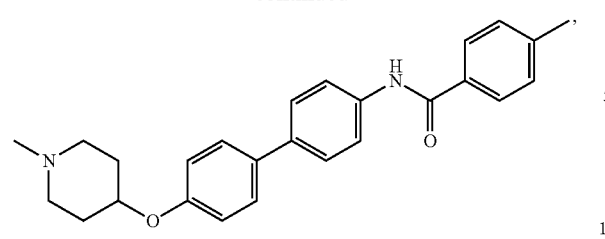
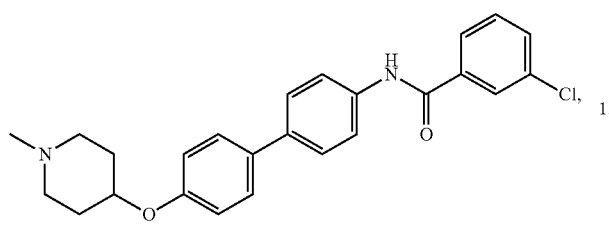
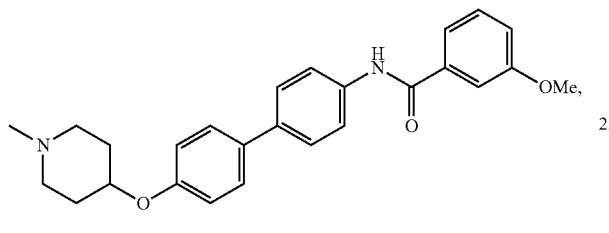
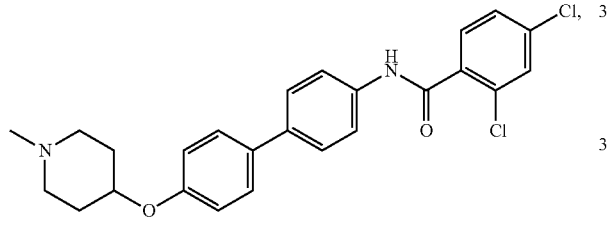
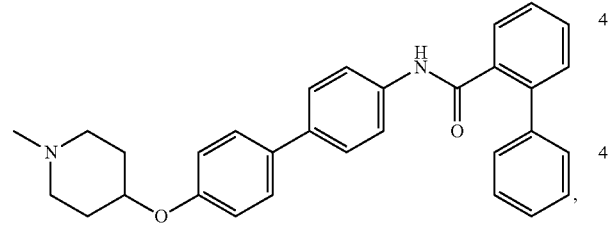
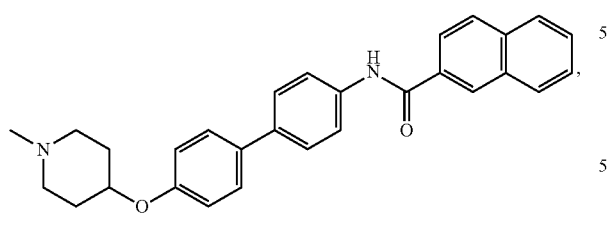
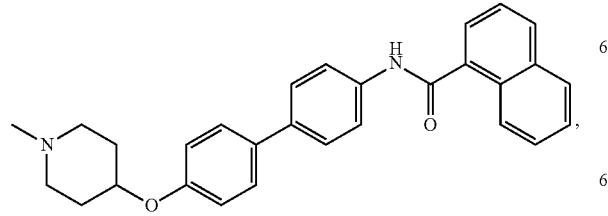
-continued
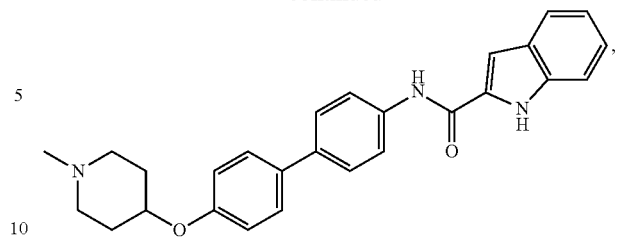
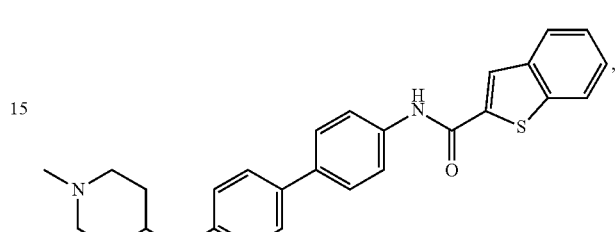
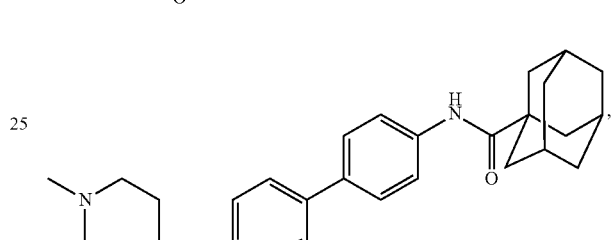
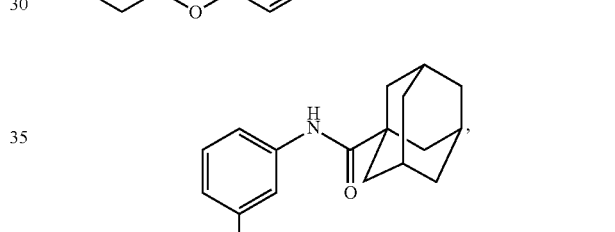
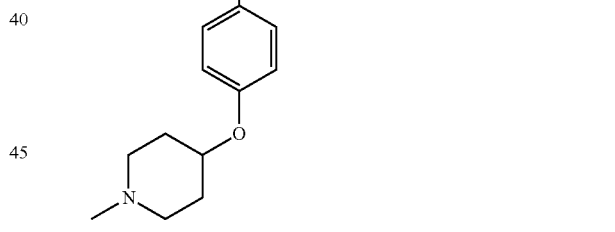
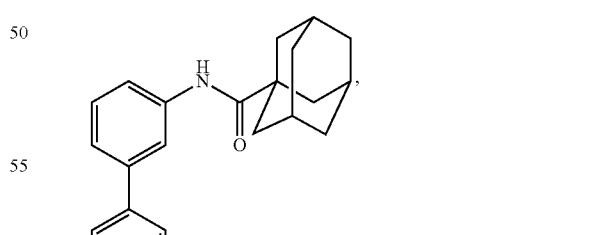
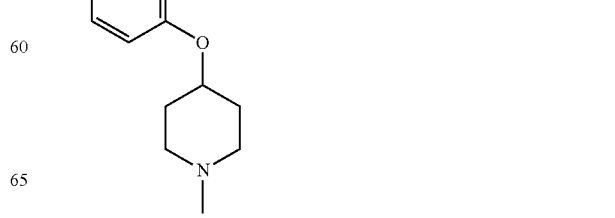

27
-continued
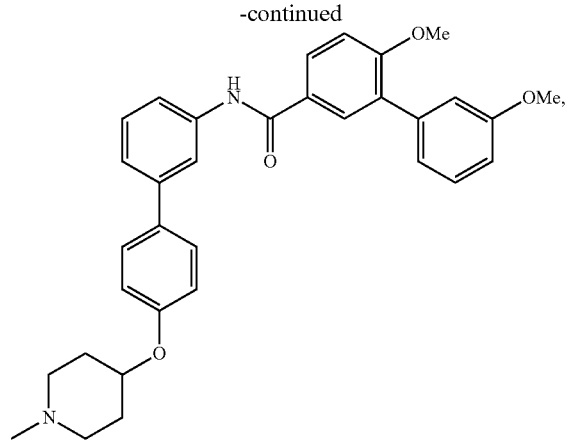
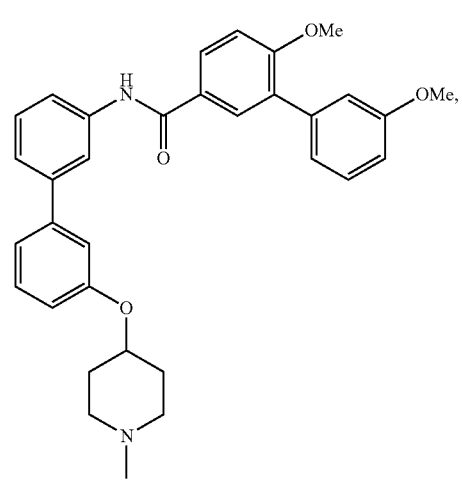
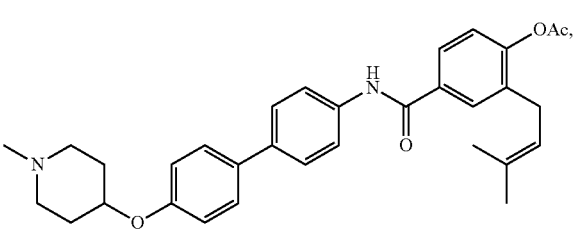
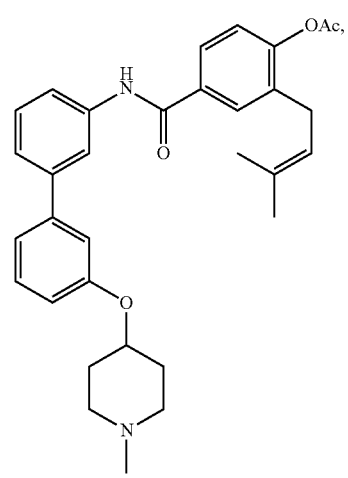
28
-continued
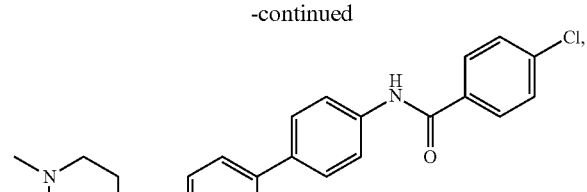
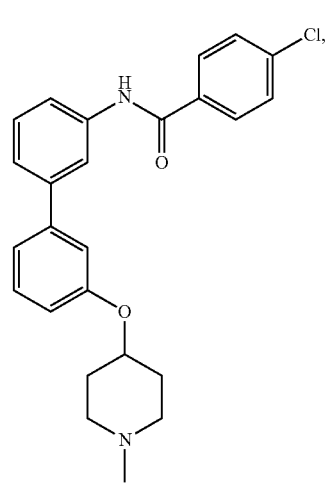
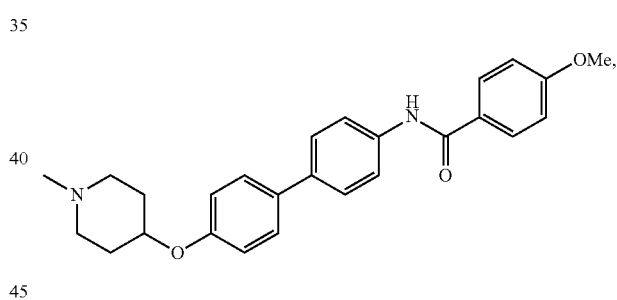
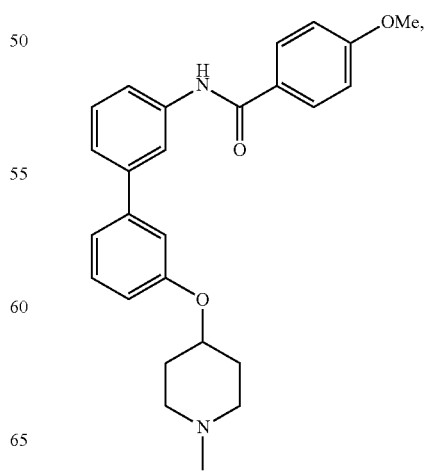

29
-continued
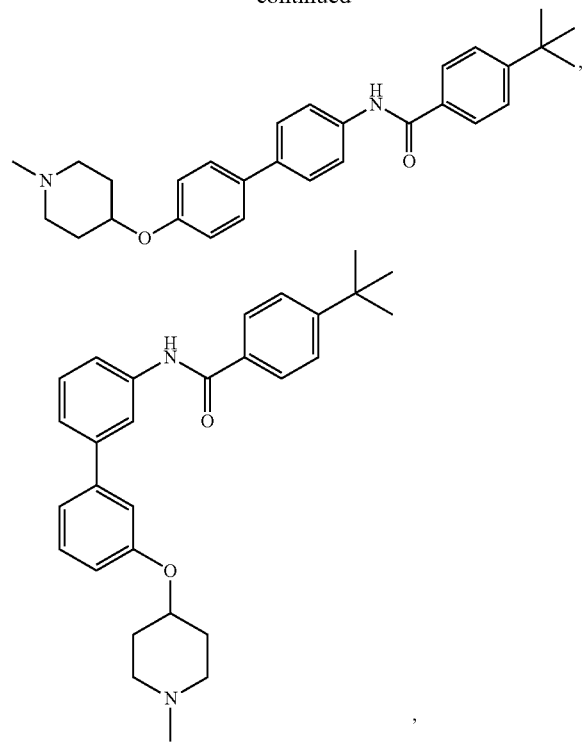
30
-continued
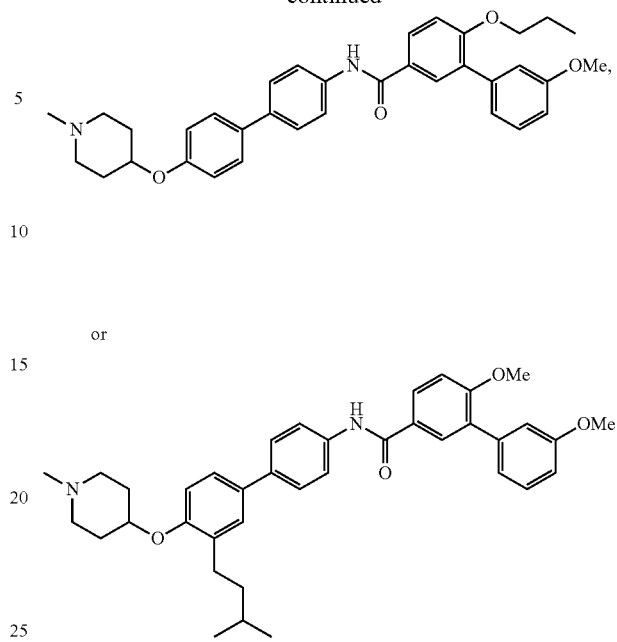
or
or a pharmaceutically acceptable salt thereof. In some embodiments, the present disclosure also provides a compound of the formula:
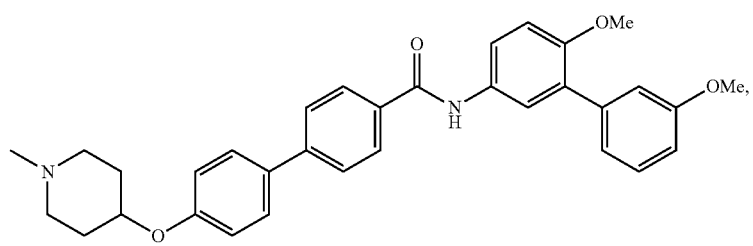
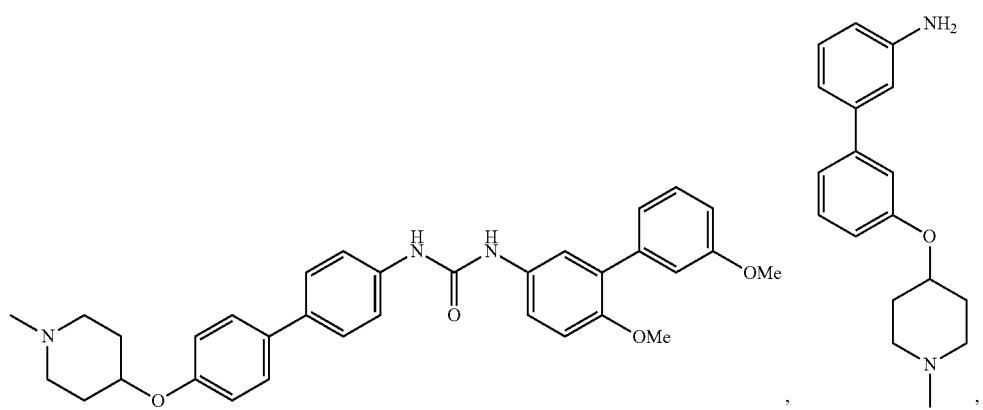

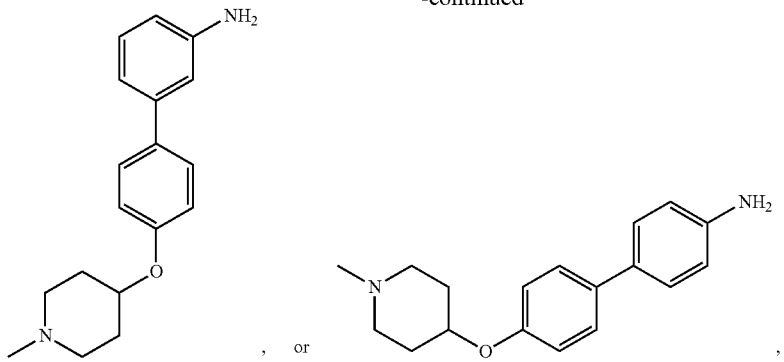

, or or a pharmaceutically acceptable salt thereof.

In yet another aspect, the present disclosure provides a pharmaceutical composition comprising a compound of the present disclosure and an excipient. In some embodiments, the composition is formulated for administration: orally, intraadiposally, intraarterially, intraarticularly, intracranially, intradermally, intralesionally, intramuscularly, intranasally, intraocularly, intrapericardially, intraperitoneally, intrapleurally, intraprostatically, intrarectally, intrathecally, intratracheally, intratumorally, intraumbilically, intravaginally, intravenously, intravesicularlly, intravitreally, liposomally, locally, mucosally, parenterally, rectally, subconjunctival, subcutaneously, sublingually, topically, transbuccally, transdermally, vaginally, in crèmes, in lipid compositions, via a catheter, via a lavage, via continuous infusion, via infusion, via inhalation, via injection, via local delivery, or via localized perfusion.

In yet another embodiments, the present disclosure provides a method of treating a disease or disorder comprising administering to a patient in need thereof a pharmaceutically acceptable amount of a compound or a pharmaceutical composition comprising a compound of the present disclosure. In some embodiments, the disease or disorder is cancer. In some embodiments, the cancer is a carcinoma, sarcoma, lymphoma, leukemia, melanoma, mesothelioma, multiple myeloma, or seminoma. In some embodiments, the cancer is a cancer of the bladder, blood, bone, brain, breast, central nervous system, cervix, colon, endometrium, esophagus, gall bladder, genitalia, genitourinary tract, head, kidney, larynx, liver, lung, muscle tissue, neck, oral or nasal mucosa, ovary, pancreas, prostate, skin, spleen, small intestine, large intestine, stomach, testicle, or thyroid. In some embodiments, the cancer is breast cancer. In some embodiments, the method further comprises administering the compound with a second therapeutic agent or modality. In some embodiments, the second therapeutic agent is a second chemotherapeutic agent. In some embodiments, the second chemotherapeutic agent is a C-terminus Hsp90 inhibitor. In some embodiments, the second therapeutic modality is surgery, radiotherapy, or immunotherapy. In some embodiments, the method comprises administering the compound and the second therapeutic agent or modality simultaneously. In some embodiments, the method comprises administering the compound and the second therapeutic agent or modality sequentially. In some embodiments, the method comprises administering an amount of compound sufficient to inhibit cancer cell growth, propagation, or migration.

In still yet another aspect, the present disclosure provides a method of inhibiting Hsp90 comprising administering to a patient an effective amount of a compound or composition comprising a compound of the present disclosure. In some embodiments, the inhibition of Hsp90 is effective to treat cancer.

In yet another aspect, the present disclosure provides a compound of the formula:

$$X_1\text{-}A\text{-}Z\text{—}Y_1 \tag{XI}$$

wherein: $X_1$ is heteroarenediyl$_{(C \leq 12)}$-$X_3$, substituted heteroarenediyl$_{(C \leq 12)}$-$X_3$;

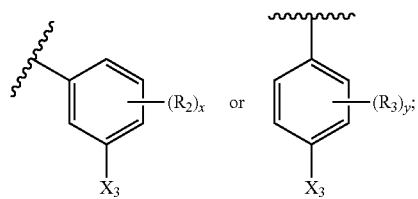

wherein: $X_3$ is heterocycloalkoxy$_{(C \leq 12)}$, -alkoxydiyl$_{(C \leq 8)}$-heterocycloalkyl$_{(C \leq 12)}$, -alkoxydiyl$_{(C \leq 8)}$-dialkylamino$_{(C \leq 12)}$, or a substituted version of any of these groups; each $R_2$ and $R_3$ are each independently selected from hydrogen, amino, cyano, halo, hydroxy, mercapto, nitro, sulfato, sulfamido, alkyl$_{(C \leq 12)}$, substituted alkyl$_{(C \leq 12)}$, alkoxy$_{(C \leq 12)}$, substituted alkoxy$_{(C \leq 12)}$, acyl$_{(C \leq 12)}$, substituted acyl$_{(C \leq 12)}$, amido$_{(C \leq 12)}$, or substituted amido$_{(C \leq 12)}$; x or y are each independently selected from 0, 1, 2, 3, or 4; A is arenediyl$_{(C \leq 60)}$, heteroarenediyl$_{(C \leq 60)}$, or a substituted version of either of these groups wherein the substituted version is a formula wherein one or more hydrogen atoms is replaced with —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, —S(O)$_2$OH, —S(O)$_2$NH$_2$, alkyl$_{(C \leq 12)}$, substituted alkyl$_{(C \leq 12)}$, alkoxy$_{(C \leq 12)}$, substituted alkoxy$_{(C \leq 12)}$, acyl$_{(C \leq 12)}$, substituted acyl$_{(C \leq 12)}$, amido$_{(C \leq 12)}$, or substituted amido$_{(C \leq 12)}$; Z is —C(O)NR$_4$—, —NR$_5$C(O)—, or —NR$_6$C(O)NR$_7$—; wherein: $R_4$, $R_5$, $R_6$, and $R_7$ are each independently selected from hydrogen, alkyl$_{(C \leq 8)}$, or substituted alkyl$_{(C \leq 8)}$; and $Y_1$ is cycloalkyl$_{(C \leq 18)}$, aryl$_{(C \leq 24)}$, heteroaryl$_{(C \leq 24)}$, -arenediyl$_{(C \leq 18)}$-alkyl$_{(C \leq 8)}$, -arenediyl$_{(C \leq 18)}$-alkenyl$_{(C \leq 8)}$, -arenediyl$_{(C \leq 18)}$-alkoxy$_{(C \leq 8)}$, or a substituted version of any of these groups; or a pharmaceutically acceptable salt thereof. In some embodiments, the compound is further defined as:

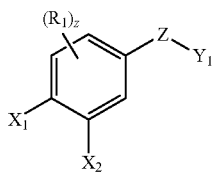
(XII)

wherein: $X_1$ are each independently selected from hydrogen, amino, cyano, halo, hydroxy, mercapto, nitro, sulfato, sulfamido, alkyl$_{(C\le12)}$, substituted alkyl$_{(C\le12)}$, alkoxy$_{(C\le12)}$, substituted alkoxy$_{(C\le12)}$, acyl$_{(C\le12)}$, substituted acyl$_{(C\le12)}$, amido$_{(C\le12)}$, substituted amido$_{(C\le12)}$,

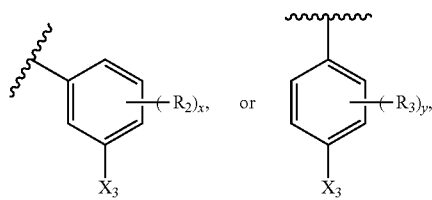

provided either $X_1$ or $X_2$ is

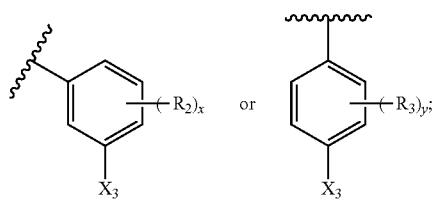

wherein: $X_3$ is heterocycloalkoxy$_{(C\le12)}$, -alkoxydiyl$_{(C\le8)}$-heterocycloalkyl$_{(C\le12)}$, -alkoxydiyl$_{(C\le8)}$-dialkylamino$_{(C\le12)}$, or a substituted version of any of these groups; each $R_2$ and $R_3$ are each independently selected from hydrogen, amino, cyano, halo, hydroxy, mercapto, nitro, sulfato, sulfamido, alkyl$_{(C\le12)}$, substituted alkyl$_{(C\le12)}$, alkoxy$_{(C\le12)}$, substituted alkoxy$_{(C\le12)}$, acyl$_{(C\le12)}$, substituted acyl$_{(C\le12)}$, amido$_{(C\le12)}$, or substituted amido$_{(C\le12)}$; x or y are each independently selected from 0, 1, 2, 3, or 4; z is 0, 1, 2, or 3; each $R_1$ is independently selected from hydrogen, amino, cyano, halo, hydroxy, mercapto, nitro, sulfato, sulfamido, alkyl$_{(C\le12)}$, substituted alkyl$_{(C\le12)}$, alkoxy$_{(C\le12)}$, substituted alkoxy$_{(C\le12)}$, acyl$_{(C\le12)}$, substituted acyl$_{(C\le12)}$, amido$_{(C\le12)}$, or substituted amido$_{(C\le12)}$; Z is —C(O)NR$_4$—, —NR$_5$C(O)—, or —NR$_6$C(O)NR$_7$—; wherein: $R_4$, $R_5$, $R_6$, and $R_7$ are each independently selected from hydrogen, alkyl$_{(C\le8)}$, or substituted alkyl$_{(C\le8)}$; and $Y_1$ is cycloalkyl$_{(C\le18)}$, aryl$_{(C\le24)}$, heteroaryl$_{(C\le24)}$, -arenediyl$_{(C\le18)}$-alkyl$_{(C\le8)}$, -arenediyl$_{(C\le18)}$-alkenyl$_{(C\le8)}$, -arenediyl$_{(C\le18)}$-alkoxy$_{(C\le8)}$, or a substituted version of any of these groups; or a pharmaceutically acceptable salt thereof. In some embodiments, the compound is further defined as:

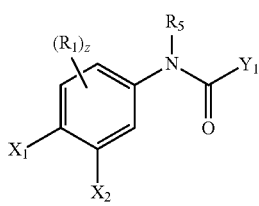
(XIII)

wherein: $X_1$ and $X_2$ are each independently selected from hydrogen, amino, cyano, halo, hydroxy, mercapto, nitro, sulfato, sulfamido, alkyl$_{(C\le12)}$, substituted alkyl$_{(C\le12)}$, alkoxy$_{(C\le12)}$, substituted alkoxy$_{(C\le12)}$, acyl$_{(C\le12)}$, substituted acyl$_{(C\le12)}$, amido$_{(C\le12)}$, substituted amido$_{(C\le12)}$,

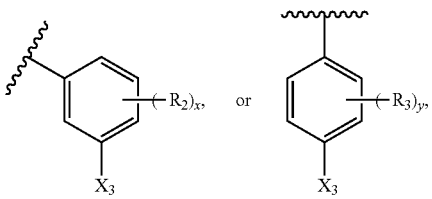

provided either $X_1$ or $X_2$ is

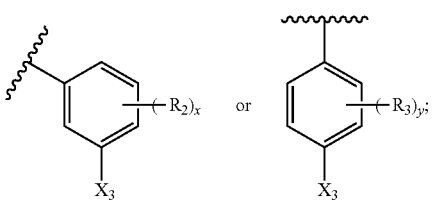

wherein: $X_3$ is heterocycloalkoxy$_{(C\le12)}$, -alkoxydiyl$_{(C\le8)}$-heterocycloalkyl$_{(C\le12)}$, -alkoxydiyl$_{(C\le8)}$-dialkylamino$_{(C\le12)}$, or a substituted version of any of these groups; each $R_2$ and $R_3$ are each independently selected from hydrogen, amino, cyano, halo, hydroxy, mercapto, nitro, sulfato, sulfamido, alkyl$_{(C\le12)}$, substituted alkyl$_{(C\le12)}$, alkoxy$_{(C\le12)}$, substituted alkoxy$_{(C\le12)}$, acyl$_{(C\le12)}$, substituted acyl$_{(C\le12)}$, amido$_{(C\le12)}$, or substituted amido$_{(C\le12)}$; $R_5$ is hydrogen, alkyl$_{(C\le8)}$, or substituted alkyl$_{(C\le8)}$; and $Y_1$ is cycloalkyl$_{(C\le18)}$, aryl$_{(C\le24)}$, heteroaryl$_{(C\le24)}$, -arenediyl$_{(C\le18)}$-alkyl$_{(C\le8)}$, -arenediyl$_{(C\le18)}$-alkenyl$_{(C\le8)}$, -arenediyl$_{(C\le18)}$-alkoxy$_{(C\le8)}$, or a substituted version of any of these groups; or a pharmaceutically acceptable salt thereof. In some embodiments, the compound is further defined as:

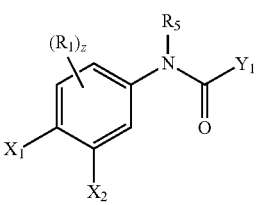
(XIII)

wherein: $X_1$ is

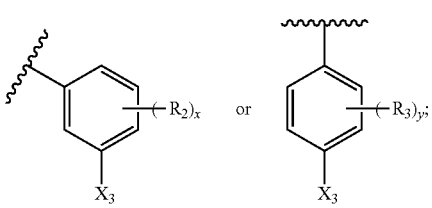

wherein: X₃ is heterocycloalkoxy$_{(C≤12)}$, -alkoxydiyl$_{(C≤8)}$-heterocycloalkyl$_{(C≤12)}$, -alkoxydiyl$_{(C≤8)}$-dialkylamino$_{(C≤12)}$, or a substituted version of any of these groups; each R₂ and R₃ are each independently selected from hydrogen, amino, cyano, halo, hydroxy, mercapto, nitro, sulfato, sulfamido, alkyl$_{(C≤12)}$, substituted alkyl$_{(C≤12)}$, alkoxy$_{(C≤12)}$, substituted alkoxy$_{(C≤12)}$, acyl$_{(C≤12)}$, substituted acyl$_{(C≤12)}$, amido$_{(C≤12)}$, or substituted amido$_{(C≤12)}$; x or y are each independently selected from 0, 1, 2, 3, or 4; X₂ is hydrogen, amino, cyano, halo, hydroxy, mercapto, nitro, sulfato, sulfamido, alkyl$_{(C≤12)}$, substituted alkyl$_{(C≤12)}$, alkoxy$_{(C≤12)}$, substituted alkoxy$_{(C≤12)}$, acyl$_{(C≤12)}$, substituted acyl$_{(C≤12)}$, amido$_{(C≤12)}$, or substituted amido$_{(C≤12)}$; z is 0, 1, 2, or 3; each R₁ is independently selected from hydrogen, amino, cyano, halo, hydroxy, mercapto, nitro, sulfato, sulfamido, alkyl$_{(C≤12)}$, substituted alkyl$_{(C≤12)}$, alkoxy$_{(C≤12)}$, substituted alkoxy$_{(C≤12)}$, acyl$_{(C≤12)}$, substituted acyl$_{(C≤12)}$, amido$_{(C≤12)}$, or substituted amido$_{(C≤12)}$; R₅ is hydrogen, alkyl$_{(C≤8)}$, or substituted alkyl$_{(C≤8)}$; and Y₁ is cycloalkyl$_{(C≤18)}$, aryl$_{(C≤24)}$, heteroaryl$_{(C≤24)}$, -arenediyl$_{(C≤18)}$-alkyl$_{(C≤8)}$, -arenediyl$_{(C≤18)}$-alkenyl$_{(C≤8)}$, -arenediyl$_{(C≤18)}$-alkoxy$_{(C≤8)}$, or a substituted version of any of these groups; or a pharmaceutically acceptable salt thereof. In some embodiments, the compound is further defined as:

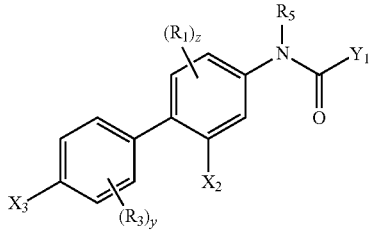

(XIV)

wherein: X₃ is heterocycloalkoxy$_{(C≤12)}$, -alkoxydiyl$_{(C≤8)}$-heterocycloalkyl$_{(C≤12)}$, -alkoxydiyl$_{(C≤8)}$-dialkylamino$_{(C≤12)}$, or a substituted version of any of these groups; each R₃ is independently selected from hydrogen, amino, cyano, halo, hydroxy, mercapto, nitro, sulfato, sulfamido, alkyl$_{(C≤12)}$, substituted alkyl$_{(C≤12)}$, alkoxy$_{(C≤12)}$, substituted alkoxy$_{(C≤12)}$, acyl$_{(C≤12)}$, substituted acyl$_{(C≤12)}$, amido$_{(C≤12)}$, or substituted amido$_{(C≤12)}$; y are each independently selected from 0, 1, 2, 3, or 4; X₂ is hydrogen, amino, cyano, halo, hydroxy, mercapto, nitro, sulfato, sulfamido, alkyl$_{(C≤12)}$, substituted alkyl$_{(C≤12)}$, alkoxy$_{(C≤12)}$, substituted alkoxy$_{(C≤12)}$, acyl$_{(C≤12)}$, substituted acyl$_{(C≤12)}$, amido$_{(C≤12)}$, or substituted amido$_{(C≤12)}$; z is 0, 1, 2, or 3; each R₁ is independently selected from hydrogen, amino, cyano, halo, hydroxy, mercapto, nitro, sulfato, sulfamido, alkyl$_{(C≤12)}$, substituted alkyl$_{(C≤12)}$, alkoxy$_{(C≤12)}$, substituted alkoxy$_{(C≤12)}$, acyl$_{(C≤12)}$, substituted acyl$_{(C≤12)}$, amido$_{(C≤12)}$, or substituted amido$_{(C≤12)}$; R₅ is hydrogen, alkyl$_{(C≤8)}$, or substituted alkyl$_{(C≤8)}$; and Y₁ is cycloalkyl$_{(C≤18)}$, aryl$_{(C≤24)}$, heteroaryl$_{(C≤24)}$, -arenediyl$_{(C≤18)}$-alkyl$_{(C≤8)}$, -arenediyl$_{(C≤18)}$-alkenyl$_{(C≤8)}$, -arenediyl$_{(C≤18)}$-alkoxy$_{(C≤8)}$, or a substituted version of any of these groups; or a pharmaceutically acceptable salt thereof. In some embodiments, the compound is further defined as:

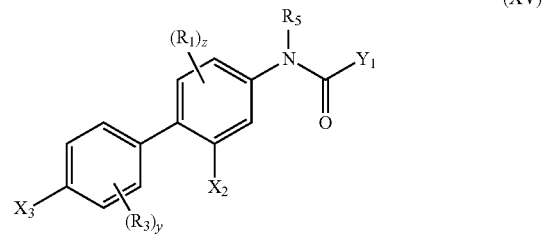

(XV)

wherein: X₃ is heterocycloalkoxy$_{(C≤12)}$ or substituted heterocycloalkoxy$_{(C≤12)}$; each R₃ is independently selected from hydrogen, amino, cyano, halo, hydroxy, mercapto, nitro, sulfato, sulfamido, alkyl$_{(C≤12)}$, substituted alkyl$_{(C≤12)}$, alkoxy$_{(C≤12)}$, substituted alkoxy$_{(C≤12)}$, acyl$_{(C≤12)}$, substituted acyl$_{(C≤12)}$, amido$_{(C≤12)}$, or substituted amido$_{(C≤12)}$; y are each independently selected from 0, 1, 2, 3, or 4; X₂ is hydrogen, amino, cyano, halo, hydroxy, mercapto, nitro, sulfato, sulfamido, alkyl$_{(C≤12)}$, substituted alkyl$_{(C≤12)}$, alkoxy$_{(C≤12)}$, substituted alkoxy$_{(C≤12)}$, acyl$_{(C≤12)}$, substituted acyl$_{(C≤12)}$, amido$_{(C≤12)}$, or substituted amido$_{(C≤12)}$; z is 0, 1, 2, or 3; each R₁ is independently selected from hydrogen, amino, cyano, halo, hydroxy, mercapto, nitro, sulfato, sulfamido, alkyl$_{(C≤12)}$, substituted alkyl$_{(C≤12)}$, alkoxy$_{(C≤12)}$, substituted alkoxy$_{(C≤12)}$, acyl$_{(C≤12)}$, substituted acyl$_{(C≤12)}$, amido$_{(C≤12)}$, or substituted amido$_{(C≤12)}$; and Y₁ is aryl$_{(C≤24)}$ or substituted aryl$_{(C≤24)}$; or a pharmaceutically acceptable salt thereof. In some embodiments, the compound is further defined as:

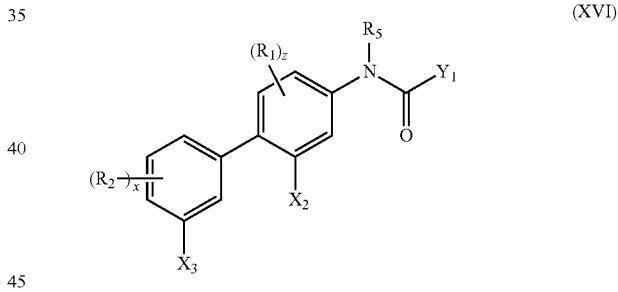

(XVI)

wherein: X₃ is heterocycloalkoxy$_{(C≤12)}$, -alkoxydiyl$_{(C≤8)}$-heterocycloalkyl$_{(C≤12)}$, -alkoxydiyl$_{(C≤8)}$-dialkylamino$_{(C≤12)}$, or a substituted version of any of these groups; each R₂ is independently selected from hydrogen, amino, cyano, halo, hydroxy, mercapto, nitro, sulfato, sulfamido, alkyl$_{(C≤12)}$, substituted alkyl$_{(C≤12)}$, alkoxy$_{(C≤12)}$, substituted alkoxy$_{(C≤12)}$, acyl$_{(C≤12)}$, substituted acyl$_{(C≤12)}$, amido$_{(C≤12)}$, or substituted amido$_{(C≤12)}$; x is 0, 1, 2, 3, or 4; X₂ is hydrogen, amino, cyano, halo, hydroxy, mercapto, nitro, sulfato, sulfamido, alkyl$_{(C≤12)}$, substituted alkyl$_{(C≤12)}$, alkoxy$_{(C≤12)}$, substituted alkoxy$_{(C≤12)}$, acyl$_{(C≤12)}$, substituted acyl$_{(C≤12)}$, amido$_{(C≤12)}$, or substituted amido$_{(C≤12)}$; z is 0, 1, 2, or 3; each R₁ is independently selected from hydrogen, amino, cyano, halo, hydroxy, mercapto, nitro, sulfato, sulfamido, alkyl$_{(C≤12)}$, substituted alkyl$_{(C≤12)}$, alkoxy$_{(C≤12)}$, substituted alkoxy$_{(C≤12)}$, acyl$_{(C≤12)}$, substituted acyl$_{(C≤12)}$, amido$_{(C≤12)}$, or substituted amido$_{(C≤12)}$; R₅ is hydrogen, alkyl$_{(C≤8)}$, or substituted alkyl$_{(C≤8)}$; and Y₁ is cycloalkyl$_{(C≤18)}$, aryl$_{(C≤24)}$, heteroaryl$_{(C≤24)}$, -arenediyl$_{(C≤18)}$-alkyl$_{(C≤8)}$, -arenediyl$_{(C≤18)}$-alkenyl$_{(C≤8)}$, -arenediyl$_{(C≤18)}$-alkoxy$_{(C≤8)}$, or a substituted version of any of these groups; or a pharmaceutically acceptable salt thereof. In some embodiments, the compound is further defined as:

(XVII)

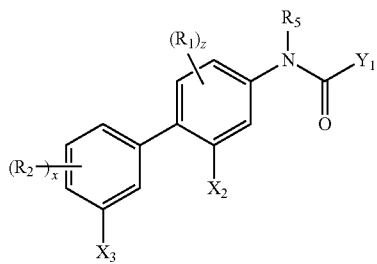

wherein: $X_3$ is heterocycloalkoxy$_{(C \leq 12)}$ or substituted heterocycloalkoxy$_{(C \leq 12)}$; each $R_2$ is independently selected from hydrogen, amino, cyano, halo, hydroxy, mercapto, nitro, sulfato, sulfamido, alkyl$_{(C \leq 12)}$, substituted alkyl$_{(C \leq 12)}$, alkoxy$_{(C \leq 12)}$, substituted alkoxy$_{(C \leq 12)}$, acyl$_{(C \leq 12)}$, substituted acyl$_{(C \leq 12)}$, amido$_{(C \leq 12)}$, or substituted amido$_{(C \leq 12)}$; x is 0, 1, 2, 3, or 4; $X_2$ is hydrogen, amino, cyano, halo, hydroxy, mercapto, nitro, sulfato, sulfamido, alkyl$_{(C \leq 12)}$, substituted alkyl$_{(C \leq 12)}$, alkoxy$_{(C \leq 12)}$, substituted alkoxy$_{(C \leq 12)}$, acyl$_{(C \leq 12)}$, substituted acyl$_{(C \leq 12)}$, amido$_{(C \leq 12)}$, or substituted amido$_{(C \leq 12)}$; z is 0, 1, 2, or 3; each $R_1$ is independently selected from hydrogen, amino, cyano, halo, hydroxy, mercapto, nitro, sulfato, sulfamido, alkyl$_{(C \leq 12)}$, substituted alkyl$_{(C \leq 12)}$, alkoxy$_{(C \leq 12)}$, substituted alkoxy$_{(C \leq 12)}$, acyl$_{(C \leq 12)}$, substituted acyl$_{(C \leq 12)}$, amido$_{(C \leq 12)}$, or substituted amido$_{(C \leq 12)}$; $R_5$, is hydrogen, alkyl$_{(C \leq 8)}$, or substituted alkyl$_{(C \leq 8)}$; and $Y_1$ is cycloalkyl$_{(C \leq 18)}$, aryl$_{(C \leq 24)}$, heteroaryl$_{(C \leq 24)}$, -arenediyl$_{(C \leq 18)}$-alkyl$_{(C \leq 8)}$, -arenediyl$_{(C \leq 18)}$-alkenyl$_{(C \leq 8)}$, -arenediyl$_{(C \leq 18)}$-alkoxy$_{(C \leq 8)}$, or a substituted version of any of these groups; or a pharmaceutically acceptable salt thereof. In some embodiments, the compound is further defined as:

(XIII)

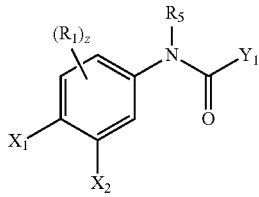

wherein: $X_1$ is hydrogen, amino, cyano, halo, hydroxy, mercapto, nitro, sulfato, sulfamido, alkyl$_{(C \leq 12)}$, substituted alkyl$_{(C \leq 12)}$, alkoxy$_{(C \leq 12)}$, substituted alkoxy$_{(C \leq 12)}$, acyl$_{(C \leq 12)}$, substituted acyl$_{(C \leq 12)}$, amido$_{(C \leq 12)}$, or substituted amido$_{(C \leq 12)}$; $X_2$ is

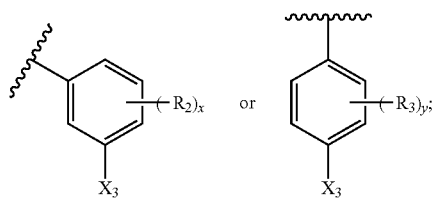

wherein: $X_3$ is heterocycloalkoxy$_{(C \leq 12)}$, -alkoxydiyl$_{(C \leq 8)}$-heterocycloalkyl$_{(C \leq 12)}$, -alkoxydiyl$_{(C \leq 8)}$-dialkylamino$_{(C \leq 12)}$, or a substituted version of any of these groups; each $R_2$ and $R_3$ are each independently selected from hydrogen, amino, cyano, halo, hydroxy, mercapto, nitro, sulfato, sulfamido, alkyl$_{(C \leq 12)}$, substituted alkyl$_{(C \leq 12)}$, alkoxy$_{(C \leq 12)}$, substituted alkoxy$_{(C \leq 12)}$, acyl$_{(C \leq 12)}$, substituted acyl$_{(C \leq 12)}$, amido$_{(C \leq 12)}$, or substituted amido$_{(C \leq 12)}$; x or y are each independently selected from 0, 1, 2, 3, or 4; z is 0, 1, 2, or 3; each $R_1$ is independently selected from hydrogen, amino, cyano, halo, hydroxy, mercapto, nitro, sulfato, sulfamido, alkyl$_{(C \leq 12)}$, substituted alkyl$_{(C \leq 12)}$, alkoxy$_{(C \leq 12)}$, substituted alkoxy$_{(C \leq 12)}$, acyl$_{(C \leq 12)}$, substituted acyl$_{(C \leq 12)}$, amido$_{(C \leq 12)}$, or substituted amido$_{(C \leq 12)}$; $R_5$ is hydrogen, alkyl$_{(C \leq 8)}$, or substituted alkyl$_{(C \leq 8)}$; and $Y_1$ is cycloalkyl$_{(C \leq 18)}$, aryl$_{(C \leq 24)}$, heteroaryl$_{(C \leq 24)}$, -arenediyl$_{(C \leq 18)}$-alkyl$_{(C \leq 8)}$, -arenediyl$_{(C \leq 18)}$-alkenyl$_{(C \leq 8)}$, -arenediyl$_{(C \leq 18)}$-alkoxy$_{(C \leq 8)}$, or a substituted version of any of these groups; or a pharmaceutically acceptable salt thereof. In some embodiments, the compound is further defined as:

(XVIII)

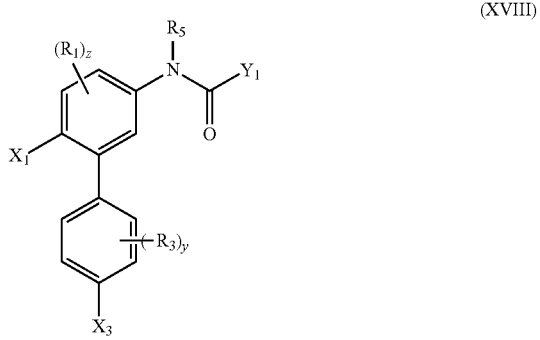

wherein: $X_1$ is hydrogen, amino, cyano, halo, hydroxy, mercapto, nitro, sulfato, sulfamido, alkyl$_{(C \leq 12)}$, substituted alkyl$_{(C \leq 12)}$, alkoxy$_{(C \leq 12)}$, substituted alkoxy$_{(C \leq 12)}$, acyl$_{(C \leq 12)}$, or substituted acyl$_{(C \leq 12)}$; $X_3$ is heterocycloalkoxy$_{(C \leq 12)}$, -alkoxydiyl$_{(C \leq 8)}$-heterocycloalkyl$_{(C \leq 12)}$, -alkoxydiyl$_{(C \leq 8)}$-dialkylamino$_{(C \leq 12)}$, or a substituted version of any of these groups; each $R_3$ is independently selected from hydrogen, amino, cyano, halo, hydroxy, mercapto, nitro, sulfato, sulfamido, alkyl$_{(C \leq 12)}$, substituted alkyl$_{(C \leq 12)}$, alkoxy$_{(C \leq 12)}$, substituted alkoxy$_{(C \leq 12)}$, acyl$_{(C \leq 12)}$, substituted acyl$_{(C \leq 12)}$, amido$_{(C \leq 12)}$, or substituted amido$_{(C \leq 12)}$; y is 0, 1, 2, 3, or 4; z is 0, 1, 2, or 3; each $R_1$ is independently selected from hydrogen, amino, cyano, halo, hydroxy, mercapto, nitro, sulfato, sulfamido, alkyl$_{(C \leq 12)}$, substituted alkyl$_{(C \leq 12)}$, alkoxy$_{(C \leq 12)}$, substituted alkoxy$_{(C \leq 12)}$, acyl$_{(C \leq 12)}$, substituted acyl$_{(C \leq 12)}$, amido$_{(C \leq 12)}$, or substituted amido$_{(C \leq 12)}$; $R_5$ is hydrogen, alkyl$_{(C \leq 8)}$, or substituted alkyl$_{(C \leq 8)}$; and $Y_1$ is cycloalkyl$_{(C \leq 18)}$, aryl$_{(C \leq 24)}$, heteroaryl$_{(C \leq 24)}$, -arenediyl$_{(C \leq 18)}$-alkyl$_{(C \leq 8)}$, -arenediyl$_{(C \leq 18)}$-alkenyl$_{(C \leq 8)}$, -arenediyl$_{(C \leq 18)}$-alkoxy$_{(C \leq 8)}$, or a substituted version of any of these groups; or a pharmaceutically acceptable salt thereof. In some embodiments, the compound is further defined as:

(XVIII)

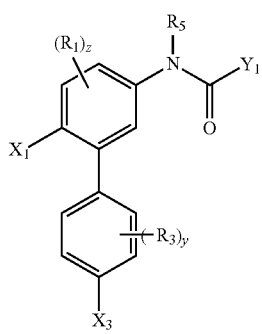

wherein: X₁ is hydrogen, amino, cyano, halo, hydroxy, mercapto, nitro, sulfato, sulfamido, alkyl$_{(C≤12)}$, substituted alkyl$_{(C≤12)}$, alkoxy$_{(C≤12)}$, substituted alkoxy$_{(C≤12)}$, acyl$_{(C≤12)}$, or substituted acyl$_{(C≤12)}$; X₃ is heterocycloalkoxy$_{(C≤12)}$ or substituted heterocycloalkoxy$_{(C≤12)}$; each R₃ is independently selected from hydrogen, amino, cyano, halo, hydroxy, mercapto, nitro, sulfato, sulfamido, alkyl$_{(C≤12)}$, substituted alkyl$_{(C≤12)}$, alkoxy$_{(C≤12)}$, substituted alkoxy$_{(C≤12)}$, acyl$_{(C≤12)}$, or substituted acyl$_{(C≤12)}$; y is 0, 1, 2, 3, or 4; z is 0, 1, 2, or 3; each R₁ is independently selected from hydrogen, amino, cyano, halo, hydroxy, mercapto, nitro, sulfato, sulfamido, alkyl$_{(C≤12)}$, substituted alkyl$_{(C≤12)}$, alkoxy$_{(C≤12)}$, substituted alkoxy$_{(C≤12)}$, acyl$_{(C≤12)}$, or substituted acyl$_{(C≤12)}$; R₅ is hydrogen, alkyl$_{(C≤8)}$, or substituted alkyl$_{(C≤8)}$; and Y₁ is cycloalkyl$_{(C≤18)}$, aryl$_{(C≤24)}$, heteroaryl$_{(C≤24)}$, -arenediyl$_{(C≤18)}$-alkyl$_{(C≤8)}$, -arenediyl$_{(C≤18)}$-alkenyl$_{(C≤8)}$, -arenediyl$_{(C≤18)}$-alkoxy$_{(C≤8)}$, or a substituted version of any of these groups; or a pharmaceutically acceptable salt thereof. In some embodiments, the compound is further defined as:

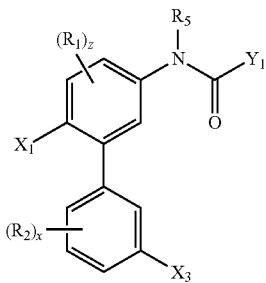

(XIX)

wherein: X₁ is hydrogen, amino, cyano, halo, hydroxy, mercapto, nitro, sulfato, sulfamido, alkyl$_{(C≤12)}$, substituted alkyl$_{(C≤12)}$, alkoxy$_{(C≤12)}$, substituted alkoxy$_{(C≤12)}$, acyl$_{(C≤12)}$, or substituted acyl$_{(C≤12)}$; X₃ is heterocycloalkoxy$_{(C≤12)}$, -alkoxydiyl$_{(C≤8)}$-heterocycloalkyl$_{(C≤12)}$, -alkoxydiyl$_{(C≤8)}$-dialkylamino$_{(C≤12)}$, or a substituted version of any of these groups; each R₂ is independently selected from hydrogen, amino, cyano, halo, hydroxy, mercapto, nitro, sulfato, sulfamido, alkyl$_{(C≤12)}$, substituted alkyl$_{(C≤12)}$, alkoxy$_{(C≤12)}$, substituted alkoxy$_{(C≤12)}$, acyl$_{(C≤12)}$, or substituted acyl$_{(C≤12)}$; x is 0, 1, 2, 3, or 4; z is 0, 1, 2, or 3; each R₁ is independently selected from hydrogen, amino, cyano, halo, hydroxy, mercapto, nitro, sulfato, sulfamido, alkyl$_{(C≤12)}$, substituted alkyl$_{(C≤12)}$, alkoxy$_{(C≤12)}$, substituted alkoxy$_{(C≤12)}$, acyl$_{(C≤12)}$, or substituted acyl$_{(C≤12)}$; R₅ is hydrogen, alkyl$_{(C≤8)}$, or substituted alkyl$_{(C≤8)}$; and Y₁ is cycloalkyl$_{(C≤18)}$, aryl$_{(C≤24)}$, heteroaryl$_{(C≤24)}$, -arenediyl$_{(C≤18)}$-alkyl$_{(C≤8)}$, -arenediyl$_{(C≤18)}$-alkenyl$_{(C≤8)}$, -arenediyl$_{(C≤18)}$-alkoxy$_{(C≤8)}$, or a substituted version of any of these groups; or a pharmaceutically acceptable salt thereof. In some embodiments, the compound is further defined as:

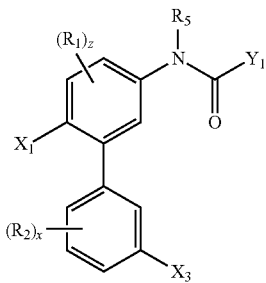

(XIX)

wherein: X₁ is hydrogen, amino, cyano, halo, hydroxy, mercapto, nitro, sulfato, sulfamido, alkyl$_{(C≤12)}$, substituted alkyl$_{(C≤12)}$, alkoxy$_{(C≤12)}$, substituted alkoxy$_{(C≤12)}$, acyl$_{(C≤12)}$, or substituted acyl$_{(C≤12)}$; X₃ is heterocycloalkoxy$_{(C≤12)}$ or substituted heterocycloalkoxy$_{(C≤12)}$; each R₂ is independently selected from hydrogen, amino, cyano, halo, hydroxy, mercapto, nitro, sulfato, sulfamido, alkyl$_{(C≤12)}$, substituted alkyl$_{(C≤12)}$, alkoxy$_{(C≤12)}$, substituted alkoxy$_{(C≤12)}$, acyl$_{(C≤12)}$, or substituted acyl$_{(C≤12)}$; x is 0, 1, 2, 3, or 4; z is 0, 1, 2, or 3; each R₁ is independently selected from hydrogen, amino, cyano, halo, hydroxy, mercapto, nitro, sulfato, sulfamido, alkyl$_{(C≤12)}$, substituted alkyl$_{(C≤12)}$, alkoxy$_{(C≤12)}$, substituted alkoxy$_{(C≤12)}$, acyl$_{(C≤12)}$, or substituted acyl$_{(C≤12)}$; R₅ is hydrogen, alkyl$_{(C≤8)}$, or substituted alkyl$_{(C≤8)}$; and Y₁ is cycloalkyl$_{(C≤18)}$, aryl$_{(C≤24)}$, heteroaryl$_{(C≤24)}$, -arenediyl$_{(C≤18)}$-alkyl$_{(C≤8)}$, -arenediyl$_{(C≤18)}$-alkenyl$_{(C≤8)}$, -arenediyl$_{(C≤18)}$-alkoxy$_{(C≤8)}$, or a substituted version of any of these groups; or a pharmaceutically acceptable salt thereof. In some embodiments, the compound is further defined by the formula:

$$X_1\text{-}A\text{-}Z\text{—}Y_1 \quad (XI)$$

wherein: X₁ is arenediyl$_{(C≤12)}$-X₃ substituted arenediyl$_{(C≤12)}$-X₃, heteroarenediyl$_{(C≤12)}$-X₃ or substituted heteroarenediyl$_{(C≤12)}$-X₃; wherein: X₃ is heterocycloalkoxy$_{(C≤12)}$, -alkoxydiyl$_{(C≤8)}$-heterocycloalkyl$_{(C≤12)}$, -alkoxydiyl$_{(C≤8)}$-dialkylamino$_{(C≤12)}$, or a substituted version of any of these groups; A is arenediyl$_{(C≤12)}$-X₃ substituted arenediyl$_{(C≤12)}$-X₃, heteroarenediyl$_{(C≤12)}$ or substituted heteroarenediyl$_{(C≤12)}$; Z is —C(O)NR₄—, —NR₅C(O)—, or —NR₆C(O)NR₇—; wherein: R₄, R₅, R₆, and R₇ are each independently selected from hydrogen, alkyl$_{(C≤8)}$, or substituted alkyl$_{(C≤8)}$; and Y₁ is cycloalkyl$_{(C≤18)}$, aryl$_{(C≤24)}$, heteroaryl$_{(C≤24)}$, -arenediyl$_{(C≤18)}$-alkyl$_{(C≤8)}$, -arenediyl$_{(C≤18)}$-alkenyl$_{(C≤8)}$, -arenediyl$_{(C≤18)}$-alkoxy$_{(C≤8)}$, or a substituted version of any of these groups; provided either X₁ or A is heteroarenediyl$_{(C≤12)}$; or a pharmaceutically acceptable salt thereof. In some embodiments, the compound is further defined as:

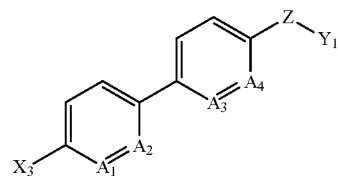

(XX)

wherein: A₁, A₂, A₃, or A₄ are each independently selected from N or CH; X₃ is heterocycloalkoxy$_{(C≤12)}$, -alkoxydiyl$_{(C≤8)}$-heterocycloalkyl$_{(C≤12)}$, -alkoxydiyl$_{(C≤8)}$-dialkylamino$_{(C≤12)}$, or a substituted version of any of these groups; Z is —C(O)NR₄—, —NRSC(O)—, or —NR₆C(O)NR₇—; wherein: R₄, R₅, R₆, and R₇ are each independently selected from hydrogen, alkyl$_{(C≤8)}$, or substituted alkyl$_{(C≤8)}$; and Y₁ is cycloalkyl$_{(C≤18)}$, aryl$_{(C≤24)}$, heteroaryl$_{(C≤24)}$, -arenediyl$_{(C≤18)}$-alkyl$_{(C≤8)}$, -arenediyl$_{(C≤18)}$-alkenyl$_{(C≤8)}$, -arenediyl$_{(C≤18)}$-alkoxy$_{(C≤8)}$, or a substituted version of any of these groups; or a pharmaceutically acceptable salt thereof. In some embodiments, the compound is further defined by the formula:

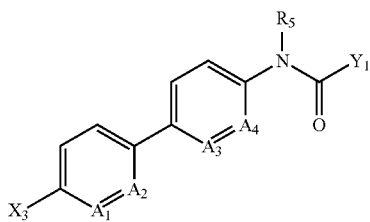

(XXI)

wherein: $A_1$, $A_2$, $A_3$, or $A_4$ are each independently selected from N or CH; $X_3$ is heterocycloalkoxy$_{(C\le12)}$, -alkoxydiyl$_{(C\le8)}$-heterocycloalkyl$_{(C\le12)}$, -alkoxydiyl$_{(C\le8)}$-dialkylamino$_{(C\le12)}$, or a substituted version of any of these groups; $R_5$ is hydrogen, alkyl$_{(C\le8)}$, or substituted alkyl$_{(C\le8)}$; and $Y_1$ is cycloalkyl$_{(C\le18)}$, aryl$_{(C\le24)}$, heteroaryl$_{(C\le24)}$, -arenediyl$_{(C\le18)}$-alkyl$_{(C\le8)}$, -arenediyl$_{(C\le18)}$-alkenyl$_{(C\le8)}$, -arenediyl$_{(C\le18)}$-alkoxy$_{(C\le8)}$, or a substituted version of any of these groups; or a pharmaceutically acceptable salt thereof. In some embodiments, the compound is further defined as:

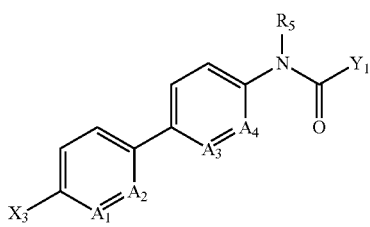

(XXI)

wherein: $A_1$, $A_2$, $A_3$, or $A_4$ are each independently selected from N or CH; $X_3$ is heterocycloalkoxy$_{(C\le12)}$ or substituted heterocycloalkoxy$_{(C\le12)}$; $R_5$ is hydrogen, alkyl$_{(C\le8)}$, or substituted alkyl$_{(C\le8)}$; and $Y_1$ is cycloalkyl$_{(C\le18)}$, aryl$_{(C\le24)}$, heteroaryl$_{(C\le24)}$, -arenediyl$_{(C\le12)}$-alkyl$_{(C\le8)}$, -arenediyl$_{(C\le12)}$-alkenyl$_{(C\le8)}$, -arenediyl$_{(C\le12)}$-alkoxy$_{(C\le8)}$, or a substituted version of any of these groups; or a pharmaceutically acceptable salt thereof. In some embodiments, the compound is further defined as:

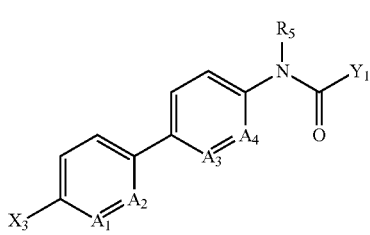

(XXI)

wherein: $A_1$, $A_2$, $A_3$, or $A_4$ are each independently selected from N or CH; $X_3$ is heterocycloalkoxy$_{(C\le12)}$ or substituted heterocycloalkoxy$_{(C\le12)}$; $R_5$ is hydrogen, alkyl$_{(C\le8)}$, or substituted alkyl$_{(C\le8)}$; and $Y_1$ is aryl$_{(C\le24)}$ or substituted aryl$_{(C\le24)}$; or a pharmaceutically acceptable salt thereof. In some embodiments, $X_3$ is heterocycloalkoxy$_{(C\le8)}$ or heterocycloalkoxy$_{(C\le8)}$. In some embodiments, $X_3$ is heterocycloalkoxy$_{(C\le8)}$. In some embodiments, $X_3$ is

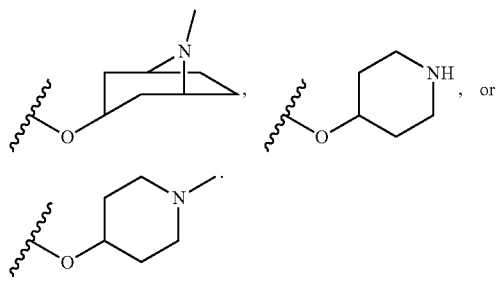

In some embodiments, $X_3$ is

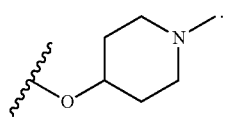 [SMILES: *OC1CCN(C)CC1]

In other embodiments, $X_3$ is -alkoxydiyl$_{(C\le8)}$-heterocycloalkyl$_{(C\le12)}$ or substituted -alkoxydiyl$_{(C\le8)}$-heterocycloalkyl$_{(C\le12)}$. In some embodiments, $X_3$ is -alkoxydiyl$_{(C\le8)}$-heterocycloalkyl$_{(C\le8)}$. In some embodiments, $X_3$ is —OCH$_2$CH$_2$-heterocycloalkyl$_{(C\le8)}$. In some embodiments, $X_3$ is

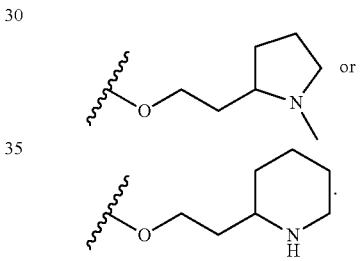

In other embodiments, $X_3$ is -alkoxydiyl$_{(C\le8)}$-dialkylamino$_{(C\le12)}$ or substituted -alkoxydiyl$_{(C\le8)}$-dialkylamino$_{(C\le12)}$. In some embodiments, $X_3$ is -alkoxydiyl$_{(C\le8)}$-dialkylamino$_{(C\le8)}$. In some embodiments, $X_3$ is —OCH$_2$CH$_2$-dialkylamino$_{(C\le8)}$ or —OCH$_2$CH$_2$CH$_2$-dialkylamino$_{(C\le8)}$. In some embodiments, $X_3$ is

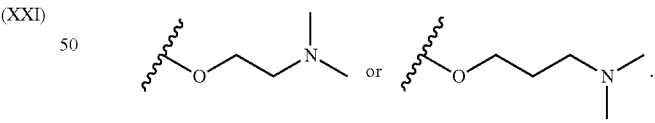

In some embodiments, $R_5$ is hydrogen. In some embodiments, $Y_1$ is aryl$_{(C\le18)}$ or substituted aryl$_{(C\le18)}$. In some embodiments, $Y_1$ is aryl$_{(C\le18)}$. In some embodiments, $Y_1$ is phenyl, 4-methylphenyl, 3-methylphenyl, 4-t-butylphenyl, naphthyl, or biphenyl. In some embodiments, $Y_1$ is substituted aryl$_{(C\le18)}$. In some embodiments, $Y_1$ is 3-methoxyphenyl, 4-methoxyphenyl, 4-acetoxyphenyl, 2-chlorophenyl, 3-chlorophenyl, 4-chlorophenyl, 4-bromophenyl, 3,4-dichlorophenyl, 2,4-dichlorophenyl, 3,5-dichlorophenyl, 3-iodo-4-methylphenyl, 3-bromo-4-methylphenyl, 3-chloro-4-methylphenyl, 4-iodophenyl, or 3-methyl-4-chlorophenyl. In some embodiments, $Y_1$ is substituted biphenyl$_{(C\le18)}$. In some embodiments, $Y_1$ is

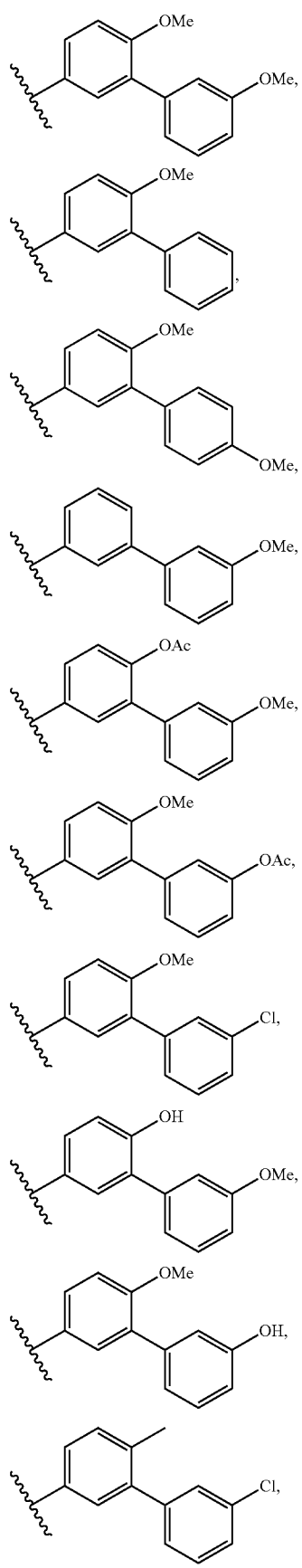
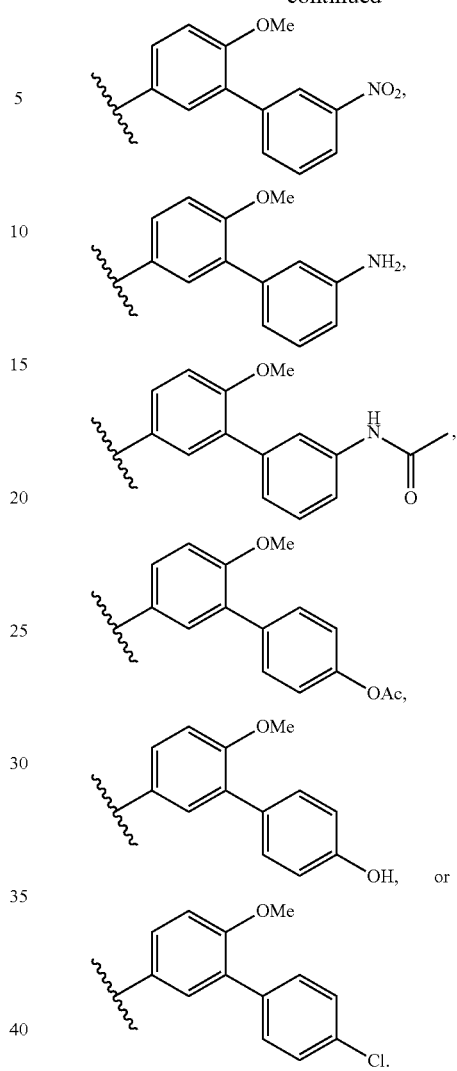

In other embodiments, $Y_1$ is heteroaryl$_{(C≤18)}$ or substituted heteroaryl$_{(C≤8)}$. In some embodiments, $Y_1$ is heteroaryl$_{(C≤18)}$. In some embodiments, $Y_1$ is 2-quinolyl, 6-quinolyl, 2-indolyl, or 2-benzo[b]thiophenyl. In some embodiments, $Y_1$ is -arenediyl$_{(C≤12)}$-alkenyl$_{(C≤8)}$ or substituted -arenediyl$_{(C≤12)}$-alkenyl$_{(C≤8)}$. In some embodiments, $Y_1$ is -arenediyl$_{(C≤12)}$—CH$_2$CH(CH$_3$)$_2$ or substituted -arenediyl$_{(C≤12)}$-CH$_2$CH(CH$_3$)$_2$. In some embodiments, $Y_1$ is —C$_6$H$_4$—CH$_2$CH(CH$_3$)$_2$. In some embodiments, $Y_1$ is

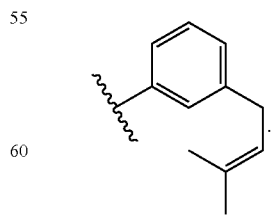

In some embodiments, $Y_1$ is —C$_6$H$_3$(OH)—CH$_2$CH(CH$_3$)$_2$ or —C$_6$H$_3$(OAc)—CH$_2$CH(CH$_3$)$_2$. In some embodiments, $Y_1$ is

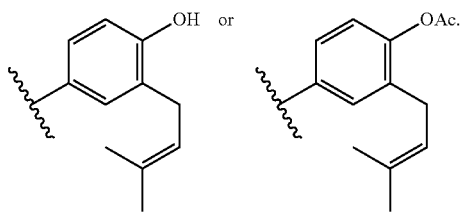 [SMILES: *c1ccc(O)c(CC=C(C)C)c1 ; *c1ccc(OC(C)=O)c(CC=C(C)C)c1]

In other embodiments, $Y_1$ is -arenediyl$_{(C \leq 15)}$-alkoxy$_{(C \leq 8)}$ or substituted -arenediyl$_{(C \leq 15)}$-alkoxy$_{(C \leq 8)}$. In some embodiments, $Y_1$ is -arenediyl$_{(C \leq 15)}$-OCH$_2$CH$_2$CH$_3$ or substituted -arenediyl$_{(C \leq 15)}$-OCH$_2$CH$_2$CH$_3$. In some embodiments, $Y_1$ is

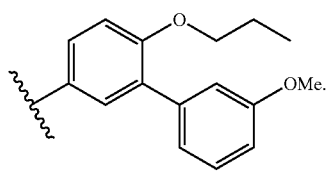 [SMILES: *c1ccc(OCCC)c(-c2cccc(OC)c2)c1]

In some embodiments, $Y_1$ is cycloalkyl$_{(C \leq 12)}$ or substituted cycloalkyl$_{(C \leq 12)}$. In some embodiments, $Y_1$ is cycloalkyl$_{(C \leq 12)}$. In some embodiments, $Y_1$ is adamantanyl. In some embodiments, $R_1$ is alkyl$_{(C \leq 12)}$ or substituted alkyl$_{(C \leq 12)}$. In some embodiments, $R_1$ is alkyl$_{(C \leq 8)}$ or substituted alkyl$_{(C \leq 8)}$. In some embodiments, $R_1$ is alkyl$_{(C \leq 8)}$. In some embodiments, $R_1$ is methyl. In some embodiments, $R_1$ is alkoxy$_{(C \leq 12)}$ or substituted alkoxy$_{(C \leq 12)}$. In other embodiments, $R_1$ is alkoxy$_{(C \leq 8)}$ or substituted alkoxy$_{(C \leq 8)}$. In some embodiments, $R_1$ is alkoxy$_{(C \leq 8)}$. In some embodiments, $R_1$ is methoxy. In other embodiments, $R_1$ is amino. In other embodiments, $R_1$ is halo. In some embodiments, $R_1$ is chloro or bromo. In some embodiments, $R_1$ is chloro. In other embodiments, $R_1$ is nitro. In other embodiments, $R_1$ is amido$_{(C \leq 12)}$ or substituted amido$_{(C \leq 12)}$. In some embodiments, $R_1$ is amido$_{(C \leq 8)}$ or substituted amido$_{(C \leq 8)}$. In some embodiments, $R_1$ is amido$_{(C \leq 8)}$. In some embodiments, $R_1$ is —NHC(O)CH$_3$. In other embodiments, $R_1$ is hydrogen. In some embodiments, z is 0, 1, or 2. In some embodiments, z is 1 or 2. In some embodiments, $R_2$ is alkyl$_{(C \leq 12)}$ or substituted alkyl$_{(C \leq 12)}$. In some embodiments, $R_2$ is alkyl$_{(C \leq 8)}$ or substituted alkyl$_{(C \leq 8)}$. In some embodiments, $R_2$ is alkyl$_{(C \leq 8)}$. In some embodiments, $R_2$ is methyl. In other embodiments, $R_2$ is alkoxy$_{(C \leq 12)}$ or substituted alkoxy$_{(C \leq 12)}$. In some embodiments, $R_2$ is alkoxy$_{(C \leq 8)}$ or substituted alkoxy$_{(C \leq 8)}$. In some embodiments, $R_2$ is alkoxy$_{(C \leq 8)}$. In some embodiments, $R_2$ is methoxy. In other embodiments, $R_2$ is amino. In other embodiments, $R_2$ is halo. In some embodiments, $R_2$ is chloro or bromo. In some embodiments, $R_2$ is chloro. In other embodiments, $R_2$ is nitro. In other embodiments, $R_2$ is amido$_{(C \leq 12)}$ or substituted amido$_{(C \leq 12)}$. In some embodiments, $R_2$ is amido$_{(C \leq 8)}$ or substituted amido$_{(C \leq 8)}$. In some embodiments, $R_2$ is amido$_{(C \leq 8)}$. In some embodiments, $R_2$ is —NHC(O)CH$_3$. In other embodiments, $R_2$ is hydrogen. In some embodiments, x is 0, 1, or 2. In some embodiments, x is 1 or 2. In some embodiments, $R_3$ is alkyl$_{(C \leq 12)}$ or substituted alkyl$_{(C \leq 12)}$. In some embodiments, $R_3$ is alkyl$_{(C \leq 8)}$ or substituted alkyl$_{(C \leq 8)}$. In some embodiments, $R_3$ is alkyl$_{(C \leq 8)}$. In some embodiments, $R_3$ is methyl. In other embodiments, $R_3$ is alkoxy$_{(C \leq 12)}$ or substituted alkoxy$_{(C \leq 12)}$. In some embodiments, $R_3$ is alkoxy$_{(C \leq 8)}$ or substituted alkoxy$_{(C \leq 8)}$. In some embodiments, $R_3$ is alkoxy$_{(C \leq 8)}$. In some embodiments, $R_3$ is methoxy. In other embodiments, $R_3$ is amino. In other embodiments, $R_3$ is halo. In some embodiments, $R_3$ is chloro or bromo. In some embodiments, $R_3$ is chloro. In other embodiments, $R_3$ is nitro. In other embodiments, $R_3$ is amido$_{(C \leq 12)}$ or substituted amido$_{(C \leq 12)}$. In some embodiments, $R_3$ is amido$_{(C \leq 8)}$ or substituted amido$_{(C \leq 8)}$. In some embodiments, $R_3$ is amido$_{(C \leq 8)}$. In some embodiments, $R_3$ is —NHC(O)CH$_3$. In other embodiments, $R_3$ is hydrogen. In some embodiments, y is 0, 1, or 2. In some embodiments, y is 1 or 2.

In yet another aspect, the present disclosure provides a compound of the formula:

$$X_1\text{—O-A-Z—NH}_2 \quad (XXII)$$

wherein: $X_1$ is heterocycloalkyl$_{(C \leq 12)}$, -alkanediyl$_{(C \leq 8)}$-amino, -alkanediyl$_{(C \leq 8)}$-hetero-cycloalkyl$_{(C \leq 8)}$, -alkanediyl$_{(C \leq 8)}$-alkylamino$_{(C \leq 8)}$, -alkanediyl$_{(C \leq 8)}$-dialkylamino$_{(C \leq 8)}$, or a substituted version of any of theses groups; A is arenediyl$_{(C \leq 12)}$, heteroarenediyl$_{(C \leq 12)}$, or a substituted version of any of these groups; Z is arenediyl$_{(C \leq 12)}$, heteroarenediyl$_{(C \leq 12)}$, or a substituted version of any of these groups; or a salt thereof. In some embodiments, $X_1$ is

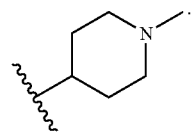 [SMILES: *C1CCN(C)CC1]

In some embodiments, the compound is further defined as:

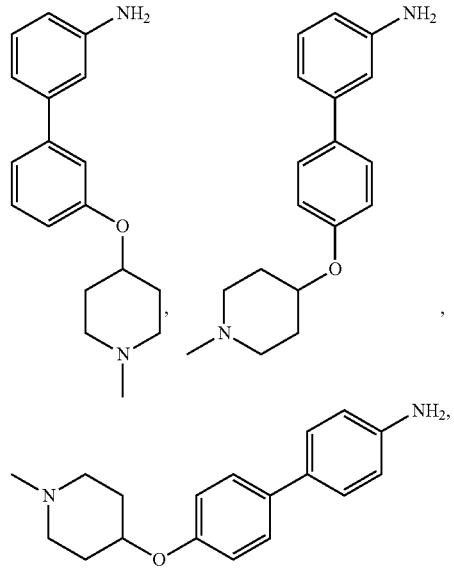

or a salt thereof.

In still yet another aspect, the present disclosure provides a compound of the formula:

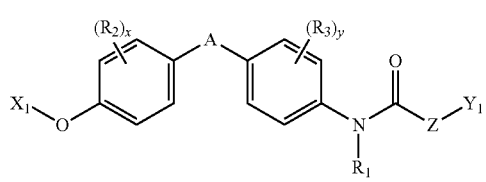
(XXIII)

wherein: $X_1$ is heteorcycloalkyl$_{(C\leq12)}$, -alkanediyl$_{(C\leq8)}$-amino, -alkanediyl$_{(C\leq8)}$-hetero-cycloalkyl$_{(C\leq8)}$, -alkanediyl$_{(C\leq8)}$-alkylamino$_{(C\leq8)}$, -alkanediyl$_{(C\leq8)}$-dialkylamino$_{(C\leq8)}$, or a substituted version of any of theses groups; A is —O—, —S—, or —NR$_4$—, wherein R$_4$ is hydrogen, alkyl$_{(C\leq8)}$, or substituted alkyl$_{(C\leq8)}$; Z is a covalent bond or —NR$_4$—, wherein: R$_5$ is hydrogen, alkyl$_{(C\leq8)}$, or substituted alkyl$_{(C\leq8)}$; Y$_1$ is cycloalkyl$_{(C\leq18)}$, aryl$_{(C\leq18)}$, heteroaryl$_{(C\leq18)}$, or a substituted version of any of these groups; R$_1$ is hydrogen, alkyl$_{(C\leq8)}$, or substituted alkyl$_{(C\leq8)}$; each R$_2$ and R$_3$ are independently selected from amino, cyano, halo, hydroxy, nitro, sulfato, sulfamido, acyl$_{(C\leq12)}$, substituted acyl$_{(C\leq12)}$, acyloxy$_{(C\leq12)}$, substituted acyloxy$_{(C\leq12)}$, alkoxy$_{(C\leq12)}$, substituted alkoxy$_{(C\leq12)}$, alkyl$_{(C\leq12)}$, substituted alkyl$_{(C\leq12)}$, amido$_{(C\leq12)}$, and substituted amido$_{(C\leq12)}$; and x and y are each independently 0, 1, 2, 3, or 4; or a pharmaceutically acceptable salt thereof. In some embodiments, the compound is further defined as:

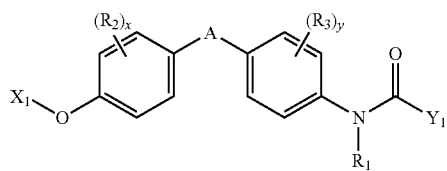
(XXIV)

wherein: $X_1$ is heteorcycloalkyl$_{(C\leq12)}$, -alkanediyl$_{(C\leq8)}$-amino, -alkanediyl$_{(C\leq8)}$-hetero-cycloalkyl$_{(C\leq8)}$, -alkanediyl$_{(C\leq8)}$-alkylamino$_{(C\leq8)}$, -alkanediyl$_{(C\leq8)}$-dialkylamino$_{(C\leq8)}$, or a substituted version of any of theses groups; A is —O—, —S—, or —NR$_4$—, wherein R$_4$ is hydrogen, alkyl$_{(C\leq8)}$, or substituted alkyl$_{(C\leq8)}$; Y$_1$ is cycloalkyl$_{(C\leq18)}$, aryl$_{(C\leq18)}$, heteroaryl$_{(C\leq18)}$, or a substituted version of any of these groups; R$_1$ is hydrogen, alkyl$_{(C\leq8)}$, or substituted alkyl$_{(C\leq8)}$; each R$_2$ and R$_3$ are independently selected from amino, cyano, halo, hydroxy, nitro, sulfato, sulfamido, acyl$_{(C\leq12)}$, substituted acyl$_{(C\leq12)}$, acyloxy$_{(C\leq12)}$, substituted acyloxy$_{(C\leq12)}$, alkoxy$_{(C\leq12)}$, substituted alkoxy$_{(C\leq12)}$, alkyl$_{(C\leq12)}$, substituted alkyl$_{(C\leq12)}$, amido$_{(C\leq12)}$, and substituted amido$_{(C\leq12)}$; and x and y are each independently 0, 1, 2, 3, or 4; or a pharmaceutically acceptable salt thereof. In some embodiments, the compound is further defined as:

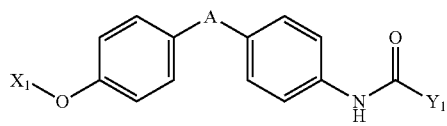
(XXV)

wherein: $X_1$ is heteorcycloalkyl$_{(C\leq12)}$, -alkanediyl$_{(C\leq18)}$-amino, -alkanediyl$_{(C\leq18)}$-hetero-cycloalkyl$_{(C\leq8)}$, -alkanediyl$_{(C\leq18)}$-alkylamino$_{(C\leq8)}$, -alkanediyl$_{(C\leq18)}$-dialkylamino$_{(C\leq8)}$, or a substituted version of any of theses groups; A is —O—, —S—, or —NR$_4$—, wherein R$_4$ is hydrogen, alkyl$_{(C\leq8)}$, or substituted alkyl$_{(C\leq8)}$; and Y$_1$ is cycloalkyl$_{(C\leq18)}$, aryl$_{(C\leq18)}$, heteroaryl$_{(C\leq18)}$, or a substituted version of any of these groups; or a pharmaceutically acceptable salt thereof. In some embodiments, the compound is further defined as:

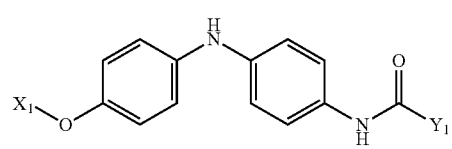
(XXVI)

wherein: $X_1$ is heteorcycloalkyl$_{(C\leq12)}$, -alkanediyl$_{(C\leq8)}$-amino, -alkanediyl$_{(C\leq8)}$-hetero-cycloalkyl$_{(C\leq8)}$, -alkanediyl$_{(C\leq8)}$-alkylamino$_{(C\leq8)}$, -alkanediyl$_{(C\leq8)}$-dialkylamino$_{(C\leq8)}$, or a substituted version of any of theses groups; and Y$_1$ is cycloalkyl$_{(C\leq18)}$, aryl$_{(C\leq18)}$, heteroaryl$_{(C\leq18)}$, or a substituted version of any of these groups; or a pharmaceutically acceptable salt thereof. In some embodiments, X$_1$ is heterocyclo-alkyl$_{(C\leq12)}$ or substituted heterocyclo-alkyl$_{(C\leq12)}$. In some embodiments, X$_1$ is heterocylco-alkyl$_{(C\leq8)}$. In some embodiments, X$_1$ is

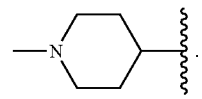

In some embodiments, Y$_1$ is aryl$_{(C\leq12)}$ or substituted aryl$_{(C\leq12)}$. In some embodiments, Y$_1$ is aryl$_{(C\leq12)}$. In some embodiments, Y$_1$ is 2-napthyl or 4-t-butylphenyl. In some embodiments, Y$_1$ is substituted aryl$_{(C\leq12)}$. In some embodiments, Y$_1$ is 4-chlorophenyl or 4-methoxyphenyl. In some embodiments, Z is a covalent bond. In some embodiments, each R$_2$ is selected from amino, cyano, halo, hydroxy, nitro, sulfato, sulfamido, acyl$_{(C\leq6)}$, substituted acyl$_{(C\leq6)}$, acyloxy$_{(C\leq6)}$, substituted acyloxy$_{(C\leq6)}$, alkoxy$_{(C\leq6)}$, substituted alkoxy$_{(C\leq6)}$, alkyl$_{(C\leq6)}$, substituted alkyl$_{(C\leq6)}$, amido$_{(C\leq6)}$, and substituted amido$_{(C\leq6)}$. In some embodiments, each R$_3$ is selected from amino, cyano, halo, hydroxy, nitro, sulfato, sulfamido, acyl$_{(C\leq6)}$, substituted acyl$_{(C\leq6)}$, acyloxy$_{(C\leq6)}$, substituted acyloxy$_{(C\leq6)}$, alkoxy$_{(C\leq6)}$, substituted alkoxy$_{(C\leq6)}$, alkyl$_{(C\leq6)}$, substituted alkyl$_{(C\leq6)}$, amido$_{(C\leq6)}$, and substituted amido$_{(C\leq6)}$. In some embodiments, x is 0, 1, or 2. In some embodiments, y is 0, 1, or 2. In some embodiments, R$_1$ is hydrogen. In some embodiments, A is NR$_4$. In some embodiments, R$_4$ is hydrogen. In some embodiments, the compound is further defined as:

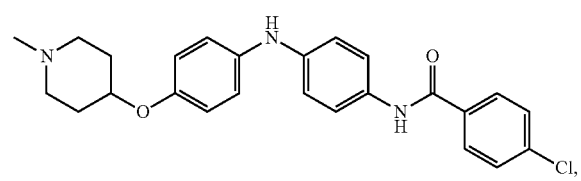

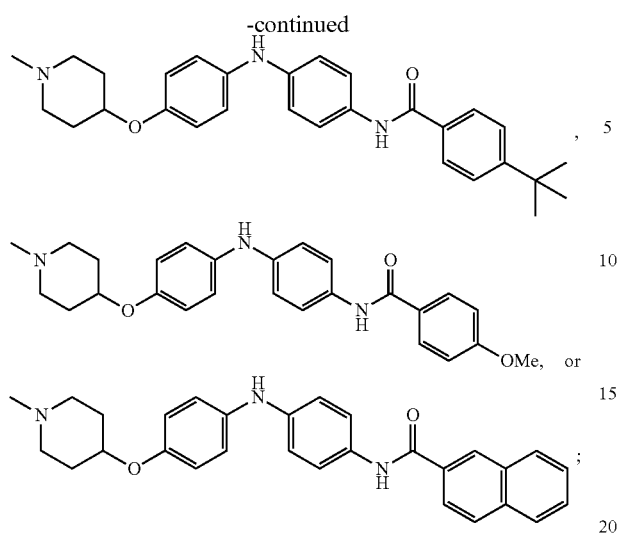

or a pharmaceutically acceptable salt thereof.

In still yet another aspect, the present disclosure provides a biphenylamine that is an HSP90 inhibitor having a structure in accordance with a scaffold as illustrated herein or a derivative thereof, the derivative having any chemical substituent. In some embodiments, the biphenylamine has the structure of:

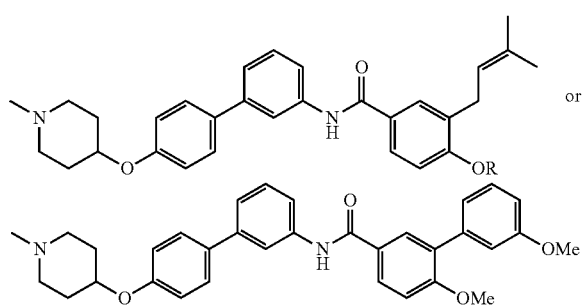

wherein R is Ac or H. In some embodiments, biphenylamine has the structure of:

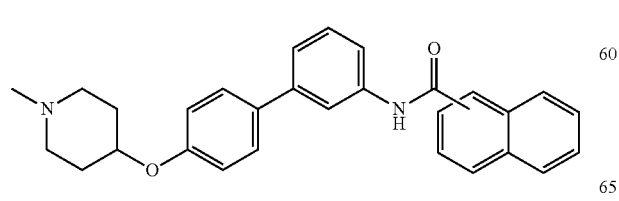

wherein R is H, p-CH$_3$, nr-CH$_3$, p-t-butyl, p-methoxy, m-methoxy, p-Cl, m-Cl, o-Cl, p-Br, 3,4-dichloro, 2,4-dichloro, or 3,5-dichloro, or

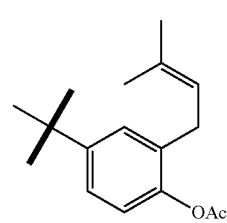

as either 1-naphthoyl or 2-naphthoyl. In some embodiments, the biphenylamine has the structure of:

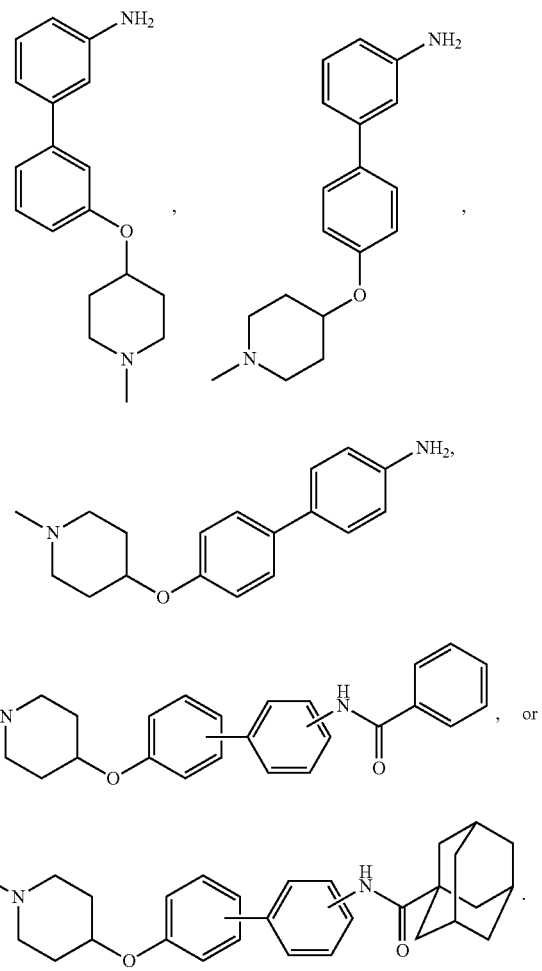

In some embodiments, the biphenylamine has the structure of:

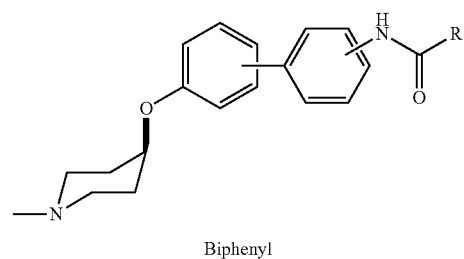

wherein: A is

A or B is

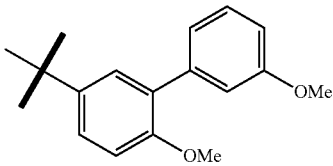

| Biphenyl | R |
|---|---|
| para-meta | A |
| meta-meta | A |
| para-para | A |
| para-meta | B |
| meta-meta | B |
| para-para | B |
| para-meta | para-t-butyl |
| meta-meta | para-t-butyl |
| para-para | para-t-butyl |
| para-meta | para-chlorophenyl |
| meta-meta | para-chlorophenyl |
| para-para | para-chlorophenyl |
| para-meta | para-methoxyphenyl |
| meta-meta | para-methoxyphenyl |
| para-para | para-methoxyphenyl |
| para-meta | adamantanyl |
| meta-meta | adamantanyl |
| para-para | adamantanyl. |

In some embodiments, the biphenylamine has the structure of:

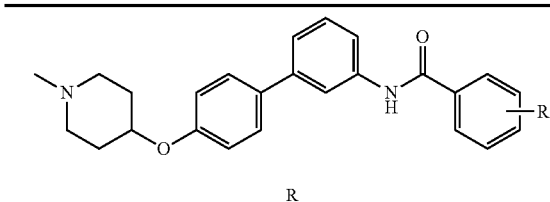

| R |
|---|
| H |
| p-CH$_3$ |
| m-CH$_3$ |
| p-t-butyl |
| p-methoxy |
| m-methoxy |
| p-Cl |
| m-Cl |
| o-Cl |
| p-Br |
| 3,4-dichloro |
| 2,4-dichloro |
| 3,5-dichloro |
| -(2-naphthoyl) |
| -(1-naphthoyl). |

In some embodiments, the biphenylamine has the structure of:

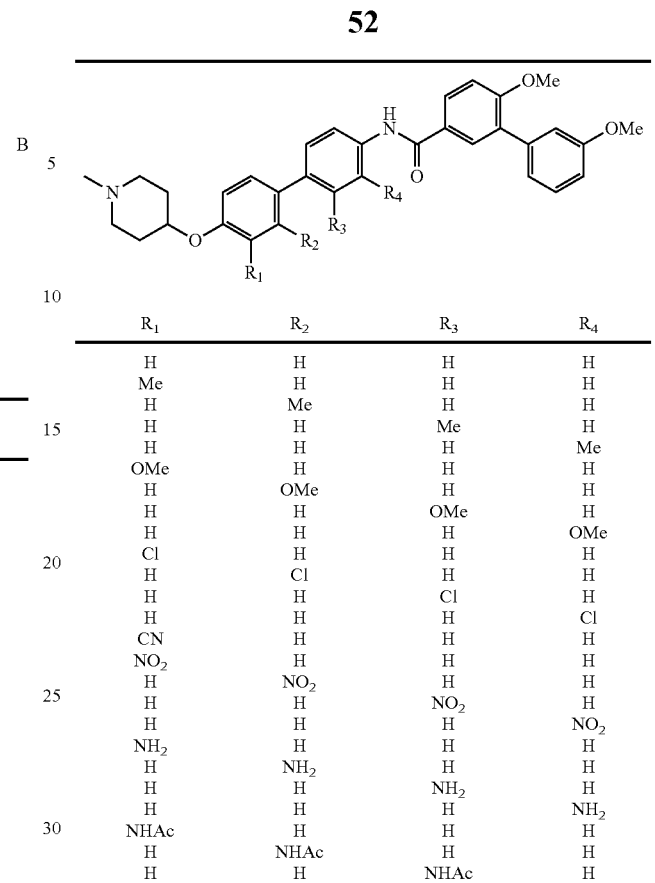

| R$_1$ | R$_2$ | R$_3$ | R$_4$ |
|---|---|---|---|
| H | H | H | H |
| Me | H | H | H |
| H | Me | H | H |
| H | H | Me | H |
| H | H | H | Me |
| OMe | H | H | H |
| H | OMe | H | H |
| H | H | OMe | H |
| H | H | H | OMe |
| Cl | H | H | H |
| H | Cl | H | H |
| H | H | Cl | H |
| H | H | H | Cl |
| CN | H | H | H |
| NO$_2$ | H | H | H |
| H | NO$_2$ | H | H |
| H | H | NO$_2$ | H |
| H | H | H | NO$_2$ |
| NH$_2$ | H | H | H |
| H | NH$_2$ | H | H |
| H | H | NH$_2$ | H |
| H | H | H | NH$_2$ |
| NHAc | H | H | H |
| H | NHAc | H | H |
| H | H | NHAc | H |
| H | H | H | NHAc. |

In some embodiments, the biphenylamine has the structure of:

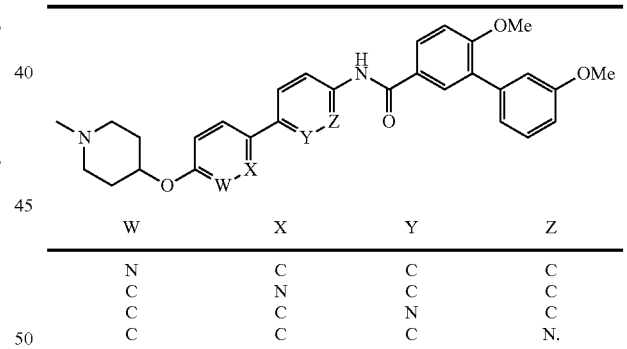

| W | X | Y | Z |
|---|---|---|---|
| N | C | C | C |
| C | N | C | C |
| C | C | N | C |
| C | C | C | N. |

In some embodiments, the biphenylamine has the structure:

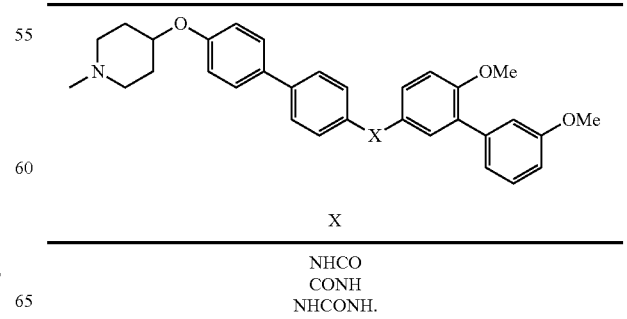

| X |
|---|
| NHCO |
| CONH |
| NHCONH. |

In some embodiments, the biphenylamine has the structure:
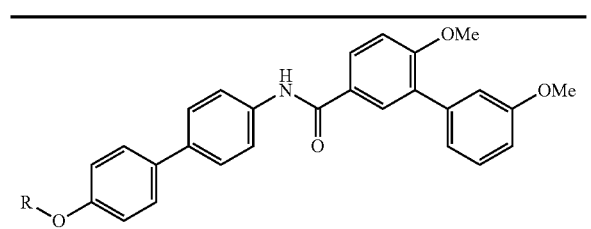
R
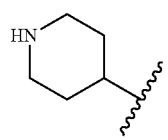
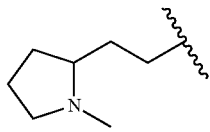
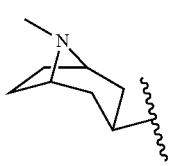 [SMILES: *C1CC2CCC(C1)N2C]
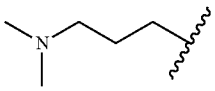 [SMILES: *CCCN(C)C]
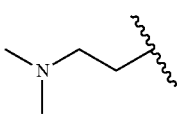
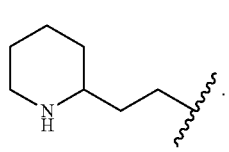 [SMILES: *CCC1CCCCN1]
In some embodiments, the biphenylamine has the structure:
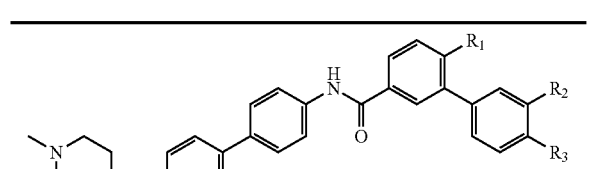
| $R_1$ | $R_2$ | $R_3$ |
|---|---|---|
| OMe | OMe | H |
| OMe | H | OMe |
-continued
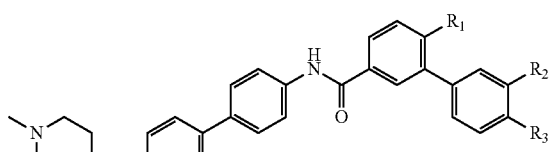
| $R_1$ | $R_2$ | $R_3$ |
|---|---|---|
| OMe | H | H |
| H | OMe | H |
| H | H | H |
| OAc | OMe | H |
| OH | OMe | H |
| OMe | OAc | H |
| OMe | OH | H |
| OMe | H | OAc |
| OMe | H | OH |
| OMe | Cl | H |
| OMe | H | Cl |
| OMe | $NO_2$ | H |
| OMe | $NH_2$ | H |
| OMe | NHAc | H. |
In some embodiments, the biphenylamine has the structure of:
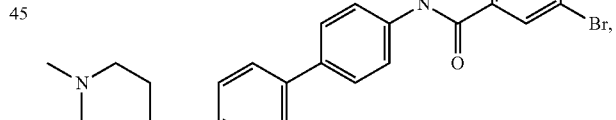
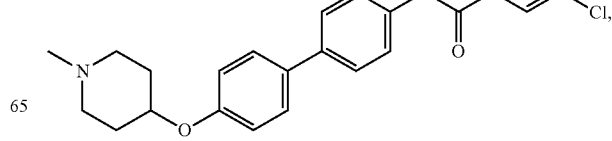

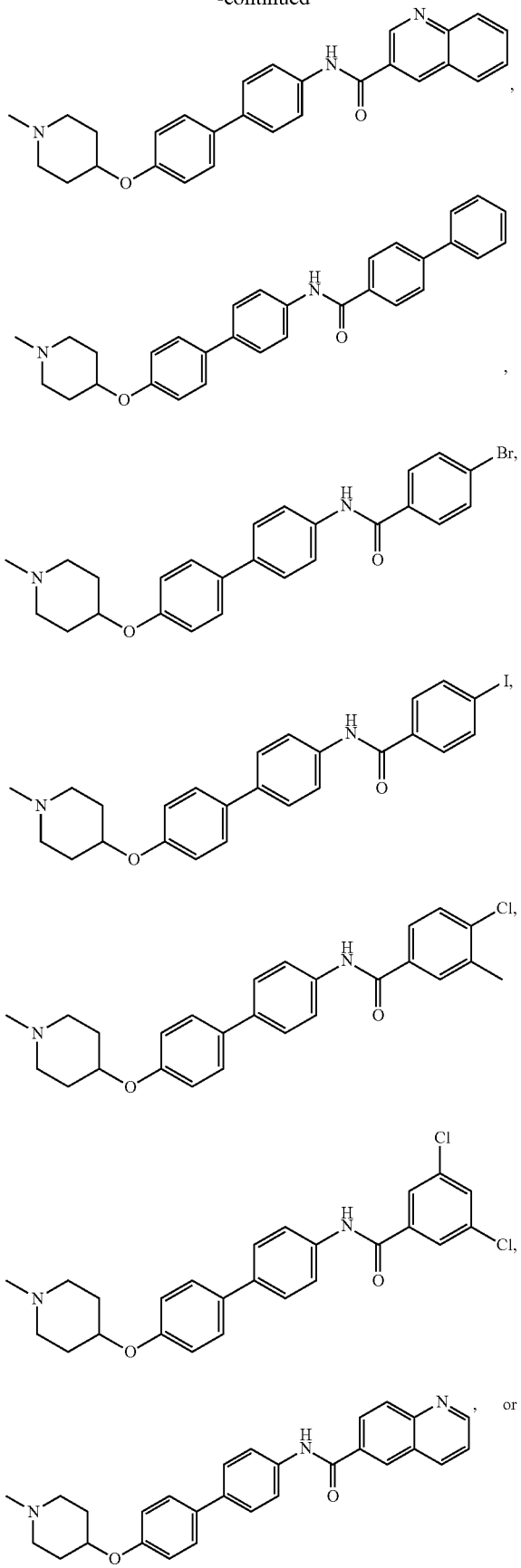

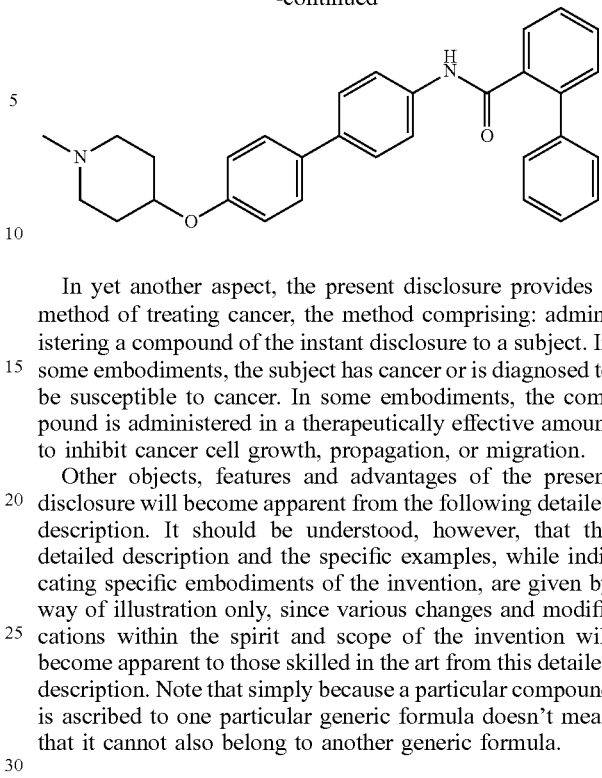

In yet another aspect, the present disclosure provides a method of treating cancer, the method comprising: administering a compound of the instant disclosure to a subject. In some embodiments, the subject has cancer or is diagnosed to be susceptible to cancer. In some embodiments, the compound is administered in a therapeutically effective amount to inhibit cancer cell growth, propagation, or migration.

Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description. Note that simply because a particular compound is ascribed to one particular generic formula doesn't mean that it cannot also belong to another generic formula.

BRIEF DESCRIPTION OF THE DRAWINGS

The following drawings form part of the present specification and are included to further demonstrate certain aspects of the present disclosure. The invention may be better understood by reference to one of these drawings in combination with the detailed description of specific embodiments presented herein.

DESCRIPTION OF ILLUSTRATIVE EMBODIMENTS

Figure 1:
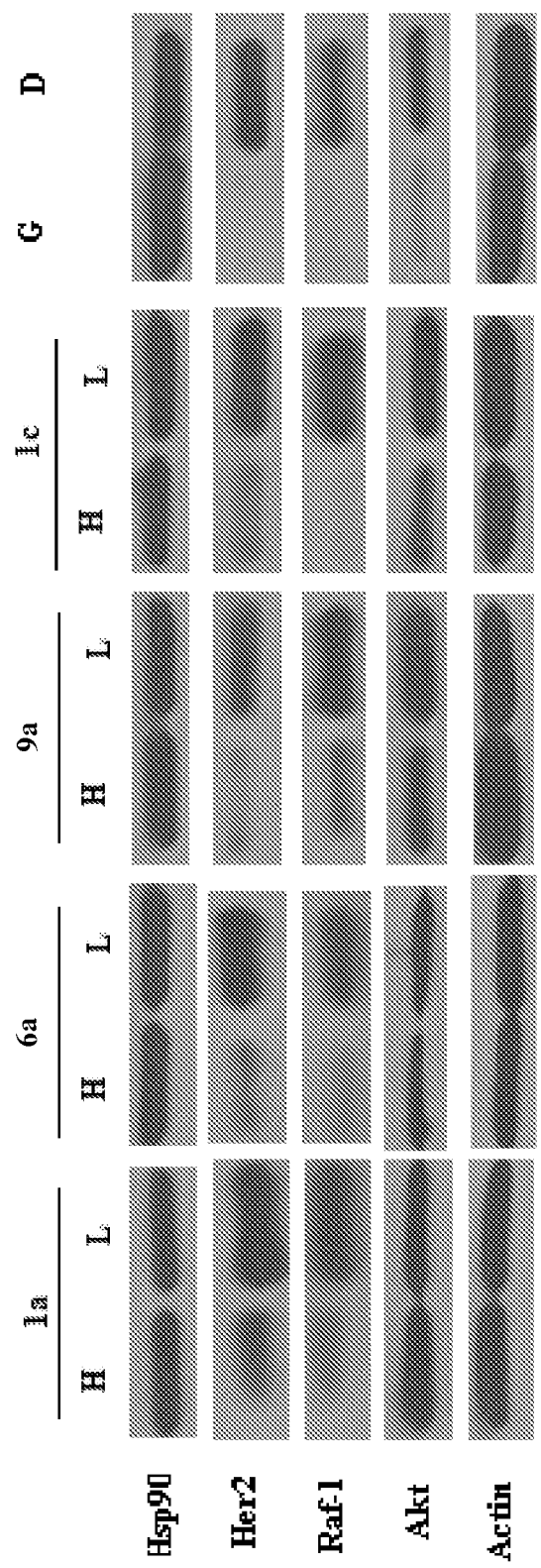
FIG. 1—Western blot analyses of Hsp90-dependent client proteins from MCF-7 breast cancer cell lysate upon treatment with biphenyl derivatives. H represents a concentration equal to 5-fold of the anti-proliferative activity. L represents a concentration ½ of the anti-proliferative activity. Geldanamycin (G, 0.5 μM) and dimethylsulfoxide (D, 100%) were employed as positive and negative controls.

The present disclosure provides new compounds which may be used to inhibit Hsp90 in some embodiments. Without being bound by theory, in some embodiments, inhibition of Hsp90 may be effected by binding to the C-terminus nucleotide binding pocket of the protein. In some embodiments, the biphenyl compounds are useful in the treatment of a disease or disorder, including, for example, cancer.

I. Definitions

When used in the context of a chemical group: "hydrogen" means —H; "hydroxy" means —OH; "oxo" means =O; "carbonyl" means —C(=O)—; "carboxy" means —C(=O)OH (also written as —COOH or —CO$_2$H); "halo" means independently —F, —Cl, —Br or —I; "amino" means —NH$_2$; "hydroxyamino" means —NHOH; "nitro" means —NO$_2$; imino means =NH; "cyano" means —CN; "isocyanate" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means=S; "sulfato" means —S(O)$_2$OH; "sulfamido" means —S(O)$_2$NH$_2$; "sulfonyl" means —S(O)$_2$—; and "sulfinyl" means —S(O)—.

In the context of chemical formulas, the symbol "—" means a single bond, "=" means a double bond, and "≡" means triple bond. The symbol "----" represents an optional bond, which if present is either single or double. The symbol "⩴" represents a single bond or a double bond. Thus, for example, the formula includes and And it is uiersood that no one such ring atom forms part of more than one double bond. Furthermore, it is noted that the covalent bond symbol "—", when connecting one or two stereogenic atoms, does not indicate any preferred stereochemistr ppas iRT covers all stereoisomers as well as mixtures thereof. The symbol "〰", when drawn perpendicularly across a bond (e.g.,

for methyl) indicates a point of attachment of the group. It is noted that the point of attachment is typically only identified in this manner for larger groups in order to assist the reader in unambiguously identifying a point of attachment. The symbol "◂" means a single bond where the group attached to the thick end of the wedge is "out of the page." The symbol "⫽" means a single bond where the group attached to the thick end of the wedge is "into the page". The symbol "〰" means a 〰 single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a group "R" is depicted as a "floating group" on a ring system, for example, in the formula:

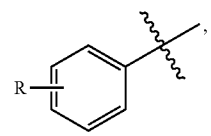

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

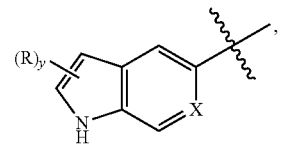

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the groups and classes below, the number of carbon atoms in the group is as indicated as follows: "Cn" defines the exact number (n) of carbon atoms in the group/class. "C≤n" defines the maximum number (n) of carbon atoms that can be in the group/class, with the minimum number as small as possible for the group in question, e.g., it is understood that the minimum number of carbon atoms in the group "alkenyl$_{(C≤8)}$" or the class "alkene$_{(C≤8)}$" is two. Compare with "alkoxy$_{(C≤10)}$", which designates alkoxy groups having from 1 to 10 carbon atoms. "Cn-n'" defines both the minimum (n) and maximum number (n') of carbon atoms in the group. Thus, "alkyl$_{(C2-10)}$" designates those alkyl groups having from 2 to 10 carbon atoms. Typically the carbon number indicator follows the group it modifies, is enclosed with parentheses, and is written entirely in subscript; however, the indicator may also precede the group, or be written

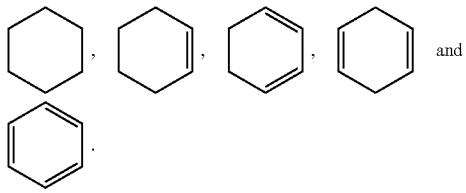

without parentheses, without signifying any change in meaning. Thus, the terms "C5 olefin", "C5-olefin", "olefin$_{(C5)}$", and "olefin$_{C5}$" are all synonymous.

The term "saturated" when used to modify a compound or an atom means the compound or atom has no carbon-carbon double and no carbon-carbon triple bonds, except as noted below. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded. When the term "saturated" is used to modify a solution of a substance, it means that no more of that substance can dissolve in that solution.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single carbon-carbon bonds (alkanes/alkyl), or unsaturated, with one or more carbon-carbon double bonds (alkenes/alkenyl) or with one or more carbon-carbon triple bonds (alkynes/alkynyl).

The term "alkyl" when used without the "substituted" modifier refers to a monovalent saturated aliphatic group with a carbon atom as the point of attachment, a linear or branched acyclic structure, and no atoms other than carbon and hydrogen. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), and —CH$_2$C(CH$_3$)$_3$ (neo-pentyl) are non-limiting examples of alkyl groups. The term "alkanediyl" when used without the "substituted" modifier refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups —CH$_2$— (methylene), —CH$_2$CH$_2$—, —CH$_2$C(CH$_3$)$_2$CH$_2$—, and —CH$_2$CH$_2$CH$_2$— are non-limiting examples of alkanediyl groups. The term "alkylidene" when used without the "substituted" modifier refers to the divalent group =CRR' in which R and R' are independently hydrogen or alkyl. Non-limiting examples of alkylidene groups include: =CH$_2$, =CH(CH$_2$CH$_3$), and =C(CH$_3$)$_2$. An "alkane" refers to the compound H—R, wherein R is alkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which the hydrogen atom replacement is limited to halo (i.e. —F, —Cl, —Br, or —I) such that no other atoms aside from carbon, hydrogen and halogen are present. The group, —CH$_2$Cl is a non-limiting example of a haloalkyl. The term "fluoroalkyl" is a subset of substituted alkyl, in which the hydrogen atom replacement is limited to fluoro such that no other atoms aside from carbon, hydrogen and fluorine are present. The groups —CH$_2$F, —CF$_3$, and —CH$_2$CF$_3$ are non-limiting examples of fluoroalkyl groups.

The term "cycloalkyl" when used without the "substituted" modifier refers to a monovalent saturated aliphatic group with a carbon atom as the point of attachment, said carbon atom forming part of one or more non-aromatic ring structures, no carbon-carbon double or triple bonds, and no atoms other than carbon and hydrogen. Non-limiting examples include: —CH(CH$_2$)$_2$ (cyclopropyl), cyclobutyl, cyclopentyl, or cyclohexyl (Cy). The term "cycloalkanediyl" when used without the "substituted" modifier refers to a divalent saturated aliphatic group with two carbon atoms as points of attachment, no carbon-carbon double or triple bonds, and no atoms other than carbon and hydrogen. The group

is a non-limiting example of cycloalkanediyl group. A "cycloalkane" refers to the compound H—R, wherein R is cycloalkyl as this term is defined above. The group "adamantyl" is a subset of cycloalkyl wherein the cycloalkyl group is defined by the structure:

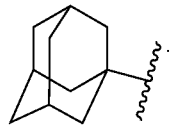 [SMILES: *C12CC3CC(CC(C3)C1)C2]

When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. A "substituted adamantyl" group is a group with the adamantyl carbon ring structure as described above and one or more hydrogen has been replaced as defined above.

The term "alkenyl" when used without the "substituted" modifier refers to an monovalent unsaturated aliphatic group with a carbon atom as the point of attachment, a linear or branched, acyclic structure, at least one nonaromatic carbon-carbon double bond, no carbon-carbon triple bonds, and no atoms other than carbon and hydrogen. Non-limiting examples include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CHCH=CH$_2$. The term "alkenediyl" when used without the "substituted" modifier refers to a divalent unsaturated aliphatic group, with two carbon atoms as points of attachment, a linear or branched, a linear or branched acyclic structure, at least one nonaromatic carbon-carbon double bond, no carbon-carbon triple bonds, and no atoms other than carbon and hydrogen. The groups —CH=CH—, —CH=C(CH$_3$)CH$_2$—, —CH=CHCH$_2$—, and —CH$_2$CH=CHCH$_2$— are non-limiting examples of alkenediyl groups. It is noted that while the alkenediyl group is aliphatic, once connected at both ends, this group is not precluded from forming part of an aromatic structure. The terms "alkene" or "olefin" are synonymous and refer to a compound having the formula H—R, wherein R is alkenyl as this term is defined above. A "terminal alkene" refers to an alkene having just one carbon-carbon double bond, wherein that bond forms a vinyl group at one end of the molecule. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups —CH=CHF, —CH=CHCl and —CH=CHBr are non-limiting examples of substituted alkenyl groups.

The term "alkynyl" when used without the "substituted" modifier refers to a monovalent unsaturated aliphatic group with a carbon atom as the point of attachment, a linear or branched acyclic structure, at least one carbon-carbon triple bond, and no atoms other than carbon and hydrogen. As used herein, the term alkynyl does not preclude the presence of one or more non-aromatic carbon-carbon double bonds. The groups —C≡CH, —C≡CCH$_3$, and —CH$_2$C≡CCH$_3$ are non-limiting examples of alkynyl groups. An "alkyne" refers to the compound H—R, wherein R is alkynyl. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl or aralkyl groups (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and a monovalent group derived from biphenyl. The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl, aryl or aralkyl groups (carbon number limitation permitting) attached to the first aromatic ring or any additional aromatic ring present. If more than one ring is present, the rings may be fused or unfused. Unfused rings may be connected via one or more of the following: a covalent bond, alkanediyl, or alkenediyl groups (carbon number limitation permitting). Non-limiting examples of arenediyl groups include:

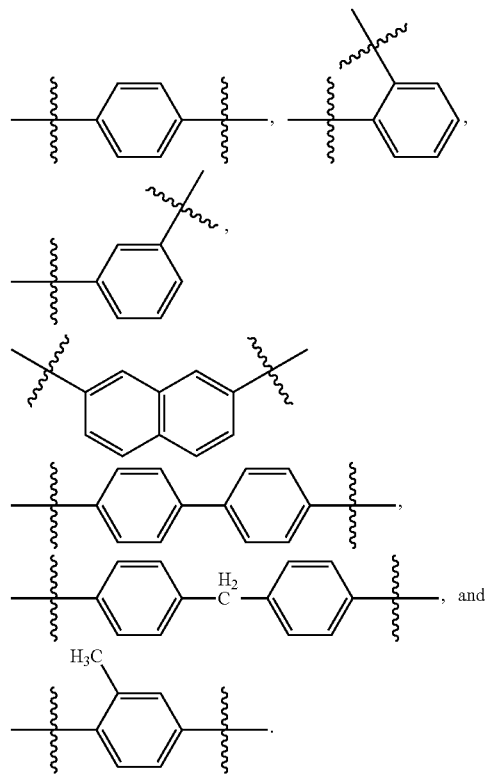

An "arene" refers to the compound H—R, wherein R is aryl as that term is defined above. Benzene and toluene are non-limiting examples of arenes. The term "biphenyl" is a subset of the term "aryl" wherein the group is defined by the aromatic ring structure:

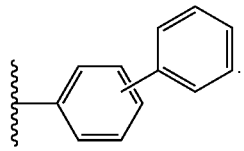

When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "aralkyl" when used without the "substituted" modifier refers to the monovalent group -alkanediyl-aryl, in which the terms alkanediyl and aryl are each used in a manner consistent with the definitions provided above. Non-limiting examples are: phenylmethyl (benzyl, Bn) and 2-phenyl-ethyl. When the term aralkyl is used with the "substituted" modifier one or more hydrogen atom from the alkanediyl and/or the aryl group has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. If more than one ring is present, the rings may be fused or unfused. As used herein, the term does not preclude the presence of one or more alkyl, aryl, and/or aralkyl groups (carbon number limitation permitting) attached to the aromatic ring or aromatic ring system. Non-limiting examples of heteroaryl groups include furanyl, imidazolyl, indolyl, indazolyl (Im), isoxazolyl, methylpyridinyl, oxazolyl, phenylpyridinyl, pyridinyl (pyridyl), pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. A "heteroarene" refers to the compound H—R, wherein R is heteroaryl. Pyridine and quinoline are non-limiting examples of heteroarenes. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. If more than one ring is present, the rings may be fused or unfused. Unfused rings may be connected via one or more of the following: a covalent bond, alkanediyl, or alkenediyl groups (carbon number limitation permitting). As used herein, the term does not preclude the presence of one or more alkyl, aryl, and/or aralkyl groups (carbon number limitation permitting) attached to the aromatic ring or aromatic ring system. Non-limiting examples of heteroarenediyl groups include:

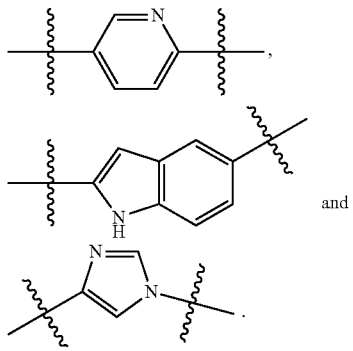

When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "heterocycloalkyl" when used without the "substituted" modifier refers to a monovalent non-aromatic group with a carbon atom or nitrogen atom as the point of attachment, said carbon atom or nitrogen atom forming part of one or more non-aromatic ring structures wherein at least one of the ring atoms is nitrogen, oxygen or sulfur, and wherein the heterocycloalkyl group consists of no atoms other than carbon, hydrogen, nitrogen, oxygen and sulfur. If more than one ring is present, the rings may be fused or unfused. As used herein, the term does not preclude the presence of one or more alkyl groups (carbon number limitation permitting) attached to the ring or ring system. Also, the term does not preclude the presence of one or more double bonds in the ring or ring system, provided that the resulting group remains non-aromatic. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, pyranyl, oxiranyl, and oxetanyl. The term "N-heterocycloalkyl" refers to a heterocycloalkyl group with a nitrogen atom as the point of attachment. N-pyrrolidinyl is an example of such a group. The term "heterocycloalkanediyl" when used without the "substituted" modifier refers to an divalent cyclic group, with two carbon atoms, two nitrogen atoms, or one carbon atom and one nitrogen atom as the two points of attachment, said atoms forming part of one or more ring structure(s) wherein at least one of the ring atoms is nitrogen, oxygen or sulfur, and wherein the divalent group consists of no atoms other than carbon, hydrogen, nitrogen, oxygen and sulfur. If more than one ring is present, the rings may be fused or unfused. Unfused rings may be connected via one or more of the following: a covalent bond, alkanediyl, or alkenediyl groups (carbon number limitation permitting). As used herein, the term does not preclude the presence of one or more alkyl groups (carbon number limitation permitting) attached to the ring or ring system. Also, the term does not preclude the presence of one or more double bonds in the ring or ring system, provided that the resulting group remains non-aromatic. Non-limiting examples of heterocycloalkanediyl groups include:

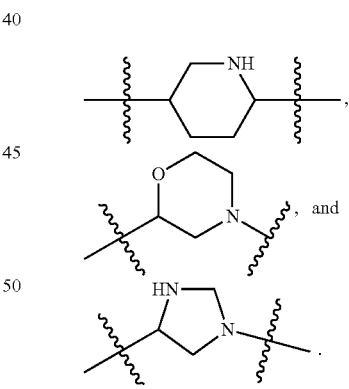

When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "acyl" when used without the "substituted" modifier refers to the group —C(O)R, in which R is a hydrogen, alkyl, cycloalkyl, alkenyl, aryl, aralkyl or heteroaryl, as those terms are defined above. The groups, —CHO, —C(O)CH$_3$ (acetyl, Ac), —C(O)CH$_2$CH$_3$, —C(O)

$CH_2CH_2CH_3$, —$C(O)CH(CH_3)_2$, —$C(O)CH(CH_2)_2$, —$C(O)C_6H_5$, —$C(O)C_6H_4CH_3$, —$C(O)CH_2C_6H_5$, —$C(O)$(imidazolyl) are non-limiting examples of acyl groups. A "thioacyl" is defined in an analogous manner, except that the oxygen atom of the group —$C(O)R$ has been replaced with a sulfur atom, —$C(S)R$. The term "aldehyde" corresponds to an alkane, as defined above, wherein at least one of the hydrogen atoms has been replaced with a —CHO group. When any of these terms are used with the "substituted" modifier one or more hydrogen atom (including a hydrogen atom directly attached to the carbon atom of the carbonyl or thiocarbonyl group, if any) has been independently replaced by —OH, —F, —Cl, —Br, —I, —$NH_2$, —$NO_2$, —$CO_2H$, —$CO_2CH_3$, —CN, —SH, —$OCH_3$, —$OCH_2CH_3$, —$C(O)CH_3$, —$NHCH_3$, —$NHCH_2CH_3$, —$N(CH_3)_2$, —$C(O)NH_2$, —$C(O)NHCH_3$, —$C(O)N(CH_3)_2$, —$OC(O)CH_3$, —$NHC(O)CH_3$, —$S(O)_2OH$, or —$S(O)_2NH_2$. The groups, —$C(O)CH_2CF_3$, —$CO_2H$ (carboxyl), —$CO_2CH_3$ (methylcarboxyl), —$CO_2CH_2CH_3$, —$C(O)NH_2$ (carbamoyl), and —$CON(CH_3)_2$, are non-limiting examples of substituted acyl groups.

The term "alkoxy" when used without the "substituted" modifier refers to the group —OR, in which R is an alkyl, as that term is defined above. Non-limiting examples include: —$OCH_3$ (methoxy), —$OCH_2CH_3$ (ethoxy), —$OCH_2CH_2CH_3$, —$OCH(CH_3)_2$ (isopropoxy), —$OC(CH_3)_3$ (tert-butoxy), —$OCH(CH_2)_2$, —O-cyclopentyl, and —O-cyclohexyl. The terms "cycloalkoxy", "alkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is cycloalkyl, alkenyl, alkynyl, aryl, aralkyl, heteroaryl, heterocycloalkyl, and acyl, respectively. The term "alkylthio" and "acylthio" when used without the "substituted" modifier refers to the group —SR, in which R is an alkyl and acyl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy group. When any of these terms is used with the "substituted" modifier one or more hydrogen atom has been independently replaced by —OH, —F, —Cl, —Br, —I, —$NH_2$, —$NO_2$, —$CO_2H$, —$CO_2CH_3$, —CN, —SH, —$OCH_3$, —$OCH_2CH_3$, —$C(O)CH_3$, —$NHCH_3$, —$NHCH_2CH_3$, —$N(CH_3)_2$, —$C(O)NH_2$, —$C(O)NHCH_3$, —$C(O)N(CH_3)_2$, —$OC(O)CH_3$, —$NHC(O)CH_3$, —$S(O)_2OH$, or —$S(O)_2NH_2$.

The term "alkylamino" when used without the "substituted" modifier refers to the group —NHR, in which R is an alkyl, as that term is defined above. Non-limiting examples include: —$NHCH_3$ and —$NHCH_2CH_3$. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —$N(CH_3)_2$ and —$N(CH_3)(CH_2CH_3)$. The terms "cycloalkylamino", "alkenylamino", "alkynylamino", "arylamino", "aralkylamino", "heteroarylamino", "heterocycloalkylamino", "alkoxyamino", and "alkylsulfonylamino" when used without the "substituted" modifier, refers to groups, defined as —NHR, in which R is cycloalkyl, alkenyl, alkynyl, aryl, aralkyl, heteroaryl, heterocycloalkyl, alkoxy, and alkylsulfonyl, respectively. A non-limiting example of an arylamino group is —$NHC_6H_5$. The term "amido" (acylamino), when used without the "substituted" modifier, refers to the group —NHR, in which R is acyl, as that term is defined above. A non-limiting example of an amido group is —$NHC(O)CH_3$. The term "alkylimino" when used without the "substituted" modifier refers to the divalent group =NR, in which R is an alkyl, as that term is defined above. When any of these terms is used with the "substituted" modifier one or more hydrogen atom attached to a carbon atom has been independently replaced by —OH, —F, —Cl, —Br, —I, —$NH_2$, —$NO_2$, —$CO_2H$, —$CO_2CH_3$, —CN, —SH, —$OCH_3$, —$OCH_2CH_3$, —$C(O)CH_3$, —$NHCH_3$, —$NHCH_2CH_3$, —$N(CH_3)_2$, —$C(O)NH_2$, —$C(O)NHCH_3$, —$C(O)N(CH_3)_2$, —$OC(O)CH_3$, —$NHC(O)CH_3$, —$S(O)_2OH$, or —$S(O)_2NH_2$. The groups —$NHC(O)OCH_3$ and —$NHC(O)NHCH_3$ are non-limiting examples of substituted amido groups.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to a subject or patient for treating a disease, is sufficient to effect such treatment for the disease.

As used herein, the term "$IC_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

The term "pharmaceutically acceptable carrier," as used herein means a pharmaceutically-acceptable material, composition or vehicle, such as a liquid or solid filler, diluent, excipient, solvent or encapsulating material, involved in carrying or transporting a chemical agent.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

Other abbreviations used herein are as follows: DMSO, dimethyl sulfoxide;

The above definitions supersede any conflicting definition in any reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

II. Compounds and Synthetic Methods

The compounds provided by the present disclosure are shown, for example, above in the summary of the invention section and in the claims below. They may be made using the methods outlined in the Examples section. These methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein.

Additionally, the compounds of the present disclosure can be synthesized using the general methods provided herein such as those summarized below. For example, in some embodiments, compounds of the present disclosure may be synthesized according to the following synthetic schemes and modifications thereof.

Scheme 1: Synthesis of Para-Meta Biphenyl Compounds

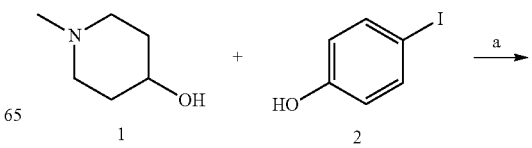

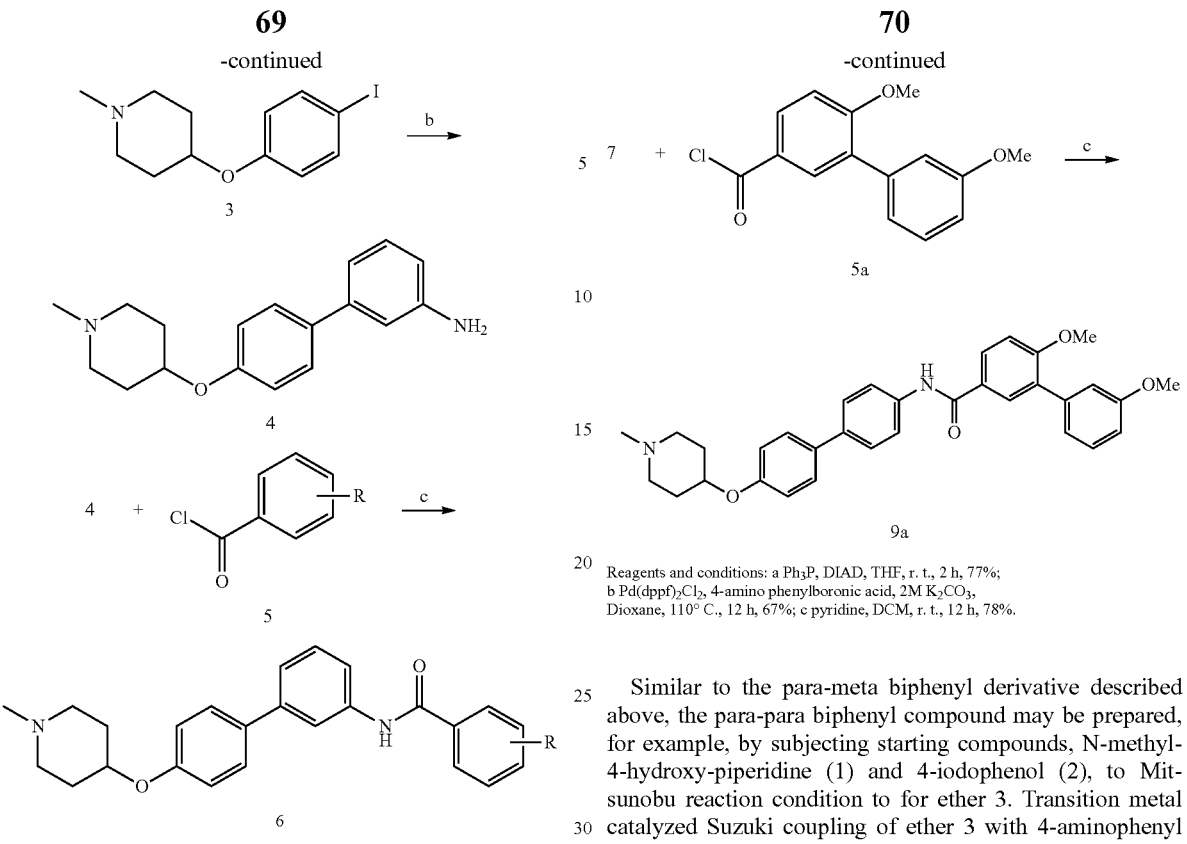

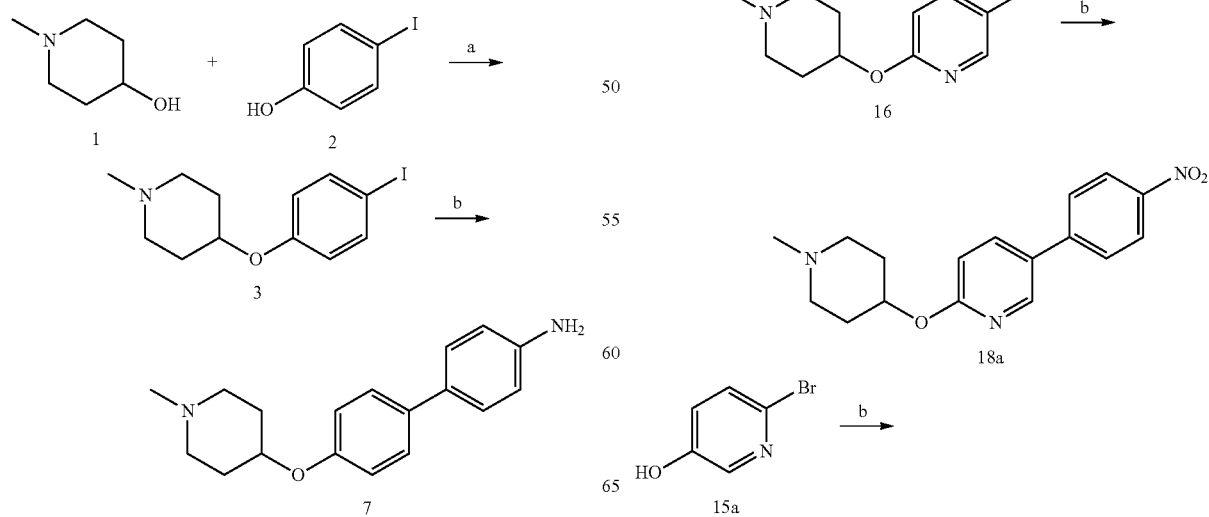

Reagents and conditions: a Ph₃P, DIAD, THF, r. t., 2 h, 77%;
b Pd(dppf)₂Cl₂, 3-amino phenylboronic acid, 2M K₂CO₃,
Dioxane, 110° C., 12 h, 67%; c pyridine, DCM, r. t., 12 h, 52%~78%.

Starting compounds, N-methyl-4-hydroxy-piperidine (1) and 4-iodophenol (2), were subjected to Mitsunobu reaction conditions to for ether 3. Transition metal catalyzed Suzuki coupling of ether 3 with 3-aminophenyl boronic acid resulted in the biphenyl amine 4. The biphenyl amine 4 was reacted with the appropriate acid chloride and a base such as pyridine or triethylamine to produce the appropriate para-meta biphenyl derivatives.

Scheme 2: Synthesis of Para-Para Biphenyl Compounds

Reagents and conditions: a Ph₃P, DIAD, THF, r. t., 2 h, 77%;
b Pd(dppf)₂Cl₂, 4-amino phenylboronic acid, 2M K₂CO₃,
Dioxane, 110° C., 12 h, 67%; c pyridine, DCM, r. t., 12 h, 78%.

Similar to the para-meta biphenyl derivative described above, the para-para biphenyl compound may be prepared, for example, by subjecting starting compounds, N-methyl-4-hydroxy-piperidine (1) and 4-iodophenol (2), to Mitsunobu reaction condition to for ether 3. Transition metal catalyzed Suzuki coupling of ether 3 with 4-aminophenyl boronic acid resulted in the biphenyl amine 7. The biphenyl amine 7 was reacted with the appropriate acid chloride and a base such as pyridine or triethylamine to produce the para-para biphenyl derivatives.

Scheme 3: Synthesis of Heteroatom Substituted Biphenyl Compounds

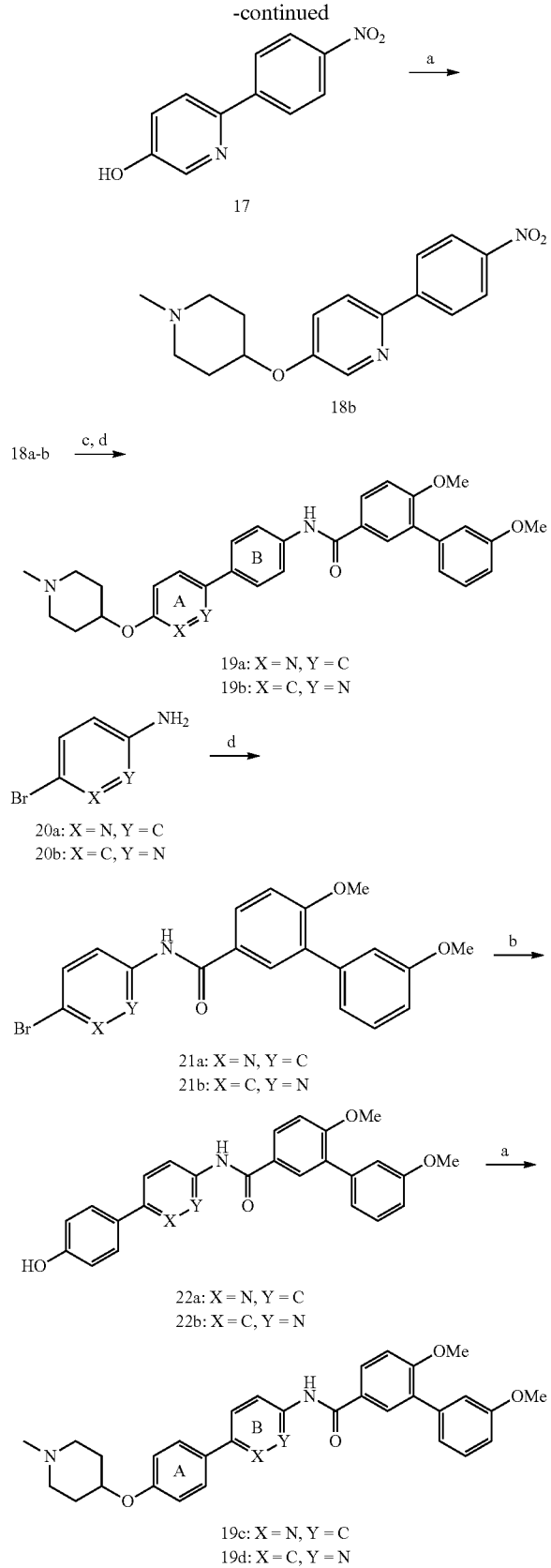
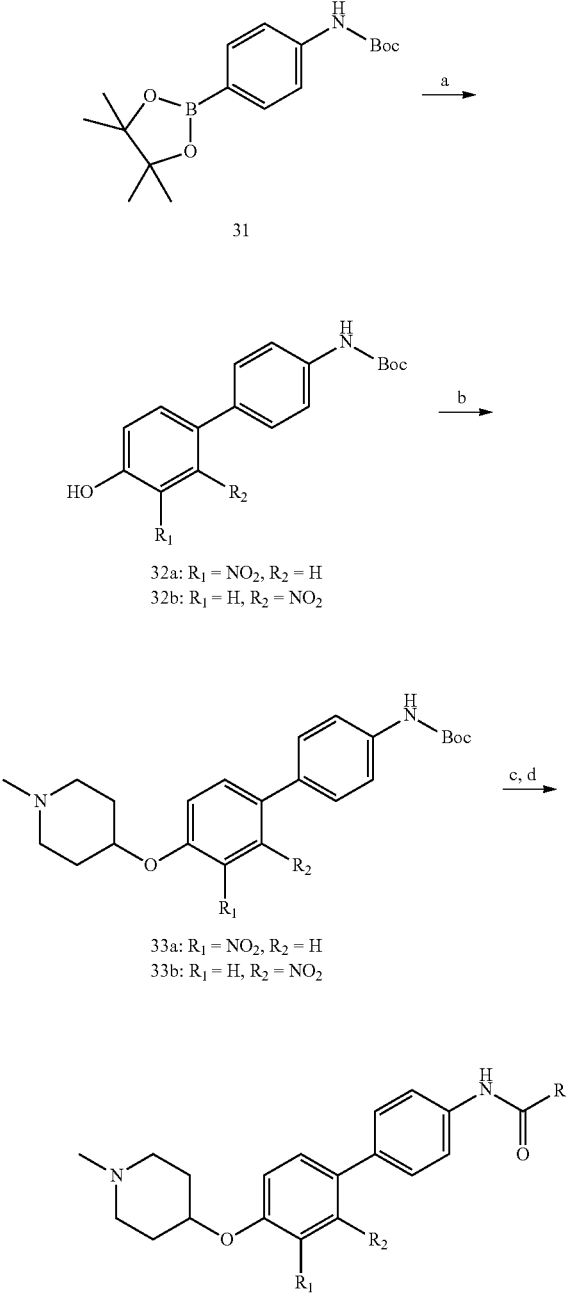
Synthesis 4: Synthesis of Substituted Biphenyl Core Compounds
Reagents and conditions: a Ph₃P, DIAD, THF, r. t., 12 h, 58%~68%; b Pd(dppf)₂Cl₂, 2M K₂CO₃, Dioxane, 110° C., 12 h, 75% %~92%; c Pd/C, MeOH, r. t., 2 h, 100%; d pyridine, DCM, r. t., 4 h, 45%-87%.

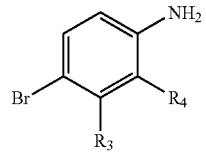

35a: R₃ = NO₂, R₄ = H
35b: R₃ = H, R₄ = NO₂

↓ e

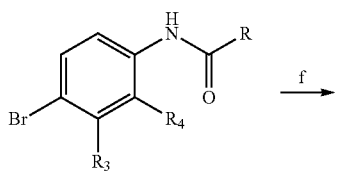

36a: R₃ = NO₂, R₄ = H
36b: R₃ = H, R₄ = NO₂

↓ f

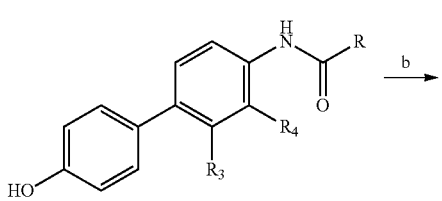

37a: R₃ = NO₂, R₄ = H
37b: R₃ = H, R₄ = NO₂

↓ b

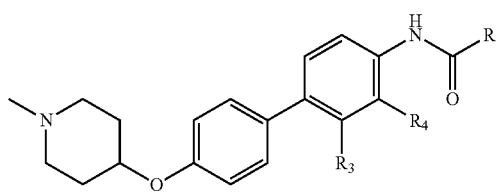

34c: R₃ = NO₂, R₄ = H
34d: R₃ = H, R₄ = NO₂

34a-d —g→

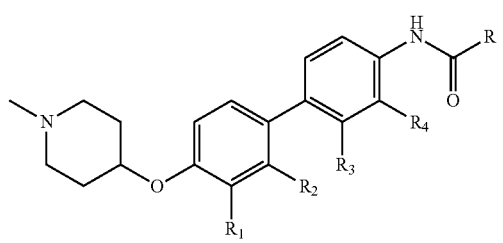

38a: R₁ = NH₂, R₂ = H, R₃ = H, R₄ = H
38b: R₁ = H, R₂ = NH₂, R₃ = H, R₄ = H
38c: R₁ = H, R₂ = H, R₃ = NH₂, R₄ = H
38d: R₁ = H, R₂ = H, R₃ = H, R₄ = NH₂

↓ h

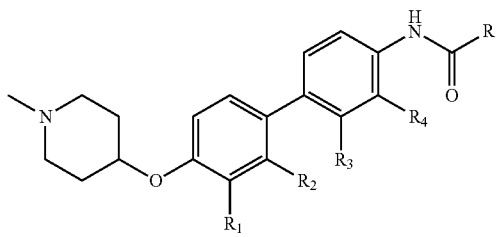

39a: R₁ = NHAc, R₂ = H, R₃ = H, R₄ = H
39b: R₁ = H, R₂ = NHAc, R₃ = H, R₄ = H
39c: R₁ = H, R₂ = H, R₃ = NHAc, R₄ = H
39d: R₁ = H, R₂ = H, R₃ = H, R₄ = NHAc

Reagents and conditions: a Pd(PPh₃)₄, 2M K₂CO₃, Dioxane, 110° C., 12 h, 60%~72%; b Ph₃P, DIAD, THF, r. t., 12 h, 39%~89%; c 10% TFA/DCM, r. t., 2 h, 98%; d pyridine, DCM, r. t., 4 h, 63%; d pyridine, DMF, 90° C., 12 h, 43%~90%; f Pd(dppf)₂Cl₂, 2M K₂CO₃, Dioxane, 120° C., 12 h, 41%~65%; g Pd/C, MeOH, AcOH(cat.), r. t., 12 h, 100%; h Ac₂O, pyridine, r. t., 12 h, 85%~90%.

R =:

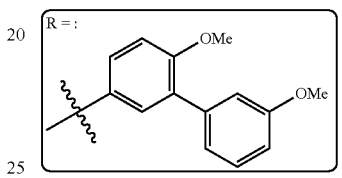

Similarly, in some aspects, the biphenyl derivatives, the heteroatom substituted biphenyl derivatives and the substituted biphenyl core derivatives were prepared in an analogous manner abet with the order varied depending on the particular starting material. These methods are shown in Schemes 3 and 4 above. The methylpiperidine is attached to the phenol via Mitsunobu reaction conditions. The biphenyl core is prepared through Suzuki coupling between an appropriate boronic acid and aryl halide coupling partners in the presence of a transition metal catalyst. In some embodiments, the terminal amine group of aniline core is prepared from the reduction of a nitro compound with hydrogen gas in the presence of a transition metal catalyst. In other embodiments, the amine is protected to prevent reacting with the other functional groups in the molecule. In still other embodiments, the amine is introduced in the construction of the core after the other reactive functional groups have undergone their final transformation. Finally, the benzylamide or biphenylamide groups is prepared through the reaction of the aniline derivative with an acid chloride to produce the desired final product.

Scheme 5: Synthesis of Substituted Biphenylamide Compounds

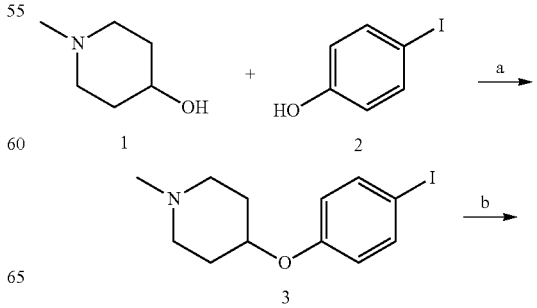

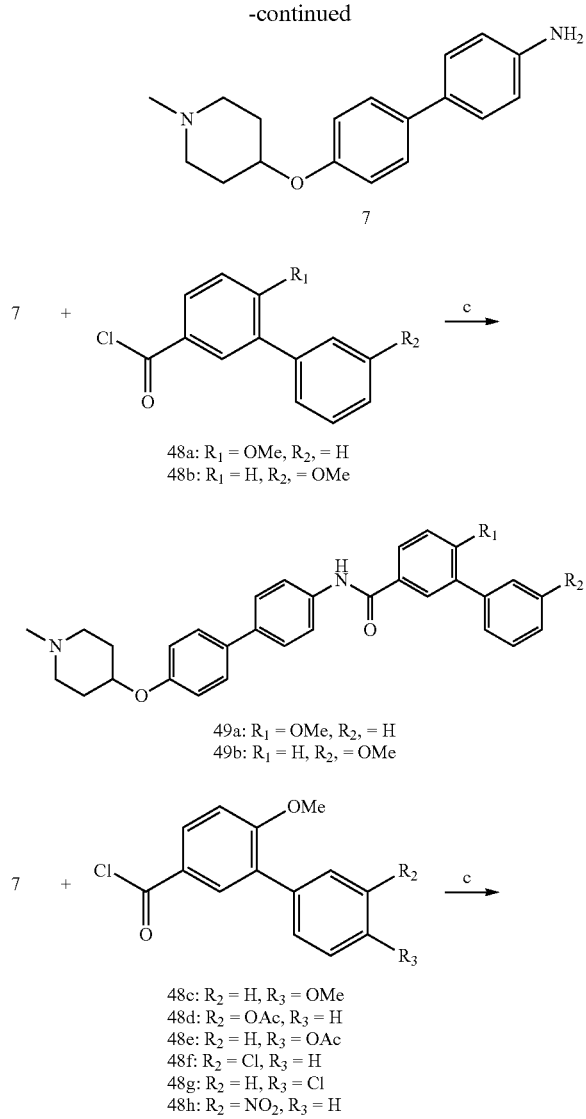

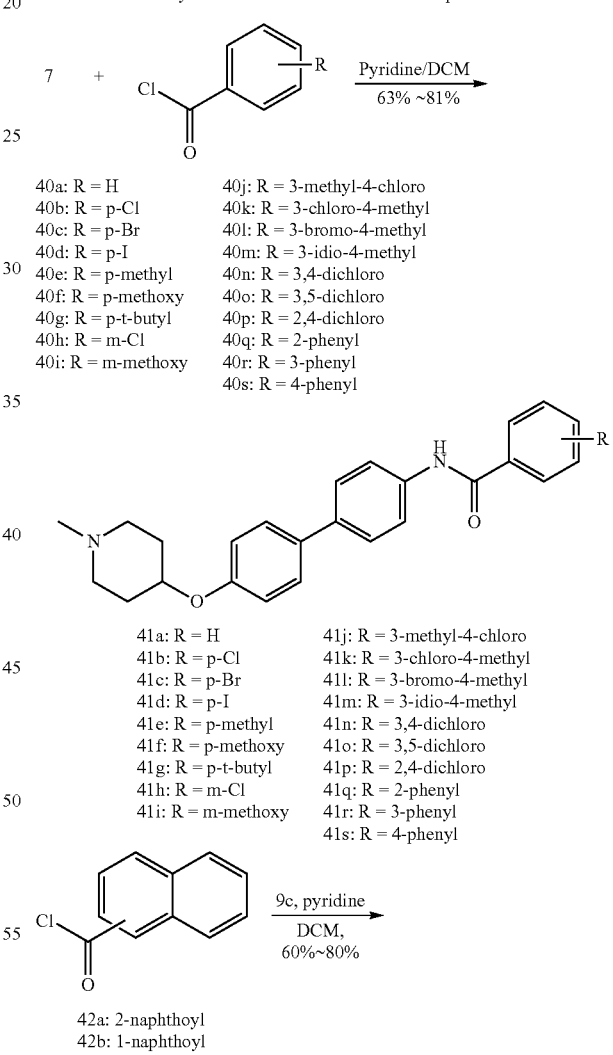

through Suzuki coupling to produce the biphenyl aniline derivative 7. This compound is then joined to the biphenylamide group through the reaction of an acid chloride derivative of that compound with the aniline in the presence of a base. In some embodiments, the biphenylamide group can be further modified once it is attached to the biphenyl core. In some embodiments, these modification can include reduction of nitro groups to amines in the presence of hydrogen gas and a transition metal catalyst, removal of acetyl group to generate a free hydroxy in the presence of a base, or the acetylation of the amine with acetic anhydride in the presence of a base. Analogous, other acid chlorides can be utilized in other embodiments to produce compounds containing other groups such as aryl, heteroaryl, or substituted versions of these groups attached to the amide of the biphenyl core as is shown in Scheme 6 below.

Scheme 5 illustrates the synthetic methods employed to construct para-para biphenyl core molecules which contained modified biphenylamides. The core para-para substituted biphenyl core is constructed by first attaching the methylpiperidine to the first aromatic ring using Mitsunobu reaction conditions. The two aromatic rings are joined

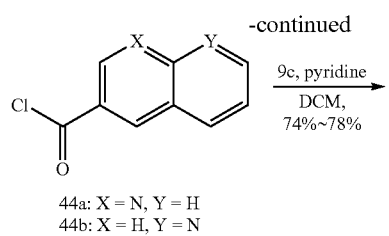
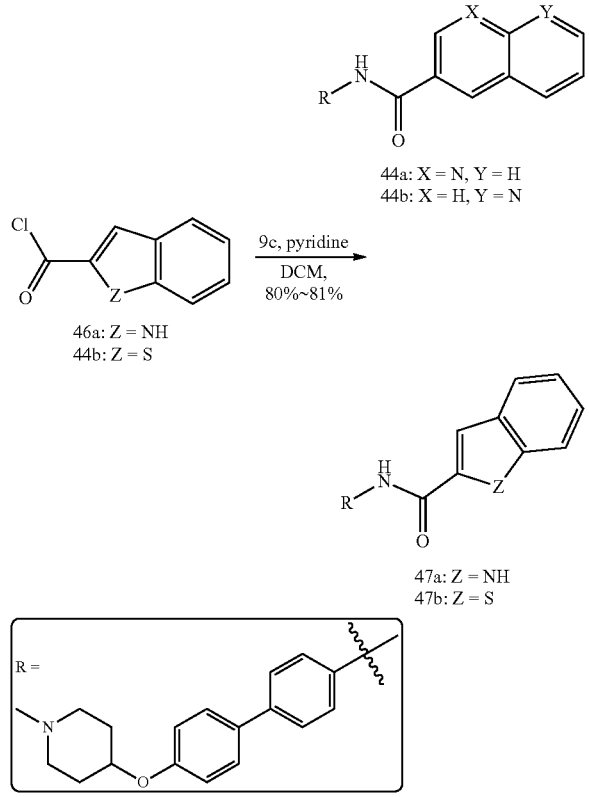

Compounds of the invention may contain one or more asymmetrically-substituted carbon or nitrogen atoms, and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present invention can have the S or the R configuration.

Chemical formulas used to represent compounds of the invention will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given compound, and regardless of which one is most prevalent, all tautomers of a given chemical formula are intended.

Compounds of the invention may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

Compounds of the present invention may also exist in prodrug form. Since prodrugs are known to enhance numerous desirable qualities of pharmaceuticals (e.g., solubility, bioavailability, manufacturing, etc.), the compounds employed in some methods of the invention may, if desired, be delivered in prodrug form. Thus, the invention contemplates prodrugs of compounds of the present invention as well as methods of delivering prodrugs. Prodrugs of the compounds employed in the invention may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a subject, cleaves to form a hydroxy, amino, or carboxylic acid, respectively.

It should be recognized that the particular anion or cation forming a part of any salt form of a compound provided herein is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

Those skilled in the art of organic chemistry will appreciate that many organic compounds can form complexes with solvents in which they are reacted or from which they are precipitated or crystallized. These complexes are known as "solvates." For example, a complex with water is known as a "hydrate." Solvates of the compounds provided herein are within the scope of the invention. It will also be appreciated by those skilled in organic chemistry that many organic compounds can exist in more than one crystalline form. For example, crystalline form may vary from solvate to solvate. Thus, all crystalline forms of the compounds provided herein or the pharmaceutically acceptable solvates thereof are within the scope of the present invention.

III. Biological Activity

Biological activity of these compounds of the present disclosure may be measured using a variety of different methods and techniques. In some embodiments of the present disclosure, the activity is measuring using anti-proliferation assays to determine an $IC_{50}$ value for particular cell lines such as JMAR and MCF-7. Additionally, in other embodiments, the activity of the instant compounds is measuring using Western blot and measuring protein expression in a variety of different downstream poteins regulated by Hsp90.

1. Anti-Proliferation Assays

Cells were maintained in a 1:1 mixture of Advanced DMEM/F12 (Gibco) supplemented with non-essential amino acids, L-glutamine (2 mM), streptomycin (500 µg/mL), penicillin (100 units/mL), and 10% FBS. Cells were grown to confluence in a humidified atmosphere (37° C., 5%

$CO_2$), seeded (2000/well, 100 μL) in 96-well plates, and allowed to attach overnight. Compound at varying concentrations in DMSO (1% DMSO final concentration) was added, and cells were returned to the incubator for 72 h. At 72 h, the number of viable cells was determined using an MTS/PMS cell proliferation kit (Promega) per the manufacturer's instructions. Cells incubated in 1% DMSO were used at 100% proliferation, and values were adjusted accordingly. $IC_{50}$ values were calculated from separate experiments performed in triplicate using GraphPad Prism.

2. Western Blot Analyses

MCF-7 cells were cultured as described above and treated with various concentrations of drug, GDA in DMSO (1% DMSO final concentration), or vehicle (DMSO) for 24 h. Cells were harvested in cold PBS and lysed in RIPA lysis buffer containing 1 mM PMSF, 2 mM sodium orthovanadate, and protease inhibitors on ice for 1 h. Lysates were clarified at 14000 g for 10 min at 4° C. Protein concentrations were determined using the Pierce BCA protein assay kit per the manufacturer's instructions. Equal amounts of protein (20 μg) were electrophoresed under reducing conditions, transferred to a nitrocellulose membrane, and immunoblotted with the corresponding specific antibodies. Membranes were incubated with an appropriate horseradish peroxidase-labeled secondary antibody, developed with a chemiluminescent substrate, and visualized.

IV. Hsp90 Protein and Hyperproliferative Diseases

The compound of the present disclosure may be useful in the treatment of diseases or disorders with result from the unnatural proliferation of cells. In some aspects, this disease or disorder is cancer. Without being bound by theory, the compounds of the present disclosure bind to the C terminus of the Hsp90 protein and thus prevent the binding of the natural substrate to the protein. The Hsp90 is a molecular chaperone protein, which in addition to assisting in protein folding, protein degration, and mitigating heat stress, is implicated in stabilizing a number of proteins associated with cancer. Inhibition of the Hsp90 protein has been shown to lead to apoptosis of the cancerous cells. Without being bound by theory, a number of different molecular pathways are implicated in the Hsp90 protein's role in cancer development and proliferation. For example, the protein is implicated in stabilizing mutant oncogenic proteins such as v-Src, Bcr/Abl, and p53, stabilizing several growth factors and signaling molecules such as EGFR, PI3K, and AKT proteins which leads to growth factor signaling pathway promotion, and promotes the induction of VEGF, nitric oxide synthase, and the matrix metalloproteinase MMP2 which promote angiogenesis and metathesis of the cancerous cells. Many different cancer types and subtypes rely on pathways mediated by the Hsp90 protein for proliferation and tumor development thus inhibitors of the highly conserved Hsp90 protein may be used to treat a wide variety of cancers.

The compound may be used to treat cancer cells according to the embodiments include but are not limited to cells from the bladder, blood, bone, bone marrow, brain, breast, colon, esophagus, gastrointestine, gum, head, kidney, liver, lung, nasopharynx, neck, ovary, prostate, skin, stomach, pancreas, testis, tongue, cervix, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. In certain aspects, the tumor may comprise an osteosarcoma, angiosarcoma, rhabdosarcoma, leiomyosarcoma, Ewing sarcoma, glioblastoma, neuroblastoma, or leukemia.

V. Pharmaceutical Formulations and Routes of Administration

The compounds of the present disclosure may be administered by a variety of methods, e.g., orally or by injection (e.g. subcutaneous, intravenous, intraperitoneal, etc.). Depending on the route of administration, the active compounds may be coated in a material to protect the compound from the action of acids and other natural conditions which may inactivate the compound. They may also be administered by continuous perfusion/infusion of a disease or wound site.

To administer the therapeutic compound by other than parenteral administration, it may be necessary to coat the compound with, or co-administer the compound with, a material to prevent its inactivation. For example, the therapeutic compound may be administered to a patient in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al., 1984).

The therapeutic compound may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (such as, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic compound in the required amount in an appropriate solvent with one or a combination of ingredients enumerated above, as required, followed by filtered sterilization. Generally, dispersions are prepared by incorporating the therapeutic compound into a sterile carrier which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (i.e., the therapeutic compound) plus any additional desired ingredient from a previously sterile-filtered solution thereof.

The therapeutic compound can be orally administered, for example, with an inert diluent or an assimilable edible carrier. The therapeutic compound and other ingredients may also be enclosed in a hard or soft shell gelatin capsule, compressed into tablets, or incorporated directly into the subject's diet. For oral therapeutic administration, the therapeutic compound may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic compound in such therapeutically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical carrier. The specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of a selected condition in a patient.

The therapeutic compound may also be administered topically to the skin, eye, or mucosa. Alternatively, if local delivery to the lungs is desired the therapeutic compound may be administered by inhalation in a dry-powder or aerosol formulation.

Active compounds are administered at a therapeutically effective dosage sufficient to treat a condition associated with a condition in a patient. For example, the efficacy of a compound can be evaluated in an animal model system that may be predictive of efficacy in treating the disease in humans, such as the model systems shown in the examples and drawings.

The actual dosage amount of a compound of the present disclosure or composition comprising a compound of the present disclosure administered to a subject may be determined by physical and physiological factors such as age, sex, body weight, severity of condition, the type of disease being treated, previous or concurrent therapeutic interventions, idiopathy of the subject and on the route of administration. These factors may be determined by a skilled artisan. The practitioner responsible for administration will typically determine the concentration of active ingredient(s) in a composition and appropriate dose(s) for the individual subject. The dosage may be adjusted by the individual physician in the event of any complication.

An effective amount typically will vary from about 0.001 mg/kg to about 1000 mg/kg, from about 0.01 mg/kg to about 750 mg/kg, from about 100 mg/kg to about 500 mg/kg, from about 1.0 mg/kg to about 250 mg/kg, from about 10.0 mg/kg to about 150 mg/kg in one or more dose administrations daily, for one or several days (depending of course of the mode of administration and the factors discussed above). Other suitable dose ranges include 1 mg to 10000 mg per day, 100 mg to 10000 mg per day, 500 mg to 10000 mg per day, and 500 mg to 1000 mg per day. In some particular embodiments, the amount is less than 10,000 mg per day with a range of 750 mg to 9000 mg per day.

The effective amount may be less than 1 mg/kg/day, less than 500 mg/kg/day, less than 250 mg/kg/day, less than 100 mg/kg/day, less than 50 mg/kg/day, less than 25 mg/kg/day or less than 10 mg/kg/day. It may alternatively be in the range of 1 mg/kg/day to 200 mg/kg/day. For example, the effective dosing amount that may be used is an amount sufficient to cause greater than 10% reduction in number of cancerous cells. In other embodiments, an effective dosing amount is sufficient to reduce the tumor volume by greater than 10% over a given time period compared to the volume before administration of the compound. In other embodiments, the effective amount is measured based upon the treatment with the compound and one or more different pharmaceutical agents or modalities.

In other non-limiting examples, a dose may also comprise from about 1 micro-gram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In certain embodiments, a pharmaceutical composition of the present disclosure may comprise, for example, at least about 0.01% of a compound of the present disclosure. In other embodiments, the compound of the present disclosure may comprise between about 2% to about 75% of the weight of the unit, or between about 25% to about 60%, for example, and any range derivable therein.

Single or multiple doses of the agents are contemplated. Desired time intervals for delivery of multiple doses can be determined by one of ordinary skill in the art employing no more than routine experimentation. As an example, subjects may be administered two doses daily at approximately 12 hour intervals. In some embodiments, the agent is administered once a day.

The agent(s) may be administered on a routine schedule. As used herein a routine schedule refers to a predetermined designated period of time. The routine schedule may encompass periods of time which are identical or which differ in length, as long as the schedule is predetermined. For instance, the routine schedule may involve administration twice a day, every day, every two days, every three days, every four days, every five days, every six days, a weekly basis, a monthly basis or any set number of days or weeks therebetween. Alternatively, the predetermined routine schedule may involve administration on a twice daily basis for the first week, followed by a daily basis for several months, etc. In other embodiments, the invention provides that the agent(s) may be taken orally and that the timing of which is or is not dependent upon food intake. Thus, for example, the agent can be taken every morning and/or every evening, regardless of when the subject has eaten or will eat.

VI. Combination Therapy

In addition to being used as a monotherapy, the compounds of the present disclosure may also be used in combination therapies. In some embodiments, effective combination therapy is achieved with a single composition or pharmacological formulation that includes both agents, or with two distinct compositions or formulations, administered at the same time, wherein one composition includes a compound of this invention, and the other includes the second agent(s). Alternatively, in other embodiments, the therapy precedes or follows the other agent treatment by intervals ranging from minutes to months.

A wide range of second therarpies may be used in conjunction with the compounds of the present disclosure. Such second therapies include, but are not limited to, surgery, immunotherapy, radiotherapy, or a second chemotherapeutic agent. In some embodiments, the second chemotherapeutic agent is a N-terminus Hsp90 inhibitor such as geldanamycin, radicicol, the geldanamycin derivative 17AAG, or gamitrinib.

VII. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Compound Activity in Cancer Cell Lines

Anti-proliferative studies with the compounds described herein were performed against the SKBr3 (estrogen receptor negative, HER2 over-expressing breast cancer cells) and MCF-7 (estrogen receptor positive breast cancer cells) breast cancer cell lines. As shown in Tables 1, all three compounds manifested low micromolar activity against both breast cancer cell lines. These activities are in close proximity to their coumarin counterparts, suggesting the biphenyl moiety represents an attractive surrogate for the coumarin ring system. In some embodiments, in contrast to the novobiocin derivatives, which usually manifest better antiproliferative activities against the SKBr3 cell line, the biphenyl derivatives described herein were more efficacious against the MCF-7 cell line. In general, all substitutions on the phenyl ring were determined to be beneficial, consistent with the existence of a hydrophobic pocket in this region of the Hsp90 C-terminal binding site.

TABLE 1

Activity of Ortho, Meta, and Para Biphenyl Cores

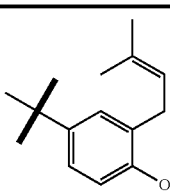

| Entry | Biphenyl | R | SKBr3 (IC$_{50}$, μM) | MCF-7 (IC$_{50}$, μM) |
|---|---|---|---|---|
| 61e | para-meta | A | 3.47 ± 0.47[a] | 2.71 ± 0.40 |
| 61f | meta-meta | A | 1.76 ± 0.16 | 1.70 ± 0.21 |
| 61j | para-para | A | 1.82 ± 0.21 | 1.37 ± 0.18 |
| 6a | para-meta | B | 3.65 ± 0.14 | 1.25 ± 0.02 |
| 61d | meta-meta | B | 1.62 ± 0.07 | 2.00 ± 0.07 |
| 9a | para-para | B | 0.47 ± 0.06 | 0.71 ± 0.02 |
| 6e | para-meta | para-t-butylphenyl | 1.51 ± 0.31 | 3.45 ± 0.02 |
| 61i | meta-meta | para-t-butylphenyl | 3.36 ± 0.20 | 1.93 ± 0.33 |
| 41g | para-para | para-t-butylphenyl | 1.26 ± 0.37 | 1.08 ± 0.08 |
| 6h | para-meta | para-chlorophenyl | 3.63 ± 1.03 | 2.23 ± 0.05 |
| 61g | meta-meta | para-chlorophenyl | 4.15 ± 0.96 | 4.89 ± 0.08 |
| 41b | para-para | para-chlorophenyl | 0.57 ± 0.01 | 0.52 ± 0.03 |
| 6f | para-meta | para-methoxyphenyl | 10.1 ± 0.93 | 5.52 ± 0.01 |
| 61h | meta-meta | para-methoxyphenyl | 13.24 ± 1.97 | 8.20 ± 0.00 |
| 41f | para-para | para-methoxyphenyl | 0.49 ± 0.01 | 0.65 ± 0.04 |
| 61a | para-meta | admantanyl | 1.25 ± 0.04 | 0.77 ± 0.08 |
| 61b | meta-meta | admantanyl | 2.60 ± 0.71 | 2.07 ± 0.09 |
| 61c | para-para | admantanyl | 2.07 ± 0.35 | 2.77 ± 0.23 |

A:

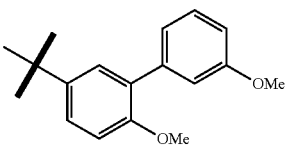

B:

TABLE 2

Activity of Para-Meta Biphenyl Core with Substituted Benzylamide

| Entry | R | SKBr3 (IC$_{50}$, μM) | MCF-7 (IC$_{50}$, μM) |
|---|---|---|---|
| 6b | H | 18.86 ± 0.95 | 12.02 ± 0.57 |
| 6c | p-CH$_3$ | 5.27 ± 0.29 [a] | 3.92 ± 0.13 |
| 6d | m-CH$_3$ | 11.38 ± 1.37 | 7.73 ± 1.90 |
| 6e | p-t-butyl | 1.51 ± 0.31 | 3.45 ± 0.02 |
| 6f | p-methoxy | 10.1 ± 0.93 | 5.52 ± 0.01 |
| 6g | m-methoxy | 8.36 ± 1.35 | 4.50 ± 0.46 |
| 6h | p-Cl | 3.63 ± 1.03 | 2.23 ± 0.05 |
| 6i | m-Cl | 4.29 ± 0.43 | 2.11 ± 0.42 |
| 6k | o-Cl | 7.87 ± 0.48 | 5.17 ± 0.49 |
| 6l | p-Br | 1.94 ± 0.11 | 0.88 ± 0.07 |
| 6m | 3,4-dichloro | 2.24 ± 0.11 | 2.17 ± 0.37 |
| 6n | 2,4-dichloro | 5.91 ± 0.15 | 3.93 ± 0.47 |
| 6o | 3,5-dichloro | 4.23 ± 0.09 | 3.72 ± 0.15 |

TABLE 2-continued

Activity of Para-Meta Biphenyl Core with Substituted Benzylamide

| Entry | R | SKBr3 (IC$_{50}$, μM) | MCF-7 (IC$_{50}$, μM) |
|---|---|---|---|
| 6q | -(2-naphthoyl) | 2.09 ± 0.34 | 1.66 ± 0.27 |
| 6p | -(1-naphthoyl) | 1.64 ± 0.13 | 1.10 ± 0.17 |

TABLE 3

Activity of Substituted Para-Para Biphenyl Core

| Entry | R$^1$ | R$^2$ | R$^3$ | R$^4$ | SKBr3 (IC$_{50}$, μM) | MCF-7 (IC$_{50}$, μM) |
|---|---|---|---|---|---|---|
| 9a | H | H | H | H | 0.47 ± 0.06 | 0.71 ± 0.02 |
| 29a | Me | H | H | H | 0.83 ± 0.03 | 1.69 ± 0.08 |
| 29b | H | Me | H | H | 1.18 ± 0.11 | 1.21 ± 0.03 |
| 29c | H | H | Me | H | 0.97 ± 0.01 | 1.57 ± 0.56 |
| 29d | H | H | H | Me | 2.47 ± 0.39 | 1.43 ± 0.35 |
| 29e | OMe | H | H | H | 0.68 ± 0.13 | 1.32 ± 0.08 |
| 29f | H | OMe | H | H | 1.41 ± 0.35 | 1.35 ± 0.16 |
| 29g | H | H | OMe | H | 0.90 ± 0.08 | 1.50 ± 0.08 |
| 29h | H | H | H | OMe | 3.92 ± 0.21 | 1.22 ± 0.04 |
| 29i | Cl | H | H | H | 1.84 ± 0.57 | 1.48 ± 0.12 |
| 29j | H | Cl | H | H | 3.68 | 3.12 1.71 |
| 29k | H | H | Cl | H | 2.21 ± 0.18 | 3.44 ± 0.21 |
| 29l | H | H | H | Cl | 4.75 | 1.80 ± 0.19 |
| 29m | CN | H | H | H | 2.77 ± 1.16 | 3.70 ± 0.61 |
| 34a | NO$_2$ | H | H | H | 1.95 | 1.25 ± 0.28 |
| 34b | H | NO$_2$ | H | H | 1.07 | 1.30 ± 0.12 |
| 34c | H | H | NO$_2$ | H | 2.48 ± 0.77 | 3.32 ± 0.25 |
| 34d | H | H | H | NO$_2$ | 0.92 | 1.15 ± 0.01 |
| 38a | NH$_2$ | H | H | H | 2.23 ± 0.49 | 5.95 ± 1.22 |
| 38b | H | NH$_2$ | H | H | 2.13 ± 0.06 | 1.76 ± 0.37 |
| 38c | H | H | NH$_2$ | H | 3.90 ± 0.18 | 2.07 ± 0.23 |
| 38d | H | H | H | NH$_2$ | 3.21 ± 0.45 | 2.25 ± 0.49 |
| 39a | NHAc | H | H | H | 2.66 ± 0.76 | 1.84 ± 0.43 |
| 39b | H | NHAc | H | H | 3.39 ± 0.66 | 1.36 ± 0.23 |
| 39c | H | H | NHAc | H | 2.52 ± 0.26 | 4.66 ± 0.49 |
| 39d | H | H | H | NHAc | 3.51 ± 0.56 | 1.66 ± 0.59 |

TABLE 4

Activity of Para-Para Heteroatom Substituted Biphenyl Core

| Entry | W | X | Y | Z | SKBr3 (IC$_{50}$, μM) | MCF-7 (IC$_{50}$, μM) |
|---|---|---|---|---|---|---|
| 19a | N | C | C | C | 1.67 ± 0.09 | 1.56 ± 0.19 |
| 19b | C | N | C | C | 1.91 ± 0.21 | 1.30 ± 0.15 |
| 19c | C | C | N | C | 1.21 ± 0.13 | 1.02 ± 0.01 |
| 19d | C | C | C | N | 1.07 ± 0.01 | 1.02 ± 0.01 |

TABLE 5

Activity of Modified Linkers in Para-Para Biphenyl Core

| Entry | X | SKBr3 (IC$_{50}$, μM) | MCF-7 (IC$_{50}$, μM) |
|---|---|---|---|
| 9a | —NHC(O)— | 0.47 ± 0.06 | 0.71 ± 0.02 |
| 60 | —C(O)NH— | 1.64 ± 0.79 | 1.22 ± 0.13 |
| 52 | —NHC(O)NH— | 0.91 ± 0.08 | 1.26 ± 0.13 |

TABLE 6

Activity of Para-Para Biphenyl Core with Substituted Benzylamide

| Entry | R | SKBr3 (IC$_{50}$, μM) | MCF-7 (IC$_{50}$, μM) |
|---|---|---|---|
| 41a | phenyl | 4.13 ± 0.22 | 3.95 ± 0.13 |
| 41b | 4-chlorophenyl | 0.57 ± 0.01 | 0.52 ± 0.03 |
| 41c | 4-bromophenyl | 0.52 ± 0.21 | 0.52 ± 0.15 |
| 41d | 4-iodophenyl | 0.31 ± 0.09 | 0.58 ± 0.01 |
| 41e | 4-methylphenyl | 0.98 ± 0.19 | 1.27 ± 0.13 |
| 41f | 4-methoxyphenyl | 0.49 ± 0.01 | 0.65 ± 0.04 |
| 41g | 4-t-butylphenyl | 1.26 ± 0.37 | 1.08 ± 0.08 |
| 41h | 3-chlorophenyl | 1.94 ± 0.37 | 2.83 ± 0.69 |
| 41i | 3-methoxyphenyl | 2.87 ± 0.51 | 5.31 ± 0.70 |
| 41j | 3-methyl-4-chlorophenyl | 1.11 ± 0.42 | 1.03 ± 0.16 |
| 41k | 3-chloro-4-methylphenyl | 1.96 ± 0.24 | 2.28 ± 0.49 |
| 41l | 3-bromo-4-methylphenyl | 2.80 ± 0.18 | 3.35 ± 0.36 |
| 41m | 3-iodo-4-methylphenyl | 0.93 ± 0.20 | 1.17 ± 0.20 |
| 41n | 3,4-dichlorophenyl | 1.20 ± 0.08 | 1.60 ± 0.16 |
| 41o | 3,5-dichlorophenyl | 0.81 ± 0.28 | 1.68 ± 0.13 |
| 41p | 2,4-dichlorophenyl | 0.80 ± 0.22 | 1.37 ± 0.33 |
| 41q | 2-biphenyl | 6.26 ± 1.54 | 6.67 ± 0.83 |

TABLE 6-continued

Activity of Para-Para Biphenyl Core with Substituted Benzylamide

| Entry | R | SKBr3 (IC$_{50}$, μM) | MCF-7 (IC$_{50}$, μM) |
|---|---|---|---|
| 41r | 3-biphenyl | 0.73 ± 0.07 | 1.15 ± 0.18 |
| 41s | 4-biphenyl | 4.59 ± 0.06 | 4.44 ± 0.60 |
| 43a | 1-naphthoyl | 0.22 ± 0.13 | 0.58 ± 0.02 |
| 43b | 2-naphthoyl | 0.35 ± 0.02 | 0.49 ± 0.11 |
| 45a | 2-quinolinyl | 2.42 ± 0.62 | 2.76 ± 0.76 |
| 45b | 6-quinolinyl | 1.31 ± 0.18 | 2.07 ± 0.16 |
| 47a | 2-indolyl | 0.64 ± 0.08 | 0.58 ± 0.02 |
| 47b | 2-benzo[b]thiophenyl | 1.32 ± 0.23 | 2.01 ± 0.58 |

TABLE 7

Activity of Para-Para Biphenyl Core with Modified Ether Groups

| Entry | R | SKBr3 (IC$_{50}$, μM) | MCF-7 (IC$_{50}$, μM) |
|---|---|---|---|
| 9a | N-methylpiperidin-4-yl | 0.47 ± 0.06 | 0.71 ± 0.02 |
| 56e | piperidin-4-yl (HN) | 1.05 ± 0.08 | 1.18 ± 0.21 |
| 56d | (1-methylpyrrolidin-2-yl)ethyl | 1.75 ± 0.24 | 1.28, 3.89 |
| 56b | tropan-3-yl (N-methyl bicyclic) | 1.67 ± 0.60 | 1.32 ± 0.23 |
| 56c | 3-(dimethylamino)propyl | 1.02 ± 0.05 | 0.87 ± 0.04 |
| 56f | 2-(dimethylamino)ethyl | 1.17 ± 0.08 | 1.64 ± 0.16 |
| 56a | (piperidin-2-yl)ethyl | 0.85 ± 0.20 | 0.95± |

TABLE 8

Activity of Para-Para Biphenyl Core with Substituted Biphenylamide Group

| Entry | R$^1$ | R$^2$ | R$^3$ | SKBr3 (IC$_{50}$, μM) | MCF-7 (IC$_{50}$, μM) |
|---|---|---|---|---|---|
| 9a | OMe | OMe | H | 0.47 ± 0.06 | 0.71 ± 0.02 |
| 49c | OMe | H | OMe | 0.63 ± 0.04 | 0.79 ± 0.13 |
| 49a | OMe | H | H | 0.51 ± 0.11 | 0.84 ± 0.01 |
| 49b | H | OMe | H | 0.81 ± 0.14 | 1.02 ± 0.08 |
| 41r | H | H | H | 0.73 ± 0.07 | 1.15 ± 0.18 |
| 49i | OAc | OMe | H | 1.90 ± 0.47 | 1.62 ± 0.04 |
| 49j | OH | OMe | H | 2.78 ± 0.35 | 2.71 ± 0.45 |
| 49d | OMe | OAc | H | 0.27 ± 0.05 | 0.62 ± 0.07 |
| 50a | OMe | OH | H | 1.56 ± 0.35 | 1.08 ± 0.34 |
| 49e | OMe | H | OAc | 0.14 ± 0.01 | 0.64 ± 0.08 |
| 50b | OMe | H | OH | 0.13 ± 0.02 | 0.50 ± 0.01 |
| 49f | OMe | Cl | H | 0.33 ± 0.03 | 0.32 ± 0.09 |
| 49g | OMe | H | Cl | 1.06 ± 0.05 | 0.82 ± 0.13 |
| 49k | Me | Cl | H | 3.16 ± 0.37 | 1.60 ± 0.11 |
| 49h | OMe | NO$_2$ | H | 0.40 ± 0.07 | 1.09 ± 0.28 |
| 50c | OMe | NH$_2$ | H | 1.52 ± 0.55 | 1.67 ± 0.68 |
| 50d | OMe | NHAc | H | 3.37 ± 0.74 | 1.43 ± 0.28 |

TABLE 9
Activity of Para-Meta Biphenyl Core with Prenylated Benzylamide
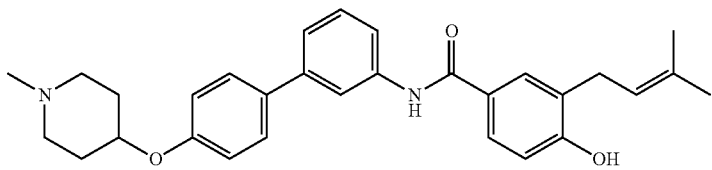 [SMILES: CC(C)=CCc1cc(C(=O)Nc2cccc(-c3ccc(OC4CCN(C)CC4)cc3)c2)ccc1O]
3a
| Entry | SKBr3 (IC$_{50}$, µM) | MCF-7 (IC$_{50}$, µM) |
|---|---|---|
| 1a | 3.65 ± 0.14 | 1.45 ± 0.02 |
| 3a | 2.94 ± 0.11 | 2.21 ± 0.06 |
| 6a | 3.47 ± 0.47 | 2.71 ± 0.40 |
TABLE 10
Activity of Longer Alkyl Chain Substituted Biphenyl Core
| Compound | SKBr3 (IC$_{50}$, µM) | MCF-7 (IC$_{50}$, µM) |
|---|---|---|
|  | 1.03 ± 0.04 | 1.66 ± 0.12 |
|  | 1.18 ± 0.04 | 1.43 ± 0.22 |
TABLE 11
Activity of Heteroatom Linked Biphenyl Core
| Compound | SKBr3 (IC$_{50}$, µM) | MCF-7 (IC$_{50}$, µM) |
|---|---|---|
|  | 6.44 ± 2.61 | 7.1 |

TABLE 11-continued
Activity of Heteroatom Linked Biphenyl Core
| Compound | SKBr3 (IC$_{50}$, μM) | MCF-7 (IC$_{50}$, μM) |
|---|---|---|
| 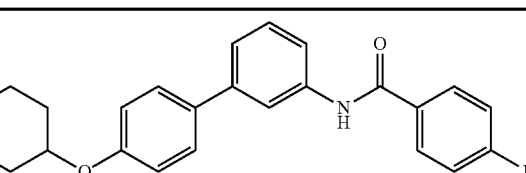 | 2.17 ± 0.03 | 3.37 ± 1.63 |
|  | 18.20 ± 2.19 | 2.83 ± 1.87 |
|  | 4.60 ± 0.25 | 2.15 ± 0.01 |
TABLE 12
Activity of Compounds in Cancer Cell Lines
| Compound | Cancer Cell Line | IC$_{50}$ (μM) |
|---|---|---|
| 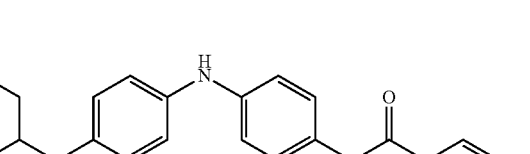 | JMAR (Head and Neck Cancer) | 0.11 |
|  | JMAR (Head and Neck Cancer) | 0.0097 |
| 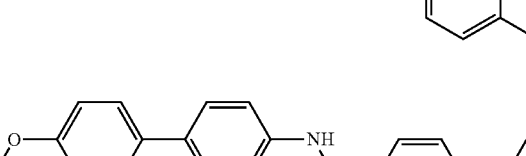 | SKME128 (Melanoma) | 0.48 |

To confirm that the anti-proliferative activities observed by these biphenyl analogues resulted from Hsp90 inhibition, western blot analyses of cell lysates following administration of biphenyl compounds was performed. The result shown in FIG. 1 shows that in MCF-7 cells, the Hsp90-dependent client proteins Her2, Raf, and Akt underwent degradation in a concentration-dependent manner upon treatment with 1a, 1c, 6a, and 9a at the same concentration needed to manifest anti-proliferative activity, thereby linking Hsp90 inhibition to cell viability. The non-Hsp90-dependent protein, actin, was not affected, and indicates the selective degradation of Hsp90-dependent proteins. In addition, Hsp90 levels remained constant at all concentrations tested, which is consistent with prior studies involving Hsp90 C-terminal inhibitors.

Figure 2A:
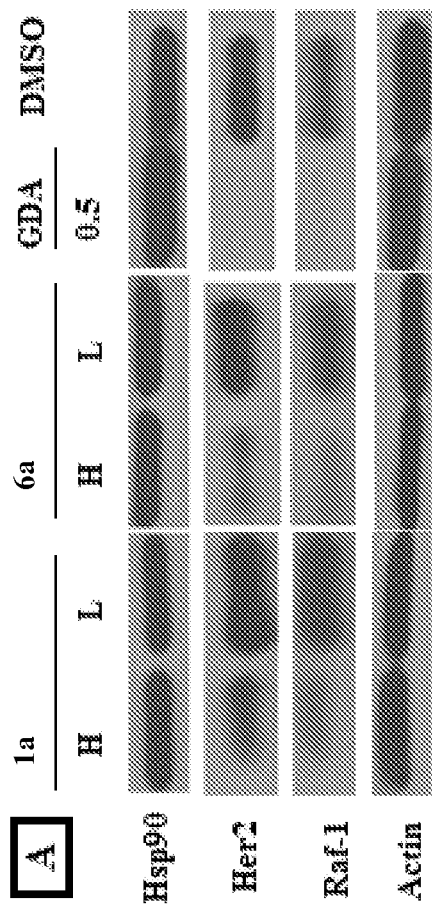
FIGS. 2A & 2B—Western blot analyses of Hsp90-dependent client proteins from MCF-7 breast cancer cell lysate upon treatment with biphenyl derivatives. Concentrations (in μM) were indicated above each line. H represents a concentration equal to 5-fold of the anti-proliferative activity. L represents a concentration equal to 0.5-fold of the anti-proliferative activity. Geldanamycin (GDA, 0.5 μM) and dimethylsulfoxide (DMSO, 100%) were employed as positive and negative controls.
Figure 2B:
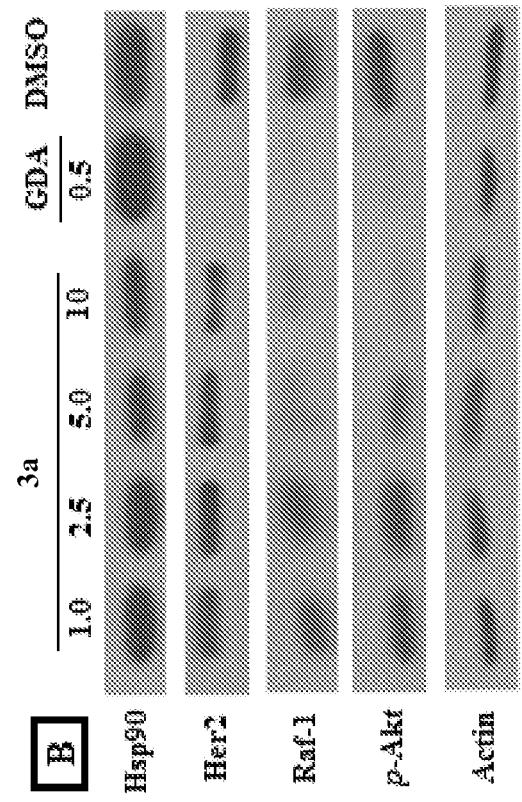

Confirmation that these compounds manifested their anti-proliferative activity through Hsp90 inhibition was performed by Western blot analyses of several Hsp90 client protein levels in MCF-7 cell lysates. Actin, a protein that is not dependent on Hsp90 for its function, was chosen as a control. As shown in FIG. 2A, two Hsp90 client proteins, Her2 and Raf-1, were degraded upon treatment with 1a or 6a at concentrations that mirror their anti-proliferative $IC_{50}$ values. Concentration-dependent analysis of MCF-7 cell lysates upon the administration of 3a showed the degradation of Her2, Raf-1 and p-Akt (FIG. 2B). These high-low and gradient-concentration Westen blot analyses suggest that inhibition of the Hsp90 protein folding machinery is responsible for the observed anti-proliferative activity, suggesting that the biphenyl moiety can serve as a replacement for the coumarin system.

Figure 3:
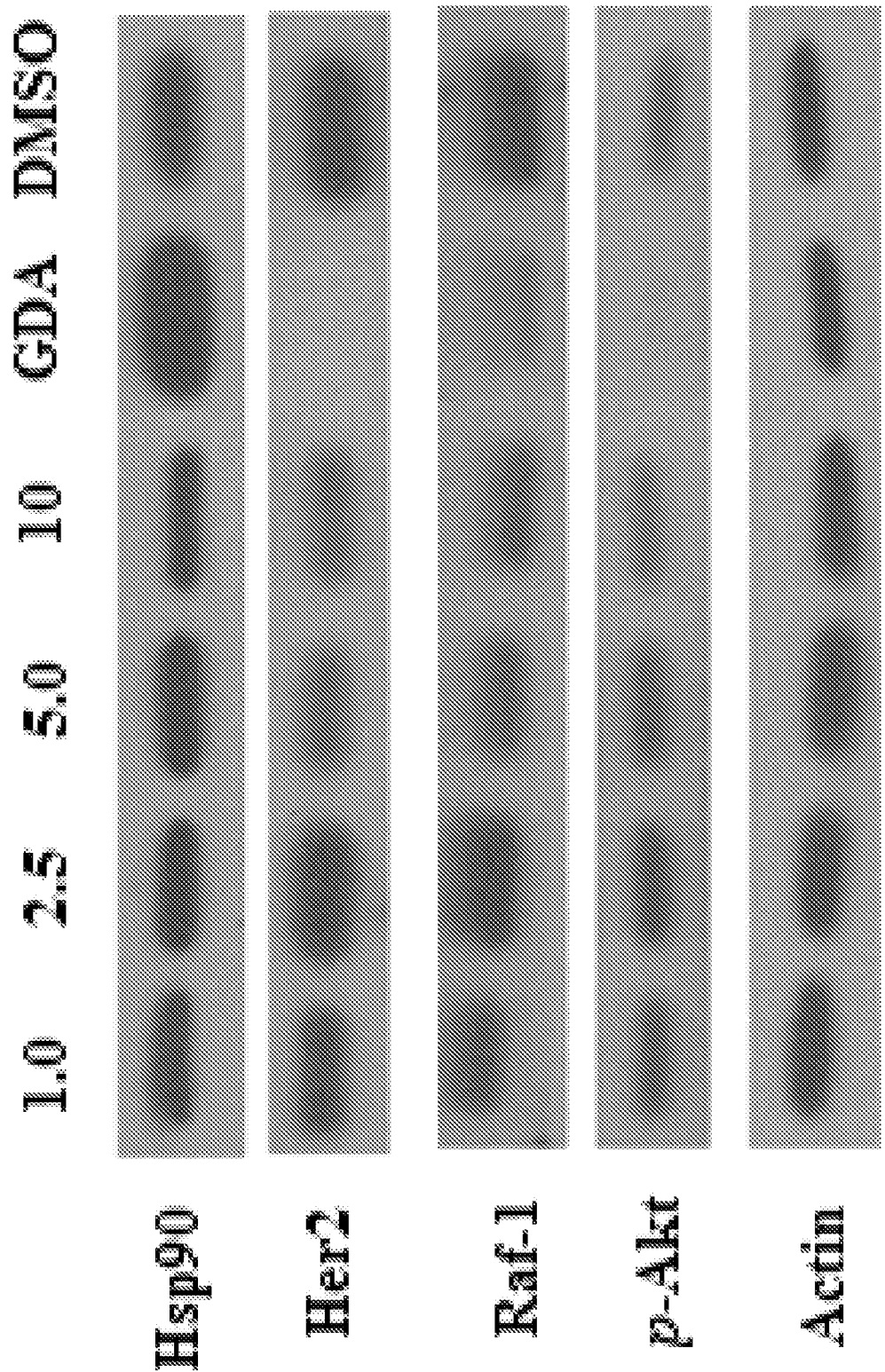
FIG. 3—Western blot analyses of Hsp90-dependent client proteins from MCF-7 breast cancer cell lysate upon treatment with compound 6l. Concentrations (in μM) were indicated above each line, and geldanamycin (GDA, 0.5 μM) and dimethylsulfoxide (DMSO) were employed as positive and negative controls.

Western blot analyses of several Hsp90 client protein levels were examined in MCF-7 cell lysates treated with the most active compound, 6l. As shown in FIG. 3, the Hsp90-dependent client proteins Her2, Raf-1 and p-Akt, were degraded in a concentration dependent manner, while actin levels remained constant. Hsp90 levels also remained unchanged, a characteristic feature shared by Hsp90 C-terminal inhibitors (Zhao, et al., 2013; Zhao, et al., 2011; Zhao, et al., 2012; and Tran, et al., 2010)

Example 2

Compounds and Synthesis 4-(4-iodophenoxy)-1-methylpiperidine (3)

Diisopropylazodicarboxylate (1.89 g, 9.36 mmol) was added to a solution of 4-iodophenol (0.92 g, 4.18 mmol), N-methyl-4-hydroxy-piperidine (480 mg, 4.18 mmol) and triphenylphosphine (2.46 g, 9.36 mmol) in anhydrous THF (50 mL). After 2 h, the solvent was removed and the residue purified via column chromatography ($SiO_2$, 10:1, DCM:methanol) to afford desired product 6 as a colorless amorphous solid (1.02 g, 77%). $^1$H NMR (500 MHz, chloroform-d) δ 7.54 (d, J=8.9 Hz, 2H), 6.69 (d, J=2.0 Hz, 2H), 4.27 (m, 1H), 2.73-2.59 (m, 2H), 2.31 (s, 1H), 2.30 (m, 2H), 1.98 (m, 2H), 1.82 (m, 2H). $^{13}$C NMR (101 MHz, $CDCl_3$) δ 157.34, 138.34, 118.50, 82.91, 72.18, 52.61, 46.28, 30.71. HRMS (ESI+) m/z: [M+H$^+$] calcd for $C_{12}H_{17}INO$ 318.0355. found 318.0357.

4'-((1-methylpiperidin-4-yl)oxy)-[1,1'-biphenyl]-3-amine (4)

A mixture of iodide 11a (250 mg, 0.79 mmol) aminophenylboronic acid (216 mg, 1.58 mmol), potassium carbonate solution (2M, 100 μL) and [1,1'-Bis(diphenylphosphino)ferrocene]dichloropalladium(II) (57 mg, 0.08 mmol) was suspended in dry dioxane (15 mL) and purged with argon for 15 min. After 15 min, the mixture was heated in a sealed tube at 110° C. for 12 hours before concentrated to dryness. The residue so obtained was purified via column chromatography ($SiO_2$, 10:1, $CH_2Cl_2$:methanol) to afford a brownish amorphous solid (149 mg, 67%). $^1$H NMR (500 MHz, chloroform-d) δ 7.50 (d, J=8.7 Hz, 2H), 7.22 (t, J=7.8 Hz, 1H), 6.99-6.92 (m, 3H), 6.88 (s, 1H), 6.66 (dd, J=7.9, 2.3 Hz, 1H), 4.45-4.34 (m, 1H), 3.74 (s, 2H), 2.79 (ddd, J=11.8, 7.8, 3.8 Hz, 2H), 2.48-2.42 (m, 2H), 2.39 (s, 3H), 2.11 (ddt, J=11.5, 7.3, 3.6 Hz, 2H), 1.94 (ddt, J=14.0, 7.9, 3.7 Hz, 2H). $^{13}$C NMR (126 MHz, $CDCl_3$) δ 156.77, 146.69, 141.94, 134.13, 129.65, 128.16, 117.28, 116.15, 113.60, 113.49, 71.45, 52.37, 45.96, 30.42. HRMS (ESI$^+$) m/z: [M+H$^+$] calcd for $C_{18}H_{23}N_2O$ 283.1810. found, 283.1808.

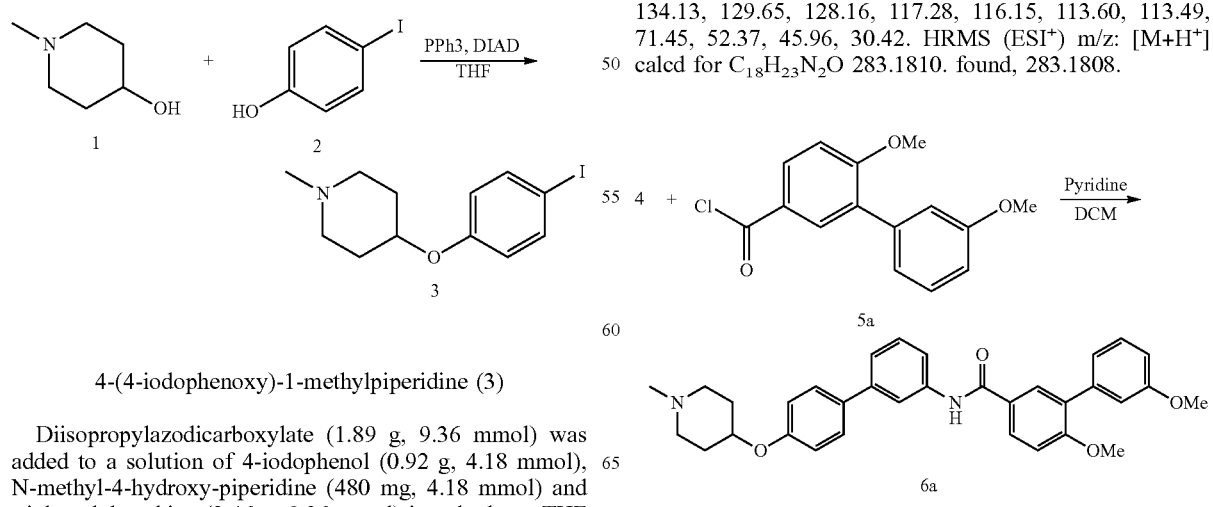

3',6-dimethoxy-N-(4'-((1-methylpiperidin-4-yl)oxy)-[1,1'-biphenyl]-3-yl)-[1,1'-biphenyl]-3-carboxamide (6a)

A solution of acid chloride (5a, 0.27 mmol), in anhydrous dichloromethane (2 mL) was added to a solution of the amine (4, 0.18 mmol) and anhydrous triethylamine (0.13 mL, 0.94 mmol) in anhydrous dichloromethane (5 mL). After 12 h, the solvent was removed and the residue purified via column chromatography (SiO$_2$, 10:1, DCM:methanol) to afford 6a as a colorless amorphous solid (55%). $^1$H NMR (500 MHz, Chloroform-d) δ 7.97 (s, 1H), 7.90-7.82 (m, 2H), 7.78 (s, 1H), 7.52-7.44 (m, 3H), 7.36-7.21 (m, 3H), 7.09-6.92 (m, 3H), 6.90-6.79 (m, 3H), 4.47 (s, 1H), 2.93 (ddd, J=13.3, 10.4, 3.4 Hz, 2H), 2.84-2.73 (m, 2H), 2.26 (td, J=10.5, 4.9 Hz, 2H), 2.04-1.91 (m, 2H). $^{13}$C NMR (126 MHz, CDCl$_3$) δ 165.26, 159.37, 159.32, 156.30, 141.41, 138.81, 138.61, 133.98, 130.67, 129.62, 129.43, 129.16, 128.47, 127.02, 122.66, 121.99, 118.63, 118.58, 116.15, 115.34, 112.93, 111.08, 68.68, 55.87, 55.35, 51.03, 44.81, 28.52. HRMS (ESI+) m/z: [M+H$^+$] calcd for C$_{33}$H$_{35}$N$_2$O$_4$ 523.2597. found 523.2599.

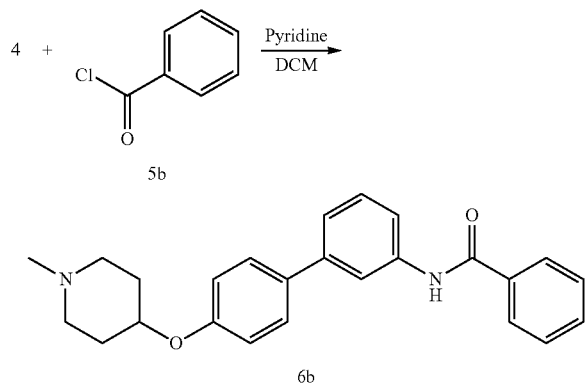

N-(4'-((1-methylpiperidin-4-yl)oxy)-[1,1'-biphenyl]-3-yl)benzamide (6b)

A solution of acid chloride (5b, 0.27 mmol), in anhydrous dichloromethane (2 mL) was added to a solution of the amine (4, 0.18 mmol) and anhydrous triethylamine (0.13 mL, 0.94 mmol) in anhydrous dichloromethane (5 mL). After 12 h, the solvent was removed and the residue purified via column chromatography (SiO$_2$, 10:1, DCM:methanol) to afford 6b as a colorless amorphous solid (64%). $^1$H NMR (400 MHz, chloroform-d) δ 7.86-7.80 (m, 3H), 7.52-7.43 (m, 4H), 7.42-7.35 (m, 2H), 7.31 (t, J=7.8 Hz, 1H), 7.25-7.21 (m, 1H), 6.88 (d, J=8.3 Hz, 2H), 4.51 (m, 1H), 3.08-2.75 (m, 4H), 2.56 (s, 3H), 2.19 (m, 2H), 2.01 (m, 3H). $^{13}$C NMR (126 MHz, CDCl$_3$) δ 167.03, 156.17, 141.31, 138.64, 134.89, 134.26, 131.85, 129.31, 128.63, 128.46, 127.32, 122.89, 119.17, 119.10, 116.21, 67.37, 50.36, 44.27, 28.25. HRMS (ESI+) m/z: [M+H$^+$] calcd for C$_{25}$H$_{27}$N$_2$O$_2$ 387.2073. found 387.2071.

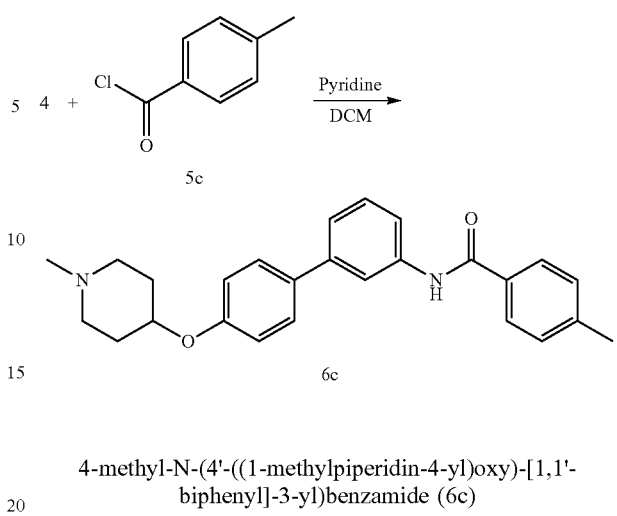

4-methyl-N-(4'-((1-methylpiperidin-4-yl)oxy)-[1,1'-biphenyl]-3-yl)benzamide (6c)

A solution of acid chloride (5c, 0.27 mmol), in anhydrous dichloromethane (2 mL) was added to a solution of the amine (4, 0.18 mmol) and anhydrous triethylamine (0.13 mL, 0.94 mmol) in anhydrous dichloromethane (5 mL). After 12 h, the solvent was removed and the residue purified via column chromatography (SiO$_2$, 10:1, DCM:methanol) to afford 6c as a colorless amorphous solid (60%). $^1$H NMR (500 MHz, chloroform-d) δ 7.93 (s, 1H, NH), 7.88 (t, J=2.0 Hz, 1H), 7.80 (d, J=8.2 Hz, 2H), 7.57 (ddd, J=8.0, 2.3, 1.1 Hz, 1H), 7.54 (d, J=8.7 Hz, 2H), 7.41 (t, J=7.8 Hz, 1H), 7.34 (dt, J=7.8, 1.4 Hz, 1H), 7.30 (d, J=8.0 Hz, 2H), 6.97 (d, J=8.7 Hz, 2H), 4.50-4.27 (m, 1H), 2.76 (m, 2H), 2.43 (s, 3H), 2.42-2.38 (m, 2H), 2.37 (s, 3H), 2.08 (m, 2H), 1.92 (m, 2H). $^{13}$C NMR (126 MHz, CDCl$_3$) δ 165.91, 157.23, 142.65, 141.92, 138.63, 133.56, 132.25, 129.67, 129.60, 128.49, 127.23, 122.99, 118.69, 118.63, 116.45, 71.79, 52.61, 46.21, 30.69, 21.72. HRMS (ESI+) m/z: [M+H$^+$] calcd for C$_{26}$H$_{29}$N$_2$O$_2$ 401.2229. found 401.2232.

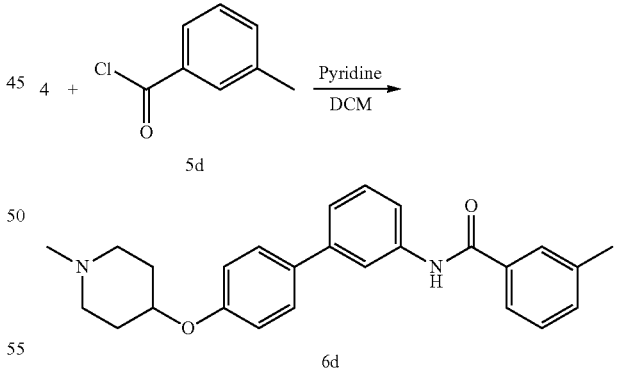

3-methyl-N-(4'-((1-methylpiperidin-4-yl)oxy)-[1,1'-biphenyl]-3-yl)benzamide (6d)

A solution of acid chloride (5d, 0.27 mmol), in anhydrous dichloromethane (2 mL) was added to a solution of the amine (4, 0.18 mmol) and anhydrous triethylamine (0.13 mL, 0.94 mmol) in anhydrous dichloromethane (5 mL). After 12 h, the solvent was removed and the residue purified via column chromatography (SiO$_2$, 10:1, DCM:methanol) to afford 6d as a colorless amorphous solid (58%). $^1$H NMR (500 MHz, chloroform-d) δ 7.90 (s, 1H, NH), 7.85 (s, 1H), 7.65 (s, 1H), 7.61 (dt, J=6.5, 2.2 Hz, 1H), 7.51-7.46 (m, 3H), 7.34 (t, J=7.8 Hz, 1H), 7.31 (m, 2H), 7.25 (dt, J=6.5, 2.2 Hz, 1H), 6.89 (d, J=8.7 Hz, 2H), 4.43 (m, 1H), 2.85 (m, 2H), 2.66 (m, 2H), 2.45 (s, 3H), 2.37 (s, 3H), 2.19 (m, 2H), 1.95 (m, 2H). $^{13}$C NMR (126 MHz, CDCl$_3$) δ 166.16, 156.77, 141.77, 138.95, 138.65, 135.09, 133.97, 132.87, 131.13, 129.64, 128.89, 128.63, 128.00, 124.20, 123.04, 118.75, 116.39, 69.91, 51.65, 45.39, 29.37, 21.63. HRMS (ESI+) m/z: [M+H$^+$] calcd for C$_{26}$H$_{29}$N$_2$O$_2$ 401.2229. found 401.2229.

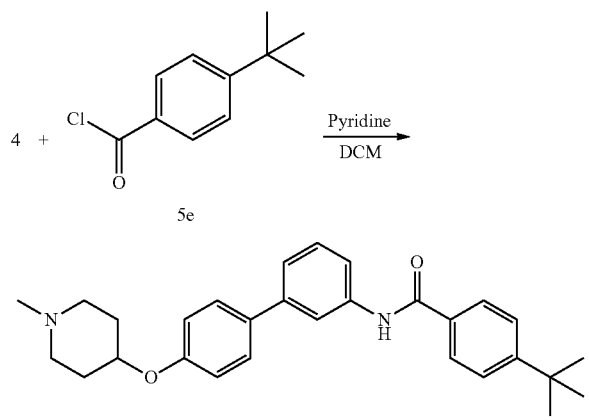

4-(tert-butyl)-N-(4'-((1-methylpiperidin-4-yl)oxy)-[1,1'-biphenyl]-3-yl)benzamide (6e)

A solution of acid chloride (5e, 0.27 mmol), in anhydrous dichloromethane (2 mL) was added to a solution of the amine (4, 0.18 mmol) and anhydrous triethylamine (0.13 mL, 0.94 mmol) in anhydrous dichloromethane (5 mL). After 12 h, the solvent was removed and the residue purified via column chromatography (SiO$_2$, 10:1, DCM:methanol) to afford 6e as a colorless amorphous solid (55%). $^1$H NMR (400 MHz, chloroform-d) δ 8.34 (s, 1H), 7.94 (s, 1H), 7.86 (d, J=8.4 Hz, 1H), 7.59 (dd, J=7.9, 2.1 Hz, 1H), 7.51 (d, J=8.7 Hz, 2H), 7.46 (d, J=8.4 Hz, 2H), 7.37 (t, J=7.8 Hz, 1H), 7.29 (d, J=1.5 Hz, 1H), 6.92 (d, J=8.7 Hz, 1H), 4.40 (m, 1H), 2.81 (m, 2H), 2.54 (m, 2H), 2.41 (s, 3H), 2.17-2.07 (m, 2H), 1.92 (m, 2H), 1.33 (s, 9H). $^{13}$C NMR (101 MHz, CDCl$_3$) δ 165.89, 156.71, 155.40, 141.49, 138.67, 133.59, 131.96, 129.35, 128.32, 127.06, 125.67, 122.66, 118.71, 118.68, 116.20, 70.00, 51.84, 45.48, 34.99, 31.17, 29.70. HRMS (ESI+) m/z: [M+H$^+$] calcd for C$_{29}$H$_{35}$N$_2$O$_2$: 443.2699. found 443.2702.

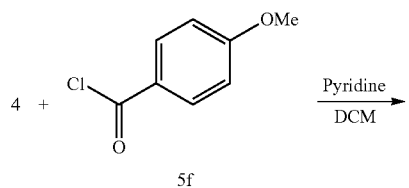

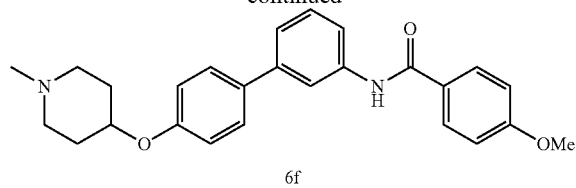

4-methoxy-N-(4'-((1-methylpiperidin-4-yl)oxy)-[1,1'-biphenyl]-3-yl)benzamide (6f)

A solution of acid chloride (5f, 0.27 mmol), in anhydrous dichloromethane (2 mL) was added to a solution of the amine (4, 0.18 mmol) and anhydrous triethylamine (0.13 mL, 0.94 mmol) in anhydrous dichloromethane (5 mL). After 12 h, the solvent was removed and the residue purified via column chromatography (SiO$_2$, 10:1, DCM:methanol) to afford 6f as a colorless amorphous solid (57%). $^1$H NMR (500 MHz, chloroform-d) δ 7.92 (t, J=2.1 Hz, 1H), 7.89 (d, J=8.9 Hz, 2H), 7.54 (d, J=8.8 Hz, 2H), 7.39-7.33 (m, 2H), 7.29 (dt, J=7.9, 1.4 Hz, 1H), 6.95 (m, 4H), 4.65 (m, 1H), 3.27-3.03 (m, 4H), 2.74 (s, 3H), 2.33 (m, 3H), 2.18-1.96 (m, 2H). $^{13}$C NMR (126 MHz, CDCl$_3$+CH$_3$OH) δ 166.54, 162.47, 155.89, 141.10, 138.81, 134.44, 131.60, 129.27, 128.43, 126.92, 122.61, 119.24, 119.13, 116.13, 113.76, 68.52, 55.36, 50.19, 43.69, 27.42. HRMS (ESI+) m/z: [M+H$^+$] calcd for C$_{26}$H$_{29}$N$_2$O$_3$ 417.2178. found 417.2180.

3-methoxy-N-(4'-((1-methylpiperidin-4-yl)oxy)-[1,1'-biphenyl]-3-yl)benzamide (6g)

A solution of acid chloride (5g, 0.27 mmol), in anhydrous dichloromethane (2 mL) was added to a solution of the amine (4, 0.18 mmol) and anhydrous triethylamine (0.13 mL, 0.94 mmol) in anhydrous dichloromethane (5 mL). After 12 h, the solvent was removed and the residue purified via column chromatography (SiO$_2$, 10:1, DCM:methanol) to afford 6g as a colorless amorphous solid (57%). $^1$H NMR (500 MHz, chloroform-d) δ 8.28 (s, 1H, NH), 7.99-7.93 (s, 1H), 7.61-7.57 (m, 1H), 7.54 (d, J=8.5 Hz, 2H), 7.49 (t, J=2.1 Hz, 1H), 7.47 (d, J=7.6 Hz, 1H), 7.39 (dt, J=10.8, 7.8 Hz, 2H), 7.32 (d, J=7.8 Hz, 1H), 7.08 (dd, J=8.2, 2.6 Hz, 1H), 6.93 (d, J=8.6 Hz, 2H), 4.49 (s, 1H), 3.86 (s, 3H), 2.93 (m, 2H), 2.80-2.67 (m, 2H), 2.52 (s, 3H), 2.25 (m, 2H), 2.01 (m, 2H). $^{13}$C NMR (126 MHz, CDCl$_3$) δ 165.88, 160.10, 156.63, 141.61, 138.67, 136.50, 133.97, 129.92, 129.58, 128.58, 122.99, 119.08, 118.91, 118.87, 118.30, 116.35, 112.68, 69.41, 55.69, 51.40, 45.12, 29.03. HRMS (ESI+) m/z: [M+H⁺] calcd for $C_{26}H_{29}N_2O_3$ 417.2178. found 417.2182.

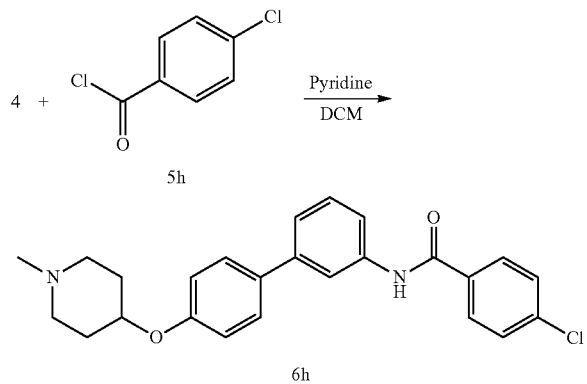

4-Chloro-N-(4'-((1-methylpiperidin-4-yl)oxy)-[1,1'-biphenyl]-3-yl)benzamide (6h)

A solution of acid chloride (5h, 0.27 mmol), in anhydrous dichloromethane (2 mL) was added to a solution of the amine (4, 0.18 mmol) and anhydrous triethylamine (0.13 mL, 0.94 mmol) in anhydrous dichloromethane (5 mL). After 12 h, the solvent was removed and the residue purified via column chromatography (SiO₂, 10:1, DCM:methanol) to afford 6h as a colorless amorphous solid (59%). ¹H NMR (500 MHz, chloroform-d) δ 7.93 (s, 1H), 7.87 (d, J=8.6 Hz, 2H), 7.54 (d, J=8.7 Hz, 2H), 7.42 (d, J=8.6 Hz, 2H), 7.39-7.23 (m, 3H), 6.96 (d, J=8.7 Hz, 2H), 4.65 (m, 2H), 3.21 (m, 4H), 2.75 (s, 3H), 2.30 (m, Hz, 2H), 2.17-2.09 (m, 2H). ¹³C NMR (126 MHz, CDCl₃+CH₃OH) δ 166.15, 155.91, 148.85, 141.12, 138.61, 137.89, 134.39, 133.25, 129.19, 128.95, 128.67, 128.40, 122.89, 119.30, 116.14, 66.83, 50.19, 43.54, 27.40. HRMS (ESI+) m/z: [M+H⁺] calcd for $C_{25}H_{26}ClN_2O_2$ 421.1683. found 421.1689.

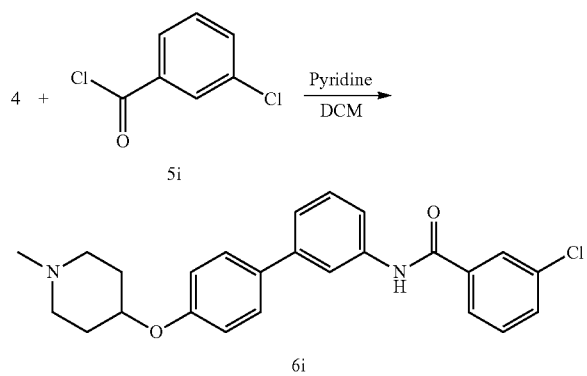

3-Chloro-N-(4'-((1-methylpiperidin-4-yl)oxy)-[1,1'-biphenyl]-3-yl)benzamide (6i)

A solution of acid chloride (5i, 0.27 mmol), in anhydrous dichloromethane (2 mL) was added to a solution of the amine (4, 0.18 mmol) and anhydrous triethylamine (0.13 mL, 0.94 mmol) in anhydrous dichloromethane (5 mL). After 12 h, the solvent was removed and the residue purified via column chromatography (SiO₂, 10:1, DCM:methanol) to afford 6i as a colorless amorphous solid (62%). ¹H NMR (500 MHz, chloroform-d) δ 8.09 (s, 1H), 7.90 (m, 2H), 7.79 (d, J=7.7 Hz, 1H), 7.60-7.49 (m, 3H), 7.44 (d, J=8.1 Hz, 1H), 7.41 (d, J=8.2 Hz, 1H), 7.35 (d, J=7.7 Hz, 1H), 6.96 (d, J=8.3 Hz, 2H), 4.47 (s, 1H), 2.87 (m, 2H), 2.77-2.55 (m, 2H), 2.47 (s, 3H), 2.27-2.09 (m, 2H), 2.07-1.95 (m, 2H). ¹³C NMR (126 MHz, CDCl₃) δ 164.67, 156.95, 149.99, 141.86, 138.28, 136.90, 135.17, 133.71, 132.11, 130.32, 129.68, 128.57, 127.65, 125.41, 123.38, 118.90, 116.42, 70.25, 51.56, 45.58, 29.71. HRMS (ESI+) m/z: [M+H⁺] calcd for $C_{25}H_{26}ClN_2O_2$ 421.1683. found 421.1686.

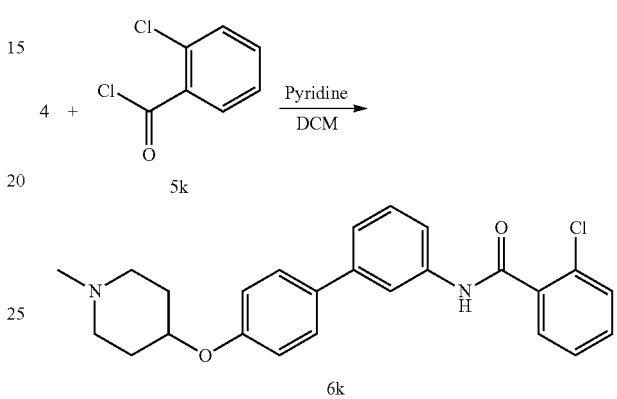

2-Chloro-N-(4'-((1-methylpiperidin-4-yl)oxy)-[1,1'-biphenyl]-3-yl)benzamide (6k)

A solution of acid chloride (5k, 0.27 mmol), in anhydrous dichloromethane (2 mL) was added to a solution of the amine (4, 0.18 mmol) and anhydrous triethylamine (0.13 mL, 0.94 mmol) in anhydrous dichloromethane (5 mL). After 12 h, the solvent was removed and the residue purified via column chromatography (SiO₂, 10:1, DCM:methanol) to afford 6k as a colorless amorphous solid (61%). ¹H NMR (500 MHz, chloroform-d) δ 7.90 (s, 1H), 7.58 (dd, J=7.3, 2.0 Hz, 1H), 7.55-7.48 (m, 3H), 7.42 (d, J=7.9 Hz, 1H), 7.40-7.34 (m, 2H), 7.31 (t, J=7.2 Hz, 2H), 6.95 (d, J=8.3 Hz, 2H), 4.62 (s, 1H), 3.11 (m, 4H), 2.70 (s, 3H), 2.37-2.22 (m, 2H), 2.11 (m, 2H). ¹³C NMR (126 MHz, CDCl₃+CH₃OH) δ 166.07, 156.05, 148.97, 141.36, 138.37, 136.01, 134.29, 131.30, 130.10, 129.35, 129.22, 128.49, 127.02, 123.07, 118.76, 118.64, 116.17, 67.49, 50.52, 43.88, 27.68. HRMS (ESI+) m/z: [M+H⁺] calcd for $C_{25}H_{26}ClN_2O_2$ 421.1683. found 421.1682.

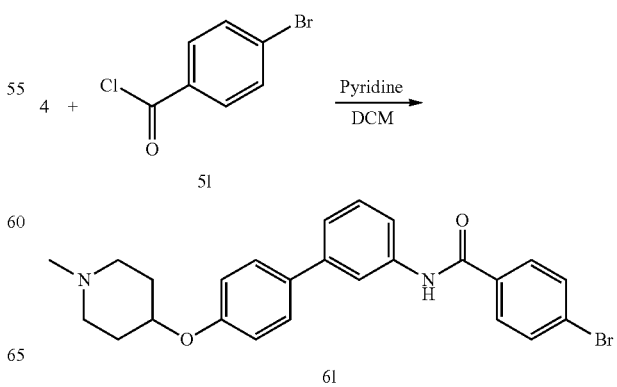

4-Bromo-N-(4'-((1-methylpiperidin-4-yl)oxy)-[1,1'-biphenyl]-3-yl)benzamide (6l)

A solution of acid chloride (5l, 0.27 mmol), in anhydrous dichloromethane (2 mL) was added to a solution of the amine (4, 0.18 mmol) and anhydrous triethylamine (0.13 mL, 0.94 mmol) in anhydrous dichloromethane (5 mL). After 12 h, the solvent was removed and the residue purified via column chromatography (SiO$_2$, 10:1, DCM:methanol) to afford 6l as a colorless amorphous solid (56%). $^1$H NMR (500 MHz, chloroform-d) δ 7.88 (s, 1H), 7.77 (d, J=8.1 Hz, 2H), 7.63-7.56 (m, 2H), 7.57-7.49 (m, 3H), 7.38 (t, J=7.8 Hz, 1H), 7.31 (dd, J=7.6, 1.7 Hz, 1H), 6.93 (d, J=8.4 Hz, 2H), 4.47 (m, 1H), 2.86 (m, 2H), 2.70 (m, 2H), 2.48 (s, 3H), 2.21-2.11 (m, 2H), 2.00-1.86 (m, 2H). $^{13}$C NMR (126 MHz, CDCl$_3$) δ 165.51, 156.67, 149.46, 141.63, 138.44, 133.90, 133.88, 132.03, 129.52, 129.04, 128.50, 126.67, 123.18, 123.16, 119.01, 118.98, 116.36, 69.62, 51.49, 45.22, 29.17. HRMS (ESI+) m/z: [M+H$^+$] calcd for C$_{25}$H$_{26}$BrN$_2$O$_2$ 465.1178. found 465.1181.

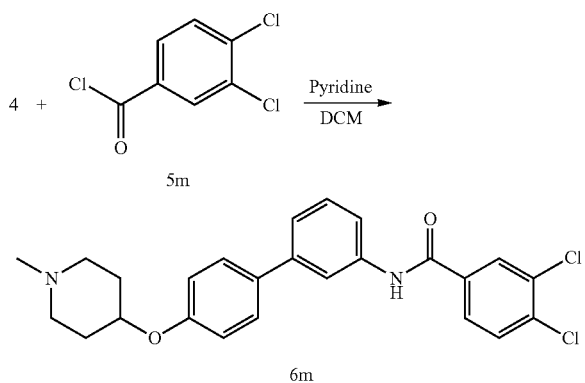

2,4-Dichloro-N-(4'-((1-methylpiperidin-4-yl)oxy)-[1,1'-biphenyl]-3-yl)benzamide (6m)

A solution of acid chloride (5l, 0.27 mmol), in anhydrous dichloromethane (2 mL) was added to a solution of the amine (4, 0.18 mmol) and anhydrous triethylamine (0.13 mL, 0.94 mmol) in anhydrous dichloromethane (5 mL). After 12 h, the solvent was removed and the residue purified via column chromatography (SiO$_2$, 10:1, DCM:methanol) to afford 6l as a colorless amorphous solid (56%). $^1$H NMR (500 MHz, Methanol-d$_4$) δ 7.93 (d, J=2.1 Hz, 1H), 7.79 (s, 1H), 7.66 (dd, J=8.4, 2.1 Hz, 1H), 7.44-7.35 (m, 4H), 7.24 (t, J=7.8 Hz, 1H), 7.17 (dt, J=7.7, 1.4 Hz, 1H), 6.83 (d, J=8.7 Hz, 2H), 4.56 (s, 1H), 3.20-3.00 (m, 4H), 2.68 (s, 3H), 2.25-2.15 (m, 2H), 2.05 (d, J=14.9 Hz, 2H). $^{13}$C NMR (126 MHz, CDCl$_3$+CH$_3$OH) δ 164.78, 155.76, 141.04, 138.41, 135.88, 134.68, 134.40, 132.71, 130.44, 129.62, 129.15, 128.36, 126.78, 122.98, 119.40, 119.28, 116.07, 65.77, 49.66, 43.34, 26.95. HRMS (ESI+) m/z: [M+H$^+$] calcd for C$_{25}$H$_{25}$Cl$_2$N$_2$O$_2$ 455.1293. found 455.1291.

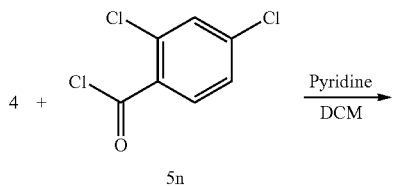

2,4-Dichloro-N-(4'-((1-methylpiperidin-4-yl)oxy)-[1,1'-biphenyl]-3-yl)benzamide (6n)

A solution of acid chloride (5n, 0.27 mmol), in anhydrous dichloromethane (2 mL) was added to a solution of the amine (4, 0.18 mmol) and anhydrous triethylamine (0.13 mL, 0.94 mmol) in anhydrous dichloromethane (5 mL). After 12 h, the solvent was removed and the residue purified via column chromatography (SiO$_2$, 10:1, DCM:methanol) to afford 6n as a colorless amorphous solid (54%). $^1$H NMR (500 MHz, chloroform-d) δ 7.99 (s, 1H, NH), 7.87 (s, 1H), 7.76 (d, J=8.3 Hz, 1H), 7.57-7.52 (m, 3H), 7.50 (d, J=2.0 Hz, 1H), 7.43 (t, J=7.8 Hz, 1H), 7.41-7.35 (m, 2H), 6.98 (d, J=8.7 Hz, 2H), 4.48 (s, 1H), 2.87 (m, 2H), 2.65 (m, 2H), 2.48 (s, 3H), 2.18 (m, 2H), 1.99 (m, 2H). $^{13}$C NMR (126 MHz, CDCl$_3$) δ 163.68, 157.07, 142.05, 137.96, 137.55, 133.68, 133.64, 131.76, 130.45, 129.75, 128.62, 128.03, 126.85, 123.65, 118.72, 118.69, 116.45, 70.90, 51.54, 45.60, 29.92. HRMS (ESI+) m/z: [M+H$^+$] calcd for C$_{25}$H$_{25}$Cl$_2$N$_2$O$_2$ 455.1293. found 455.1290.

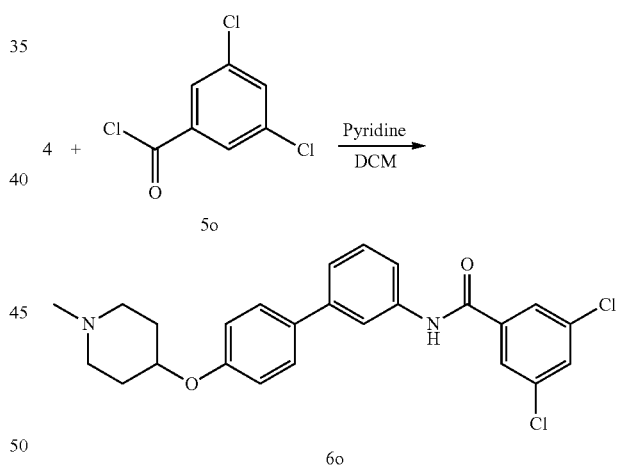

3,5-Dichloro-N-(4'-((1-methylpiperidin-4-yl)oxy)-[1,1'-biphenyl]-3-yl)benzamide (6o)

A solution of acid chloride (5o, 0.27 mmol), in anhydrous dichloromethane (2 mL) was added to a solution of the amine (4, 0.18 mmol) and anhydrous triethylamine (0.13 mL, 0.94 mmol) in anhydrous dichloromethane (5 mL). After 12 h, the solvent was removed and the residue purified via column chromatography (SiO$_2$, 10:1, DCM:methanol) to afford 6o as a colorless amorphous solid (65%). $^1$H NMR (500 MHz, chloroform-d) δ 8.31 (s, 1H), 7.87 (s, 1H), 7.80 (d, J=1.9 Hz, 2H), 7.58 (ddd, J=8.1, 2.3, 1.2 Hz, 1H), 7.54-7.48 (m, 3H), 7.40 (t, J=7.8 Hz, 1H), 7.35 (dt, J=7.8, 1.4 Hz, 1H), 6.94 (d, J=8.7 Hz, 1H), 4.45 (s, 1H), 2.88 (ddd, J=12.4, 9.3, 3.4 Hz, 2H), 2.66 (s, 2H), 2.48 (s, 3H), 2.19 (ddt, J=13.0, 9.3, 3.6 Hz, 2H), 2.03-1.86 (m, 2H). $^{13}$C NMR (126 MHz, CDCl$_3$) δ 163.51, 156.90, 141.79, 138.06, 137.94, 135.79, 133.63, 131.83, 129.68, 128.53, 126.07, 123.57, 119.14, 119.07, 116.40, 70.15, 51.73, 45.43, 29.54. HRMS (ESI+) m/z: [M+H$^+$] calcd for C$_{25}$H$_{25}$Cl$_2$N$_2$O$_2$ 455.1293. found 455.1289.

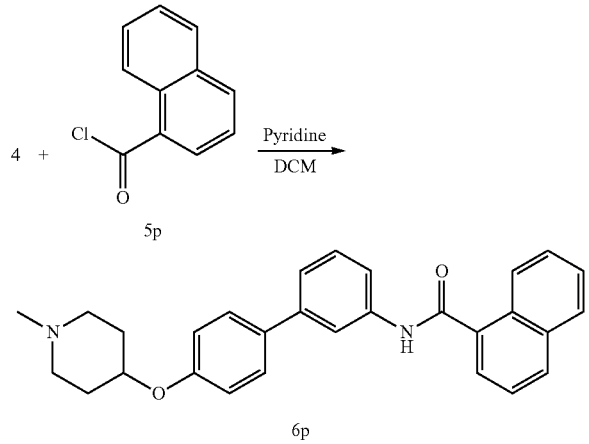

N-(4'-((1-methylpiperidin-4-yl)oxy)-[1,1'-biphenyl]-3-yl)-1-naphthamide (6p)

A solution of acid chloride (5p, 0.27 mmol), in anhydrous dichloromethane (2 mL) was added to a solution of the amine (4, 0.18 mmol) and anhydrous triethylamine (0.13 mL, 0.94 mmol) in anhydrous dichloromethane (5 mL). After 12 h, the solvent was removed and the residue purified via column chromatography (SiO$_2$, 10:1, DCM:methanol) to afford 6p as a colorless amorphous solid (68%). $^1$H NMR (500 MHz, chloroform-d) δ 8.30 (d, J=7.3 Hz, 1H), 7.98 (d, J=2.3 Hz, 1H), 7.95 (d, J=8.3 Hz, 1H), 7.88 (d, J=8.3 Hz, 1H), 7.73 (d, J=7.2 Hz, 1H), 7.63-7.60 (m, 1H), 7.58-7.47 (m, 4H), 7.41 (t, J=7.9 Hz, 1H), 7.36-7.31 (m, 2H), 6.97 (d, J=8.7 Hz, 2H), 4.62-4.39 (m, 1H), 2.97 (m, 2H), 2.83 (s, 2H), 2.55 (s,3H), 2.31-2.14 (m, 2H), 2.10-1.89 (m, 2H). $^{13}$C NMR (126 MHz, CDCl$_3$+CH$_3$OH) δ 168.80, 156.37, 148.96, 141.47, 138.77, 136.91, 134.47, 133.67, 130.79, 130.07, 129.35, 128.40, 127.17, 126.47, 125.23, 125.13, 124.73, 122.93, 118.72, 118.65, 116.24, 69.35, 51.17, 44.65, 28.56. HRMS (ESI+) m/z: [M+H$^+$] calcd for C$_{29}$H$_{29}$N$_2$O$_2$ 437.2229. found 437.2231.

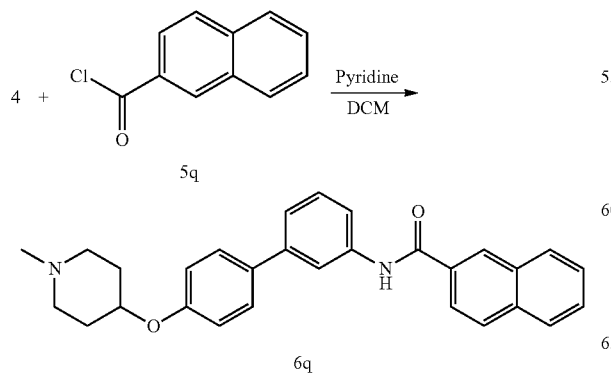

N-(4'-((1-methylpiperidin-4-yl)oxy)-[1,1'-biphenyl]-3-yl)-1-naphthamide (6q)

A solution of acid chloride (5q, 0.27 mmol), in anhydrous dichloromethane (2 mL) was added to a solution of the amine (4, 0.18 mmol) and anhydrous triethylamine (0.13 mL, 0.94 mmol) in anhydrous dichloromethane (5 mL). After 12 h, the solvent was removed and the residue purified via column chromatography (SiO$_2$, 10:1, DCM:methanol) to afford 6q as a colorless amorphous solid (65%). $^1$H NMR (500 MHz, chloroform-d) δ 8.43 (s, 1H), 8.14 (s, 1H), 7.97 (q, J=1.4 Hz, 3H), 7.94-7.88 (m, 1H), 7.66-7.53 (m, 4H), 7.48-7.42 (m, 1H), 7.39-7.33 (m, 1H), 7.28 (s, 1H), 7.01-6.94 (m, 2H), 4.48 (m, 1H), 2.99-2.84 (m, 2H), 2.63 (m, 2H), 2.47 (s, 3H), 2.20 (m, 2H), 2.00 (m, 2H). $^{13}$C NMR (126 MHz, CDCl$_3$) δ 166.04, 156.97, 141.89, 138.64, 135.10, 133.82, 132.82, 132.32, 129.69, 129.20, 129.02, 128.61, 128.18, 128.04, 127.79, 127.21, 123.75, 123.16, 118.81, 118.78, 116.43, 70.63, 52.07, 45.69, 29.87. HRMS (ESI+) m/z: [M+H$^+$] calcd for C$_{29}$H$_{29}$N$_2$O$_2$ 437.2229. found 437.2227.

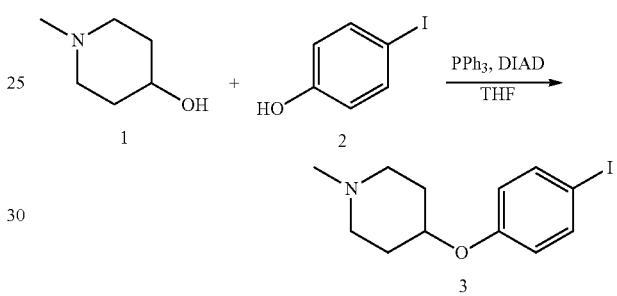

4-(4-iodophenoxy)-1-methylpiperidine (3)

Diisopropylazodicarboxylate (1.89 g, 9.36 mmol) was added to a solution of 4-iodophenol (0.92 g, 4.18 mmol), N-methyl-4-hydroxy-piperidine (480 mg, 4.18 mmol) and triphenylphosphine (2.46 g, 9.36 mmol) in anhydrous THF (50 mL). After 2 h, the solvent was removed and the residue purified via column chromatography (SiO$_2$, 10:1, DCM: methanol) to afford desired product 6 as a colorless amorphous solid (1.02 g, 77%). $^1$H NMR (500 MHz, chloroform-d) δ 7.54 (d, J=8.9 Hz, 2H), 6.69 (d, J=2.0 Hz, 2H), 4.27 (m, 1H), 2.73-2.59 (m, 2H), 2.31 (s, 1H), 2.30 (m, 2H), 1.98 (m, 2H), 1.82 (m, 2H). 13C NMR (101 MHz, CDCl$_3$) δ 157.34, 138.34, 118.50, 82.91, 72.18, 52.61, 46.28, 30.71. HRMS (ESI+) m/z: [M+H$^+$] calcd for C$_{12}$H$_{17}$INO 318.0355. found 318.0357.

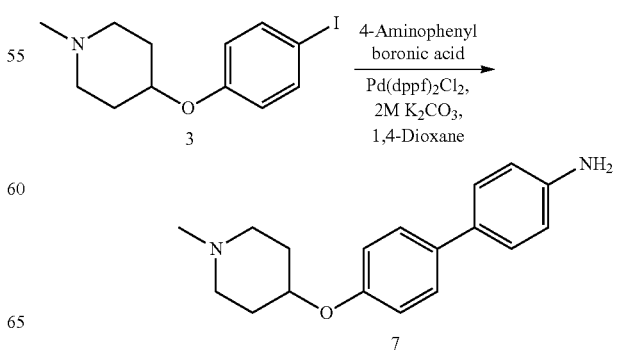

4'-((1-methylpiperidin-4-yl)oxy)-[1,1'-biphenyl]-3-amine (7)

A mixture of iodide 11a (250 mg, 0.79 mmol) aminophenylboronic acid (216 mg, 1.58 mmol), potassium carbonate solution (2M, 100 µL) and [1,1'-Bis(diphenylphosphino)ferrocene]dichloropalladium(II) (57 mg, 0.08 mmol) was suspended in dry dioxane (15 mL) and purged with argon for 15 min. After 15 min, the mixture was heated in a sealed tube at 110° C. for 12 hours before concentrated to dryness. The residue so obtained was purified via column chromatography (SiO$_2$, 10:1, CH$_2$Cl$_2$:methanol) to afford a brownish amorphous solid (149 mg, 67%). $^1$H NMR (500 MHz, chloroform-d) δ 7.50 (d, J=8.7 Hz, 2H), 7.22 (t, J=7.8 Hz, 1H), 6.99-6.92 (m, 3H), 6.88 (s, 1H), 6.66 (dd, J=7.9, 2.3 Hz, 1H), 4.45-4.34 (m, 1H), 3.74 (s, 2H), 2.79 (ddd, J=11.8, 7.8, 3.8 Hz, 2H), 2.48-2.42 (m, 2H), 2.39 (s, 3H), 2.11 (ddt, J=11.5, 7.3, 3.6 Hz, 2H), 1.94 (ddt, J=14.0, 7.9, 3.7 Hz, 2H). $^{13}$C NMR (126 MHz, CDCl$_3$) δ 156.77, 146.69, 141.94, 134.13, 129.65, 128.16, 117.28, 116.15, 113.60, 113.49, 71.45, 52.37, 45.96, 30.42. HRMS (ESI$^+$) m/z: [M+H$^+$] calcd for C$_{18}$H$_{23}$N$_2$O 283.1810. found, 283.1808.

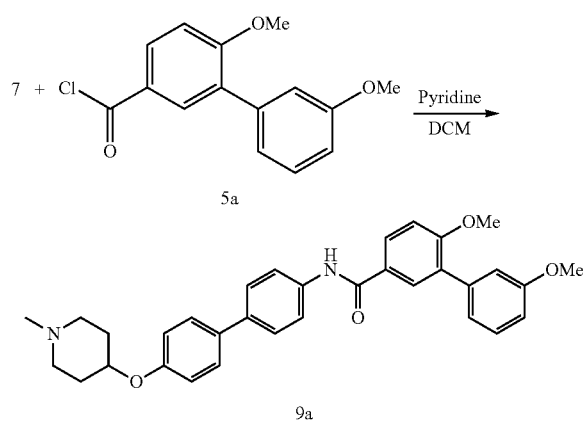

3',6-dimethoxy-N-(4'-((1-methylpiperidin-4-yl)oxy)-[1,1'-biphenyl]-4-yl)-[1,1'-biphenyl]-3-carboxamide (9a)

A solution of acid chloride (5a, 0.27 mmol), in anhydrous dichloromethane (2 mL) was added to a solution of the aniline (7, 0.18 mmol) and anhydrous triethylamine (0.94 mmol) in anhydrous dichloromethane (5 mL). After 12 h, the solvent was removed and the residue purified via column chromatography (SiO$_2$, 10:1, DCM:methanol) to afford 9a as a white amorphous solid (78%). $^1$H NMR (500 MHz, chloroform-d) δ 7.93 (dd, J=8.6, 2.4 Hz, 1H), 7.89 (d, J=2.4 Hz, 1H), 7.71 (d, J=8.6 Hz, 2H), 7.51 (d, J=7.2 Hz, 2H), 7.49 (d, J=7.2 Hz, 2H), 7.32 (t, J=7.9 Hz, 1H), 7.12 (dt, J=7.6, 1.3 Hz, 1H), 7.09 (dd, J=2.6, 1.6 Hz, 1H), 7.04 (d, J=8.7 Hz, 1H), 6.95 (d, J=8.8 Hz, 2H), 6.89 (ddd, J=8.3, 2.6, 1.0 Hz, 1H), 4.57 (m, 1H), 3.86 (s, 3H), 3.82 (s, 3H), 3.05 (m, 2H), 2.99 (m, 2H), 2.63 (s, 3H), 2.20 (ddt, J=14.3, 10.4, 3.4 Hz, 2H), 2.12-1.98 (m, 2H). $^{13}$C NMR (126 MHz, CDCl$_3$+CH$_3$OH) δ 166.41, 159.27, 159.17, 155.86, 148.91, 138.93, 137.31, 136.39, 134.01, 130.38, 130.07, 129.04, 128.58, 128.00, 126.91, 122.01, 121.08, 116.23, 115.26, 112.75, 110.88, 68.10, 55.69, 55.21, 50.60, 44.10, 28.06. HRMS (ESI$^+$) m/z: [M+H$^+$] calcd for C$_{33}$H$_{35}$N$_2$O$_4$ 523.2597. found 523.2561.

5-bromo-2-((1-methylpiperidin-4-yl)oxy)pyridine (16)

Diisopropylazodicarboxylate (809 mg, 4.0 mmol) was added to a solution of 5-bromopyridin-2-ol (348 mg, 2.0 mmol), N-methyl-4-hydroxy-piperidine (230 mg, 2.0 mmol) and triphenylphosphine (1.08 g, 4.0 mmol) in anhydrous THF (40 mL), and the resulting mixture was stirred at room temperature for 12 hours. After 12 hours, the reaction mixture was concentrated to dryness. The residue was purified via column chromatography (SiO$_2$, 10:1, CH$_2$Cl$_2$:methanol) to afford desired product as a thick oil (368 mg, 68%). $^1$H NMR (500 MHz, chloroform-d) δ 8.15 (s, 1H), 7.62 (dd, J=8.8, 2.5 Hz, 1H), 6.62 (dd, J=8.8, 0.8 Hz, 1H), 5.01 (dt, J=8.3, 4.2 Hz, 1H), 2.72 (m, 2H), 2.40-2.33 (m, 2H), 2.32 (s, 3H), 2.10-2.00 (m, 2H), 1.83 (m, 2H). $^{13}$C NMR (126 MHz, CDCl$_3$) δ 162.13, 147.58, 141.33, 113.49, 111.53, 70.64, 53.11, 46.28, 30.90. HRMS (ESI$^+$) m/z: [M+H$^+$] calcd for C$_{11}$H$_{16}$BrN$_2$O 271.0446. found 271.0442.

2-((1-methylpiperidin-4-yl)oxy)-5-(4-nitrophenyl)pyridine (18a)

[1,1'-Bis(diphenylphosphino)ferrocene]dichloropalladium(II) (43 mg, 0.05 mmol) and potassium carbonate solution (2M, 100 µL) were added to a solution of bromide 16 (250 mg, 0.92 mmol) and 4-nitrophenylboronic acid (462 mg, 2.76 mmol) in dioxane (15 mL) and purged with argon for 15 min. After 15 min, the mixture was heated at 110° C. for 12 hours before concentrated to dryness. The brown residue so obtained was purified via column chromatography (SiO$_2$, 10:1, CH$_2$Cl$_2$:methanol) to afford desired product as a brown amorphous solid (246 mg, 85%). $^1$H NMR (500 MHz, chloroform-d) δ 8.31 (d, J=2.6 Hz, 1H), 8.21 (d, J=8.8 Hz, 2H), 7.78 (dd, J=8.6, 2.6 Hz, 1H), 7.61 (d, J=8.8 Hz, 2H), 6.77 (d, J=8.6 Hz, 1H), 5.07 (m, 1H), 2.72 (m, 2H), 2.41 (m, 2H), 2.29 (s, 3H), 2.04 (m, 2H), 1.92-1.76 (m, 2H). $^{13}$C NMR (126 MHz, CDCl$_3$+CH$_3$OH) δ 163.45, 147.00, 145.46, 144.39, 137.76, 127.77, 127.17, 124.37, 112.09, 69.69, 52.49, 45.60, 30.15. HRMS (ESI$^+$) m/z: [M+H$^+$] calcd for C$_{17}$H$_{20}$N$_3$O$_3$ 314.1505. found 314.1502.

6-(4-nitrophenyl)pyridin-3-ol (17)

[1,1'-Bis(diphenylphosphino)ferrocene]dichloropalladium(II) (42 mg, 0.05 mmol) and potassium carbonate solution (2M, 100 µL) were added to a solution of 6-bromopyridin-3-ol (174 mg, 1.0 mmol) and 4-nitrophenylboronic acid (334 mg, 2.0 mmol) in dioxane (15 mL) and purged with argon for 15 min. After 15 min, the mixture was heated at 110° C. for 12 hours before concentrated to dryness. The brown residue was purified via column chromatography (SiO$_2$, 100:1, CH$_2$Cl$_2$:acetone) to afford desired product as a brown amorphous solid (162 mg, 75%). $^1$H NMR (500 MHz, chloroform-d) δ 8.17 (m, 3H), 7.92 (dd, J=9.1, 2.0 Hz, 2H), 7.59 (dd, J=8.7, 1.6 Hz, 1H), 7.22-7.14 (m, 1H). $^{13}$C NMR (126 MHz, CDCl$_3$+CH$_3$OH) δ 154.26, 147.30, 146.13, 145.30, 138.20, 126.93, 124.01, 123.67, 122.60. HRMS (ESI$^+$) m/z: [M+H$^+$] calcd for C$_{11}$H$_{18}$N$_2$O$_3$ 226.1317. found 226.1319.

5-((1-methylpiperidin-4-yl)oxy)-2-(4-nitrophenyl)pyridine (18b)

Diisopropyl azodicarboxylate (279 mg, 1.38 mmol) was added to a solution of pridinol 17 (150 mg, 0.69 mmol), N-methyl-4-hydroxy-piperidine (80 mg, 0.69 mmol) and triphenylphosphine (362 mg, 1.38 mmol) in anhydrous THF (20 mL), and the resulting mixture was stirred at room temperature for 12 hours. After 12 hours, the reaction mixture was concentrated to the dryness and the remaining residue was purified via column chromatography (SiO$_2$, 10:1, CH$_2$Cl$_2$:methanol) to afford desired product as a light brown solid (126 mg, 58%). $^1$H NMR (500 MHz, Chloroform-d) δ 8.46-8.38 (m, 1H), 8.28 (d, J=8.9 Hz, 2H), 8.09 (d, J=8.9 Hz, 2H), 7.74 (dd, J=8.8, 0.7 Hz, 1H), 7.30 (dd, J=8.7, 2.9 Hz, 1H), 4.45 (m, 1H), 2.72 (m, 2H), 2.40-2.35 (m, 1H), 2.33 (s, 3H), 2.11-2.00 (m, 2H), 1.92-1.86 (m, 2H). $^{13}$C NMR (126 MHz, CDCl$_3$) δ 154.01, 147.65, 147.22, 145.14, 139.63, 127.05, 124.20, 123.12, 121.88, 72.94, 52.50, 46.27, 30.70. HRMS (ESI$^+$) m/z: [M+H$^+$] calcd for C$_{17}$H$_{20}$N$_3$O$_3$ 314.1505. found 314.1506.

3',6-dimethoxy-N-(4-(6-((1-methylpiperidin-4-yl)oxy)pyridin-3-yl)phenyl)-[1,1'-biphenyl]-3-carboxamide (19a)

General Procedure for the Synthesis of 19a-b Through Reduction/Amide Coupling

Palladium on carbon (10 mg) was added to a solution of nitro phenyl 18a (82 mg, 0.27 mmol) in dry methanol (5 mL). The resulting mixture was stirred under hydrogen atmosphere for 2 hours. After 2 hours, the reaction mixture was filtered through celite. The filtrate was concentrated to dryness and used as such without further purification in the next step.

The amine (from the previous step) was dissolved in dry dichloromethane (0.5 ml) and added dropwise to an ice-cooled solution of acid chloride 5a (150 mg, 0.54 mmol) and pyridine (42 mg, 0.54 mmol) in dry dichloromethane (1 ml). The resulting mixture was stirred at room temperature for additional 4 hours before concentrated to dryness. The remaining residue was purified via column chromatography (SiO$_2$, 10:1, CH$_2$Cl$_2$:methanol) to afford desired product as a light brown solid (68 mg, 48%). $^1$H NMR (500 MHz, chloroform-d) δ 8.21 (s, 1H), 7.85 (dd, J=7.7, 3.1 Hz, 1H), 7.80 (d, J=2.5 Hz, 1H), 7.72-7.70 (m, 1H), 7.68-7.63 (m, 2H), 7.40 (d, J=8.9 Hz, 2H), 7.23 (dd, J=9.5, 6.4 Hz, 1H), 7.00 (m, 3H), 6.82-6.78 (m, 1H), 6.70 (d, J=8.7 Hz, 1H), 5.13 (s, 1H), 3.78 (s, 3H), 3.74 (s, 3H), 2.98 (m, 2H), 2.90-2.71 (m, 2H), 2.52 (s, 3H), 2.16 (m, 2H), 2.02 (m, 2H). $^{13}$C NMR (126 MHz, CDCl$_3$+CH$_3$OH) δ 166.42, 161.69, 159.35, 159.22, 144.52, 138.95, 137.98, 137.73, 133.34, 130.45, 130.07, 129.08, 128.65, 126.98, 126.96, 122.04, 121.22, 121.18, 115.32, 112.79, 111.38, 110.93, 66.64, 55.75, 55.26, 51.48, 44.36, 28.65. HRMS (ESI$^+$) m/z: [M+H$^+$] calcd for C$_{32}$H$_{34}$N$_3$O$_4$ 524.2549. found 524.2551.

3',6-dimethoxy-N-(4-(5-((1-methylpiperidin-4-yl)oxy)pyridin-2-yl)phenyl)-[1,1'-biphenyl]-3-carboxamide (19b)

Palladium on carbon (10 mg) was added to a solution of nitro phenyl 18b (0.27 mmol) in dry methanol (5 mL). The resulting mixture was stirred under hydrogen atmosphere for 2 hours. After 2 hours, the reaction mixture was filtered through Celite®. The filtrate was concentrated to dryness and used as such without further purification in the next step.

The amine (from the previous step) was dissolved in dry dichloromethane (0.5 ml) and added dropwise to an ice-cooled solution of acid chloride 5a (0.54 mmol) and pyridine (0.54 mmol) in dry dichloromethane (1 ml). The resulting mixture was stirred at room temperature for additional 4 hours before concentrated to dryness. The remaining residue was purified via column chromatography (SiO$_2$, 10:1, CH$_2$Cl$_2$:methanol) to afford desired product as a light brown solid (45%). $^1$H NMR (400 MHz, methanol-d$_4$) δ 8.33 (d, J=2.9 Hz, 1H), 7.99 (dd, J=8.6, 2.4 Hz, 1H), 7.95 (d, J=2.4 Hz, 1H), 7.89-7.79 (m, 4H), 7.72 (d, J=8.7 Hz, 1H), 7.42 (dd, J=8.8, 3.0 Hz, 1H), 7.36 (t, J=7.9 Hz, 1H), 7.16 (dt, J=7.6, 1.2 Hz, 1H), 7.13 (dd, J=2.6, 1.5 Hz, 1H), 7.11 (d, J=8.7 Hz, 1H), 6.93 (ddd, J=8.3, 2.7, 1.0 Hz, 1H), 4.79 (m, 1H), 3.91, (s, 3H), 3.87 (s, 3H), 3.36 (m, 4H), 2.87 (s, 3H), 2.48-2.40 (sm 2H), 2.34-2.16 (m, 2H). $^{13}$C NMR (126 MHz, CDCl$_3$) δ 166.57, 159.31, 159.15, 151.72, 150.82, 139.02, 138.89, 138.36, 134.22, 130.38, 130.13, 128.98, 128.58, 126.97, 126.86, 123.72, 121.96, 121.47, 120.79, 115.19, 112.72, 110.83, 66.83, 55.63, 55.13, 49.50, 43.31, 26.93. HRMS (ESI$^+$) m/z: [M+H$^+$] calcd for C$_{32}$H$_{34}$N$_3$O$_4$ 524.2549. found 524.2546.

5'-((6-bromopyridin-3-yl)carbamoyl)-2'-methoxy-[1,1'-biphenyl]-3-yl acetate (21a)

A solution of acid chloride 10b (300 mg, 1.16 mmol) in dichloromethane (1 ml) was added to a solution of 6-bromopyridin-3-amine (200 mg, 1.16 mmol) and pyridine (162 mg, 2.32 mmol) in dry dichloromethane (5 mL). The solution was then stirred at room temperature for 4 hours. After 4 hours, the reaction mixture was concentrated to dryness and the remaining residue was purified via column chromatography (SiO$_2$, 10:1, CH$_2$Cl$_2$:methanol) to afford desired product as a light brown solid (416 mg, 87%). $^1$H NMR (500 MHz, chloroform-d) δ 8.47 (d, J=2.8 Hz, 1H), 8.21 (s, 1H, NH), 8.17 (dd, J=8.7, 2.9 Hz, 1H), 7.88 (dd, J=8.6, 2.4 Hz, 1H), 7.78 (d, J=2.4 Hz, 1H), 7.44 (d, J=8.6 Hz, 1H), 7.32 (t, J=7.9 Hz, 1H), 7.09-6.98 (m, 3H), 6.90 (dd, J=8.2, 2.7 Hz, 1H), 3.88 (s, 3H), 3.83 (s, 3H). $^{13}$C NMR (126 MHz, CDCl$_3$) δ 165.77, 159.94, 159.48, 141.64, 138.72, 136.00, 134.87, 130.96, 130.41, 129.84, 129.37, 128.84, 128.23, 126.05, 122.07, 115.57, 113.06, 111.32, 56.07, 55.52. HRMS (ESI$^+$) m/z: [M+H$^+$] calcd for C$_{21}$H$_{18}$BrN$_2$O$_4$ 441.0450. found 441.0453.

5'-((5-bromopyridin-2-yl)carbamoyl)-2'-methoxy-[1,1'-biphenyl]-3-yl acetate (21b)

A solution of acid chloride 10b (300 mg, 1.16 mmol) in dichloromethane (1 ml) was added to a solution of 5-bromopyridin-2-amine (200 mg, 1.16 mmol) and pyridine (162 mg, 2.32 mmol) in dry dichloromethane (5 mL). The solution was then stirred at room temperature for 4 hours. After 4 hours, the reaction mixture was concentrated to dryness and the remaining residue was purified via column chromatography (SiO$_2$, 10:1, CH$_2$Cl$_2$:methanol) to afford desired product as a light brown solid (392 mg, 82%). $^1$H NMR (500 MHz, chloroform-d) δ 8.47 (t, J=2.3 Hz, 1H), 8.19 (dt, J=8.7, 3.0 Hz, 1H), 7.89 (dd, J=8.6, 2.4 Hz, 1H), 7.81 (d, J=2.4 Hz, 1H), 7.43 (d, J=8.6 Hz, 1H), 7.32 (t, J=7.9 Hz, 1H), 7.10-7.06 (m, 1H), 7.05 (dd, J=2.6, 1.6 Hz, 1H), 7.02 (d, J=8.7 Hz, 1H), 6.90 (dd, J=8.4, 2.6 Hz, 1H), 3.87 (s, 3H), 3.83 (s, 3H). $^{13}$C NMR (126 MHz, CDCl$_3$) δ 165.93, 159.87, 159.43, 141.61, 138.79, 135.73, 135.03, 130.84, 130.44, 129.97, 129.33, 128.90, 128.18, 126.10, 122.09, 115.56, 112.99, 111.24, 56.03, 55.50. HRMS (ESI$^+$) m/z: [M+H$^+$] calcd for C$_{21}$H$_{18}$BrN$_2$O$_4$ 441.0450. found 441.0452.

N-(6-(4-hydroxyphenyl)pyridin-3-yl)-3',6-dimethoxy-[1,1'-biphenyl]-3-carboxamide (22a)

[1,1'-Bis(diphenylphosphino)ferrocene]dichloropalladium(II) (42 mg, 0.05 mmol) and potassium carbonate solution (2M, 100 µL) were added to a solution of bromide 21a (150 mg, 0.36 mmol) and 4-hydrophenylboronic acid (99 mg, 0.72 mmol) in dioxane (10 mL). The mixture was heated at 110° C. for 12 hours. After 12 hours, the reaction mixture was concentrated to dryness. The brown residue so obtained was purified via column chromatography (SiO$_2$, 100:1, CH$_2$Cl$_2$:acetone) to afford desired product as a brown amorphous solid (117 mg, 76%). $^1$H NMR (500 MHz, chloroform-d) δ 8.54 (d, J=2.6 Hz, 1H), 8.28 (dd, J=8.7, 2.6 Hz, 1H), 7.94-7.81 (m, 2H), 7.63 (d, J=8.7 Hz, 2H), 7.54 (d, J=8.7 Hz, 1H), 7.24 (t, J=7.9 Hz, 1H), 7.04 (dt, J=7.6, 1.3 Hz, 1H), 7.01 (d, J=2.6 Hz, 1H), 6.97 (d, J=8.6 Hz, 1H), 6.83-6.77 (m, 3H), 3.78 (s, 3H), 3.74 (s, 3H). $^{13}$C NMR (126 MHz, CDCl$_3$+CH$_3$OH) δ 166.82, 159.50, 159.21, 157.87, 153.08, 140.97, 138.90, 133.90, 130.48, 130.30, 130.28, 129.38, 129.06, 128.76, 128.10, 126.42, 122.04, 120.40, 115.64, 115.27, 112.82, 110.90, 55.73, 55.24. HRMS (ESI$^+$) m/z: [M+H$^+$] calcd for C$_{26}$H$_{23}$N$_2$O$_4$ 427.1658. found 427.1655.

5'-((5-(4-hydroxyphenyl)pyridin-2-yl)carbamoyl)-2'-methoxy-[1,1'-biphenyl]-3-yl acetate (22b)

[1,1'-Bis(diphenylphosphino)ferrocene]dichloropalladium(II) (40 mg, 0.05 mmol) and potassium carbonate solution (2M, 100 µL) were added to a solution of bromide 21b (116 mg, 0.28 mmol) and 4-hydrophenylboronic acid (78 mg, 0.56 mmol) in dioxane (10 mL). The mixture was heated at 110° C. for 12 hours. After 12 hours, the reaction mixture was concentrated to dryness. The brown residue so obtained was purified via column chromatography (SiO$_2$, 100:1, CH$_2$Cl$_2$:acetone) to afford desired product as a brown amorphous solid (110 mg, 92%). $^1$H NMR (500 MHz, chloroform-d) δ 8.46-8.38 (m, 2H), 7.98-7.93 (m, 2H), 7.91 (dd, J=8.6, 2.5 Hz, 1H), 7.42 (d, J=8.6 Hz, 2H), 7.35 (t, J=7.9 Hz, 1H), 7.12 (dt, J=7.6, 1.2 Hz, 1H), 7.10 (dd, J=2.6, 1.5 Hz, 1H), 7.06 (d, J=8.4 Hz, 1H), 6.92 (dd, J=8.9, 2.3 Hz, 3H), 3.89 (s, 3H), 3.85 (s, 3H). $^{13}$C NMR (126 MHz, CDCl$_3$) δ 165.44, 159.91, 159.44, 156.76, 150.25, 145.29, 138.87, 136.84, 133.07, 131.02, 130.26, 129.32, 129.21, 128.66, 128.15, 126.31, 122.20, 116.18, 115.38, 114.33, 113.28, 111.25, 56.03, 55.51. HRMS (ESI$^+$) m/z: [M+H$^+$] calcd for C$_{26}$H$_{23}$N$_2$O$_4$ 427.1658. found 427.1660.

3',6-dimethoxy-N-(6-(4-((1-methylpiperidin-4-yl)oxy)phenyl)pyridin-3-yl)-[1,1'-biphenyl]-3-carboxamide (19c)

Diisopropylazodicarboxylate (36 mg, 0.18 mmol) was added to a solution of phenol 22a (38 mg, 0.09 mmol), N-methyl-4-hydroxy-piperidine (21 mg, 0.18 mmol) and triphenylphosphine (47 mg, 0.18 mmol) in anhydrous THF (1 mL), and the resulting mixture was stirred at room temperature for 12 hours. After 12 hours, the reaction mixture was concentrated to dryness and the remaining residue was purified via column chromatography (SiO$_2$, 10:1, CH$_2$Cl$_2$:methanol) to afford desired product as a light brown solid (31 mg, 67%). $^1$H NMR (500 MHz, chloroform-d) δ 8.73 (d, J=2.6 Hz, 1H), 8.56 (s, 1H), 8.32 (dd, J=8.7, 2.7 Hz, 1H), 7.93 (dd, J=8.6, 2.5 Hz, 1H), 7.88-7.82 (m, 3H), 7.62 (d, J=8.6 Hz, 1H), 7.31 (t, J=7.9 Hz, 1H), 7.11-7.05 (m, 2H), 6.99 (d, J=8.6 Hz, 1H), 6.95 (d, J=8.8 Hz, 2H), 6.89 (ddd, J=8.3, 2.6, 1.0 Hz, 1H), 4.48-4.31 (m, 1H), 3.85 (s, 3H), 3.82 (s, 3H), 2.76 (m, 2H), 2.47 (m, 2H), 2.37 (s, 3H), 2.08 (m, 2H), 1.91 (m, 2H). $^{13}$C NMR (126 MHz, CDCl$_3$+CH$_3$OH) δ 165.91, 159.65, 159.43, 157.97, 152.85, 141.46, 138.87, 133.61, 131.94, 130.76, 130.03, 129.29, 128.80, 128.71, 128.11, 126.57, 122.12, 119.94, 116.25, 115.50, 113.04, 111.15, 71.14, 55.99, 55.47, 52.24, 45.89, 30.22. HRMS (ESI$^+$) m/z: [M+H$^+$] calcd for C$_{32}$H$_{34}$N$_3$O$_4$ 524.2549. found 524.2549.

3',6-dimethoxy-N-(5-(4-((1-methylpiperidin-4-yl)oxy)phenyl)pyridin-2-yl)-[1,1'-biphenyl]-3-carboxamide (19d)

Diisopropylazodicarboxylate (40 mg, 0.2 mmol) was added to a solution of phenol 22b (43 mg, 0.1 mmol), N-methyl-4-hydroxy-piperidine (24 mg, 0.2 mmol) and triphenylphosphine (52 mg, 0.2 mmol) in anhydrous THF (5 mL), and the resulting mixture was stirred at room temperature for 12 hours. After 12 hours, the reaction mixture was concentrated to dryness and the remaining residue was purified via column chromatography (SiO$_2$, 10:1, CH$_2$Cl$_2$:methanol) to afford desired product as a light brown solid (34 mg, 65%). $^1$H NMR (500 MHz, chloroform-d) δ 8.35 (d, J=2.5 Hz, 1H), 8.30 (d, J=8.7 Hz, 1H), 7.90-7.81 (m, 3H), 7.42 (d, J=8.6 Hz, 2H), 7.24 (t, J=8.0 Hz, 1H), 7.04-6.98 (m, 3H), 6.92 (d, J=8.7 Hz, 2H), 6.82-6.78 (m, 1H), 4.58 (m, 1H), 3.80 (s, 3H), 3.75 (s, 3H), 3.08 (m, 4H), 2.65 (s, 3H), 2.25 (m, 2H), 2.06 (m, 2H). $^{13}$C NMR (126 MHz, CDCl$_3$+CH$_3$OH) δ 165.73, 159.79, 159.20, 156.29, 150.46, 145.25, 138.69, 136.70, 132.33, 130.75, 130.71, 130.14, 129.08, 128.51, 128.13, 125.97, 121.96, 116.43, 115.17, 114.38, 112.96, 111.07, 66.72, 55.76, 55.21, 50.22, 43.80, 27.47. HRMS (ESI$^+$) m/z: [M+H$^+$] calcd for C$_{32}$H$_{34}$N$_3$O$_4$ 524.2549. found 524.2548.

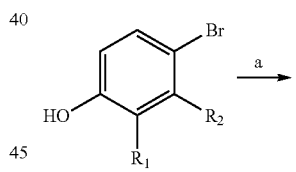

23a: R$_1$ = Me, R$_2$ = H
23b: R$_1$ = H, R$_2$ = Me
23c: R$_1$ = OMe, R$_2$ = H
23d: R$_1$ = H, R$_2$ = OMe
23e: R$_1$ = Cl, R$_2$ = H
23f: R$_1$ = H, R$_2$ = Cl

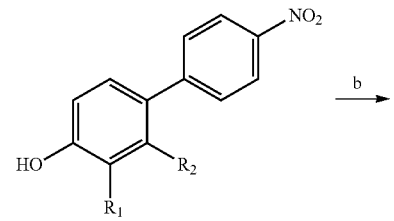

24a: R$_1$ = Me, R$_2$ = H
24b: R$_1$ = H, R$_2$ = Me
24c: R$_1$ = OMe, R$_2$ = H
24d: R$_1$ = H, R$_2$ = OMe
24e: R$_1$ = Cl, R$_2$ = H
24f: R$_1$ = H, R$_2$ = Cl

113
-continued

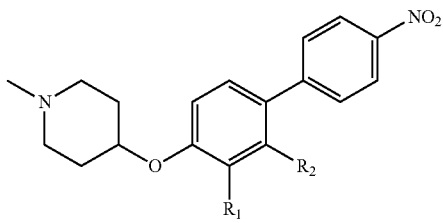

25a: R₁ = Me, R₂ = H
25b: R₁ = H, R₂ = Me
25c: R₁ = OMe, R₂ = H
25d: R₁ = H, R₂ = OMe
25e: R₁ = Cl, R₂ = H
25f: R₁ = H, R₂ = Cl

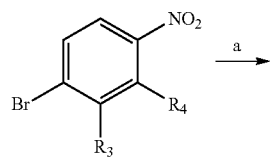

26a: R₃ = Me, R₄ = H
26b: R₃ = H, R₄ = Me
26c: R₃ = OMe, R₄ = H
26d: R₃ = H, R₄ = OMe
26e: R₃ = Cl, R₄ = H
26f: R₃ = H, R₄ = Cl

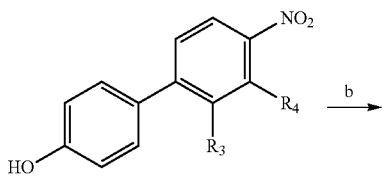

27a: R₃ = Me, R₄ = H
27b: R₃ = H, R₄ = Me
27c: R₃ = OMe, R₄ = H
27d: R₃ = H, R₄ = OMe
27e: R₃ = Cl, R₄ = H
27f: R₃ = H, R₄ = Cl

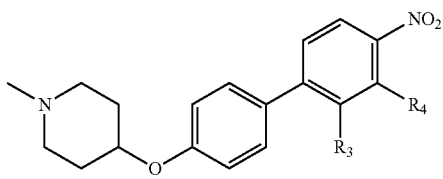

28a: R₃ = Me, R₄ = H
28b: R₃ = H, R₄ = Me
28c: R₃ = OMe, R₄ = H
28d: R₃ = H, R₄ = OMe
28e: R₃ = Cl, R₄ = H
28f: R₃ = H, R₄ = Cl

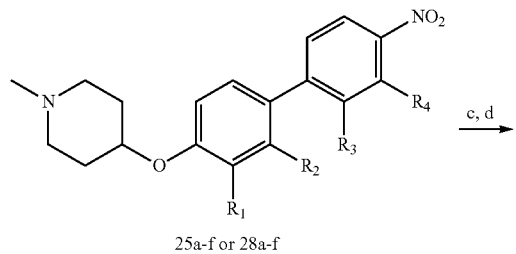

25a-f or 28a-f

114
-continued

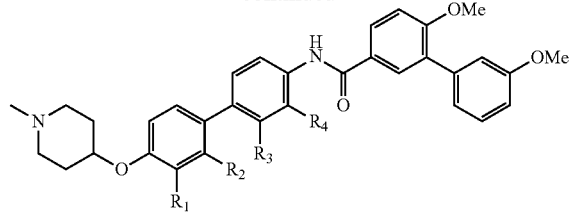

29a: R₁ = Me, R₂ = H, R₃ = H, R₄ = H
29b: R₁ = H, R₂ = Me, R₃ = H, R₄ = H
29c: R₁ = H, R₂ = H, R₃ = Me, R₄ = H
29d: R₁ = H, R₂ = H, R₃ = H, R₄ = Me
29e: R₁ = OMe, R₂ = H, R₃ = H, R₄ = H
29f: R₁ = H, R₂ = OMe, R₃ = H, R₄ = H
29g: R₁ = H, R₂ = H, R₃ = OMe, R₄ = H
29h: R₁ = H, R₂ = H, R₃ = H, R₄ = OMe
29i: R₁ = Cl, R₂ = H, R₃ = H, R₄ = H
29j: R₁ = H, R₂ = Cl, R₃ = H, R₄ = H
29k: R₁ = H, R₂ = H, R₃ = Cl, R₄ = H
29l: R₁ = H, R₂ = H, R₃ = H, R₄ = Cl

Reagents and conditions: a Pd(dppf)₂Cl₂, 2M K₂CO₃, Dioxane, 110° C., 12 h, 17%~74%; b Ph₃P, DIAD, THF, r.t., 12 h, 46%~80%; c Pd/C, MeOH, r.t., 2 h, 100%; d 5a, pyridine, DCM, r.t., 4 h, 39%~87%.

3-methyl-4'-nitro-[1,1'-biphenyl]-4-ol (24a)

General Procedure for the Synthesis of 24a-f Through Suzuki Coupling

[1,1'-Bis(diphenylphosphino)ferrocene]dichloropalladium(II) (42 mg, 0.05 mmol) and potassium carbonate solution (2M, 100 µL) were added to a solution of bromide 23a (187 mg, 1.00 mmol) and 4-nitrophenylboronic acid (249 mg, 1.50 mmol) in dioxane (5 mL). The mixture was refluxed at 110° C. for 12 hours before concentrated to dryness. The resulted brown residue was purified via column chromatography (SiO₂, 100:1, CH₂Cl₂:acetone) to afford desired product as a yellow amorphous solid (134 mg, 59%). ¹H NMR (400 MHz, chloroform-d+CD₃OD) δ 8.28 (d, J=8.9 Hz, 2H), 7.70 (d, J=8.9 Hz, 2H), 7.44 (s, 1H), 7.42-7.36 (m, 1H), 6.91 (d, J=8.3 Hz, 1H), 2.36 (s, 3H). ¹³C NMR (126 MHz, CDCl₃) δ 154.94, 146.75, 145.29, 129.30, 129.07, 125.97, 125.05, 123.15, 122.42, 114.36, 15.18. HRMS (ESI⁺) m/z: [M+H⁺] calcd for C₁₃H₁₂NO₃: 230.0817. found 230.0815.

2-methyl-4'-nitro-[1,1'-biphenyl]-4-ol (24b)

[1,1'-Bis(diphenylphosphino)ferrocene]dichloropalladium(II) (0.05 mmol) and potassium carbonate solution (2M, 100 µL) were added to a solution of bromide (23b, 1.00 mmol) and 4-nitrophenylboronic acid (1.50 mmol) in dioxane (5 mL). The mixture was refluxed at 110° C. for 12 hours before concentrated to dryness. The resulted brown residue was purified via column chromatography (SiO₂, 100:1, CH₂Cl₂:acetone) to afford desired product as a yellow amorphous solid (40%). ¹H NMR (400 MHz, chloroform-d) δ 8.13 (d, J=2.4 Hz, 1H), 8.06 (dd, J=8.4, 2.5 Hz, 1H), 7.35 (d, J=8.4 Hz, 1H), 7.26-7.14 (m, 2H), 7.00-6.91 (m, 2H), 2.37 (s, 3H). ¹³C NMR (126 MHz, CDCl₃) δ 155.57, 148.36, 146.85, 137.40, 132.38, 130.81, 130.34, 125.35, 121.08, 115.49, 20.90. HRMS (ESI⁺) m/z: [M+H⁺] calcd for C₁₃H₁₂NO₃: 230.0817. found 230.0822.

3-chloro-4'-nitro-[1,1'-biphenyl]-4-ol (24c)

[1,1'-Bis(diphenylphosphino)ferrocene]dichloropalladium(II) (0.05 mmol) and potassium carbonate solution (2M, 100 µL) were added to a solution of bromide (23c, 1.00 mmol) and 4-nitrophenylboronic acid (1.50 mmol) in dioxane (5 mL). The mixture was refluxed at 110° C. for 12 hours before concentrated to dryness. The resulted brown residue was purified via column chromatography (SiO$_2$, 100:1, CH$_2$Cl$_2$:acetone) to afford desired product as a yellow amorphous solid (74%). $^1$H NMR (500 MHz, CDCl$_3$) δ 8.34-8.23 (m, 2H), 7.71-7.64 (m, 2H), 7.62 (d, J=2.3 Hz, 1H), 7.48 (dd, J=8.5, 2.3 Hz, 1H), 7.15 (d, J=8.5 Hz, 1H), 5.74 (s, 1H). $^{13}$C NMR (126 MHz, CDCl$_3$) δ 152.10, 146.93, 145.83, 132.28, 127.88, 127.50, 127.24 (2C), 124.24 (2C), 120.75, 116.95. HRMS (ESI) m/z [M–H$^+$] calcd for C$_{12}$H$_8$ClNO$_3$ 248.0114. found 248.0117.

2-chloro-4'-nitro-[1,1'-biphenyl]-4-ol (24d)

[1,1'-Bis(diphenylphosphino)ferrocene]dichloropalladium(II) (0.05 mmol) and potassium carbonate solution (2M, 100 µL) were added to a solution of bromide (23d, 1.00 mmol) and 4-nitrophenylboronic acid (1.50 mmol) in dioxane (5 mL). The mixture was refluxed at 110° C. for 12 hours before concentrated to dryness. The resulted brown residue was purified via column chromatography (SiO$_2$, 100:1, CH$_2$Cl$_2$:acetone) to afford desired product as a yellow amorphous solid (74%). $^1$H NMR (500 MHz, chloroform-d) δ 8.25-8.14 (m, 2H), 7.58-7.43 (m, 2H), 7.11 (dt, J=8.4, 1.8 Hz, 1H), 6.92 (t, J=2.4 Hz, 1H), 6.80-6.71 (m, 1H). $^{13}$C NMR (126 MHz, CDCl$_3$) δ 158.21, 146.82, 146.34, 132.64, 131.88, 130.64, 129.48, 123.32, 117.12, 114.74. HRMS (ESI$^-$) m/z [M+K]$^+$ calcd for C$_{12}$H$_8$ClNO$_3$ 288.0214. found 288.2896.

3-methoxy-4'-nitro-[1,1'-biphenyl]-4-ol (24e)

[1,1'-Bis(diphenylphosphino)ferrocene]dichloropalladium(II) (0.05 mmol) and potassium carbonate solution (2M, 100 µL) were added to a solution of bromide (23e, 1.00 mmol) and 4-nitrophenylboronic acid (1.50 mmol) in dioxane (5 mL). The mixture was refluxed at 110° C. for 12 hours before concentrated to dryness. The resulted brown residue was purified via column chromatography (SiO$_2$, 100:1, CH$_2$Cl$_2$:acetone) to afford desired product as a yellow amorphous solid (56%). $^1$H NMR (400 MHz, chloroform-d) δ 8.27 (d, J=8.9 Hz, 2H), 7.68 (d, J=8.9 Hz, 2H), 7.17 (dd, J=8.2, 2.1 Hz, 1H), 7.10 (d, J=2.1 Hz, 1H), 7.03 (d, J=8.2 Hz, 1H), 5.78 (s, 1H, OH), 3.99 (s, 3H). $^{13}$C NMR (126 MHz, CDCl$_3$) δ 147.70, 147.16, 146.86, 131.21, 127.37, 124.28, 120.99, 115.22, 109.76, 56.23. HRMS (ESI+) m/z: [M+H$^+$] calcd for C$_{13}$H$_{12}$NO$_4$: 246.0766. found 246.0762.

2-methoxy-4'-nitro-[1,1'-biphenyl]-4-ol (24f)

[1,1'-Bis(diphenylphosphino)ferrocene]dichloropalladium(II) (0.05 mmol) and potassium carbonate solution (2M, 100 µL) were added to a solution of bromide (23f, 1.00 mmol) and 4-nitrophenylboronic acid (1.50 mmol) in dioxane (5 mL). The mixture was refluxed at 110° C. for 12 hours before concentrated to dryness. The resulted brown residue was purified via column chromatography (SiO$_2$, 100:1, CH$_2$Cl$_2$:acetone) to afford desired product as a yellow amorphous solid (44%). $^1$H NMR (500 MHz, chloroform-d) δ 8.23 (d, J=8.8 Hz, 2H), 7.66 (d, J=8.8 Hz, 2H), 7.21 (d, J=8.2 Hz, 1H), 6.62-6.45 (m, 2H), 4.96 (s, 1H, OH), 3.82 (s, 3H). $^{13}$C NMR (126 MHz, CDCl$_3$) δ 157.18, 156.88, 145.60, 144.69, 130.92, 129.41, 122.65, 120.40, 107.07, 98.88, 55.01. HRMS (ESI+) m/z: [M+H$^+$] calcd for C$_{13}$H$_{12}$NO$_4$: 246.0766. found 246.0769.

2'-methyl-4'-nitro-[1,1'-biphenyl]-4-ol (27a)

General Procedure for the Synthesis of 27a, 27c and 27e-f Through Suzuki Coupling

[1,1'-Bis(diphenylphosphino)ferrocene]dichloropalladium(II) (82 mg, 0.10 mmol) and potassium carbonate solution (2M, 100 µL) were added to a solution of 26a (621 mg, 2.36 mmol) and 4-hydroxyphenylboronic acid (326 mg, 2.36 mmol) in dioxane (4 mL). The mixture was refluxed at 110° C. for 12 hours before concentrated to dryness. The resulted brown residue was purified via column chromatography (SiO$_2$, 100:1, CH$_2$Cl$_2$:acetone) to afford desired product as a yellow amorphous solid (120 mg, 46%). $^1$H NMR (500 MHz, chloroform-d) δ 8.14 (s, 1H), 8.08 (dd, J=8.4, 2.4 Hz, 1H), 7.36 (d, J=8.4 Hz, 1H), 7.21 (d, J=8.5 Hz, 2H), 6.94 (d, J=8.6 Hz, 2H), 5.03 (s, 1H, OH), 2.38 (s, 3H). $^{13}$C NMR (126 MHz, CDCl$_3$) δ 155.63, 148.42, 146.92, 137.46, 132.45, 130.88, 130.41, 125.42, 121.14, 115.56, 20.97. HRMS (ESI$^+$) m/z: [M+H$^+$] calcd for C$_{13}$H$_{12}$NO$_3$: 230.0817. found 230.0819.

3'-methyl-4'-nitro-[1,1'-biphenyl]-4-ol (27b)

A mixture of boronic acid (300 mg, 2.175 mmol), 4-chloro-2-methyl-1-nitrobenzene (373 mg, 2.175 mmol), Pd(OAc)$_2$ (5 mg, 0.022 mmol), TBAB (723 mg, 2.175 mmol) and 2M Na$_2$CO$_3$ was irradiated by microwave at 175° C. for 10 min. The reaction mixture was then extracted by ethyl acetate. The organic layer was collected, dried (over Na$_2$SO$_4$) and concentrated under reduced pressure. The brown residue was purified by flash column chromatography (SiO$_2$, 10:1, EtOAc:Hexane) to afford desired product as a yellowish amorphous solid (80 mg, 17%). $^1$H NMR (500 MHz, chloroform-d) δ 8.09 (d, J=9.0 Hz, 1H), 7.62-7.40 (m, 4H), 7.03-6.85 (m, 2H), 4.89 (s, 1H), 2.69 (s, 3H). $^{13}$C NMR (126 MHz, CDCl$_3$) δ 155.97, 147.51, 145.34, 144.15, 134.24, 133.92, 131.29, 130.48, 128.50, 125.32, 124.59, 115.74, 20.87. HRMS (ESI$^+$) m/z [M$^+$] calcd for C$_{13}$H$_{11}$NO$_3$ 229.0739. found 229.0742.

2'-methoxy-4'-nitro-[1,1'-biphenyl]-4-ol (27c)

[1,1'-Bis(diphenylphosphino)ferrocene]dichloropalladium(II) (0.10 mmol) and potassium carbonate solution (2M, 100 µL) were added to a solution of bromide (26c, 2.36 mmol) and 4-hydroxyphenylboronic acid (2.36 mmol) in dioxane (4 mL). The mixture was refluxed at 110° C. for 12 hours before concentrated to dryness. The resulted brown residue was purified via column chromatography (SiO$_2$, 100:1, CH$_2$Cl$_2$:acetone) to afford desired product as a yellow amorphous solid (27%). $^1$H NMR (500 MHz, chloroform-d) δ 7.91 (dd, J=8.4, 2.2 Hz, 1H), 7.82 (d, J=2.2 Hz, 1H), 7.46 (d, J=8.6 Hz, 1H), 7.45 (s, 1H), 6.93 (d, J=8.6 Hz, 2H), 3.93 (s, 3H). $^{13}$C NMR (126 MHz, CDCl$_3$) δ 156.87, 155.93, 147.77, 137.21, 131.11, 130.84, 129.03, 116.38, 115.45, 106.37, 56.29. HRMS (ESI+) m/z: [M+H$^+$] calcd for C$_{13}$H$_{12}$NO$_4$: 246.0766. found 246.0763.

3'-methoxy-4'-nitro-[1,1'-biphenyl]-4-ol (27d)

A mixture of boronic acid (300 mg, 2.18 mmol), 4-chloro-2-methoxy-1-nitrobenzene (408 mg, 2.18 mmol), Pd(OAc)$_2$ (5 mg, 0.022 mmol), TBAB (723 mg, 2.18 mmol) and 2M Na$_2$CO$_3$ (3.27 ml, 6.54 mmol) was irradiated by microwave at 175° C. for 10 min. The reaction mixture was then extracted by ethyl acetate. The organic layer was collected, dried (over Na$_2$SO$_4$) and concentrated under reduced pressure. The brown residue was purified by column chromatography (SiO$_2$, 10:1, EtOAc:Hexane) to afford desired product as a yellowish amorphous solid (95 mg, 18%). $^1$H NMR (400 MHz, chloroform-d) δ 7.93 (d, J=8.5 Hz, 1H), 7.48-7.42 (m, 2H), 7.19-7.11 (m, 2H), 6.95-6.87 (m, 2H), 4.00 (s, 3H). $^{13}$C NMR (126 MHz, CDCl$_3$) δ 156.80, 152.76, 146.98, 136.59, 129.71, 127.71, 125.69, 117.48, 115.07, 110.41, 55.59. Exact Mass, Calculated for C$_{13}$H$_{11}$NO$_4$ (M−H): 244.0546. found (M−H): 244.0542.

2'-chloro-4'-nitro-[1,1'-biphenyl]-4-ol (27e)

[1,1'-Bis(diphenylphosphino)ferrocene]dichloropalladium(II) (0.10 mmol) and potassium carbonate solution (2M, 100 μL) were added to a solution of bromide (26c, 2.36 mmol) and 4-hydroxyphenylboronic acid (2.36 mmol) in dioxane (4 mL). The mixture was refluxed at 110° C. for 12 hours before concentrated to dryness. The resulted brown residue was purified via column chromatography (SiO$_2$, 100:1, CH$_2$Cl$_2$:acetone) to afford desired product as a yellow amorphous solid (59%). $^1$H NMR (500 MHz, CDCl$_3$) δ 8.36 (d, J=2.4 Hz, 1H), 8.16 (dd, J=8.5, 2.3 Hz, 1H), 7.51 (d, J=8.5 Hz, 1H), 7.44-7.31 (m, 2H), 6.99-6.91 (m, 2H), 4.91 (s, 1H). $^{13}$C NMR (126 MHz, CDCl$_3$) δ 156.08, 147.01, 146.55, 133.51, 131.81, 130.77 (2C), 129.87, 125.33, 121.83, 115.35 (2C). HRMS (ESI$^-$) m/z [M−H$^+$] calcd for C$_{12}$H$_8$ClNO$_3$ 248.0114. found 248.0118.

3'-chloro-4'-nitro-[1,1'-biphenyl]-4-ol (27f)

[1,1'-Bis(diphenylphosphino)ferrocene]dichloropalladium(II) (0.10 mmol) and potassium carbonate solution (2M, 100 μL) were added to a solution of bromide (26c, 2.36 mmol) and 4-hydroxyphenylboronic acid (2.36 mmol) in dioxane (4 mL). The mixture was refluxed at 110° C. for 12 hours before concentrated to dryness. The resulted brown residue was purified via column chromatography (SiO$_2$, 100:1, CH$_2$Cl$_2$:acetone) to afford desired product as a yellow amorphous solid (42%). $^1$H NMR (500 MHz, chloroform-d) δ 7.95 (d, J=8.5 Hz, 1H), 7.67 (d, J=1.9 Hz, 1H), 7.52 (dd, J=8.5, 2.0 Hz, 1H), 7.47-7.41 (m, 2H), 6.95-6.86 (m, 2H). $^{13}$C NMR (126 MHz, CDCl$_3$+CH$_3$OH) δ 154.32, 142.77, 141.49, 125.48, 124.80, 124.64, 123.86, 122.46, 121.13, 112.19. HRMS (ESI$^-$) m/z [M−H$^+$] calcd for C$_{12}$H$_8$ClNO$_3$ 248.0114. found 248.0108.

1-methyl-4-((3-methyl-4'-nitro-[1,1'-biphenyl]-4-yl)oxy)piperidine (25a)

General Procedure for the Synthesis of 25a-f and 28a-f

Diisopropylazodicarboxylate (0.94 mL, 2.40 mmol) was added to a solution of phenol (280 mg, 1.20 mmol), PPh$_3$ (1.28 g, 2.40 mmol) and 4-hydroxy N-methyl piperidine (280 mg, 2.40 mmol) in THF (8 mL) at room temperature. The reaction mixture was stirred for 18 hours before the removal of solvent under reduced pressure. The remaining residue was purified by silica gel column chromatography (eluting with methylene chloride:methanol=99:1 to 20:1) to yield 25a as a light brown amorphous solid (180 mg, 46%). $^1$H NMR (500 MHz, chloroform-d) δ 8.35-8.18 (m, 2H), 7.75-7.62 (m, 2H), 7.49-7.36 (m, 2H), 6.92 (d, J=8.4 Hz, 1H), 4.45 (s, 1H), 2.66 (s, 2H), 2.44-2.34 (m, 2H), 2.33 (s, 3H), 2.31 (s, 3H), 2.11-1.86 (m, 4H). $^{13}$C NMR (126 MHz, CDCl$_3$) δ 156.59, 147.57, 146.54, 130.70, 130.04, 128.86, 127.15, 124.23, 113.06, 52.57, 46.47, 30.92, 29.85, 16.80. Exact Mass Calculated for C$_{19}$H$_{23}$N$_2$O$_3$ (M+H$^+$): 327.1709. found (M+H$^+$) 327.1724.

1-methyl-4-((2-methyl-4'-nitro-[1,1'-biphenyl]-4-yl)oxy)piperidine (25b)

Diisopropylazo dicarboxylate (2.40 mmol) was added to a solution of phenol (1.20 mmol), PPh$_3$ (2.40 mmol) and 4-hydroxy N-methyl piperidine (2.40 mmol) in THF (8 mL) at room temperature. The reaction mixture was stirred for 18 hours before the removal of solvent under reduced pressure. The remaining residue was purified by silica gel column chromatography (eluting with methylene chloride:methanol=99:1 to 20:1) to yield a light brown amorphous solid (61%). $^1$H NMR (500 MHz, chloroform-d) δ 8.26 (d, J=8.9 Hz, 2H), 7.68 (d, J=8.9 Hz, 2H), 7.47-7.37 (m, 2H), 6.92 (d, J=8.5 Hz, 1H), 4.49 (s, 1H), 2.77-2.68 (m, 2H), 2.50 (s, 2H), 2.39 (s, 3H), 2.31 (s, 3H), 2.15-2.08 (m, 2H), 2.02-1.92 (m, 2H). $^{13}$C NMR (126 MHz, CDCl$_3$) δ 156.51, 147.61, 146.68, 130.96, 130.20, 127.28, 124.35, 113.11, 52.42, 46.27, 30.57, 16.90. IR 2954, 2923, 2852, 2358, 2341, 1593, 1514, 1485, 1340, 1307, 1274, 1247, 1135, 1108, 1039 cm$^{-1}$. Exact Mass: Calculated for C$_{19}$H$_{22}$N$_2$O$_3$ (M+Na$^+$) 349.1528. found 349.1528.

4-((3-methoxy-4'-nitro-[1,1'-biphenyl]-4-yl)oxy)-1-methylpiperidine (25c)

Diisopropylazo dicarboxylate (2.40 mmol) was added to a solution of phenol (1.20 mmol), PPh$_3$ (2.40 mmol) and 4-hydroxy N-methyl piperidine (2.40 mmol) in THF (8 mL) at room temperature. The reaction mixture was stirred for 18 hours before the removal of solvent under reduced pressure. The remaining residue was purified by silica gel column chromatography (eluting with methylene chloride:methanol=99:1 to 20:1) to yield a yellow amorphous solid (80%). $^1$H NMR (500 MHz, chloroform-d:acetone-d$_6$ (10:1)) δ 8.25 (d, J=8.9 Hz, 2H), 7.67 (d, J=8.8 Hz, 2H), 7.18-7.08 (m, 2H), 7.00 (d, J=8.4 Hz, 1H), 4.44 (dp, J=6.9, 3.4 Hz, 1H), 3.92 (s, 3H), 2.90 (ddd, J=11.9, 8.6, 3.4 Hz, 2H), 2.70-2.60 (m, 1H), 2.43 (s, 3H), 2.11 (ddd, J=12.5, 8.5, 3.8 Hz, 2H), 1.99 (s, 3H). $^{13}$C NMR (126 MHz, CDCl$_3$:acetone-d$_6$ (10:1)) δ 176.70, 151.31, 146.78, 132.86, 127.43, 124.20, 120.20, 117.41, 111.54, 56.26, 44.99, 22.83. Exact Mass: Calculated for C$_{19}$H$_{22}$N$_2$O$_4$Na (M+Na) 365.1477. found 365.1473.

4-((2-methoxy-4'-nitro-[1,1'-biphenyl]-4-yl)oxy)-1-methylpiperidine (25d)

Diisopropylazo dicarboxylate (2.40 mmol) was added to a solution of phenol (1.20 mmol), PPh$_3$ (2.40 mmol) and 4-hydroxy N-methyl piperidine (2.40 mmol) in THF (8 mL) at room temperature. The reaction mixture was stirred for 18 hours before the removal of solvent under reduced pressure. The remaining residue was purified by silica gel column chromatography (eluting with methylene chloride:methanol=99:1 to 20:1) to yield a yellow amorphous solid (78%). $^1$H NMR (500 MHz, chloroform-d) δ 8.23 (d, J=8.9 Hz, 2H), 7.67 (d, J=8.8 Hz, 2H), 7.25 (d, J=8.8 Hz, 1H), 6.59 (m, 2H), 4.41 (m, 1H), 3.82 (s, 3H), 2.75 (m, 2H), 2.38 (m, 2H), 2.36 (s, 3H), 2.06 (m, 2H), 2.00-1.82 (m, 2H). $^{13}$C NMR (126 MHz, CDCl$_3$) δ 159.53, 157.90, 146.38, 145.52, 131.49, 130.18, 123.45, 121.25, 106.92, 101.09, 70.09, 55.80, 52.72, 46.31, 30.88. Exact Mass: Calculated for $C_{19}H_{22}N_2O_4$ (M+H) 343.1658. found 365.1658.

4-((3-chloro-4'-nitro-[1,1'-biphenyl]-4-yl)oxy)-1-methylpiperidine (25e)

Diisopropylazo dicarboxylate (2.40 mmol) was added to a solution of phenol (1.20 mmol), $PPh_3$ (2.40 mmol) and 4-hydroxy N-methyl piperidine (2.40 mmol) in THF (8 mL) at room temperature. The reaction mixture was stirred for 18 hours before the removal of solvent under reduced pressure. The remaining residue was purified by silica gel column chromatography (eluting with methylene chloride:methanol=99:1 to 20:1) to yield a yellow amorphous solid (83%). $^1$H NMR (500 MHz, $CDCl_3$) δ 8.22 (d, J=8.8 Hz, 2H), 7.77-7.52 (m, 3H), 7.46 (dd, J=8.5, 2.4 Hz, 1H), 7.06 (d, J=8.6 Hz, 1H), 4.81 (m, 1H), 3.49-3.37 (m, 2H), 3.23 (m, 2H), 2.87 (s, 3H), 2.32 (m, 2H), 2.24-2.10 (m, 2H). $^{13}$C NMR (126 MHz, $CDCl_3+CH_3OH$) δ 147.99, 142.90, 141.28, 129.32, 125.35, 123.24, 123.19, 122.97, 120.71, 120.08, 120.04, 111.82, 67.46, 54.11, 44.12, 26.76. HRMS ($ESI^+$) m/z [M+H$^+$] calcd for $C_{18}H_{19}ClN_2O_3$ 347.1163. found 347.1159.

4-((2-chloro-4'-nitro-[1,1'-biphenyl]-4-yl)oxy)-1-methylpiperidine (25f)

Diisopropylazo dicarboxylate (2.40 mmol) was added to a solution of phenol (1.20 mmol), $PPh_3$ (2.40 mmol) and 4-hydroxy N-methyl piperidine (2.40 mmol) in THF (8 mL) at room temperature. The reaction mixture was stirred for 18 hours before the removal of solvent under reduced pressure. The remaining residue was purified by silica gel column chromatography (eluting with methylene chloride:methanol=99:1 to 20:1) to yield a yellow amorphous solid (78%). $^1$H NMR (500 MHz, chloroform-d) δ 8.28 (d, J=8.7 Hz, 2H), 7.60 (d, J=8.7 Hz, 2H), 7.27 (d, J=0.7 Hz, 1H), 7.07 (d, J=2.5 Hz, 1H), 6.92 (dd, J=8.5, 2.5 Hz, 1H), 4.42 (m, 1H), 2.76 (m, 2H), 2.42 (m, 2H), 2.39 (s, 3H), 2.11 (m, 2H), 1.93 (m, 2H). $^{13}$C NMR (126 MHz, $CDCl_3+CH_3OH$) δ 158.30, 147.19, 145.92, 133.15, 131.99, 130.72, 126.23, 123.55, 117.64, 115.13, 72.44, 52.65, 46.15, 30.40. HRMS ($ESI^+$) m/z [M+H$^+$] calcd for $C_{18}H_{19}ClN_2O_3$ 347.1163. found 347.1158.

1-methyl-4-((2'-methyl-4'-nitro-[1,1'-biphenyl]-4-yl)oxy)piperidine (28a)

Diisopropylazo dicarboxylate (2.40 mmol) was added to a solution of phenol (1.20 mmol), $PPh_3$ (2.40 mmol) and 4-hydroxy N-methyl piperidine (2.40 mmol) in THF (8 mL) at room temperature. The reaction mixture was stirred for 18 hours before the removal of solvent under reduced pressure. The remaining residue was purified by silica gel column chromatography (eluting with methylene chloride:methanol=99:1 to 20:1) to yield a yellow amorphous solid (73%). $^1$H NMR (500 MHz, methanol-$d_4$) δ 8.14 (d, J=2.4 Hz, 1H), 8.09-8.02 (m, 1H), 7.39 (d, J=8.4 Hz, 1H), 7.31-7.24 (m, 2H), 7.03 (d, J=8.7 Hz, 2H), 4.49 (q, J=5.1, 4.6 Hz, 1H), 2.76 (s, 2H), 2.50-2.40 (m, 2H), 2.37 (s, 3H), 2.33 (s, 3H), 2.05 (ddd, J=12.7, 6.5, 3.1 Hz, 2H), 1.91-1.81 (m, 2H). $^{13}$C NMR (126 MHz, MeOD) δ 158.59, 149.66, 148.08, 138.64, 133.53, 131.82, 131.22, 126.00, 124.48, 121.80, 116.90, 112.62, 79.50, 53.25, 46.10, 31.30, 20.88, 16.60. Exact Mass Calculated for $C_{19}H_{22}N_2O_4Na$ (M+Na): 365.1477. found 365.1481.

1-methyl-4-((3'-methyl-4'-nitro-[1,1'-biphenyl]-4-yl)oxy)piperidine (28b)

Diisopropylazo dicarboxylate (2.40 mmol) was added to a solution of phenol (1.20 mmol), $PPh_3$ (2.40 mmol) and 4-hydroxy N-methyl piperidine (2.40 mmol) in THF (8 mL) at room temperature. The reaction mixture was stirred for 18 hours before the removal of solvent under reduced pressure. The remaining residue was purified by silica gel column chromatography (eluting with methylene chloride:methanol=99:1 to 20:1) to yield a yellow amorphous solid (75%). $^1$H NMR (500 MHz, chloroform-d) δ 8.08 (d, J=9.1 Hz, 1H), 7.55 (d, J=8.7 Hz, 2H), 7.52-7.46 (m, 2H), 7.01 (d, J=8.8 Hz, 2H), 4.46 (s, 1H), 2.83-2.79 (m, 2H), 2.69 (s, 3H), 2.56-2.48 (m, 2H), 2.42 (s, 3H), 2.18-2.14 (m, 2H), 1.98-1.94 (m, 2H). $^{13}$C NMR (126 MHz, $CDCl_3$) δ 158.10, 147.64, 145.77, 134.69, 131.60, 130.90, 128.79, 125.78, 125.02, 116.59, 71.39, 52.31, 45.99, 30.29, 21.34. Exact Mass Calculated for $C_{19}H_{22}N_2O_4$ (M+H): 327.1709. found: 327.1721.

4-((2'-methoxy-4'-nitro-[1,1'-biphenyl]-4-yl)oxy)-1-methylpiperidine (28c)

Diisopropylazo dicarboxylate (2.40 mmol) was added to a solution of phenol (1.20 mmol), $PPh_3$ (2.40 mmol) and 4-hydroxy N-methyl piperidine (2.40 mmol) in THF (8 mL) at room temperature. The reaction mixture was stirred for 18 hours before the removal of solvent under reduced pressure. The remaining residue was purified by silica gel column chromatography (eluting with methylene chloride:methanol=99:1 to 20:1) to yield a yellow amorphous solid (65%). $^1$H NMR (400 MHz, chloroform-d) δ 7.96-7.87 (m, 1H), 7.82 (d, J=2.2 Hz, 1H), 7.49 (d, J=8.8 Hz, 2H), 7.44 (d, J=8.4 Hz, 1H), 6.98 (d, J=8.8 Hz, 2H), 4.41 (m, 1H), 3.93 (s, 3H), 2.82-2.63 (m, 2H), 2.39 (m, 2H), 2.36 (s, 3H), 2.09 (m, 2H), 1.92 (m, 2H). $^{13}$C NMR (126 MHz, $CDCl_3$) δ 157.69, 156.87, 147.77, 137.20, 130.97, 130.83, 128.90, 116.39, 115.79, 106.37, 70.23, 56.30, 52.29, 45.98, 30.45. Exact Mass Calculated for $C_{19}H_{22}N_2O_4Na$ (M+Na$^+$): 365.1477. found: 327.1483.

4-((3'-methoxy-4'-nitro-[1,1'-biphenyl]-4-yl)oxy)-1-methylpiperidine (28d)

Diisopropylazo dicarboxylate (2.40 mmol) was added to a solution of phenol (1.20 mmol), $PPh_3$ (2.40 mmol) and 4-hydroxy N-methyl piperidine (2.40 mmol) in THF (8 mL) at room temperature. The reaction mixture was stirred for 18 hours before the removal of solvent under reduced pressure. The remaining residue was purified by silica gel column chromatography (eluting with methylene chloride:methanol=99:1 to 20:1) to yield a yellow amorphous solid (60%). $^1$H NMR (400 MHz, chloroform-d) δ 7.96 (d, J=8.3 Hz, 1H), 7.53 (d, J=8.7 Hz, 2H), 7.22-7.14 (m, 2H), 7.01 (d, J=8.7 Hz, 2H), 4.45 (s, 1H), 4.03 (s, 3H), 2.89-2.69 (m, 2H), 2.52-2.42 (m, 2H), 2.37 (s, 3H), 2.15 (d, J=16.9 Hz, 2H), 1.94 (s, 2H). $^{13}$C NMR (126 MHz, $CDCl_3$) δ 158.23, 153.75, 147.55, 137.94, 131.76, 128.73, 126.72, 118.62, 116.53, 111.59, 56.67, 52.30, 45.99, 30.34. Exact Mass Calculated for $C_{19}H_{22}N_2O_4$ (M+H): 343.1658. found 343.1658.

4-((2'-chloro-4'-nitro-[1,1'-biphenyl]-4-yl)oxy)-1-methylpiperidine (28e)

Diisopropylazo dicarboxylate (2.40 mmol) was added to a solution of phenol (1.20 mmol), $PPh_3$ (2.40 mmol) and 4-hydroxy N-methyl piperidine (2.40 mmol) in THF (8 mL)

at room temperature. The reaction mixture was stirred for 18 hours before the removal of solvent under reduced pressure. The remaining residue was purified by silica gel column chromatography (eluting with methylene chloride:methanol=99:1 to 20:1) to yield a yellow amorphous solid (81%). $^1$H NMR (500 MHz, chloroform-d) δ 8.35 (d, J=2.3 Hz, 1H), 8.15 (dt, J=8.4, 2.2 Hz, 1H), 7.51 (d, J=8.5 Hz, 1H), 7.43-7.34 (m, 2H), 7.05-6.94 (m, 2H), 4.41 (dt, J=7.2, 3.7 Hz, 1H), 2.83-2.65 (m, 2H), 2.34 (s, 3H), 2.07 (ddd, J=13.9, 7.1, 3.5 Hz, 2H), 1.92 (ddd, J=13.2, 7.9, 3.7 Hz, 2H). $^{13}$C NMR (126 MHz, CDCl$_3$) δ 158.01, 146.90, 146.62, 133.42, 131.78, 130.57, 129.47, 125.32, 121.80, 115.58, 71.98, 52.60, 46.17, 30.74. HRMS (ESI$^+$) m/z [M+H$^+$] calcd for C$_{18}$H$_{19}$ClN$_2$O$_3$ 347.1163. found 347.1136.

4-((3'-chloro-4'-nitro-[1,1'-biphenyl]-4-yl)oxy)-1-methylpiperidine (28f)

Diisopropylazo dicarboxylate (2.40 mmol) was added to a solution of phenol (1.20 mmol), PPh$_3$ (2.40 mmol) and 4-hydroxy N-methyl piperidine (2.40 mmol) in THF (8 mL) at room temperature. The reaction mixture was stirred for 18 hours before the removal of solvent under reduced pressure. The remaining residue was purified by silica gel column chromatography (eluting with methylene chloride:methanol=99:1 to 20:1) to yield a yellow amorphous solid (63%). $^1$H NMR (500 MHz, chloroform-d) δ 7.99 (d, J=8.5 Hz, 1H), 7.71 (d, J=1.9 Hz, 1H), 7.62-7.47 (m, 3H), 7.02 (d, J=8.7 Hz, 2H), 4.44 (m, 1H), 2.76 (m, 2H), 2.42 (m, 2H), 2.38 (s, 3H), 2.10 (m, 2H), 1.93 (m, 2H). $^{13}$C NMR (126 MHz, CDCl$_3$) δ 158.71, 146.52, 145.96, 130.06, 129.83, 128.80, 128.10, 126.65, 125.45, 116.72, 71.93, 52.54, 46.21, 30.62. HRMS (ESI$^+$) m/z [M+H$^+$] calcd for C$_{18}$H$_{19}$ClN$_2$O$_3$ 347.1163. found 347.1159.

3',6-dimethoxy-N-(3'-methyl-4'-((1-methylpiperidin-4-yl)oxy)-[1,1'-biphenyl]-4-yl)-[1,1'-biphenyl]-3-carboxamide 29a General Procedure for the Synthesis of 29a-l Palladium on carbon (10% w/w, 20 mg) was added to a solution of 25a (164 mg, 0.5 mmol) in methanol. The reaction mixture was then stirred under hydrogen atmosphere overnight before filtration. The filtrate was concentrated to dryness to get aniline. The aniline was dissolved in anhydrous dichloromethane and slowly added to an ice-cooled solution of 4-(chlorocarbonyl)-2-(3-methylbut-2-en-1-yl)phenyl acetate (276 mg, 1.0 mmol) and pyridine (0.2 mL) in anhydrous dichloromethane (2 mL). The reaction mixture was allowed to stir at room temperature for 4 hours. After 4 hours, the solvent was removed and the residue was purified via column chromatography (SiO$_2$, 10:1, CH$_2$Cl$_2$:methanol) to afford 29a as a white amorphous solid (210 mg, 78%). $^1$H NMR (500 MHz, chloroform-d) δ 8.20 (s, 1H), 7.98 (dd, J=8.6, 2.4 Hz, 1H), 7.89 (d, J=2.4 Hz, 1H), 7.75 (d, J=8.6 Hz, 1H), 7.54 (d, J=8.6 Hz, 1H), 7.42-7.40 (m, 1H), 7.37-7.32 (m, 2H), 7.17-7.14 (m, 1H), 7.12 (dd, J=2.6, 1.5 Hz, 1H), 7.07 (d, J=8.7 Hz, 1H), 6.93 (dd, J=8.3, 2.6 Hz, 1H), 6.84 (d, J=8.5 Hz, 1H), 4.58 (m, 1H), 3.90 (s, 3H), 3.86 (s, 3H), 3.00 (m, 4H), 2.64 (s, 3H), 2.45-2.34 (m, 2H), 2.30 (s, 3H), 2.17-2.06 (m, 2H). $^{13}$C NMR (126 MHz, CDCl$_3$) δ 165.23, 159.32, 154.02, 149.81, 138.84, 137.10, 136.60, 133.49, 130.61, 129.75, 129.69, 129.15, 128.51, 127.79, 127.14, 127.08, 125.22, 122.01, 120.66, 115.33, 112.94, 112.83, 111.03, 67.89, 55.85, 55.35, 50.88, 44.64, 28.28, 16.63. HRMS (ESI$^+$) m/z [M+H$^+$] calcd for C$_{34}$H$_{37}$N$_2$O$_4$ 537.2753. found 537.2754.

3',6-dimethoxy-N-(2'-methyl-4'-((1-methylpiperidin-4-yl)oxy)-[1,1'-biphenyl]-4-yl)-[1,1'-biphenyl]-3-carboxamide (29b)

Palladium on carbon (10% w/w, 20 mg) was added to a solution of 25b (0.5 mmol) in methanol. The reaction mixture was then stirred under hydrogen atmosphere overnight before filtration. The filtrate was concentrated to dryness to get aniline. The aniline was dissolved in anhydrous dichloromethane and slowly added to an ice-cooled solution of 4-(chlorocarbonyl)-2-(3-methylbut-2-en-1-yl)phenyl acetate (5a, 1.0 mmol) and pyridine (0.2 mL) in anhydrous dichloromethane (2 mL). The reaction mixture was allowed to stir at room temperature for 4 hours. After 4 hours, the solvent was removed and the residue was purified via column chromatography (SiO$_2$, 10:1, CH$_2$Cl$_2$:methanol) to afford a white amorphous solid (81%). $^1$H NMR (500 MHz, chloroform-d) δ 7.89 (s, 1H), 7.87 (dd, J=8.6, 2.4 Hz, 1H), 7.77 (d, J=2.4 Hz, 1H), 7.63 (d, J=8.6 Hz, 2H), 7.47 (d, J=8.6 Hz, 2H), 7.34-7.33 (m, 1H), 7.31-7.26 (m, 2H), 7.06 (dt, J=7.6, 1.3 Hz, 1H), 7.03 (dd, J=2.7, 1.6 Hz, 1H), 6.99 (d, J=8.6 Hz, 1H), 6.86 (dd, J=8.3, 2.7 Hz, 1H), 6.79 (d, J=8.5 Hz, 1H), 4.50 (s, 1H), 3.82 (s, 3H), 3.78 (s, 3H), 2.94-2.74 (m, 4H), 2.52 (s, 3H), 2.33-2.25 (m, 3H), 2.23 (m, 2H), 2.06-1.98 (m, 2H). $^{13}$C NMR (126 MHz, CDCl$_3$) δ 165.12, 159.34, 154.16, 138.83, 136.97, 136.71, 133.41, 130.69, 129.69, 129.60, 129.17, 128.45, 127.85, 127.61, 127.20, 127.10, 125.20, 121.99, 120.50, 115.33, 112.96, 112.87, 111.07, 68.06, 55.87, 55.35, 50.99, 44.88, 28.84, 16.64. HRMS (ESI$^+$) m/z [M+H$^+$] calcd for C$_{34}$H$_{37}$N$_2$O$_4$ 537.2753. found 537.2756.

3',6-dimethoxy-N-(2-methyl-4'-((1-methylpiperidin-4-yl)oxy)-[1,1'-biphenyl]-4-yl)-[1,1'-biphenyl]-3-carboxamide (29c)

Palladium on carbon (10% w/w, 20 mg) was added to a solution of 25c (0.5 mmol) in methanol. The reaction mixture was then stirred under hydrogen atmosphere overnight before filtration. The filtrate was concentrated to dryness to get aniline. The aniline was dissolved in anhydrous dichloromethane and slowly added to an ice-cooled solution of 4-(chlorocarbonyl)-2-(3-methylbut-2-en-1-yl)phenyl acetate (5a, 1.0 mmol) and pyridine (0.2 mL) in anhydrous dichloromethane (2 mL). The reaction mixture was allowed to stir at room temperature for 4 hours. After 4 hours, the solvent was removed and the residue was purified via column chromatography (SiO$_2$, 10:1, CH$_2$Cl$_2$:methanol) to afford a white amorphous solid (76%). $^1$H NMR (500 MHz, chloroform-d) δ 7.91 (s, 1H), 7.87 (dd, J=8.6, 2.4 Hz, 1H), 7.77 (d, J=2.3 Hz, 1H), 7.50 (d, J=2.3 Hz, 1H), 7.44 (dd, J=8.3, 2.3 Hz, 1H), 7.28 (t, J=7.9 Hz, 1H), 7.16 (d, J=8.6 Hz, 2H), 7.12 (d, J=8.3 Hz, 1H), 7.06 (dt, J=7.8, 1.2 Hz, 1H), 7.03 (dd, J=2.7, 1.5 Hz, 1H), 6.99 (d, J=8.6 Hz, 1H), 6.87-6.83 (m, 3H), 4.46 (m, 1H), 3.81 (s, 3H), 3.78 (s, 3H), 2.92 (m, 2H), 2.82-2.67 (m, 2H), 2.51 (s, 3H), 2.30-2.22 (m, 2H), 2.21 (s, 3H), 1.99 (m, 2H). $^{13}$C NMR (126 MHz, CDCl$_3$) δ 165.17, 159.33, 159.31, 155.62, 149.82, 138.85, 137.48, 137.01, 136.26, 134.56, 130.64, 130.56, 130.41, 129.62, 129.16, 128.44, 127.14, 122.00, 117.77, 115.46, 115.32, 112.95, 111.05, 69.02, 55.86, 55.35, 51.35, 44.89, 28.70, 20.75. HRMS (ESI$^+$) m/z [M+H$^+$] calcd for C$_{34}$H$_{37}$N$_2$O$_4$ 537.2753. found 537.2762.

3',6-dimethoxy-N-(3-methyl-4'-((1-methylpiperidin-4-yl)oxy)-[1,1'-biphenyl]-4-yl)-[1,1'-biphenyl]-3-carboxamide (29d)

Palladium on carbon (10% w/w, 20 mg) was added to a solution of 25d (0.5 mmol) in methanol. The reaction mixture was then stirred under hydrogen atmosphere overnight before filtration. The filtrate was concentrated to dryness to get aniline. The aniline was dissolved in anhydrous dichloromethane and slowly added to an ice-cooled solution of 4-(chlorocarbonyl)-2-(3-methylbut-2-en-1-yl)phenyl acetate (5a, 1.0 mmol) and pyridine (0.2 mL) in anhydrous dichloromethane (2 mL). The reaction mixture was allowed to stir at room temperature for 4 hours. After 4 hours, the solvent was removed and the residue was purified via column chromatography (SiO$_2$, 10:1, CH$_2$Cl$_2$:methanol) to afford a white amorphous solid (58%). $^1$H NMR (500 MHz, chloroform-d) δ 8.01 (s, NH), 7.90 (dd, J=8.5, 2.4 Hz, 1H), 7.85-7.78 (m, 2H), 7.48 (dd, J=8.4, 1.4 Hz, 2H), 7.39 (d, J=8.6 Hz, 2H), 7.35-7.30 (m, 1H), 7.12-7.08 (m, 1H), 7.08-7.03 (m, 2H), 6.93 (dd, J=8.5, 1.4 Hz, 2H), 6.91-6.87 (m, 1H), 4.52-4.38 (m, 1H), 3.86 (d, J=1.2 Hz, 3H), 3.82 (d, J=1.3 Hz, 3H), 2.92-2.54 (m, 4H), 2.44 (s, 3H), 2.34 (s, 3H), 2.11 (d, J=10.8 Hz, 2H), 1.96 (s, 2H). $^{13}$C NMR (126 MHz, CDCl$_3$) δ 165.91, 159.56, 159.44, 156.55, 139.02, 138.03, 134.74, 133.89, 130.88, 130.78, 129.94, 129.33, 128.98, 128.58, 128.29 (2C), 127.10, 125.16, 124.33, 122.17, 116.44 (2C), 115.43, 113.08, 111.25, 69.95, 55.97, 55.37, 51.73, 45.43, 29.44, 18.24. HRMS (ESI$^+$) m/z [M+H$^+$] calcd for C$_{34}$H$_{36}$N$_2$O$_4$ 537.2753. found 537.2757.

3',6-dimethoxy-N-(3'-methoxy-4'-((1-methylpiperidin-4-yl)oxy)-[1,1'-biphenyl]-4-yl)-[1,1'-biphenyl]-3-carboxamide (29e)

Palladium on carbon (10% w/w, 20 mg) was added to a solution of 25e (0.5 mmol) in methanol. The reaction mixture was then stirred under hydrogen atmosphere overnight before filtration. The filtrate was concentrated to dryness to get aniline. The aniline was dissolved in anhydrous dichloromethane and slowly added to an ice-cooled solution of 4-(chlorocarbonyl)-2-(3-methylbut-2-en-1-yl)phenyl acetate (5a, 1.0 mmol) and pyridine (0.2 mL) in anhydrous dichloromethane (2 mL). The reaction mixture was allowed to stir at room temperature for 4 hours. After 4 hours, the solvent was removed and the residue was purified via column chromatography (SiO$_2$, 10:1, CH$_2$Cl$_2$:methanol) to afford a white amorphous solid (68%). $^1$H NMR (500 MHz, DMSO-d$_6$) δ 10.25 (s, 1H, NH), 8.03 (dd, J=8.6, 2.4 Hz, 1H), 7.98 (d, J=2.4 Hz, 1H), 7.85 (d, J=8.4 Hz, 2H), 7.65 (d, J=8.4 Hz, 2H), 7.37 (t, J=7.9 Hz, 1H), 7.27 (s, 1H), 7.26 (d, J=5.7 Hz, 1H), 7.18 (d, J=9.0 Hz, 1H), 7.14-7.07 (m, 3H), 6.95 (dd, J=8.3, 2.6 Hz, 1H), 4.51-4.39 (m, 1H), 3.87 (s, 3H), 3.86 (s, 3H), 3.80 (s, 3H), 3.09 (m, 2H), 2.83 (m, 2H), 2.57 (s, 3H), 2.05 (m, 2H), 1.83 (m, 2H). $^{13}$C NMR (126 MHz, DMSO) δ 164.74, 158.92, 158.71, 150.62, 149.53, 145.14, 138.77, 138.30, 134.92, 134.04, 129.80, 129.20, 129.14, 129.10, 126.80, 126.44, 121.73, 120.62, 118.41, 115.14, 112.54, 111.40, 110.68, 71.29, 55.84, 55.67, 55.07, 51.02, 43.45, 28.64. HRMS (ESI$^+$) m/z [M+H$^+$] calcd for C$_{34}$H$_{36}$N$_2$O$_5$ 553.2702. found 553.2700.

3',6-dimethoxy-N-(2'-methoxy-4'-((1-methylpiperidin-4-yl)-oxy)-[1,1'-biphenyl]-4-yl)-[1,1'-biphenyl]-3-carboxamide (29f)

Palladium on carbon (10% w/w, 20 mg) was added to a solution of 25f (0.5 mmol) in methanol. The reaction mixture was then stirred under hydrogen atmosphere overnight before filtration. The filtrate was concentrated to dryness to get aniline. The aniline was dissolved in anhydrous dichloromethane and slowly added to an ice-cooled solution of 4-(chlorocarbonyl)-2-(3-methylbut-2-en-1-yl)phenyl acetate (5a, 1.0 mmol) and pyridine (0.2 mL) in anhydrous dichloromethane (2 mL). The reaction mixture was allowed to stir at room temperature for 4 hours. After 4 hours, the solvent was removed and the residue was purified via column chromatography (SiO$_2$, 10:1, CH$_2$Cl$_2$:methanol) to afford a white amorphous solid (72%). $^1$H NMR (500 MHz, chloroform-d) δ 7.86 (m, 2H), 7.77 (d, J=2.4 Hz, 1H), 7.60 (d, J=8.5 Hz, 2H), 7.42 (d, J=8.6 Hz, 2H), 7.29 (t, J=7.9 Hz, 1H), 7.15 (d, J=9.0 Hz, 1H), 7.06 (dd, J=7.6, 1.2 Hz, 1H), 7.03 (dd, J=2.7, 1.6 Hz, 1H), 6.99 (d, J=8.7 Hz, 1H), 6.85 (dd, J=8.3, 2.7 Hz, 1H), 6.49-6.44 (m, 1H), 4.41 (m, 1H), 3.81 (s, 3H), 3.78 (s, 3H), 3.71 (s, 3H), 2.90-2.67 (m, 2H), 2.64 (m, 2H), 2.44 (s, 3H), 2.23-2.10 (m, 2H), 2.01-1.84 (m, 2H). $^{13}$C NMR (126 MHz, CDCl$_3$) δ 165.09, 159.33, 159.30, 157.64, 138.85, 136.68, 134.22, 131.15, 130.67, 129.99, 129.61, 129.16, 128.40, 127.21, 123.46, 122.00, 119.79, 115.29, 112.99, 111.05, 106.57, 102.55, 100.79, 69.99, 55.86, 55.60, 55.35, 51.55, 45.22, 29.31. HRMS (ESI$^+$) m/z [M+H$^+$] calcd for C$_{34}$H$_{36}$N$_2$O$_5$ 553.2702. found 553.2706.

3',6-dimethoxy-N-(2-methoxy-4'-((1-methylpiperidin-4-yl)oxy)-[1,1'-biphenyl]-4-yl)-[1,1'-biphenyl]-3-carboxamide (29g)

Palladium on carbon (10% w/w, 20 mg) was added to a solution of 28a (0.5 mmol) in methanol. The reaction mixture was then stirred under hydrogen atmosphere overnight before filtration. The filtrate was concentrated to dryness to get aniline. The aniline was dissolved in anhydrous dichloromethane and slowly added to an ice-cooled solution of 4-(chlorocarbonyl)-2-(3-methylbut-2-en-1-yl)phenyl acetate (5a, 1.0 mmol) and pyridine (0.2 mL) in anhydrous dichloromethane (2 mL). The reaction mixture was allowed to stir at room temperature for 4 hours. After 4 hours, the solvent was removed and the residue was purified via column chromatography (SiO$_2$, 10:1, CH$_2$Cl$_2$:methanol) to afford a white amorphous solid (79%). $^1$H NMR (500 MHz, chloroform-d) δ 8.11 (s, 1H), 7.98 (dd, J=8.6, 2.4 Hz, 1H), 7.88 (d, J=2.4 Hz, 1H), 7.70 (d, J=2.1 Hz, 1H), 7.48 (d, J=8.6 Hz, 2H), 7.38 (t, J=7.9 Hz, 1H), 7.27 (d, J=8.3 Hz, 1H), 7.17-7.13 (m, 2H), 7.12 (s, 1H), 7.09 (d, J=8.6 Hz, 1H), 6.96-6.91 (m, 3H), 4.55 (m, 1H), 3.91 (s, 3H), 3.87 (s, 6H), 3.01 (m, 2H), 2.90 (m, 2H), 2.61 (s, 3H), 2.41-2.27 (m, 2H), 2.10-2.00 (m, 2H). $^{13}$C NMR (126 MHz, CDCl$_3$) δ 165.22, 159.39, 159.33, 156.73, 155.57, 149.83, 138.81, 138.52, 130.73, 130.68, 130.58, 129.61, 129.17, 128.48, 127.00, 125.88, 122.00, 115.44, 115.36, 112.93, 112.07, 111.09, 103.77, 68.43, 55.87, 55.67, 55.36, 50.95, 44.75, 28.50. HRMS (ESI$^+$) m/z [M+H$^+$] calcd for C$_{34}$H$_{36}$N$_2$O$_5$ 553.2702. found 553.2699.

3',6-dimethoxy-N-(3-methoxy-4'-((1-methylpiperidin-4-yl)oxy)-[1,1'-biphenyl]-4-yl)-[1,1'-biphenyl]-3-carboxamide (29h)

Palladium on carbon (10% w/w, 20 mg) was added to a solution of 28b (0.5 mmol) in methanol. The reaction mixture was then stirred under hydrogen atmosphere overnight before filtration. The filtrate was concentrated to dryness to get aniline. The aniline was dissolved in anhydrous dichloromethane and slowly added to an ice-cooled solution of 4-(chlorocarbonyl)-2-(3-methylbut-2-en-1-yl) phenyl acetate (5a, 1.0 mmol) and pyridine (0.2 mL) in anhydrous dichloromethane (2 mL). The reaction mixture was allowed to stir at room temperature for 4 hours. After 4 hours, the solvent was removed and the residue was purified via column chromatography (SiO$_2$, 10:1, CH$_2$Cl$_2$:methanol) to afford a white amorphous solid (65%). $^1$H NMR (500 MHz, chloroform-d) δ 8.55 (d, J=8.4 Hz, 1H), 8.51 (s, NH), 7.91 (dd, J=8.5, 2.4 Hz, 1H), 7.87 (d, J=2.4 Hz, 1H), 7.56-7.46 (m, 2H), 7.36 (t, J=7.9 Hz, 1H), 7.27 (s, 1H), 7.19 (dd, J=8.4, 1.9 Hz, 1H), 7.17-7.09 (m, 2H), 7.07 (dd, J=5.3, 3.4 Hz, 2H), 6.99-6.95 (m, 2H), 6.93 (ddd, J=8.2, 2.6, 1.0 Hz, 1H), 4.59 (s, 1H), 3.97 (s, 3H), 3.87 (d, J=15.2 Hz, 6H), 3.11-2.89 (m, 5H), 2.64 (s, 3H), 2.43-2.31 (m, 2H), 2.11 (dt, J=14.3, 4.6 Hz, 2H). $^{13}$C NMR (126 MHz, CDCl$_3$) δ 164.67, 159.22, 159.18, 155.89, 148.34, 138.81, 136.12, 134.27, 130.58, 129.61, 129.05, 128.10, 127.43, 126.81, 121.92, 119.95, 119.32, 116.15, 115.21, 112.87, 110.92, 108.31, 68.19, 55.82, 55.76, 55.23, 50.61, 44.45, 27.93. HRMS (ESI$^+$) m/z [M+H$^+$] calcd for C$_{34}$H$_{36}$N$_2$O$_5$ 553.2702. found 553.2713.

N-(3'-chloro-4'-((1-methylpiperidin-4-yl)oxy)-[1,1'-biphenyl]-4-yl)-3',6-dimethoxy-[1,1'-biphenyl]-3-carboxamide (29i)

Palladium on carbon (10% w/w, 20 mg) was added to a solution of 28c (0.5 mmol) in methanol. The reaction mixture was then stirred under hydrogen atmosphere overnight before filtration. The filtrate was concentrated to dryness to get aniline. The aniline was dissolved in anhydrous dichloromethane and slowly added to an ice-cooled solution of 4-(chlorocarbonyl)-2-(3-methylbut-2-en-1-yl) phenyl acetate (5a, 1.0 mmol) and pyridine (0.2 mL) in anhydrous dichloromethane (2 mL). The reaction mixture was allowed to stir at room temperature for 4 hours. After 4 hours, the solvent was removed and the residue was purified via column chromatography (SiO$_2$, 10:1, CH$_2$Cl$_2$:methanol) to afford a white amorphous solid (47%). $^1$H NMR (500 MHz, chloroform-d) δ 8.08 (s, 1H), 7.94 (dd, J=8.6, 2.4 Hz, 1H), 7.85 (d, J=2.4 Hz, 1H), 7.76-7.69 (m, 2H), 7.61 (d, J=2.3 Hz, 1H), 7.51 (d, J=8.6 Hz, 2H), 7.41 (dd, J=8.5, 2.3 Hz, 1H), 7.36 (t, J=7.9 Hz, 1H), 7.13 (dt, J=7.6, 1.2 Hz, 1H), 7.10 (dd, J=2.6, 1.6 Hz, 1H), 7.05 (d, J=8.7 Hz, 1H), 7.00 (d, J=8.6 Hz, 1H), 6.92 (ddd, J=8.2, 2.6, 1.0 Hz, 1H), 4.55 (s, 1H), 3.89 (s, 3H), 3.85 (s, 3H), 3.05-2.87 (m, 2H), 2.78 (d, J=16.2 Hz, 2H), 2.52 (s, 3H), 2.32-2.18 (m, 2H), 2.05 (dq, J=14.6, 4.6 Hz, 2H). $^{13}$C NMR (126 MHz, CDCl$_3$) δ 165.19, 159.35, 159.30, 151.60, 138.78, 137.59, 135.18, 134.98, 130.64, 129.63, 129.14, 128.77, 128.46, 127.18, 126.97, 125.98, 124.76, 121.96, 120.57, 116.34, 115.32, 112.91, 111.03, 55.84, 55.32, 51.08, 45.24, 29.69, 29.06. HRMS (ESI$^+$) m/z [M+H$^+$] calcd for C$_{33}$H$_{33}$ClN$_2$O$_4$ 557.2207. found 557.2215.

N-(2'-chloro-4'-((1-methylpiperidin-4-yl)oxy)-[1,1'-biphenyl]-4-yl)-3',6-dimethoxy-[1,1'-biphenyl]-3-carboxamide (29j)

Palladium on carbon (10% w/w, 20 mg) was added to a solution of 28d (0.5 mmol) in methanol. The reaction mixture was then stirred under hydrogen atmosphere overnight before filtration. The filtrate was concentrated to dryness to get aniline. The aniline was dissolved in anhydrous dichloromethane and slowly added to an ice-cooled solution of 4-(chlorocarbonyl)-2-(3-methylbut-2-en-1-yl) phenyl acetate (5a, 1.0 mmol) and pyridine (0.2 mL) in anhydrous dichloromethane (2 mL). The reaction mixture was allowed to stir at room temperature for 4 hours. After 4 hours, the solvent was removed and the residue was purified via column chromatography (SiO$_2$, 10:1, CH$_2$Cl$_2$:methanol) to afford a white amorphous solid (87%). $^1$H NMR (400 MHz, chloroform-d) δ 8.56 (s, 1H), 7.99 (dd, J=8.6, 2.4 Hz, 1H), 7.91 (d, J=2.3 Hz, 1H), 7.83-7.72 (m, 2H), 7.41-7.30 (m, 3H), 7.22 (d, J=8.4 Hz, 1H), 7.17-7.09 (m, 2H), 7.03 (d, J=8.6 Hz, 1H), 6.98 (d, J=2.5 Hz, 1H), 6.94-6.87 (m, 1H), 6.81 (dd, J=8.5, 2.5 Hz, 1H), 4.52 (s, 1H), 3.85 (d, J=11.2 Hz, 6H), 3.01 (d, J=8.7 Hz, 4H), 2.62 (s, 3H), 2.36 (d, J=7.4 Hz, 2H), 2.12-1.98 (m, 2H). $^{13}$C NMR (126 MHz, CDCl$_3$) δ 165.20, 159.35, 159.31, 149.80, 138.79, 137.31, 135.06, 133.06, 132.06, 131.96, 130.69, 130.22, 130.15, 129.60, 129.15, 128.41, 127.04, 121.97, 119.69, 117.24, 115.29, 114.70, 112.97, 111.03, 67.62, 55.85, 55.33, 50.82, 45.61, 29.86. HRMS (ESI$^+$) m/z [M+] calcd for C$_{33}$H$_{33}$ClN$_2$O$_4$ 557.2207. found 557.2209.

N-(2-chloro-4'-((1-methylpiperidin-4-yl)oxy)-[1,1'-biphenyl]-4-yl)-3',6-dimethoxy-[1,1'-biphenyl]-3-carboxamide (29k)

Palladium on carbon (10% w/w, 20 mg) was added to a solution of 28e (0.5 mmol) in methanol. The reaction mixture was then stirred under hydrogen atmosphere overnight before filtration. The filtrate was concentrated to dryness to get aniline. The aniline was dissolved in anhydrous dichloromethane and slowly added to an ice-cooled solution of 4-(chlorocarbonyl)-2-(3-methylbut-2-en-1-yl) phenyl acetate (5a, 1.0 mmol) and pyridine (0.2 mL) in anhydrous dichloromethane (2 mL). The reaction mixture was allowed to stir at room temperature for 4 hours. After 4 hours, the solvent was removed and the residue was purified via column chromatography (SiO$_2$, 10:1, CH$_2$Cl$_2$:methanol) to afford a white amorphous solid (39%). $^1$H NMR (500 MHz, chloroform-d) δ 7.77 (m, 3H), 7.32-7.20 (m, 1H), 7.11 (d, J=8.6 Hz, 2H), 7.07 (t, J=7.9 Hz, 1H), 7.00 (d, J=8.5 Hz, 1H), 6.88 (d, J=7.6 Hz, 1H), 6.86 (s, 1H), 6.84 (d, J=9.2 Hz, 1H), 6.72 (d, J=8.2 Hz, 2H), 6.62 (dd, J=8.3, 2.7 Hz, 1H), 4.45 (m, 1H), 3.63 (s, 3H), 3.57 (s, 3H), 3.11-2.90 (m, 4H), 2.54 (s, 3H), 2.02 (m, 2H), 1.89 (m, 2H). $^{13}$C NMR (126 MHz, CDCl$_3$+CH$_3$OH) δ 166.39, 160.09, 159.95, 140.43, 139.92, 135.32, 132.62, 131.98, 131.70, 131.14, 130.57, 130.25, 129.89, 127.79, 127.40, 122.88, 122.30, 119.94, 117.34, 116.36, 116.31, 113.42, 111.78, 69.59, 56.68, 56.10, 50.37, 44.39, 27.88. HRMS (ESI$^+$) m/z [M+H$^+$] calcd for C$_{33}$H$_{33}$ClN$_2$O$_4$ 557.2207. found 557.2211.

N-(3-chloro-4'-((1-methylpiperidin-4-yl)oxy)-[1,1'-biphenyl]-4-yl)-3',6-dimethoxy-[1,1'-biphenyl]-3-carboxamide (29l)

Palladium on carbon (10% w/w, 20 mg) was added to a solution of 28f (0.5 mmol) in methanol. The reaction mixture was then stirred under hydrogen atmosphere overnight before filtration. The filtrate was concentrated to dryness to get aniline. The aniline was dissolved in anhydrous dichloromethane and slowly added to an ice-cooled solution of 4-(chlorocarbonyl)-2-(3-methylbut-2-en-1-yl)phenyl acetate (5a, 1.0 mmol) and pyridine (0.2 mL) in anhydrous dichloromethane (2 mL). The reaction mixture was allowed to stir at room temperature for 4 hours. After 4 hours, the solvent was removed and the residue was purified via column chromatography (SiO$_2$, 10:1, CH$_2$Cl$_2$:methanol) to afford a white amorphous solid (86%). $^1$H NMR (500 MHz, chloroform-d) δ 8.61 (d, J=8.6 Hz, 1H), 8.43 (s, NH), 7.95

(dd, J=8.5, 2.4 Hz, 1H), 7.91 (d, J=2.4 Hz, 1H), 7.60 (d, J=2.1 Hz, 1H), 7.55-7.48 (m, 3H), 7.38 (t, J=7.9 Hz, 1H), 7.17-7.08 (m, 4H), 6.98 (d, J=8.8 Hz, 2H), 4.72 (s, 1H), 3.92 (s, 3H), 3.87 (s, 3H), 3.35-3.25 (m, 2H), 3.24-3.10 (m, 2H), 2.78 (s, 3H), 2.65-2.55 (m, 2H), 2.26-2.15 (m, 2H). $^{13}$C NMR (126 MHz, CDCl$_3$) δ 164.78, 159.68, 159.34, 138.69, 136.88, 133.72, 131.00, 129.84, 129.20, 128.26, 128.20, 127.27, 126.94, 126.79, 126.02, 123.38, 121.98, 121.69, 120.48, 116.24, 115.31, 113.06, 111.12, 71.59, 55.91, 55.34, 50.01, 43.62, 29.95. HRMS (ESI$^+$) m/z [M+] calcd for C$_{33}$H$_{33}$ClN$_2$O$_4$ 557.2207. found 557.2199.

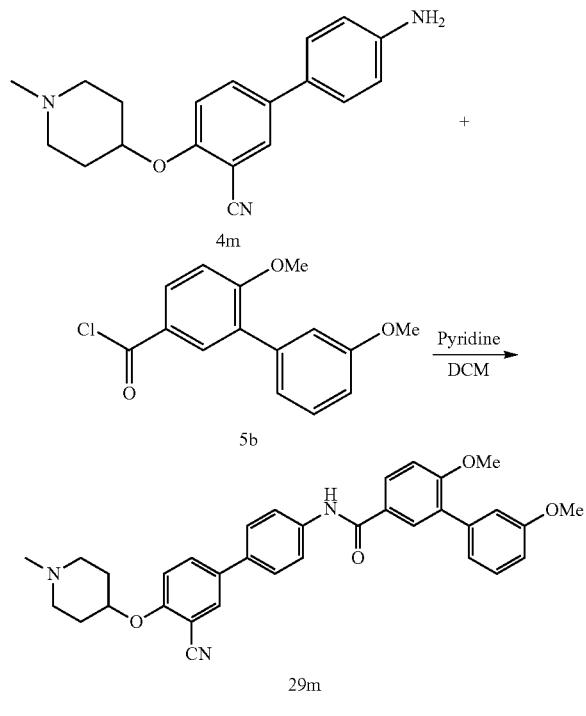

N-(3'-cyano-4'-((1-methylpiperidin-4-yl)oxy)-[1,1'-biphenyl]-4-yl)-3',6-dimethoxy-[1,1'-biphenyl]-3-carboxamide (29m)

A solution of acid chloride (5a, 0.27 mmol), in anhydrous dichloromethane (2 mL) was added to a solution of the aniline (4m, 0.18 mmol) and anhydrous pyridine (0.94 mmol) in anhydrous dichloromethane (5 mL). After 12 h, the solvent was removed and the residue purified via column chromatography (SiO$_2$, 10:1, DCM:methanol) to afford 29m as a white amorphous solid (90%). $^1$H NMR (500 MHz, chloroform-d) δ 7.93 (dd, J=8.6, 2.4 Hz, 1H), 7.84 (d, J=2.4 Hz, 1H), 7.80-7.69 (m, 4H), 7.54-7.45 (m, 2H), 7.35 (t, J=8.0 Hz, 1H), 7.12 (dd, J=7.6, 1.3 Hz, 1H), 7.10-7.01 (m, 3H), 6.91 (dd, J=8.3, 2.5 Hz, 1H), 4.86 (s, 1H), 3.86 (d, J=19.1 Hz, 6H), 3.47-3.33 (m, 2H), 3.33-3.16 (m, 2H), 2.83 (s, 3H), 2.49-2.34 (m, 2H), 2.34-2.14 (m, 2H). $^{13}$C NMR (126 MHz, CDCl$_3$+CH$_3$OH) δ 165.55, 159.40, 159.24, 157.04, 138.78, 138.20, 135.16, 133.87, 133.02, 131.71, 130.57, 129.64, 129.11, 128.57, 127.17, 126.77, 121.94, 120.81, 120.70, 116.38, 115.35, 114.51, 112.78, 111.02, 103.70, 67.98, 55.80, 55.30, 49.45, 43.84, 26.94. HRMS (ESI) m/z [M+H$^+$] calcd for C$_{34}$H$_{33}$N$_3$O$_4$ 548.2549. found 548.2545.

tert-butyl (4'-hydroxy-3'-nitro-[1,1'-biphenyl]-4-yl) carbamate (32a)

General Procedure for the Synthesis of 32a-b

Palladium tetraphenylphosphine (115 mg, 0.10 mmol) and potassium carbonate solution (2M, 100 μL) were added to a solution of 4-bromo-2-nitrophenol (150 mg, 0.69 mmol) and boronic ester (300 mg, 0.82 mmol) in dioxane (40 mL) and the mixture was refluxed at 110° C. for 12 hours. After 12 hours, the reaction mixture was concentrated to dryness and the residue so obtained was purified via column chromatography (SiO$_2$, 100:1, CH$_2$Cl$_2$:acetone) to afford desired product as a yellow amorphous solid (136 mg, 60%). $^1$H NMR (500 MHz, chloroform-d) δ 10.58 (s, 1H), 8.29 (d, J=2.3 Hz, 1H), 7.81 (dd, J=8.7, 2.4 Hz, 1H), 7.61-7.37 (m, 4H), 7.25-7.21 (m, 1H), 6.55 (s, 1H), 1.55 (s, 9H). $^{13}$C NMR (126 MHz, CDCl$_3$) δ 154.11, 151.21, 138.75, 138.34, 136.01, 135.15, 132.82, 127.25, 122.26, 120.39, 118.90, 81.15, 28.35. HRMS (ESI$^-$) m/z [M-H$^+$] calcd for C$_{17}$H$_{18}$N$_2$O$_5$ 329.1137. found 329.1133.

tert-butyl (4'-hydroxy-2'-nitro-[1,1'-biphenyl]-4-yl) carbamate (32b)

Palladium tetraphenylphosphine (0.10 mmol) and potassium carbonate solution (2M, 100 μL) were added to a solution of phenol (30b, 0.69 mmol) and boronic ester (0.82 mmol) in dioxane (10 mL) and the mixture was refluxed at 110° C. for 12 hours. After 12 hours, the reaction mixture was concentrated to dryness and the residue so obtained was purified via column chromatography (SiO$_2$, 100:1, CH$_2$Cl$_2$:acetone) to afford desired product as a yellow amorphous solid (210 mg, 72%). $^1$H NMR (500 MHz, chloroform-d) δ 7.40 (d, J=8.3 Hz, 2H), 7.32 (d, J=2.6 Hz, 1H), 7.28 (d, J=5.0 Hz, 1H), 7.23-7.17 (m, 2H), 7.07 (dd, J=8.4, 2.6 Hz, 1H), 6.53 (s, 1H), 5.47 (s, 1H), 1.54 (s, 9H). $^{13}$C NMR (126 MHz, CDCl$_3$) δ 155.35, 153.00, 149.83, 138.39, 133.34, 132.05, 129.00, 128.64, 119.86, 118.99, 111.40, 81.16, 28.64. HRMS (ESI) m/z [M-H$^+$] calcd for C$_{17}$H$_{18}$N$_2$O$_5$ 329.1137. found 329.1132.

tert-butyl (4'-((1-methylpiperidin-4-yl)oxy)-3'-nitro-[1,1'-biphenyl]-4-yl)carbamate (33a)

General Procedure for the Synthesis of 33a-b

Diisopropylazodicarboxylate (83 mg, 0.41 mmol) was added to an ice-cooled solution of phenol 32a (75 mg, 0.23 mmol), N-methyl-4-hydroxy-piperidine (31.5 mg, 0.27 mmol) and triphenylphosphine (150 mg, 0.54 mmol) in anhydrous THF (2 mL). The reaction mixture was then allowed to stir at room temperature for 12 hours. After 12 hours, the reaction mixture was concentrated under reduced pressure and the residue was purified via column chromatography (SiO$_2$, CH$_2$Cl$_2$:methanol, 10:1) to afford a yellow amorphous semi-solid (80 mg, 82%). $^1$H NMR (500 MHz, chloroform-d) δ 8.01 (d, J=2.4 Hz, 1H), 7.70 (dd, J=8.7, 2.4 Hz, 1H), 7.51-7.41 (m, 4H), 7.13 (d, J=8.8 Hz, 1H), 6.57 (s, 1NH), 4.70 (s, 1H), 2.85 (s, 2H), 2.70 (s, 2H), 2.48 (s, 3H), 2.24 (s, 2H), 2.06 (ddd, J=15.0, 7.7, 3.9 Hz, 2H), 1.54 (s, 9H). $^{13}$C NMR (126 MHz, CDCl$_3$) δ 153.49, 150.08, 141.99, 139.23, 134.69, 133.72, 132.74, 128.15, 124.54, 119.81, 117.21, 81.78, 51.83, 46.40, 30.62, 30.18, 29.24. HRMS (ESI$^+$) m/z [M+H$^+$] calcd for C$_{23}$H$_{29}$N$_3$O$_5$ 428.2186. found 428.2177.

tert-butyl (4'-((1-methylpiperidin-4-yl)oxy)-2'-nitro-[1,1'-biphenyl]-4-yl)carbamate (33b)

Diisopropylazodicarboxylate (83 mg, 0.41 mmol) was added to an ice-cooled solution of phenol 32b (75 mg, 0.23 mmol), N-methyl-4-hydroxy-piperidine (31.5 mg, 0.27 mmol) and triphenylphosphine (150 mg, 0.54 mmol) in anhydrous THF (2 mL). The reaction mixture was then allowed to stir at room temperature for 12 hours. After 12 hours, the reaction mixture was concentrated under reduced pressure and the residue was purified via column chromatography ($SiO_2$, $CH_2Cl_2$:methanol, 10:1) to afford a yellow amorphous semi-solid (175 mg, 89%). $^1$H NMR (500 MHz, chloroform-d) δ 7.41 (d, J=8.2 Hz, 2H), 7.34 (d, J=2.6 Hz, 1H), 7.29 (d, J=33.1 Hz, 1H), 7.23-7.19 (m, 2H), 7.13 (dd, J=8.6, 2.6 Hz, 1H), 6.53 (s, NH), 4.42 (s, 1H), 2.73 (s, 2H), 2.36 (s, 3H), 2.15-2.01 (m, 2H), 1.91 (d, J=11.4 Hz, 2H), 1.65-1.54 (m, 2H), 1.54 (s, 9H). $^{13}$C NMR (126 MHz, $CDCl_3$) δ 156.95, 152.90, 149.98, 138.48, 133.18, 131.97, 128.97, 128.51, 120.36, 118.84, 111.29, 81.09, 52.25, 46.19, 30.42, 30.03, 28.63. HRMS (ESI$^+$) m/z [M+H$^+$] calcd for $C_{23}H_{29}N_3O_5$ 428.2186. found 428.2182.

N-(4-bromo-3-nitrophenyl)-3',6-dimethoxy-[1,1'-biphenyl]-3-carboxamide (36a)

General Procedure for the Synthesis of 36a-b

A solution of acid chloride 5a (200 mg, 0.72 mmol) in dry dimethylformamide (0.5 ml) was added slowly to a solution of aniline 35a (150 mg, 0.69 mmol) and pyridine (160 mg, 2.30 mmol) in dimethylformamide (1 mL) and heated at 90° C. for 12 hours. After 12 hours, the reaction mixture was concentrated to dryness; diluted with water and extracted with ethyl acetate (3×10 ml). The organic layers were combined, dried over $Na_2SO_4$, and concentrated. The residue was purified via column chromatography ($SiO_2$, 100:1, $CH_2Cl_2$:acetone) to afford desired product as a light brown solid (283 mg, 90%). $^1$H NMR (400 MHz, chloroform-d) δ 8.28 (d, J=2.5 Hz, 1H), 7.97 (broad, 1H, NH), 7.90 (dd, J=8.6, 2.4 Hz, 1H), 7.79 (d, J=2.4 Hz, 1H), 7.76 (d, J=2.5 Hz, 1H), 7.70 (d, J=8.8 Hz, 1H), 7.37 (t, J=7.9 Hz, 1H), 7.13-7.05 (m, 3H), 6.94 (dd, J=8.3, 2.7 Hz, 1H), 3.91 (s, 3H), 3.86 (s, 3H). $^{13}$C NMR (126 MHz, $CDCl_3$) δ 165.35, 160.13, 159.57, 150.09, 138.71, 138.57, 135.53, 131.18, 129.76, 129.45, 128.81, 125.97, 124.32, 122.10, 116.92, 115.61, 113.18, 111.45, 108.40, 56.14, 55.56. HRMS (ESI$^+$) m/z [M+H$^+$] calcd for $C_{21}H_{18}BrN_2O_5$ 457.0399. found 457.0402.

N-(4-bromo-2-nitrophenyl)-3',6-dimethoxy-[1,1'-biphenyl]-3-carboxamide (36b)

A solution of acid chloride 5a (200 mg, 0.72 mmol) in dry dimethylformamide (0.5 ml) was added slowly to a solution of aniline 35b (150 mg, 0.69 mmol) and pyridine (160 mg, 2.30 mmol) in dimethylformamide (1 mL) and heated at 90° C. for 12 hours. After 12 hours, the reaction mixture was concentrated to dryness; diluted with water and extracted with ethyl acetate (3×10 ml). The organic layers were combined, dried over $Na_2SO_4$, and concentrated. The residue was purified via column chromatography ($SiO_2$, 100:1, $CH_2Cl_2$:acetone) to afford desired product as a yellow amorphous solid (80 mg, 43%). $^1$H NMR (500 MHz, chloroform-d) δ 11.30 (s, NH), 8.97 (d, J=9.1 Hz, 1H), 8.43 (d, J=2.4 Hz, 1H), 8.05-7.93 (m, 2H), 7.80 (dd, J=9.1, 2.4 Hz, 1H), 7.38 (t, J=7.9 Hz, 1H), 7.20-7.06 (m, 3H), 6.94 (ddd, J=8.3, 2.6, 1.0 Hz, 1H), 3.93 (s, 3H), 3.87 (s, 3H). $^{13}$C NMR (126 MHz, $CDCl_3$) δ 165.81, 160.78, 159.94, 139.61, 139.05, 137.11, 135.41, 131.81, 130.97, 129.82, 128.99, 126.57, 124.11, 122.53, 115.78, 115.65, 113.81, 111.79, 56.54, 55.92. HRMS (ESI$^+$) m/z [M+H$^+$] calcd for $C_{21}H_{17}BrN_2O_5$ 457.0399. found 457.0402.

N-(4'-hydroxy-2-nitro-[1,1'-biphenyl]-4-yl)-3',6-dimethoxy-[1,1'-biphenyl]-3-carboxamide (37a)

General Procedure for the Synthesis of 37a-b

[1,1'-Bis(diphenylphosphino)ferrocene]dichloropalladium(II) (42 mg, 0.05 mmol) and potassium carbonate solution (2M, 100 µL) were added to a solution of bromide 36a (120 mg, 0.26 mmol) and 4-hydrophenylboronic acid (72 mg, 0.52 mmol) in dioxane (10 mL) and the mixture was refluxed at 110° C. for 12 hours. After 12 hours, the reaction mixture was concentrated to dryness and the residue so obtained was purified via column chromatography ($SiO_2$, 100:1, $CH_2Cl_2$:acetone) to afford desired product as a brown amorphous solid (52 mg, 43%). $^1$H NMR (400 MHz, chloroform-d) δ 9.83 (s, 1H, NH), 8.16 (t, J=1.8 Hz, 1H), 7.91-7.83 (m, 3H), 7.29 (d, J=8.3 Hz, 1H), 7.25-7.22 (m, 1H), 7.05 (m, 3H), 7.03-6.97 (m, 2H), 6.82 (dd, J=8.3, 2.6 Hz, 1H), 6.79-6.72 (m, 2H), 3.80 (s, 3H), 3.76 (s, 3H). $^{13}$C NMR (126 MHz, $CDCl_3$) δ 166.66, 159.52, 159.17, 156.95, 149.16, 138.84, 138.32, 131.98, 131.09, 130.42, 130.24, 129.07, 129.02, 128.78, 128.18, 127.52, 126.35, 123.76, 121.98, 115.52, 115.24, 112.74, 110.87, 55.67, 55.18. HRMS (ESI$^+$) m/z [M+Na$^+$] calcd for $C_{27}H_{22}N_2O_6Na$ 493.1376. found 493.1371.

N-(4'-hydroxy-3-nitro-[1,1'-biphenyl]-4-yl)-3',6-dimethoxy-[1,1'-biphenyl]-3-carboxamide (37b)

[1,1'-Bis(diphenylphosphino)ferrocene]dichloropalladium(II) (0.05 mmol) and potassium carbonate solution (2M, 100 µL) were added to a solution of bromide 36b (0.26 mmol) and 4-hydrophenylboronic acid (0.52 mmol) in dioxane (10 mL) and the mixture was refluxed at 110° C. for 12 hours. After 12 hours, the reaction mixture was concentrated to dryness and the residue so obtained was purified via column chromatography ($SiO_2$, 100:1, $CH_2Cl_2$:acetone) to afford desired product as a brown amorphous solid (92%). $^1$H NMR (500 MHz, chloroform-d) δ 11.35 (s, OH), 9.05 (d, J=8.8 Hz, 1H), 8.45 (d, J=2.3 Hz, 1H), 8.09-7.95 (m, 2H), 7.90 (dd, J=8.8, 2.3 Hz, 1H), 7.59-7.47 (m, 2H), 7.38 (t, J=7.9 Hz, 1H), 7.21-7.05 (m, 3H), 6.98-6.89 (m, 3H), 3.93 (s, 3H), 3.88 (s, 3H). $^{13}$C NMR (126 MHz, $CDCl_3$) δ 165.90, 160.62, 159.94, 156.48, 139.16, 137.21, 136.56, 134.72, 134.65, 131.73, 131.41, 130.97, 129.81, 128.96, 128.75, 126.96, 123.77, 123.11, 122.58, 116.65, 115.77, 113.82, 111.76, 56.53, 55.93. HRMS (ESI$^+$) m/z [M+Na]$^+$ calcd for $C_{27}H_{22}N_2O_6$ 493.1376. found 493.3180.

3',6-dimethoxy-N-(4'-((1-methylpiperidin-4-yl)oxy)-3'-nitro-[1,1'-biphenyl]-4-yl)-[1,1'-biphenyl]-3-carboxamide (34a)

General Procedure for the Synthesis of 34a-b

A solution of trifluoroacetic acid (0.5 mL) in anhydrous dichloromethane (0.5 mL) was added to an ice-cooled solution of boc-protected aniline 33a (65 mg, 0.15 mmol) in anhydrous dichloromethane (0.5 ml) and allowed to stir at room temperature for 2 hours. After 2 hours, the reaction mixture was concentrated under high vacuum to afford a brownish amorphous semi-solid (48 mg, 98%), which was used as such without further purification in the next step.

Acid chloride (50 mg, 0.36 mmol) was added to a solution of aniline (50 mg, 0.18 mmol, obtained from previous step) and triethylamine (0.13 mL, 0.94 mmol) in anhydrous dichloromethane (5 mL) and stirred at room temperature for 4 hours. After 4 hours, the reaction mixture was concentrated and the residue was purified via column chromatography (SiO$_2$, 10:1, CH$_2$Cl$_2$:methanol) to afford 34a as a yellow amorphous solid (30 mg, 63%). $^1$H NMR (500 MHz, chloroform-d) δ 8.28 (s, 1H), 8.05 (d, J=2.4 Hz, 1H), 7.97 (dd, J=8.6, 2.4 Hz, 1H), 7.89 (d, J=2.4 Hz, 1H), 7.81 (d, J=8.3 Hz, 2H), 7.75 (dd, J=8.7, 2.4 Hz, 1H), 7.53 (d, J=8.4 Hz, 2H), 7.36 (t, J=7.9 Hz, 1H), 7.17-7.09 (m, 3H), 7.06 (d, J=8.7 Hz, 1H), 6.92 (ddd, J=8.3, 2.6, 1.0 Hz, 1H), 4.84 (s, 1H), 3.87 (d, J=19.2 Hz, 6H), 3.30-2.89 (m, 4H), 2.67 (s, 3H), 2.54-2.37 (m, 2H), 2.16-2.09 (m, 2H). $^{13}$C NMR (126 MHz, CDCl$_3$) δ 165.28, 159.41, 159.29, 148.60, 140.80, 138.72, 138.34, 134.09, 133.66, 132.21, 130.59, 129.71, 129.13, 128.58, 127.17, 126.81, 123.85, 121.95, 120.77, 116.04, 115.35, 112.86, 111.03, 69.03, 55.84, 55.32, 49.78, 44.39, 27.82. HRMS (ESI$^+$) m/z [M+H$^+$] calcd for C$_{33}$H$_{33}$N$_3$O$_6$ 568.2448. found 568.2445.

3',6-dimethoxy-N-(4'-((1-methylpiperidin-4-yl)oxy)-2'-nitro-[1¹'-biphenyl]-4-yl)-[1,1'-biphenyl]-3-carboxamide (34b)

A solution of trifluoroacetic acid (0.5 mL) in anhydrous dichloromethane (0.5 mL) was added to an ice-cooled solution of boc-protected aniline 33b (0.15 mmol) in anhydrous dichloromethane (0.5 mL) and allowed to stir at room temperature for 2 hours. After 2 hours, the reaction mixture was concentrated under high vacuum to afford a brownish amorphous semi-solid (97%), which was used as such without further purification in the next step.

Acid chloride (5a, 0.36 mmol) was added to a solution of aniline (0.18 mmol, obtained from previous step) and triethylamine (0.94 mmol) in anhydrous dichloromethane (5 mL) and stirred at room temperature for 4 hours. After 4 hours, the reaction mixture was concentrated and the residue was purified via column chromatography (SiO$_2$, 10:1, CH$_2$Cl$_2$:methanol) to afford 34b as a yellow amorphous solid (125 mg, 63%). $^1$H NMR (500 MHz, chloroform-d) δ 7.95 (s, 1H), 7.87 (dd, J=8.5, 2.4 Hz, 1H), 7.78 (d, J=2.4 Hz, 1H), 7.66-7.61 (m, 2H), 7.32-7.26 (m, 3H), 7.20 (d, J=2.0 Hz, 1H), 7.06 (ddd, J=9.0, 5.3, 1.9 Hz, 2H), 7.04-6.97 (m, 2H), 6.86 (ddd, J=8.3, 2.7, 1.0 Hz, 1H), 4.50 (s, 1H), 3.80 (d, J=18.6 Hz, 6H), 2.86 (t, J=10.5 Hz, 2H), 2.48 (s, 3H), 2.23 (s, 3H), 2.04-1.88 (m, 2H). $^{13}$C NMR (126 MHz, CDCl$_3$) δ 165.20, 159.43, 159.33, 156.29, 149.67, 138.77, 138.05, 133.07, 132.82, 130.74, 129.68, 129.17, 128.71, 128.56, 128.43, 126.92, 121.98, 120.33, 119.86, 115.29, 113.01, 111.24, 111.08, 70.27, 55.87, 55.35, 51.14, 44.96, 29.71. HRMS (ESI$^+$) m/z [M+H$^+$] calcd for C$_{33}$H$_{33}$N$_3$O$_6$ 568.2448. found 568.2446.

3',6-dimethoxy-N-(4'-((1-methylpiperidin-4-yl)oxy)-2-nitro-[1,1'-biphenyl]-4-yl)-[1,1'-biphenyl]-3-carboxamide (34c)

General Procedure for the Synthesis of 34c-d

Diisopropylazodicarboxylate (93 mg, 0.46 mmol) was added to an ice-cooled solution of phenol 37a (110 mg, 0.23 mmol), N-methyl-4-hydroxy-piperidine (27 mg, 0.23 mmol) and triphenylphosphine (128 mg, 0.46 mmol) in anhydrous THF (10 mL). The reaction mixture was then allowed to stir at room temperature for 12 hours. After 12 hours, the reaction mixture was concentrated under reduced pressure and the residue was purified via column chromatography (SiO$_2$, CH$_2$Cl$_2$:methanol, 10:1) to afford a yellow amorphous solid (85 mg, 65%). $^1$H NMR (500 MHz, chloroform-d) δ 8.15 (s, 1H), 7.93 (dd, J=8.5, 2.5 Hz, 2H), 7.90 (d, J=8.7 Hz, 1H), 7.85 (s, 1H), 7.31 (dd, J=8.4, 2.5 Hz, 2H), 7.30-7.27 (m, 1H), 7.17-7.13 (m, 1H), 7.07 (d, J=7.7 Hz, 1H), 7.03 (d, J=2.1 Hz, 1H), 7.01 (dd, J=8.7, 2.4 Hz, 1H), 6.85 (m, 3H), 4.35 (s, 1H), 3.82 (s, 3H), 3.78 (s, 3H), 2.70 (m, 2H), 2.52-2.40 (m, 2H), 2.30 (s, 3H), 1.99 (m, 2H), 1.85 (m, 2H). $^{13}$C NMR (126 MHz, CDCl$_3$+CH$_3$OH) δ 166.45, 159.66, 159.30, 157.16, 149.24, 138.93, 138.60, 132.22, 130.87, 130.58, 130.21, 129.71, 129.33, 129.18, 128.93, 126.43, 123.83, 122.11, 116.10, 115.66, 115.44, 112.86, 111.06, 70.57, 55.87, 55.39, 51.93, 45.64, 29.74. HRMS (ESI$^+$) m/z [M+K$^+$] calcd for C$_{33}$H$_{33}$N$_3$O$_6$K 606.2006. found 606.2007.

3',6-dimethoxy-N-(4'-((1-methylpiperidin-4-yl)oxy)-3-nitro-[1,1'-biphenyl]-4-yl)-[1,1'-biphenyl]-3-carboxamide (34d)

Diisopropylazodicarboxylate (93 mg, 0.46 mmol) was added to an ice-cooled solution of phenol 37b (110 mg, 0.23 mmol), N-methyl-4-hydroxy-piperidine (27 mg, 0.23 mmol) and triphenylphosphine (128 mg, 0.46 mmol) in anhydrous THF (10 mL). The reaction mixture was then allowed to stir at room temperature for 12 hours. After 12 hours, the reaction mixture was concentrated under reduced pressure and the residue was purified via column chromatography (SiO$_2$, CH$_2$Cl$_2$:methanol, 10:1) to afford a yellow amorphous solid (25 mg, 39%) $^1$H NMR (500 MHz, chloroform-d) δ 11.34 (s, 1H), 9.05 (d, J=8.8 Hz, 1H), 8.45 (d, J=2.3 Hz, 1H), 8.00 (d, J=8.1 Hz, 2H), 7.90 (dd, J=8.8, 2.3 Hz, 1H), 7.58-7.52 (m, 2H), 7.37 (t, J=7.9 Hz, 1H), 7.18-7.10 (m, 3H), 7.04-6.99 (m, 2H), 6.96-6.92 (m, 1H), 4.43 (s, 1H), 3.92 (s, 3H), 3.87 (s, 3H), 2.83-2.72 (m, 2H), 2.51-2.41 (m, 2H), 2.39 (s, 3H), 2.11 (ddd, J=11.3, 8.1, 3.7 Hz, 2H), 1.93 (tdd, J=10.9, 7.2, 3.5 Hz, 2H). $^{13}$C NMR (126 MHz, CDCl$_3$) δ 165.23, 159.99, 159.32, 157.55, 138.55, 136.58, 135.90, 134.07, 134.03, 131.09, 130.67, 130.34, 129.19, 128.33, 127.95, 126.34, 123.12, 122.47, 121.95, 116.52, 115.15, 113.19, 111.14, 71.62, 55.81, 55.36, 52.44, 45.84, 29.73. HRMS (ESI$^+$) m/z [M$^+$] calcd for C$_{33}$H$_{33}$N$_3$O$_6$ 567.2348. found 567.2339.

N-(3'-amino-4'-((1-methylpiperidin-4-yl)oxy)-[1,1'-biphenyl]-4-yl)-3',6-dimethoxy-[1,1'-biphenyl]-3-carboxamide (38a)

General procedure for the synthesis of 38a-d Palladium on carbon (10%, 10 mg) was added to a solution of nitro 34a (60 mg, 0.1 mmol), followed by two drops of acetic acid. The resulted suspension was degassed and stirred under hydrogen atmosphere for 12 hours before filtration. The filtrate was concentrated to dryness to afford aniline 38a as a white amorphous solid (46 mg, 85%). $^1$H NMR (400 MHz, chloroform-d) δ 7.94 (d, J=8.7 Hz, 1H), 7.84 (d, J=2.3 Hz, 1H), 7.69 (d, J=8.2 Hz, 2H), 7.53 (d, J=8.3 Hz, 2H), 7.37 (t, J=7.9 Hz, 1H), 7.14 (d, J=7.6 Hz, 1H), 7.10 (t, J=2.1 Hz, 1H), 7.08 (d, J=8.7 Hz, 1H), 7.00 (s, 1H), 6.97-6.91 (m, 2H), 6.85-6.81 (m, 1H), 4.63 (m, 1H), 3.90 (s, 3H), 3.87 (s, 3H), 3.16 (m, 4H), 2.72 (s, 3H), 2.42 (m, 2H), 2.20 (m, 2H). $^{13}$C NMR (126 MHz, CDCl$_3$) δ 165.31, 159.57, 159.54, 143.58, 139.02, 137.56, 137.24, 137.04, 135.04, 130.92, 129.77, 129.38, 128.63, 127.48, 127.28, 122.19, 120.62, 117.47, 115.54, 114.63, 114.31, 113.16, 111.29, 69.10, 56.08, 55.56, 50.61, 44.37, 28.10. HRMS (ESI$^+$) m/z [M+H$^+$] calcd for C$_{33}$H$_{36}$N$_3$O$_4$ 538.2706. found 538.2707.

N-(2'-amino-4'-((1-methylpiperidin-4-yl)oxy)-[1,1'-biphenyl]-4-yl)-3',6-dimethoxy-[1,1'-biphenyl]-3-carboxamide (38b)

Palladium on carbon (10%, 10 mg) was added to a solution of nitro 34b (0.1 mmol), followed by two drops of acetic acid. The resulted suspension was degassed and stirred under hydrogen atmosphere for 12 hours before filtration. The filtrate was concentrated to dryness to afford aniline 38b was obtained as a white amorphous solid (39%). $^1$H NMR (500 MHz, chloroform-d) δ 8.03 (d, J=2.9 Hz, 1H), 7.94 (dd, J=8.5, 2.4 Hz, 1H), 7.86 (d, J=2.5 Hz, 1H), 7.71 (dd, J=8.5, 2.7 Hz, 2H), 7.42 (dd, J=8.7, 2.6 Hz, 2H), 7.36 (td, J=7.9, 2.8 Hz, 1H), 7.17-7.09 (m, 2H), 7.05 (ddd, J=18.4, 8.5, 2.7 Hz, 2H), 6.93 (dd, J=8.2, 2.6 Hz, 1H), 6.38 (dt, J=8.5, 2.6 Hz, 1H), 6.33 (d, J=2.5 Hz, 1H), 4.42 (s, 1H), 3.89 (s, 3H), 3.86 (s, 3H), 3.80 (s, NH$_2$), 2.95-2.81 (m, 2H), 2.67 (s, 2H), 2.49 (s, 3H), 2.29-2.14 (m, 2H), 1.99 (d, J=14.2 Hz, 2H). $^{13}$C NMR (126 MHz, CDCl$_3$) δ 165.25, 159.34, 159.30, 157.35, 144.89, 138.79, 136.90, 135.13, 131.38, 130.65, 129.70, 129.63, 129.14, 128.45, 127.00, 121.96, 120.69, 120.60, 115.32, 112.91, 111.04, 106.02, 103.05, 69.81, 55.84, 55.32, 51.86, 45.30, 29.69. HRMS (ESI$^+$) m/z [M+H$^+$] calcd for C$_{33}$H$_{35}$N$_3$O$_4$ 538.2706. found 538.2704.

N-(2-amino-4'-((1-methylpiperidin-4-yl)oxy)-[1,1'-biphenyl]-4-yl)-3',6-dimethoxy-[1,1'-biphenyl]-3-carboxamide (38c)

Palladium on carbon (10%, 10 mg) was added to a solution of nitro 34c (0.1 mmol), followed by two drops of acetic acid. The resulted suspension was degassed and stirred under hydrogen atmosphere for 12 hours before filtration. The filtrate was concentrated to dryness to afford aniline 38c was obtained as a white amorphous solid (85%). $^1$H NMR (400 MHz, chloroform-d) δ 7.92 (dd, J=8.5, 2.3 Hz, 1H), 7.82 (d, J=2.4 Hz, 1H), 7.77 (s, 1H), 7.39 (d, J=8.7 Hz, 3H), 7.14 (d, J=7.9 Hz, 1H), 7.10 (d, J=2.3 Hz, 1H), 7.07 (dd, J=8.5, 2.2 Hz, 2H), 6.97 (d, J=8.5 Hz, 2H), 6.94 (dd, J=8.3, 2.7 Hz, 1H), 6.86 (dd, J=8.2, 2.1 Hz, 1H), 4.58 (m, 1H), 3.90 (s, 3H), 3.87 (s, 3H), 3.02 (m, 4H), 2.63 (s, 3H), 2.37 (m, 2H), 2.10 (m, 2H). $^{13}$C NMR (126 MHz, CDCl$_3$) δ 165.05, 159.33, 159.30, 155.73, 144.29, 138.82, 138.19, 132.21, 130.79, 130.69, 130.45, 129.51, 129.16, 128.34, 127.24, 123.26, 121.97, 116.17, 115.30, 112.96, 111.05, 110.21, 107.01, 69.03, 55.86, 55.34, 50.67, 44.57, 28.34. HRMS (ESI$^+$) m/z [M+H$^+$] calcd for C$_{33}$H$_{36}$N$_3$O$_4$ 538.2706. found 538.2709.

N-(3-amino-4'-((1-methylpiperidin-4-yl)oxy)-[1,1'-biphenyl]-4-yl)-3',6-dimethoxy-[1,1'-biphenyl]-3-carboxamide (38d)

Palladium on carbon (10%, 10 mg) was added to a solution of nitro 34d (0.1 mmol), followed by two drops of acetic acid. The resulted suspension was degassed and stirred under hydrogen atmosphere for 12 hours before filtration. The filtrate was concentrated to dryness to afford aniline 38d was obtained as a white amorphous solid (25 mg, 90%). $^1$H NMR (400 MHz, chloroform-d) δ 7.91 (dd, J=9.0, 2.4 Hz, 1H), 7.87 (s, 1H), 7.43 (d, J=8.7 Hz, 2H), 7.29 (t, J=7.9 Hz, 1H), 7.24 (d, J=7.8 Hz, 1H), 7.09-6.94 (m, 5H), 6.89 (d, J=8.8 Hz, 2H), 6.85 (dd, J=8.3, 2.6 Hz, 1H), 4.51 (m, 1H), 3.83 (s, 3H), 3.79 (s, 3H), 2.99-2.74 (m, 4H), 2.54 (s, 3H), 2.15 (m, 2H), 2.06-1.94 (m, 2H). $^{13}$C NMR (126 MHz, CDCl$_3$) δ 159.52, 159.32, 156.19, 141.22, 139.75, 138.96, 134.13, 130.65, 130.31, 129.19, 128.84, 128.42, 128.27, 126.33, 126.25, 123.71, 122.11, 118.33, 116.42, 116.23, 115.37, 112.96, 111.03, 68.80, 55.88, 55.39, 50.92, 44.54, 28.39. HRMS (ESI$^+$) m/z [M+K$^+$] calcd for C$_{33}$H$_{35}$N$_3$O$_4$K 576.2265. found 576.2264.

N-(3'-acetamido-4'-((1-methylpiperidin-4-yl)oxy)-[1,1'-biphenyl]-4-yl)-3',6-dimethoxy-[1,1'-biphenyl]-3-carboxamide (39a)

General Procedure for the Synthesis of 39a-d

Aniline 38a (23 mg, 0.04 mmol) was added to a solution of acetic anhydride in pyridine (1:3, v/v) and the resulting mixture was stirred at room temperature for 4 hours before being concentrated to dryness. The remaining residue was further dried under vacuum overnight to afford acetamide 39a as a light brown amorphous solid (25 mg, 100%). $^1$H NMR (500 MHz, chloroform-d) δ 8.01 (s, 1H), 7.87 (dd, J=8.6, 2.4 Hz, 1H), 7.78 (d, J=2.4 Hz, 1H), 7.73 (s, 1H), 7.61 (d, J=8.2 Hz, 2H), 7.45 (d, J=8.1 Hz, 2H), 7.29 (t, J=7.9 Hz, 1H), 7.18-7.15 (m, 1H), 7.06 (dt, J=7.6, 1.2 Hz, 1H), 7.03 (s, 1H), 6.99 (d, J=8.7 Hz, 1H), 6.85 (ddd, J=8.3, 2.7, 1.0 Hz, 1H), 6.80 (d, J=8.6 Hz, 1H), 4.50 (m, 1H), 3.82 (s, 3H), 3.78 (s, 3H), 3.15 (m, 2H), 2.94-2.82 (m, 2H), 2.61 (s, 3H), 2.35-2.26 (m, 2H), 2.18 (s, 3H), 2.17-2.07 (m, 2H). $^{13}$C NMR (126 MHz, CDCl$_3$) δ 174.51, 168.78, 165.41, 159.58, 159.53, 139.02, 137.46, 136.40, 134.43, 130.89, 129.89, 129.37, 128.65, 127.52, 127.20, 125.01, 123.84, 123.04, 122.20, 121.88, 120.81, 115.54, 113.15, 111.26, 69.90, 56.07, 55.55, 51.00, 44.13, 29.92, 28.34. HRMS (ESI$^+$) m/z [M+K$^+$] calcd for C$_{35}$H$_{37}$N$_3$O$_5$K 618.2370. found 618.2373.

N-(2'-acetamido-4'-((1-methylpiperidin-4-yl)oxy)-[1,1'-biphenyl]-4-yl)-3',6-dimethoxy-[1,1'-biphenyl]-3-carboxamide (39b)

Aniline 38b (0.04 mmol) was added to a solution of acetic anhydride in pyridine (1:3, v/v) and the resulting mixture was stirred at room temperature for 4 hours before being concentrated to dryness. The remaining residue was further dried under vacuum overnight to afford acetamide 39b as a light brown amorphous solid (11 mg, 100%). $^1$H NMR (400 MHz, chloroform-d) δ 7.82 (dd, J=8.6, 2.4 Hz, 1H), 7.78 (d, J=2.4 Hz, 1H), 7.58 (d, J=8.6 Hz, 2H), 7.47 (d, J=2.5 Hz, 1H), 7.23-7.15 (m, 3H), 7.04 (d, J=8.4 Hz, 1H), 6.99 (dt, J=7.7, 1.3 Hz, 1H), 6.97-6.93 (m, 2H), 6.78-6.74 (m, 1H), 6.63 (dd, J=8.5, 2.6 Hz, 1H), 4.42 (m, 1H), 3.75 (s, 3H), 3.70 (s, 3H), 2.89 (m, 2H), 2.73 (m, 2H), 2.44 (s, 3H), 2.12-2.00 (m, 2H), 1.99-1.92 (m, 2H), 1.89 (s, 3H). $^{13}$C NMR (126 MHz, CDCl$_3$+CH$_3$OH) δ 168.45, 165.21, 158.75, 158.51, 138.57, 138.17, 135.32, 132.82, 130.44, 129.80, 129.30, 128.91, 128.75, 128.52, 126.81, 126.77, 121.55, 120.50, 120.40, 114.95, 112.09, 110.31, 110.24, 70.60, 55.30, 54.76, 51.21, 44.76, 29.06, 23.74. HRMS (ESI$^+$) m/z [M+K$^+$] calcd for C$_{35}$H$_{37}$N$_3$O$_5$K 618.2370. found 618.2372.

N-(2-acetamido-4'-((1-methylpiperidin-4-yl)oxy)-[1,1'-biphenyl]-4-yl)-3',6-dimethoxy-[1,1'-biphenyl]-3-carboxamide (39c)

Aniline 38c (23 mg, 0.04 mmol) was added to a solution of acetic anhydride in pyridine (1:3, v/v) and the resulting mixture was stirred at room temperature for 4 hours before being concentrated to dryness. The remaining residue was further dried under vacuum overnight to afford acetamide 39c was obtained as a white amorphous solid (15 mg, 100%). $^1$H NMR (500 MHz, chloroform-d) δ 7.76 (dd, J=8.5, 2.4 Hz, 1H), 7.73 (d, J=2.4 Hz, 1H), 7.69 (d, J=2.2 Hz, 1H), 7.56 (dd, J=8.4, 2.2 Hz, 1H), 7.14 (t, J=7.9 Hz, 1H), 7.10 (d, J=8.6 Hz, 2H), 7.07 (d, J=8.4 Hz, 1H), 6.96-6.93 (m, 1H), 6.92 (s, 1H), 6.90 (d, J=8.6 Hz, 1H), 6.80 (d, J=8.6 Hz, 2H), 6.71 (dd, J=8.2, 2.6 Hz, 1H), 4.42 (m, 1H), 3.70 (s, 3H), 3.65 (s, 3H), 2.91 (m, 2H), 2.80 (m, 2H), 2.47 (s, 3H), 2.02 (m, 2H), 1.92-1.87 (m, 2H), 1.82 (s, 3H). $^{13}$C NMR (126 MHz, CDCl$_3$+CH$_3$OH) δ 170.20, 166.68, 159.26, 159.09, 156.03, 138.85, 137.89, 134.07, 131.30, 130.75, 130.48, 130.34, 130.26, 130.12, 128.87, 128.49, 126.70, 121.88, 118.69, 117.00, 115.93, 115.06, 112.68, 110.74, 69.73, 55.51, 50.71, 43.95, 29.51, 28.22. HRMS (ESI$^+$) m/z [M+K$^+$] calcd for C$_{35}$H$_{37}$N$_3$O$_5$K 618.2370. found 618.2367.

N-(3-acetamido-4'-((1-methylpiperidin-4-yl)oxy)-[1,1'-biphenyl]-4-yl)-3',6-dimethoxy-[1,1'-biphenyl]-3-carboxamide (39d)

Aniline 38d (23 mg, 0.04 mmol) was added to a solution of acetic anhydride in pyridine (1:3, v/v) and the resulting mixture was stirred at room temperature for 4 hours before being concentrated to dryness. The remaining residue was further dried under vacuum overnight to afford acetamide 39d was obtained as a white amorphous solid (10 mg, 100%). $^1$H NMR (400 MHz, chloroform-d) δ 7.81 (m, 2H), 7.61 (d, J=8.4 Hz, 1H), 7.38 (d, J=8.1 Hz, 2H), 7.36 (d, J=2.3 Hz, 1H), 7.32 (dd, J=8.4, 2.1 Hz, 1H), 7.21 (t, J=7.9 Hz, 1H), 7.02 (d, J=7.9 Hz, 1H), 7.00-6.98 (m, 1H), 6.98-6.94 (m, 1H), 6.84 (d, J=8.9 Hz, 2H), 6.77 (dd, J=8.2, 2.5 Hz, 1H), 4.46 (m, 1H), 3.77 (s, 3H), 3.72 (s, 3H), 2.91-2.75 (m, 4H), 2.50 (s, 3H), 2.09 (m, 2H), 2.06 (s, 3H), 1.95 (m, 2H). $^{13}$C NMR (126 MHz, CDCl$_3$+CH$_3$OH) δ 170.95, 166.15, 159.53, 159.19, 156.19, 138.82, 138.31, 133.28, 130.63, 130.56, 130.37, 129.94, 129.03, 128.35, 128.14, 126.19, 126.10, 124.58, 122.95, 121.96, 116.21, 115.17, 112.87, 110.98, 68.17, 55.71, 55.18, 50.64, 44.20, 28.12, 23.18. HRMS (ESI$^+$) m/z [M+K$^+$] calcd for C$_{35}$H$_{37}$N$_3$O$_5$K 618.2370. found 618.2368.

1-(3',6-dimethoxy-[1,1'-biphenyl]-3-yl)-3-(4'-((1-methylpiperidin-4-yl)oxy)-[1,1'-biphenyl]-4-yl)urea (52)

Aniline 4 (28 mg, 0.1 mmol) was added to a solution of biarylisocyanate 5d (51 mg, 0.2 mmol) in dichloromethane (2 mL) and the resulting mixture was stirred at room temperature overnight. After removing the solvent, the residue was purified via column chromatography (SiO$_2$, 10:1, CH$_2$Cl$_2$:methanol) to afford desired product as a light brown amorphous solid (33 mg, 61%). $^1$H NMR (400 MHz, chloroform-d) δ 8.03 (s, 1H, NH), 7.91 (s, 1H, NH), 7.40-7.27 (m, 8H), 7.25-7.17 (m, 1H), 7.07-6.98 (m, 2H), 6.86-6.71 (m, 4H), 4.35-4.20 (m, 1H), 3.75 (s, 3H), 3.66 (s, 3H), 2.84 (m, 2H), 2.57 (m, 2H), 2.42 (s, 3H), 2.08 (m, 2H), 1.97-1.82 (m, 2H). $^{13}$C NMR (126 MHz, CDCl$_3$) δ 159.19, 156.68, 154.05, 153.79, 139.06, 136.96, 136.28, 133.22, 131.27, 130.66, 129.03, 127.84, 127.27, 125.35, 123.00, 121.93, 121.00, 116.29, 115.23, 112.74, 112.07, 71.68, 55.92, 55.26, 52.53, 46.07, 30.60. HRMS (ESI$^+$) m/z [M+H$^+$] calcd for C$_{33}$H$_{36}$N$_3$O$_4$ 538.2706. found 538.2701.

6-methoxy-N-(4'-((1-methylpiperidin-4-yl)oxy)-[1,1'-biphenyl]-4-yl)-[1,1'-biphenyl]-3-carboxamide (49a)

A solution of acid chloride (48a, 0.27 mmol), in anhydrous dichloromethane (2 mL) was added to a solution of the aniline (7, 0.18 mmol) and anhydrous triethylamine (0.94 mmol) in anhydrous dichloromethane (5 mL). After 12 h, the solvent was removed and the residue purified via column chromatography (SiO$_2$, 10:1, DCM:methanol) to afford a white amorphous solid (78%). $^1$H NMR (500 MHz, DMSO-d$_6$) δ 10.25 (s, 1H, NH), 8.04 (dd, J=8.6, 2.4 Hz, 1H), 7.98 (d, J=2.3 Hz, 1H), 7.86 (d, J=8.6 Hz, 2H), 7.60 (dd, J=8.6, 3.5 Hz, 4H), 7.56 (d, J=7.3 Hz, 2H), 7.45 (t, J=7.6 Hz, 2H), 7.37 (t, J=7.4 Hz, 1H), 7.26 (d, J=8.7 Hz, 1H), 7.06 (d, J=8.5 Hz, 2H), 4.58 (m, 1H), 3.86 (s, 3H), 3.11-2.93 (m, 2H), 2.78 (m, 2H), 2.52 (s, 3H), 2.08 (m, 2H), 1.85 (m, 2H). $^{13}$C NMR (126 MHz, DMSO) δ 164.68, 158.68, 156.01, 138.20, 137.49, 134.70, 132.52, 129.90, 129.36, 129.09, 128.06, 127.41, 127.17, 126.93, 126.16, 120.66, 116.33, 111.36, 69.61, 55.85, 50.89, 43.61, 28.55. HRMS (ESI+) m/z: [M+H$^+$] calcd for C$_{32}$H$_{33}$N$_2$O$_3$ 493.2491. found 493.2495.

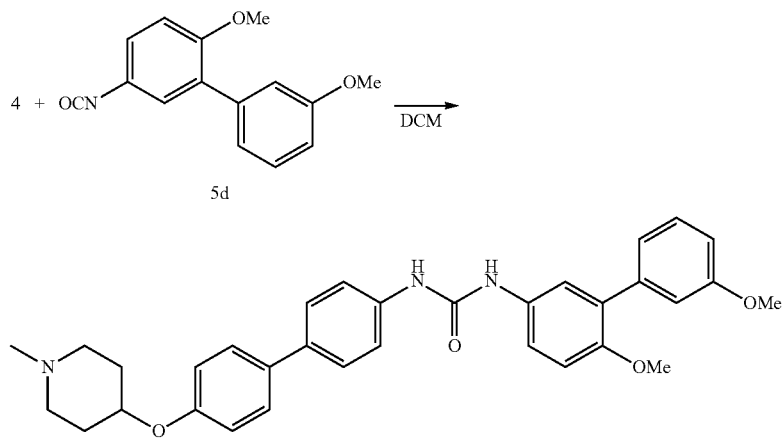

52

3'-methoxy-N-(4'-((1-methylpiperidin-4-yl)oxy)-[1,1'-biphenyl]-4-yl)-[1,1'-biphenyl]-3-carboxamide (49b)

A solution of acid chloride (48b, 0.27 mmol), in anhydrous dichloromethane (2 mL) was added to a solution of the aniline (7, 0.18 mmol) and anhydrous triethylamine (0.94 mmol) in anhydrous dichloromethane (5 mL). After 12 h, the solvent was removed and the residue purified via column chromatography (SiO$_2$, 10:1, DCM:methanol) to afford a white amorphous solid (72%). $^1$H NMR (500 MHz, DMSO-d$_6$) δ 10.44 (s, 1H, NH), 8.24 (s, 1H), 7.96 (dt, J=7.7, 1.4 Hz, 1H), 7.93-7.84 (m, 3H), 7.68-7.57 (m, 4H), 7.44 (dd, J=8.6, 7.1 Hz, 1H), 7.35 (dt, J=7.8, 1.2 Hz, 1H), 7.33 (t, J=2.1 Hz, 1H), 7.10-7.05 (m, 2H), 7.03-6.98 (m, 1H), 4.61 (m, 1H), 3.86 (s, 3H), 3.11-3.02 (m, 2H), 2.88 (s, 2H), 2.60 (s, 3H), 2.20-2.01 (m, 2H), 1.93-1.76 (m, 2H). $^{13}$C NMR (126 MHz, DMSO) δ 165.34, 159.78, 156.00, 140.99, 140.15, 138.02, 135.52, 134.95, 132.54, 130.08, 129.88, 129.06, 127.46, 126.97, 126.24, 125.86, 120.72, 119.23, 116.36, 113.34, 112.49, 69.66, 55.20, 50.77, 43.33, 28.33. HRMS (ESI+) m/z: [M+H$^+$] calcd for C$_{32}$H$_{33}$N$_2$O$_3$ 493.2491. found 493.2494.

4',6-dimethoxy-N-(4'-((1-methylpiperidin-4-yl)oxy)-[1,1'-biphenyl]-4-yl)-[1,1'-biphenyl]-3-carboxamide (49c)

A solution of acid chloride (48c, 0.27 mmol), in anhydrous dichloromethane (2 mL) was added to a solution of the aniline (7, 0.18 mmol) and anhydrous triethylamine (0.94 mmol) in anhydrous dichloromethane (5 mL). After 12 h, the solvent was removed and the residue purified via column chromatography (SiO$_2$, 10:1, DCM:methanol) to afford a white amorphous solid (56%). $^1$H NMR (500 MHz, DMSO-d$_6$) δ 10.22 (s, 1H, NH), 7.99 (dd, J=8.6, 2.4 Hz, 1H), 7.95 (d, J=2.4 Hz, 1H), 7.85 (d, J=8.7 Hz, 1H), 7.64-7.60 (m, 3H), 7.51 (d, J=8.7 Hz, 1H), 7.24 (d, J=8.7 Hz, 1H), 7.09 (d, J=8.6 Hz, 2H), 7.02 (d, J=8.8 Hz, 1H), 4.65 (m, 1H), 3.86 (s, 3H), 3.81 (s, 3H), 3.25-2.96 (m, 4H), 2.68 (s, 3H), 2.11 (m, 2H), 1.91 (m, 2H). $^{13}$C NMR (126 MHz, DMSO) δ 164.78, 158.67, 158.50, 155.86, 138.25, 134.63, 132.70, 130.48, 129.63, 129.04, 128.52, 127.44, 126.91, 126.18, 120.63, 116.40, 113.56, 113.52, 111.29, 66.97, 55.82, 55.12, 51.23, 42.74, 28.33. HRMS (ESI+) m/z: [M+H$^+$] calcd for C$_{33}$H$_{35}$N$_2$O$_4$ 523.2597. found 523.2602.

2'-methoxy-5'-((4'-((1-methylpiperidin-4-yl)oxy)-[1,1'-biphenyl]-4-yl)carbamoyl)-[1,1'-biphenyl]-3-yl acetate (49d)

A solution of acid chloride (48d, 0.27 mmol), in anhydrous dichloromethane (2 mL) was added to a solution of the aniline (7, 0.18 mmol) and anhydrous triethylamine (0.94 mmol) in anhydrous dichloromethane (5 mL). After 12 h, the solvent was removed and the residue purified via column chromatography (SiO$_2$, 10:1, DCM:methanol) to afford a white amorphous solid (76%). $^1$H NMR (500 MHz, chloroform-d) δ 7.93 (s, 1H), 7.86 (dd, J=8.7, 2.4 Hz, 1H), 7.73 (d, J=2.4 Hz, 1H), 7.63 (d, J=8.5 Hz, 2H), 7.47 (d, J=8.7 Hz, 2H), 7.45 (d, J=8.8 Hz, 2H), 7.35-7.30 (m, 1H), 7.01 (d, J=7.4 Hz, 1H), 6.98 (d, J=8.7 Hz, 1H), 6.89 (d, J=8.7 Hz, 2H), 4.43 (m, 1H), 3.81 (s, 3H), 2.90-2.79 (m, 2H), 2.66 (m, 2H), 2.45 (s, 3H), 2.25 (s, 3H), 2.19 (m, 2H), 1.95 (m, 2H). $^{13}$C NMR (126 MHz, CDCl$_3$) δ 169.64, 165.09, 159.23, 156.27, 150.37, 138.92, 137.04, 136.58, 133.73, 129.62, 129.55, 129.12, 128.82, 128.05, 127.22, 127.18, 127.03, 122.77, 120.64, 120.51, 116.27, 111.11, 69.73, 55.86, 51.43, 45.19, 29.15, 21.21. HRMS (ESI+) m/z: [M+H$^+$] calcd for C$_{34}$H$_{35}$N$_2$O$_5$ 551.2546. found 551.2543.

2'-methoxy-5'-((4'-((1-methylpiperidin-4-yl)oxy)-[1,1'-biphenyl]-4-yl)carbamoyl)-[1,1'-biphenyl]-4-yl acetate (49e)

A solution of acid chloride (48e, 0.27 mmol), in anhydrous dichloromethane (2 mL) was added to a solution of the aniline (7, 0.18 mmol) and anhydrous triethylamine (0.94 mmol) in anhydrous dichloromethane (5 mL). After 12 h, the solvent was removed and the residue purified via column chromatography (SiO$_2$, 10:1, DCM:methanol) to afford a white amorphous solid (66%). $^1$H NMR (500 MHz, chloroform-d) δ 7.98 (s, 1H), 7.86 (dd, J=8.6, 2.4 Hz, 1H), 7.74 (d, J=2.4 Hz, 1H), 7.65 (d, J=8.6 Hz, 1H), 7.46 (m, 5H), 7.06 (d, J=8.6 Hz, 1H), 6.98 (d, J=8.6 Hz, 1H), 6.89 (d, J=8.7 Hz, 2H), 4.43 (m, 1H), 3.81 (s, 3H), 2.93-2.78 (m, 2H), 2.66 (s, 2H), 2.45 (s, 3H), 2.26 (s, 3H), 2.26-2.10 (m, 2H), 1.95 (m, 2H). $^{13}$C NMR (126 MHz, CDCl$_3$) δ 169.68, 165.08, 159.28, 156.27, 149.97, 137.10, 136.56, 135.14, 133.71, 130.58, 129.83, 129.63, 128.59, 128.04, 127.18, 127.15, 121.29, 120.51, 116.27, 111.06, 69.72, 55.81, 51.41, 45.17, 29.16, 21.21. HRMS (ESI+) m/z: [M+H$^+$] calcd for C$_{34}$H$_{35}$N$_2$O$_5$ 551.2546. found 551.2545.

3'-chloro-6-methoxy-N-(4'-((1-methylpiperidin-4-yl)oxy)-[1,1'-biphenyl]-4-yl)-[1,1'-biphenyl]-3-carboxamide (49f)

A solution of acid chloride (48f, 0.27 mmol), in anhydrous dichloromethane (2 mL) was added to a solution of the aniline (7, 0.18 mmol) and anhydrous triethylamine (0.94 mmol) in anhydrous dichloromethane (5 mL). After 12 h, the solvent was removed and the residue purified via column chromatography (SiO$_2$, 10:1, DCM:methanol) to afford a white amorphous solid (80%). $^1$H NMR (500 MHz, DMSO-d$_6$) δ 10.21 (s, 1H), 8.06 (dd, J=8.6, 2.4 Hz, 1H), 8.00 (d, J=2.4 Hz, 1H), 7.84 (d, J=8.6 Hz, 2H), 7.63-7.57 (m, 54H), 7.55-7.44 (m, 3H), 7.30 (d, J=8.7 Hz, 1H), 7.02 (d, J=8.7 Hz, 2H), 4.41 (m, 1H), 3.88 (s, 3H), 2.71-2.57 (m, 2H), 2.20 (m, 5H), 2.12-1.90 (m, 2H), 1.66 (m, 2H). $^{13}$C NMR (126 MHz, DMSO) δ 164.50, 158.58, 156.38, 139.55, 138.04, 134.86, 132.73, 132.09, 129.95, 129.81, 129.71, 128.97, 128.13, 127.70, 127.35, 127.12, 127.01, 126.13, 120.67, 116.17, 111.55, 71.85, 55.98, 52.32, 45.74, 30.51. HRMS (ESI+) m/z: [M+H$^+$] calcd for C$_{32}$H$_{32}$ClN$_2$O$_3$ 527.2101. found 527.2100.

4'-chloro-6-methoxy-N-(4'-((1-methylpiperidin-4-yl)oxy)-[1,1'-biphenyl]-4-yl)-[1,1'-biphenyl]-3-carboxamide (49g)

A solution of acid chloride (48g, 0.27 mmol), in anhydrous dichloromethane (2 mL) was added to a solution of the aniline (7, 0.18 mmol) and anhydrous triethylamine (0.94 mmol) in anhydrous dichloromethane (5 mL). After 12 h, the solvent was removed and the residue purified via column chromatography (SiO$_2$, 10:1, DCM:methanol) to afford a white amorphous solid (70%). $^1$H NMR (500 MHz, DMSO-d$_6$) δ 10.23 (s, 1H, NH), 8.04 (dd, J=8.6, 2.3 Hz, 1H), 7.97 (d, J=2.3 Hz, 1H), 7.84 (d, J=8.7 Hz, 2H), 7.60 (m, 5H), 7.52 (d, J=8.5 Hz, 2H), 7.28 (d, J=8.7 Hz, 1H), 7.06 (d, J=8.7 Hz, 2H), 4.55 (m, 1H), 3.87 (s, 3H), 3.33 (s, 3H), 2.98 (m, 2H), 2.70 (m, 2H), 2.06 (m, 2H), 1.80 (m, 2H). $^{13}$C NMR (126 MHz, DMSO) δ 164.60, 158.61, 156.07, 138.16, 136.26, 134.76, 132.48, 132.02, 131.18, 129.78, 129.44, 128.10, 127.98, 127.43, 127.04, 126.19, 120.66, 116.33, 111.51, 69.88, 55.96, 51.10, 43.86, 28.74. HRMS (ESI+) m/z: [M+H$^+$] calcd for C$_{32}$H$_{32}$ClN$_2$O$_3$ 527.2101. found 527.2105.

6-methoxy-N-(4'-((1-methylpiperidin-4-yl)oxy)-[1,1'-biphenyl]-4-yl)-3'-nitro-[1,1'-biphenyl]-3-carboxamide (49h)

A solution of acid chloride (48h, 0.27 mmol), in anhydrous dichloromethane (2 mL) was added to a solution of the aniline (7, 0.18 mmol) and anhydrous triethylamine (0.94 mmol) in anhydrous dichloromethane (5 mL). After 12 h, the solvent was removed and the residue purified via column chromatography (SiO$_2$, 10:1, DCM:methanol) to afford a yellow amorphous solid (72%). $^1$H NMR (500 MHz, DMSO-d$_6$) δ 10.27 (s, 1H, NH), 8.42 (t, J=2.0 Hz, 1H), 8.26 (dd, J=8.2, 2.4 Hz, 1H), 8.11 (dd, J=8.6, 2.3 Hz, 1H), 8.08-8.03 (m, 2H), 7.86-7.83 (m, 2H), 7.78 (t, J=8.0 Hz, 1H), 7.65-7.57 (m, 4H), 7.34 (d, J=8.8 Hz, 1H), 7.05 (d, J=8.7 Hz, 2H), 4.52 (m, 1H), 3.91 (s, 3H), 2.91 (m, 2H), 2.66-2.56 (m, 2H), 2.44 (s, 3H), 2.09-1.96 (m, 2H), 1.85-1.66 (m, 2H). $^{13}$C NMR (126 MHz, DMSO) δ 164.46, 158.58, 156.14, 147.68, 138.93, 138.06, 136.08, 134.82, 132.37, 130.15, 129.96, 129.71, 127.40, 127.21, 126.80, 126.18, 123.79, 122.14, 120.68, 116.27, 111.69, 69.71, 56.10, 51.67, 44.44, 29.14. HRMS (ESI+) m/z: [M+H$^+$] calcd for C$_{32}$H$_{32}$N$_3$O$_5$ 538.2342. found 538.2346.

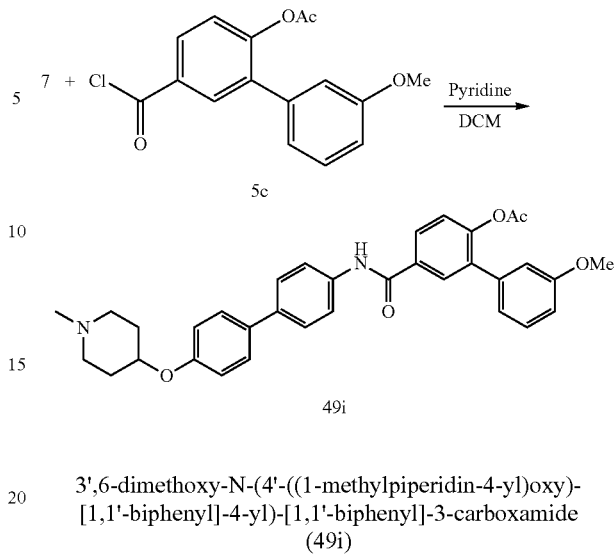

3',6-dimethoxy-N-(4'-((1-methylpiperidin-4-yl)oxy)-[1,1'-biphenyl]-4-yl)-[1,1'-biphenyl]-3-carboxamide (49i)

A solution of acid chloride (5c, 0.27 mmol), in anhydrous dichloromethane (2 mL) was added to a solution of the aniline (7, 0.18 mmol) and anhydrous pyridine (0.94 mmol) in anhydrous dichloromethane (5 mL). After 12 h, the solvent was removed and the residue purified via column chromatography (SiO$_2$, 10:1, DCM:methanol) to afford a white amorphous solid (35 mg, 76%). $^1$H NMR (500 MHz, chloroform-d) δ 8.13 (s, 1H), 7.87 (s, 1H), 7.83 (dd, J=8.3, 2.3 Hz, 1H), 7.64 (d, J=8.6 Hz, 2H), 7.46 (d, J=8.5 Hz, 2H), 7.43 (d, J=8.7 Hz, 2H), 7.26 (t, J=7.9 Hz, 1H), 7.16 (d, J=8.3 Hz, 1H), 7.00-6.77 (m, 5H), 4.40 (m, 1H), 3.76 (s, 3H), 2.82 (m, 2H), 2.63 (m, 2H), 2.41 (s, 3H), 2.12 (m, 2H), 2.06 (s, 3H), 1.97-1.86 (m, 2H). $^{13}$C NMR (126 MHz, CDCl$_3$) δ 169.13, 164.90, 159.60, 156.36, 150.41, 137.88, 136.89, 136.80, 135.26, 133.58, 133.16, 129.94, 129.51, 128.05, 127.53, 127.20, 123.50, 121.19, 120.67, 116.27, 114.39, 113.66, 69.70, 55.35, 51.31, 45.08, 29.17, 20.91.

2'-hydroxy-5'-((4'-((1-methylpiperidin-4-yl)oxy)-[1,1'-biphenyl]-4-yl)carbamoyl)-[1,1'-biphenyl]-3-yl acetate (49j)

A solution of 49i (30 mg, 0.052 mmol) in MeOH (0.5 ml) was treated with triethylamine (0.020 mL, 0.156 mmol) and stirred for 4 h. After 4 h, the RM was concentrated and residue was purified by column chromatography (SiO$_2$, 5:95 MeOH:DCM) to afford a white amorphous solid (14 mg, 49%). $^1$H NMR (500 MHz, chloroform-d) δ 7.86 (d, J=2.4 Hz, 1H), 7.77 (dd, J=8.5, 2.4 Hz, 1H), 7.69 (d, J=8.6 Hz, 2H), 7.54-7.46 (m, 4H), 7.35-7.31 (m, 1H), 7.17 (d, J=7.5 Hz, 1H), 7.14 (d, J=2.6 Hz, 1H), 6.98 (d, J=8.4 Hz, 1H), 6.95 (d, J=8.7 Hz, 2H), 6.88 (dd, J=8.4, 2.6 Hz, 1H), 4.52 (m, 1H), 3.83 (s, 3H), 3.03-2.86 (m, 2H), 2.81 (m, 2H), 2.53 (s, 3H), 2.26-2.09 (m, 2H), 2.09-1.92 (m, 2H). $^{13}$C NMR (126 MHz, CDCl$_3$+CH$_3$OH) δ 166.63, 159.37, 157.41, 156.02, 139.03, 137.26, 136.42, 133.88, 130.14, 129.26, 128.35, 128.34, 127.96, 126.93, 126.05, 121.74, 120.97, 116.26, 115.87, 114.92, 112.85, 68.65, 55.20, 51.11, 44.67, 28.69.

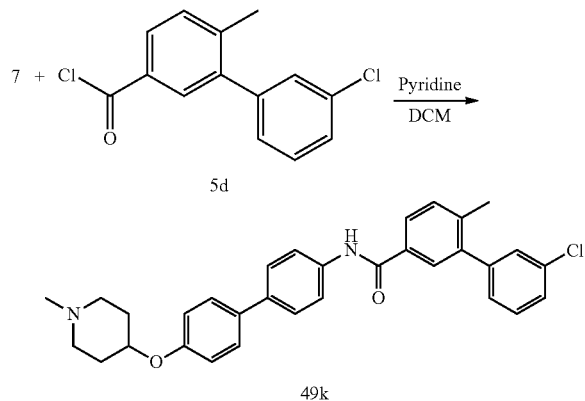

4'-chloro-6-methoxy-N-(4'-((1-methylpiperidin-4-yl)oxy)-[1,1'-biphenyl]-4-yl)-[1,1'-biphenyl]-3-carboxamide (49k)

A solution of acid chloride (5d, 0.27 mmol) in anhydrous dichloromethane (2 mL) was added to a solution of the aniline (7, 0.18 mmol) and anhydrous pyridine (0.94 mmol) in anhydrous dichloromethane (5 mL). After 12 h, the solvent was removed and the residue purified via column chromatography (SiO$_2$, 10:1, DCM:methanol) to afford a white amorphous solid (71%). $^1$H NMR (500 MHz, DMSO-d$_6$) δ 10.30 (s, 1H, NH), 7.93 (d, J=7.9 Hz, 1H), 7.88 (s, 1H), 7.84 (dd, J=8.5, 4.6 Hz, 2H), 7.62 (dd, J=8.8, 2.8 Hz, 4H), 7.54-7.46 (m, 4H), 7.41 (s, 1H), 7.08 (d, J=8.2 Hz, 2H), 4.62 (m, 1H), 3.13 (m, 2H), 2.94 (m, 2H), 2.63 (s, 3H), 2.32 (s, 3H), 2.10 (m, 2H), 1.88 (m, 2H). $^{13}$C NMR (126 MHz, DMSO) δ 164.88, 155.93, 142.60, 139.64, 138.89, 137.97, 137.40, 134.89, 133.05, 132.57, 132.42, 130.63, 130.18, 128.73, 128.52, 127.90, 127.46, 127.23, 126.20, 120.75, 116.37, 68.91, 50.47, 43.15, 28.19, 20.10.

3'-hydroxy-6-methoxy-N-(4'-((1-methylpiperidin-4-yl)oxy)-[1,1'-biphenyl]-4-yl)-[1,1'-biphenyl]-3-carboxamide (50a)

General Procedure for the Synthesis of 50a-b

Compounds 49d (20 mg, 0.036 mmol) were dissolved in a solution of 10% Et$_3$N in methanol (1 mL) and stirred at room temperature for 24 hours before concentrated to dryness. The light brown residue so obtained was purified by flash chromatography using dichloromethane and methanol (v/v, 10:1) as eluent to give 50a as a white amorphous solid (16 mg, 85%). $^1$H NMR (500 MHz, methanol-d$_4$) δ 7.95 (dd, J=8.6, 2.5 Hz, 1H), 7.91 (d, J=2.4 Hz, 1H), 7.74 (d, J=8.5 Hz, 2H), 7.56 (d, J=8.6 Hz, 2H), 7.53 (d, J=8.7 Hz, 2H), 7.27 (t, J=7.9 Hz, 1H), 7.08 (d, J=8.6 Hz, 2H), 7.05-7.03 (m, 1H), 6.99 (d, J=8.7 Hz, 2H), 6.84 (dd, J=8.0, 2.5 Hz, 1H), 4.49 (m, 1H), 3.90 (s, 3H), 2.86 (m, 2H), 2.63 (m, 2H), 2.46 (s, 3H), 2.12 (m, 2H), 2.02-1.93 (m, 2H). $^{13}$C NMR (126 MHz, CDCl$_3$+CH$_3$OH) δ 166.57, 159.32, 156.47, 156.29, 138.87, 137.19, 136.60, 133.67, 130.54, 130.01, 129.01, 128.41, 127.90, 126.91, 126.88, 121.04, 120.98, 116.35, 116.31, 114.33, 110.87, 69.62, 55.62, 51.63, 45.18, 29.42. HRMS (ESI+) m/z: [M+H$^+$] calcd for C$_{32}$H$_{33}$N$_2$O$_4$ 509.2440. found 509.2442.

4'-hydroxy-6-methoxy-N-(4'-((1-methylpiperidin-4-yl)oxy)-[1,1'-biphenyl]-4-yl)-[1,1'-biphenyl]-3-carboxamide (50b)

Compounds 49e (0.036 mmol) were dissolved in a solution of 10% Et$_3$N in methanol (1 mL) and stirred at room temperature for 24 hours before concentrated to dryness. The light brown residue so obtained was purified by flash chromatography using dichloromethane and methanol (v/v, 10:1) as eluent to give 50b as a white amorphous solid (16 mg, 90%). $^1$H NMR (500 MHz, methanol-d$_4$) δ 7.90 (dd, J=8.5, 2.4 Hz, 1H), 7.87 (d, J=2.4 Hz, 1H), 7.73 (d, J=8.6 Hz, 2H), 7.56-7.50 (m, 4H), 7.43 (d, J=8.6 Hz, 1H), 7.06 (d, J=8.6 Hz, 1H), 6.98 (d, J=8.7 Hz, 2H), 6.90 (d, J=8.6 Hz, 1H), 4.55 (m, 1H), 3.89 (s, 3H), 3.00 (m, 2H), 2.84 (m, 2H), 2.57 (s, 3H), 2.20 (m, 2H), 2.06 (m, 2H). $^{13}$C NMR (126 MHz, CDCl$_3$+CH$_3$OH) δ 166.53, 159.30, 156.25, 156.03, 137.23, 136.47, 133.88, 130.59, 130.56, 129.76, 128.81, 127.96, 127.80, 126.93, 126.91, 121.00, 116.26, 114.96, 110.79, 68.82, 55.63, 51.12, 44.67, 28.69. HRMS (ESI+) m/z [M+H$^+$] calcd for C$_{32}$H$_{33}$N$_2$O$_4$ 509.2440. found 509.2441.

3'-amino-6-methoxy-N-(4'-((1-methylpiperidin-4-yl)oxy)-[1,1'-biphenyl]-4-yl)-[1,1'-biphenyl]-3-carboxamide (50c)

Palladium on carbon (10%, 5 mg) was added to a solution of 49h (25 mg, 0.047 mmol) in methanol (1 ml), followed by two drops of acetic acid. The resulted suspension was degassed and stirred under hydrogen atmosphere for 12 hours before filtration. The filtrate was concentrated to dryness to afford aniline 50c as a white amorphous solid (18 mg, 76%). $^1$H NMR (400 MHz, chloroform-d) δ 7.85-7.81 (m, 1H), 7.78 (s, 1H), 7.64 (d, J=8.5 Hz, 2H), 7.43 (m, 4H), 7.11 (t, J=7.8 Hz, 1H), 6.95 (d, J=8.7 Hz, 1H), 6.87 (m, 3H), 6.81 (s, 1H), 6.64-6.62 (m, 1H), 4.54 (m, 1H), 3.77 (s, 3H), 3.13-2.99 (m, 4H), 2.63 (s, 3H), 2.25-2.15 (m, 2H), 2.08-2.00 (m, 2H). $^{13}$C NMR (126 MHz, CDCl$_3$+CH$_3$OH) δ 159.41, 156.00, 146.03, 138.68, 137.32, 136.51, 134.07, 130.83, 129.93, 128.98, 128.53, 128.09, 127.04, 126.93, 121.02, 120.98, 120.31, 116.69, 116.31, 114.71, 110.97, 68.71, 55.76, 50.83, 44.44, 28.31. HRMS (ESI+) m/z: [M+H$^+$] calcd for C$_{32}$H$_{34}$N$_3$O$_3$ 508.2600. found 508.2598.

3'-acetamido-6-methoxy-N-(4'-((1-methylpiperidin-4-yl)oxy)-[1,1'-biphenyl]-4-yl)-[1,1'-biphenyl]-3-carboxamide (50d)

Aniline 50c (10 mg, 0.02 mmol) was added to a solution of acetic anhydride in pyridine (1:3, v/v) and the resulting mixture was stirred at room temperature for 4 hours before being concentrated to dryness. The remaining residue was further dried under vacuum overnight to afford acetamide 50d as a light brown amorphous solid (10 mg, 100%). $^1$H NMR (500 MHz, methanol-d$_4$) δ 7.76 (dd, J=8.8, 2.7 Hz, 1H), 7.73 (s, 1H), 7.56-7.51 (m, 3H), 7.37-7.29 (m, 5H), 7.17-7.08 (m, 2H), 6.88 (d, J=8.5 Hz, 1H), 6.77 (d, J=8.6 Hz, 2H), 4.34 (m, 1H), 3.67 (s, 3H), 2.81 (m, 2H), 2.62 (s, 1H), 2.36 (m, 2H), 1.96 (s, 3H), 1.94 (m, 2H), 1.80 (m, 2H). $^{13}$C NMR (126 MHz, CDCl$_3$+CH$_3$OH) δ 170.17, 166.64, 159.19, 155.91, 138.13, 137.98, 137.25, 136.38, 133.83, 130.00, 129.93, 128.69, 128.18, 127.79, 126.78, 126.67, 125.34, 121.11, 121.07, 118.95, 116.14, 110.77, 68.98, 55.39, 51.01, 44.30, 28.59, 23.26. HRMS (ESI+) m/z [M+K+] calcd for C$_{34}$H$_{35}$N$_3$O$_4$K 588.2265. found 588.2270.

General Procedure for the Synthesis of 41a-41s, 43a-b, 45a-b, 47a-b and 49a-h

N-(4'-((1-methylpiperidin-4-yl)oxy)-[1,1'-biphenyl]-4-yl)benzamide (41a)

Acid chloride 40a (50 mg, 0.36 mmol) was added to a solution of aniline 7 (50 mg, 0.18 mmol) and triethylamine (0.13 mL, 0.94 mmol) in anhydrous dichloromethane (5 mL). After 12 h, the solvent was removed and the residue was purified via column chromatography (SiO$_2$, 10:1, CH$_2$Cl$_2$:methanol) to afford 41a as a white amorphous solid (51 mg, 74%). $^1$H NMR (500 MHz, chloroform-d) δ 7.95 (d, J=6.9 Hz, 2H), 7.77 (d, J=8.6 Hz, 2H), 7.61-7.53 (m, 5H), 7.53-7.49 (m, 2H), 7.02 (d, J=8.7 Hz, 2H), 4.71 (s, 1H), 3.27 (m, 4H), 2.82 (s, 3H), 2.43-2.29 (m, 2H), 2.25-2.11 (m, 2H). $^{13}$C NMR (126 MHz, CDCl$_3$) δ 167.69, 156.00, 137.67, 136.89, 135.17, 134.64, 132.09, 128.83, 128.43, 127.71, 127.27, 121.56, 116.58, 67.03, 50.55, 46.71, 27.76. HRMS (ESI+) m/z: [M+H+] calcd for C$_{25}$H$_{27}$N$_2$O$_2$ 387.2073. found 387.2071.

4-chloro-N-(4'-((1-methylpiperidin-4-yl)oxy)-[1,1'-biphenyl]-4-yl)benzamide (41b)

Acid chloride 40b (0.36 mmol) was added to a solution of aniline 7 (0.18 mmol) and triethylamine (0.13 mL, 0.94 mmol) in anhydrous dichloromethane (5 mL). After 12 h, the solvent was removed and the residue was purified via column chromatography (SiO$_2$, 10:1, CH$_2$Cl$_2$:methanol) to afford a white amorphous solid (65%). $^1$H NMR (500 MHz, DMSO-d$_6$) δ 8.00 (d, J=8.6 Hz, 2H), 7.84 (d, J=8.7 Hz, 2H), 7.62 (m, 4H), 7.05 (d, J=8.8 Hz, 2H), 4.53 (s, 1H), 2.93 (m, 1H), 2.68-2.55 (m, 1H), 2.45 (s, 3H), 2.03 (m, 2H), 1.79 (m, 2H). $^{13}$C NMR (126 MHz, DMSO) δ 164.32, 156.16, 137.82, 136.36, 135.08, 133.56, 132.34, 129.61, 128.44, 127.44, 126.23, 120.67, 116.29, 69.80, 51.33, 44.20, 29.09. HRMS (ESI+) m/z: [M+H+] calcd for C$_{25}$H$_{26}$ClN$_2$O$_2$ 421.1683. found 421.1681.

4-bromo-N-(4'-((1-methylpiperidin-4-yl)oxy)-[1,1'-biphenyl]-4-yl)benzamide (41c)

Acid chloride 40c (0.36 mmol) was added to a solution of aniline 7 (0.18 mmol) and triethylamine (0.13 mL, 0.94 mmol) in anhydrous dichloromethane (5 mL). After 12 h, the solvent was removed and the residue was purified via column chromatography (SiO$_2$, 10:1, CH$_2$Cl$_2$:methanol) to afford a white amorphous solid (88%). $^1$H NMR (400 MHz, chloroform-d) δ 7.66 (d, J=8.4 Hz, 2H), 7.56 (d, J=8.6 Hz, 2H), 7.46 (d, J=8.4 Hz, 2H), 7.39 (d, J=8.5 Hz, 2H), 7.36 (d, J=8.7 Hz, 2H), 6.82 (d, J=8.6 Hz, 2H), 4.31 (m, 1H), 2.65 (d, J=9.7 Hz, 2H), 2.40 (s, 2H), 2.25 (s, 3H), 1.93 (m, 2H), 1.79 (m, 2H). $^{13}$C NMR (126 MHz, DMSO) δ 164.49, 156.37, 137.82, 135.18, 133.98, 132.21, 131.43, 129.83, 127.46, 126.27, 125.36, 120.71, 116.27, 71.02, 52.10, 45.12, 29.96. HRMS (ESI+) m/z: [M+H+] calcd for C$_{25}$H$_{26}$BrN$_2$O$_2$ 465.1178. found 465.1181.

4-iodo-N-(4'-((1-methylpiperidin-4-yl)oxy)-[1,1'-biphenyl]-4-yl)benzamide (41d)

Acid chloride 41d (0.36 mmol) was added to a solution of aniline 7 (0.18 mmol) and triethylamine (0.13 mL, 0.94 mmol) in anhydrous dichloromethane (5 mL). After 12 h, the solvent was removed and the residue was purified via column chromatography (SiO$_2$, 10:1, CH$_2$Cl$_2$:methanol) to afford a white amorphous solid (80%). $^1$H NMR (400 MHz, chloroform-d) δ 7.86-7.73 (m, 2H), 7.64 (d, J=8.3 Hz, 2H), 7.59 (d, J=8.2 Hz, 2H), 7.47 (d, J=8.8 Hz, 2H), 7.44 (d, J=8.7 Hz, 2H), 6.94-6.76 (m, 2H), 4.39 (m, 1H), 2.74 (m, 2H), 2.48 (m, 2H), 2.34 (s, 3H), 2.13-1.97 (m, 2H), 1.88 (m, 2H). $^{13}$C NMR (126 MHz, CDCl$_3$) δ 166.30, 156.37, 137.69, 136.95, 136.87, 134.34, 133.60, 129.01, 127.90, 126.91, 121.11, 116.30, 98.61, 69.97, 51.89, 45.12, 29.41. HRMS (ESI+) m/z: [M+H+] calcd for C$_{25}$H$_{26}$IN$_2$O$_2$ 513.1039. found 513.1042.

4-methyl-N-(4'-((1-methylpiperidin-4-yl)oxy)-[1,1'-biphenyl]-4-yl)benzamide (41e)

Acid chloride 41e (0.36 mmol) was added to a solution of aniline 7 (0.18 mmol) and triethylamine (0.13 mL, 0.94 mmol) in anhydrous dichloromethane (5 mL). After 12 h, the solvent was removed and the residue was purified via column chromatography (SiO$_2$, 10:1, CH$_2$Cl$_2$:methanol) to afford a white amorphous solid (69%). $^1$H NMR (500 MHz, chloroform-d) δ 7.82 (d, J=8.2 Hz, 2H), 7.74-7.68 (m, 2H), 7.52 (ddd, J=8.6, 4.5, 2.2 Hz, 4H), 7.36-7.18 (m, 2H), 7.06-6.76 (m, 2H), 4.60 (d, J=10.7 Hz, 1H), 3.10 (m, 2H), 2.95 (m, 2H), 2.65 (s, 3H), 2.41 (s, 3H), 2.17 (m, 2H), 2.07 (m, 2H). $^{13}$C NMR (126 MHz, CDCl$_3$) δ 167.24, 155.74, 142.02, 137.08, 136.34, 133.76, 131.64, 128.78, 127.63, 127.13, 126.49, 121.01, 116.00, 69.53, 50.91, 43.73, 28.31, 20.66. HRMS (ESI+) m/z: [M+H+] calcd for C$_{26}$H$_{29}$N$_2$O$_2$ 401.2229. found 401.2231.

4-methoxy-N-(4'-((1-methylpiperidin-4-yl)oxy)-[1,1'-biphenyl]-4-yl)benzamide (41f)

Acid chloride 41f (0.36 mmol) was added to a solution of aniline 7 (0.18 mmol) and triethylamine (0.13 mL, 0.94 mmol) in anhydrous dichloromethane (5 mL). After 12 h, the solvent was removed and the residue was purified via column chromatography (SiO$_2$, 10:1, CH$_2$Cl$_2$:methanol) to afford a white amorphous solid (75%). $^1$H NMR (500 MHz, chloroform-d) δ 7.76 (d, J=8.8 Hz, 2H), 7.57 (d, J=8.7 Hz, 2H), 7.39 (d, J=6.6 Hz, 2H), 7.37 (d, J=6.5 Hz, 2H), 6.89-6.75 (m, 4H), 4.43 (m, 1H), 3.72 (s, 3H), 2.94-2.83 (m, 2H), 2.77 (m, 2H), 2.46 (s, 3H), 2.15-2.01 (m, 2H), 1.94-1.87 (m, 2H). $^{13}$C NMR (126 MHz, CDCl$_3$+CH$_3$OH) δ 166.65, 162.42, 155.92, 137.29, 136.42, 133.95, 129.23, 127.94, 126.85, 121.07, 116.22, 113.67, 68.59, 55.25, 50.89, 44.34, 28.40. HRMS (ESI+) m/z: [M+H+] calcd for C$_{26}$H$_{29}$N$_2$O$_3$ 417.2178. found 417.2176.

4-(tert-butyl)-N-(4'-((1-methylpiperidin-4-yl)oxy)-[1,1'-biphenyl]-4-yl)benzamide (41g)

Acid chloride 41g (0.36 mmol) was added to a solution of aniline 7 (0.18 mmol) and triethylamine (0.13 mL, 0.94 mmol) in anhydrous dichloromethane (5 mL). After 12 h, the solvent was removed and the residue was purified via column chromatography (SiO$_2$, 10:1, CH$_2$Cl$_2$:methanol) to afford a white amorphous solid (70%). $^1$H NMR (500 MHz, DMSO-d$_6$) δ 10.25 (s, 1H, NH), 7.90 (d, J=8.5 Hz, 2H), 7.85 (d, J=8.7 Hz, 2H), 7.61 (d, J=4.2 Hz, 2H), 7.59 (d, J=4.3 Hz, 2H), 7.55 (d, J=8.5 Hz, 2H), 7.06 (d, J=8.8 Hz, 2H), 4.56 (m, 1H), 3.34 (s, 3H), 2.99 (m, 2H), 2.74 (m, 2H), 2.06 (m, 2H), 1.84 (m, 2H), 1.33 (s, 9H). $^{13}$C NMR (126 MHz, DMSO) δ 165.41, 156.04, 154.37, 138.15, 134.77, 132.48, 132.21, 129.14, 127.50, 126.19, 125.12, 120.51, 116.32, 69.87, 51.08, 43.71, 34.66, 30.84, 28.67. HRMS (ESI+) m/z: [M+H$^+$] calcd for C$_{29}$H$_{35}$N$_2$O$_2$: 443.2699. found 443.2696.

3-chloro-N-(4'-((1-methylpiperidin-4-yl)oxy)-[1,1'-biphenyl]-4-yl)benzamide (41h)

Acid chloride 41h (0.36 mmol) was added to a solution of aniline 7 (0.18 mmol) and triethylamine (0.13 mL, 0.94 mmol) in anhydrous dichloromethane (5 mL). After 12 h, the solvent was removed and the residue was purified via column chromatography (SiO$_2$, 10:1, CH$_2$Cl$_2$:methanol) to afford a white amorphous solid (73%). $^1$H NMR (400 MHz, chloroform-d) δ 7.82 (s, 1H), 7.71 (d, J=7.7 Hz, 1H), 7.64-7.58 (d, J=8.3 Hz, 2H), 7.43 (d, J=8.4 Hz, 2H), 7.40 (d, J=8.6 Hz, 2H), 7.36-7.28 (m, 2H), 6.85 (d, J=7.5 Hz, 2H), 4.37 (m, 1H), 2.89-2.68 (m, 2H), 2.52 (m, 2H), 2.34 (s, 3H), 2.05-1.99 (m, 2H), 1.94-1.78 (m, 2H). $^{13}$C NMR (126 MHz, CDCl$_3$) δ 165.62, 156.37, 136.94, 136.90, 136.71, 134.53, 133.58, 131.61, 129.83, 127.91, 127.62, 126.92, 125.61, 121.14, 116.31, 70.25, 51.75, 45.20, 29.52. HRMS (ESI+) m/z: [M+H$^+$] calcd for C$_{25}$H$_{26}$ClN$_2$O$_2$ 421.1683. found 421.1685.

3-methoxy-N-(4'-((1-methylpiperidin-4-yl)oxy)-[1,1'-biphenyl]-4-yl)benzamide (41i)

Acid chloride 41i (0.36 mmol) was added to a solution of aniline 7 (0.18 mmol) and triethylamine (0.13 mL, 0.94 mmol) in anhydrous dichloromethane (5 mL). After 12 h, the solvent was removed and the residue was purified via column chromatography (SiO$_2$, 10:1, CH$_2$Cl$_2$:methanol) to afford a white amorphous solid (74%). $^1$H NMR (500 MHz, chloroform-d) δ 7.53 (d, J=8.6 Hz, 2H), 7.39-7.22 (m, 6H), 7.18 (t, J=7.9 Hz, 1H), 6.87 (dd, J=8.4, 2.6 Hz, 1H), 6.77 (d, J=8.7 Hz, 2H), 4.36 (m, 1H), 3.65 (s, 3H), 2.77 (m, 2H), 2.57 (m, 2H), 2.33 (s, 3H), 1.93 (m, 2H), 1.80 (m, 2H). $^{13}$C NMR (126 MHz, CDCl$_3$) δ 166.97, 159.49, 155.97, 136.97, 136.54, 136.01, 133.59, 129.28, 127.68, 126.59, 121.08, 119.30, 117.47, 116.09, 112.44, 69.15, 54.93, 51.18, 44.33, 28.72. HRMS (ESI+) m/z: [M+H$^+$] calcd for C$_{26}$H$_{29}$N$_2$O$_3$ 417.2178. found 417.2175.

4-chloro-3-methyl-N-(4'-((1-methylpiperidin-4-yl)oxy)-[1,1'-biphenyl]-4-yl)benzamide (41j)

Acid chloride 41j (0.36 mmol) was added to a solution of aniline 7 (0.18 mmol) and triethylamine (0.13 mL, 0.94 mmol) in anhydrous dichloromethane (5 mL). After 12 h, the solvent was removed and the residue was purified via column chromatography (SiO$_2$, 10:1, CH$_2$Cl$_2$:methanol) to afford a white amorphous solid (68%). $^1$H NMR (500 MHz, DMSO-d$_6$) δ 10.35 (s, 1H, NH), 7.97 (d, J=2.2 Hz, 1H), 7.89-7.77 (m, 3H), 7.67-7.53 (m, 5H), 7.05 (d, J=8.8 Hz, 2H), 4.51 (m, 1H), 2.88 (m, 2H), 2.63-2.52 (m, 2H), 2.43 (s, 3H), 2.40 (s, 3H), 2.02 (m, 2H), 1.77 (m, 2H). $^{13}$C NMR (126 MHz, DMSO) δ 164.48, 156.20, 137.85, 136.51, 135.61, 135.04, 133.63, 132.29, 130.40, 128.86, 127.42, 126.88, 126.21, 120.63, 116.26, 70.60, 51.57, 44.44, 29.42, 19.62. HRMS (ESI+) m/z: [M+H$^+$] calcd for C$_{26}$H$_{28}$ClN$_2$O$_2$ 435.1839. found 435.1838.

3-chloro-4-methyl-N-(4'-((1-methylpiperidin-4-yl)oxy)-[1,1'-biphenyl]-4-yl)benzamide (41k)

Acid chloride 41k (0.36 mmol) was added to a solution of aniline 7 (0.18 mmol) and triethylamine (0.13 mL, 0.94 mmol) in anhydrous dichloromethane (5 mL). After 12 h, the solvent was removed and the residue was purified via column chromatography (SiO$_2$, 10:1, CH$_2$Cl$_2$:methanol) to afford a white amorphous solid (80%). $^1$H NMR (500 MHz, chloroform-d) δ 7.88 (d, J=1.9 Hz, 1H), 7.70-7.65 (m, 3H), 7.52 (d, J=8.6 Hz, 2H), 7.48 (d, J=8.7 Hz, 2H), 7.32 (d, J=7.5 Hz, 1H), 6.94 (d, J=8.7 Hz, 2H), 4.46 (m, 1H), 2.93-2.66 (m, 2H), 2.54 (m, 2H), 2.44 (s, 3H), 2.42 (s, 3H), 2.16-2.07 (m, 2H), 1.98-1.90 (m, 2H). $^{13}$C NMR (126 MHz, CDCl$_3$+CH$_3$OH) δ 165.03, 156.52, 140.36, 137.05, 136.88, 134.89, 134.17, 133.69, 131.29, 128.14, 128.05, 127.25, 125.60, 120.91, 116.45, 70.23, 51.78, 45.40, 29.35, 20.30. HRMS (ESI+) m/z: [M+H$^+$] calcd for C$_{26}$H$_{28}$ClN$_2$O$_2$ 435.1839. found 435.1841.

3-bromo-4-methyl-N-(4'-((1-methylpiperidin-4-yl)oxy)-[1,1'-biphenyl]-4-yl)benzamide (41l)

Acid chloride 41l (0.36 mmol) was added to a solution of aniline 7 (0.18 mmol) and triethylamine (0.13 mL, 0.94 mmol) in anhydrous dichloromethane (5 mL). After 12 h, the solvent was removed and the residue was purified via column chromatography (SiO$_2$, 10:1, CH$_2$Cl$_2$:methanol) to afford a white amorphous solid (69%). $^1$H NMR (500 MHz, chloroform-d) δ 7.95 (d, J=1.9 Hz, 1H), 7.61 (dd, J=7.9, 1.9 Hz, 1H), 7.54 (d, J=8.2 Hz, 2H), 7.36 (d, J=9.0 Hz, 2H), 7.33 (d, J=8.0 Hz, 2H), 7.18 (d, J=7.9 Hz, 1H), 6.80 (d, J=8.4 Hz, 2H), 4.44-4.27 (m, 1H), 2.77 (m, 2H), 2.60 (m, 2H), 2.36 (s, 3H), 2.28 (s, 3H), 1.98 (m, 2H), 1.84 (m, 2H). $^{13}$C NMR (126 MHz, CDCl$_3$+CH$_3$OH) δ 165.52, 156.08, 141.83, 136.97, 136.71, 134.04, 133.72, 131.30, 130.68, 127.86, 126.79, 126.25, 124.74, 121.13, 116.21, 69.55, 51.13, 44.60, 28.73, 22.65. HRMS (ESI+) m/z: [M+H$^+$] calcd for C$_{26}$H$_{28}$BrN$_2$O$_2$ 479.1334. found 479.1333.

3-iodo-4-methyl-N-(4'-((1-methylpiperidin-4-yl)oxy)-[1,1'-biphenyl]-4-yl)benzamide (41m)

Acid chloride 41m (0.36 mmol) was added to a solution of aniline 7 (0.18 mmol) and triethylamine (0.13 mL, 0.94 mmol) in anhydrous dichloromethane (5 mL). After 12 h, the solvent was removed and the residue was purified via column chromatography (SiO$_2$, 10:1, CH$_2$Cl$_2$:methanol) to afford a white amorphous solid (78%). $^1$H NMR (500 MHz, DMSO-d$_6$) δ 10.33 (s, 1H, NH), 8.42 (d, J=1.8 Hz, 1H), 7.93 (dd, J=7.9, 1.9 Hz, 1H), 7.83 (d, J=8.7 Hz, 2H), 7.66-7.53 (m, 4H), 7.50 (d, J=7.9 Hz, 1H), 7.04 (d, J=8.8 Hz, 1H), 4.48 (m, 1H), 2.80 (m, 2H), 2.45 (s, 3H), 2.34 (m, 2H), 2.07-1.93 (m, 2H), 1.80-1.66 (m, 2H). $^{13}$C NMR (126 MHz, DMSO) δ 163.54, 156.27, 144.65, 137.79, 137.40, 135.07, 133.99, 132.21, 129.72, 127.70, 127.41, 126.19, 120.68, 116.23, 101.09, 71.05, 52.03, 45.16, 29.83, 27.51. HRMS (ESI+) m/z: [M+H]+ calcd for $C_{26}H_{28}IN_2O_2$ 527.1195. found 527.1192.

3,4-dichloro-N-(4'-((1-methylpiperidin-4-yl)oxy)-[1,1'-biphenyl]-4-yl)benzamide (41n)

Acid chloride 41n (0.36 mmol) was added to a solution of aniline 7 (0.18 mmol) and triethylamine (0.13 mL, 0.94 mmol) in anhydrous dichloromethane (5 mL). After 12 h, the solvent was removed and the residue was purified via column chromatography (SiO$_2$, 10:1, CH$_2$Cl$_2$:methanol) to afford a white amorphous solid (81%). $^1$H NMR (400 MHz, chloroform-d) δ 7.77 (d, J=2.1 Hz, 1H), 7.50 (dd, J=8.5, 2.1 Hz, 1H), 7.41 (d, J=8.6 Hz, 2H), 7.29-7.16 (m, 4H), 7.13 (t, J=4.1 Hz, 1H), 6.67 (d, J=8.7 Hz, 2H), 4.26 (m, 1H), 2.72 (m, 2H), 2.60 (m, 2H), 2.29 (s, 3H), 1.88 (m, 2H), 1.75 (m, 2H). $^{13}$C NMR (126 MHz, CDCl$_3$) δ 164.64, 156.20, 136.95, 136.88, 135.92, 134.79, 133.72, 132.80, 130.51, 129.65, 127.98, 126.94, 126.82, 121.18, 116.29, 69.59, 51.17, 44.80, 28.69. HRMS (ESI+) m/z: [M+H]+ calcd for $C_{25}H_{25}Cl_2N_2O_2$ 455.1293. found 455.1291.

3,5-dichloro-N-(4'-((1-methylpiperidin-4-yl)oxy)-[1,1'-biphenyl]-4-yl)benzamide (41o)

Acid chloride 41o (0.36 mmol) was added to a solution of aniline 7 (0.18 mmol) and triethylamine (0.13 mL, 0.94 mmol) in anhydrous dichloromethane (5 mL). After 12 h, the solvent was removed and the residue was purified via column chromatography (SiO$_2$, 10:1, CH$_2$Cl$_2$:methanol) to afford a white amorphous solid (70%). $^1$H NMR (400 MHz, chloroform-d) δ 7.70 (s, 2H), 7.56 (d, J=8.4 Hz, 2H), 7.37 (m, 5H), 6.82 (d, J=8.6 Hz, 2H), 4.33 (m, 1H), 2.80-2.64 (m, 2H), 2.49 (m, 2H), 2.30 (s, 3H), 1.94 (m, 2H), 1.83 (m, 2H). $^{13}$C NMR (126 MHz, DMSO) δ 162.61, 156.44, 138.09, 137.46, 135.50, 134.33, 132.09, 130.95, 127.49, 126.53, 126.31, 120.78, 116.27, 71.35, 52.01, 45.26, 30.08. HRMS (ESI+) m/z: [M+H]+ calcd for $C_{25}H_{25}Cl_2N_2O_2$ 455.1293. found 455.1296.

2,4-dichloro-N-(4'-((1-methylpiperidin-4-yl)oxy)-[1,1'-biphenyl]-4-yl)benzamide (41p)

Acid chloride 41p (0.36 mmol) was added to a solution of aniline 7 (0.18 mmol) and triethylamine (0.13 mL, 0.94 mmol) in anhydrous dichloromethane (5 mL). After 12 h, the solvent was removed and the residue was purified via column chromatography (SiO$_2$, 10:1, CH$_2$Cl$_2$:methanol) to afford a white amorphous solid (63%). $^1$H NMR (500 MHz, chloroform-d) δ 7.58 (d, J=8.3 Hz, 2H), 7.47-7.33 (m, 4H), 7.27-7.18 (m, 2H), 7.09 (dd, J=8.4, 2.1 Hz, 1H), 6.85 (d, J=8.3 Hz, 2H), 4.49 (m, 1H), 3.07-2.90 (m, 4H), 2.58 (s, 3H), 2.13 (m, 2H), 2.00-1.89 (m, 2H). $^{13}$C NMR (126 MHz, CDCl$_3$) δ 164.97, 156.32, 137.13, 136.69, 136.57, 134.57, 133.67, 131.98, 130.25, 129.90, 128.03, 127.34, 127.10, 120.61, 116.34, 69.83, 51.49, 45.06, 29.19. HRMS (ESI+) m/z: [M+H]+ calcd for $C_{25}H_{25}Cl_2N_2O_2$ 455.1293. found 455.1292.

N-(4'-((1-methylpiperidin-4-yl)oxy)-[1,1'-biphenyl]-4-yl)-[1,1'-biphenyl]-2-carboxamide (41q)

Acid chloride 41q (0.36 mmol) was added to a solution of aniline 7 (0.18 mmol) and triethylamine (0.13 mL, 0.94 mmol) in anhydrous dichloromethane (5 mL). After 12 h, the solvent was removed and the residue was purified via column chromatography (SiO$_2$, 10:1, CH$_2$Cl$_2$:methanol) to afford a white amorphous solid (66%). $^1$H NMR (400 MHz, methanol-d$_4$) δ 8.24 (d, J=4.5 Hz, 2H), 7.55-7.40 (m, 2H), 7.27 (t, J=7.5 Hz, 1H), 7.19 (m, 6H), 7.06 (m, 4H), 6.69 (dd, J=8.4, 3.0 Hz, 2H), 4.39-4.25 (m, 1H), 2.89-2.64 (m, 4H), 2.40 (s, 3H), 2.06-1.91 (m, 2H), 1.83 (m, 2H). $^{13}$C NMR (126 MHz, DMSO) δ 167.65, 155.87, 139.92, 139.09, 137.87, 136.96, 134.72, 132.51, 129.88, 129.67, 128.17, 128.13, 127.69, 127.35, 127.16, 127.11, 126.17, 119.79, 116.26, 69.25, 50.77, 43.29, 28.11. HRMS (ESI+) m/z: [M+H]+ calcd for $C_{31}H_{31}N_2O_2$ 463.2386. found 463.2389.

N-(4'-((1-methylpiperidin-4-yl)oxy)-[1,1'-biphenyl]-4-yl)-[1,1'-biphenyl]-3-carboxamide (41r)

Acid chloride 41r (0.36 mmol) was added to a solution of aniline 7 (0.18 mmol) and triethylamine (0.13 mL, 0.94 mmol) in anhydrous dichloromethane (5 mL). After 12 h, the solvent was removed and the residue was purified via column chromatography (SiO$_2$, 10:1, CH$_2$Cl$_2$:methanol) to afford a white amorphous solid (70%). $^1$H NMR (500 MHz, DMSO-d$_6$) δ 10.24 (s, 1H, NH), 8.03 (dd, J=8.6, 2.4 Hz, 1H), 7.97 (d, J=2.3 Hz, 1H), 7.85 (d, J=8.4 Hz, 2H), 7.61 (d, J=8.4 Hz, 4H), 7.56 (d, J=7.4 Hz, 2H), 7.46 (t, J=7.6 Hz, 2H), 7.38 (t, J=7.4 Hz, 1H), 7.27 (d, J=8.7 Hz, 1H), 7.08 (d, J=8.5 Hz, 2H), 4.63 (m, 1H), 3.15 (m, 2H), 2.96 (m, 2H), 2.64 (s, 3H), 2.11 (m, 2H), 1.96-1.78 (m, 2H). $^{13}$C NMR (126 MHz, DMSO) δ 164.73, 158.69, 155.89, 138.17, 137.46, 134.70, 132.63, 129.87, 129.37, 129.34, 129.08, 128.08, 127.44, 127.19, 126.88, 126.18, 120.69, 116.38, 111.38, 68.81, 50.55, 43.04, 28.02. HRMS (ESI+) m/z: [M+H]+ calcd for $C_{31}H_{31}N_2O_2$ 463.2386. found 463.2387.

N-(4'-((1-methylpiperidin-4-yl)oxy)-[1,1'-biphenyl]-4-yl)-[1,1'-biphenyl]-4-carboxamide (41s)

Acid chloride 41d (0.36 mmol) was added to a solution of aniline 7 (0.18 mmol) and triethylamine (0.13 mL, 0.94 mmol) in anhydrous dichloromethane (5 mL). After 12 h, the solvent was removed and the residue was purified via column chromatography (SiO$_2$, 10:1, CH$_2$Cl$_2$:methanol) to afford a white amorphous solid (75%). $^1$H NMR (400 MHz, chloroform-d) δ 7.90 (d, J=8.1 Hz, 2H), 7.64 (d, J=8.1 Hz, 2H), 7.61 (d, J=8.1 Hz, 2H), 7.53 (d, J=7.8 Hz, 2H), 7.43 (dd, J=13.4, 8.2 Hz, 4H), 7.36 (t, J=7.5 Hz, 2H), 7.29 (d, J=6.8 Hz, 1H), 6.86 (d, J=8.6 Hz, 2H), 4.37 (m, 1H), 2.75 (m, 2H), 2.54 (m, 2H), 2.36 (s, 3H), 2.08-1.95 (m, 2H), 1.87 (m, 2H). $^{13}$C NMR (126 MHz, DMSO) δ 165.05, 156.23, 143.05, 139.05, 138.03, 134.95, 133.63, 132.28, 129.04, 128.35, 128.13, 127.41, 126.89, 126.55, 126.20, 120.62, 116.25, 70.83, 51.67, 44.67, 29.68. HRMS (ESI+) m/z: [M+H]+ calcd for $C_{31}H_{31}N_2O_2$ 463.2386. found 463.2383.

N-(4'-((1-methylpiperidin-4-yl)oxy)-[1,1'-biphenyl]-4-yl)-2-naphthamide (43a)

Acid chloride 42a (0.36 mmol) was added to a solution of aniline 7 (0.18 mmol) and triethylamine (0.13 mL, 0.94 mmol) in anhydrous dichloromethane (5 mL). After 12 h, the solvent was removed and the residue was purified via column chromatography (SiO$_2$, 10:1, CH$_2$Cl$_2$:methanol) to afford a white amorphous solid (60%). $^1$H NMR (500 MHz, methanol-d$_4$) δ 8.35 (d, J=1.8 Hz, 1H), 7.92-7.84 (m, 3H), 7.81-7.74 (m, 1H), 7.68 (d, J=8.5 Hz, 2H), 7.55-7.35 (m, 6H), 6.87 (d, J=8.7 Hz, 2H), 4.40 (m, 1H), 2.78 (m, 2H), 2.59 (m, 2H), 2.38 (s, 3H), 2.04 (m, 2H), 1.90 (m, 2H). $^{13}$C NMR (126 MHz, CDCl$_3$+CH$_3$OH) δ 167.04, 156.35, 137.18, 136.80, 134.88, 133.69, 132.61, 132.09, 128.98, 128.44, 127.97, 127.93, 127.84, 127.73, 127.01, 126.80, 123.86, 121.08, 116.35, 70.03, 51.61, 45.21, 29.65. HRMS (ESI+) m/z: [M+H$^+$] calcd for $C_{29}H_{29}N_2O_2$ 437.2229. found 437.2227.

N-(4'-((1-methylpiperidin-4-yl)oxy)-[1,1'-biphenyl]-4-yl)-1-naphthamide (43b)

Acid chloride 42b (0.36 mmol) was added to a solution of aniline 7 (0.18 mmol) and triethylamine (0.13 mL, 0.94 mmol) in anhydrous dichloromethane (5 mL). After 12 h, the solvent was removed and the residue was purified via column chromatography (SiO2, 10:1, CH2Cl2:methanol) to afford a white amorphous solid (80%). 1H NMR (500 MHz, Chloroform-d) δ 8.17 (d, J=8.1 Hz, 1H), 7.82 (d, J=8.3 Hz, 1H), 7.79-7.73 (m, 1H), 7.65 (d, J=8.2 Hz, 2H), 7.60 (d, J=7.0 Hz, 1H), 7.44-7.37 (m, 7H), 6.85 (d, J=8.3 Hz, 2H), 4.41 (s, 1H), 2.85 (d, J=12.0 Hz, 2H), 2.67 (s, 2H), 2.41 (s, 3H), 2.04 (t, J=11.1 Hz, 2H), 1.90 (d, J=14.2 Hz, 2H). 13C NMR (126 MHz, CDCl3+CH3OH) δ 168.82, 156.12, 137.24, 136.77, 134.38, 133.81, 133.61, 130.68, 130.02, 128.27, 127.96, 127.06, 127.00, 126.37, 125.19, 125.06, 124.65, 120.63, 116.28, 69.38, 51.34, 44.66, 28.95. HRMS (ESI+) m/z: [M+H+] calcd for C29H29N2O2 437.2229. found 437.2231.

N-(4'-((1-methylpiperidin-4-yl)oxy)-[1,1'-biphenyl]-4-yl)quinoline-3-carboxamide (45a)

Acid chloride 44a (0.36 mmol) was added to a solution of aniline 7 (0.18 mmol) and triethylamine (0.13 mL, 0.94 mmol) in anhydrous dichloromethane (5 mL). After 12 h, the solvent was removed and the residue was purified via column chromatography ($SiO_2$, 10:1, $CH_2Cl_2$:methanol) to afford a white amorphous solid (78%). $^1$H NMR (500 MHz, Chloroform-d) δ 9.29 (d, J=2.3 Hz, 1H), 8.79 (d, J=2.3 Hz, 1H), 8.05 (d, J=8.5 Hz, 1H), 7.93 (dd, J=8.3, 1.4 Hz, 1H), 7.82-7.78 (m, 1H), 7.75 (d, J=8.6 Hz, 2H), 7.60 (t, J=8.2 Hz, 1H), 7.51 (d, J=8.6 Hz, 2H), 7.47 (d, J=8.7 Hz, 2H), 6.91 (d, J=8.7 Hz, 2H), 4.51-4.40 (m, 1H), 2.93-2.79 (m, 2H), 2.69 (m, 2H), 2.45 (s, 3H), 2.11-2.07 (m, 2H), 2.00-1.88 (m, 2H). $^{13}$C NMR (126 MHz, CDCl$_3$+CH$_3$OH) δ 164.54, 151.05, 148.52, 148.28, 138.45, 137.28, 137.08, 131.84, 131.14, 129.12, 128.46, 128.11, 127.97, 127.84, 127.25, 127.13, 121.24, 116.38, 68.04, 51.55, 45.14, 28.95. HRMS (ESI+) m/z: [M+H$^+$] calcd for $C_{28}H_{28}N_3O_2$ 438.2182. found 438.2181.

N-(4'-((1-methylpiperidin-4-yl)oxy)-[1,1'-biphenyl]-4-yl)quinoline-6-carboxamide (45b)

Acid chloride 44b (0.36 mmol) was added to a solution of aniline 7 (0.18 mmol) and triethylamine (0.13 mL, 0.94 mmol) in anhydrous dichloromethane (5 mL). After 12 h, the solvent was removed and the residue was purified via column chromatography ($SiO_2$, 10:1, $CH_2Cl_2$:methanol) to afford a white amorphous solid (74%). $^1$H NMR (500 MHz, DMSO-d$_6$) δ 10.61 (s, 1H, NH), 9.02 (dd, J=4.2, 1.7 Hz, 1H), 8.67 (d, J=2.0 Hz, 1H), 8.55 (dd, J=8.3, 1.7 Hz, 1H), 8.28 (dd, J=8.8, 2.0 Hz, 1H), 8.15 (d, J=8.8 Hz, 1H), 7.90 (d, J=8.7 Hz, 2H), 7.68-7.63 (m, 3H), 7.61 (d, J=8.7 Hz, 2H), 7.05 (d, J=8.7 Hz, 2H), 4.50 (m, 1H), 3.33 (m, 2H), 2.84 (m, 2H), 2.38-2.34 (m, 3H), 2.02 (m, 2H), 1.77 (m, 2H). $^{13}$C NMR (126 MHz, DMSO) δ 165.12, 156.36, 152.34, 148.73, 138.08, 137.18, 135.11, 132.80, 132.36, 129.09, 128.55, 128.14, 127.56, 127.13, 126.38, 122.37, 120.77, 116.25, 70.88, 51.89, 44.82, 29.71. HRMS (ESI+) m/z: [M+H$^+$] calcd for $C_{28}H_{28}N_3O_2$ 438.2182. found 438.2185.

N-(4'-((1-methylpiperidin-4-yl)oxy)-[1,1'-biphenyl]-4-yl)-1H-indole-2-carboxamide (47a)

Acid chloride 46a (0.36 mmol) was added to a solution of aniline 7 (0.18 mmol) and triethylamine (0.13 mL, 0.94 mmol) in anhydrous dichloromethane (5 mL). After 12 h, the solvent was removed and the residue was purified via column chromatography ($SiO_2$, 10:1, $CH_2Cl_2$:methanol) to afford a white amorphous solid (80%). $^1$H NMR (500 MHz, DMSO-d$_6$) δ 11.63 (d, J=2.2 Hz, 1H, NH), 10.15 (s, 1H, NH), 7.71 (d, J=8.7 Hz, 2H), 7.50 (dd, J=7.9, 1.1 Hz, 1H), 7.45 (d, J=8.7 Hz, 2H), 7.42 (d, J=8.7 Hz, 2H), 7.29 (dd, J=8.0, 1.0 Hz, 1H), 7.27 (d, J=2.0 Hz, 1H), 7.04 (ddd, J=8.2, 6.9, 1.2 Hz, 1H), 6.92-6.83 (m, 3H), 4.36 (m, 1H), 2.79-2.68 (m, 2H), 2.57-2.42 (m, 2H), 2.28 (s, 3H), 1.96-1.78 (m, 2H), 1.63-1.55 (m, 2H). $^{13}$C NMR (126 MHz, DMSO) δ 159.62, 156.10, 137.84, 136.78, 134.78, 132.42, 131.45, 127.42, 126.97, 126.30, 123.75, 121.70, 120.38, 119.88, 116.30, 112.34, 103.97, 69.99, 51.29, 44.04, 28.99. HRMS (ESI+) m/z: [M+H$^+$] calcd for $C_{27}H_{28}N_3O_2$ 426.2182. found 426.2179.

N-(4'-((1-methylpiperidin-4-yl)oxy)-[1,1'-biphenyl]-4-yl)benzo[b]thiophene-2-carboxamide (47b)

Acid chloride 46b (0.36 mmol) was added to a solution of aniline 7 (0.18 mmol) and triethylamine (0.13 mL, 0.94 mmol) in anhydrous dichloromethane (5 mL). After 12 h, the solvent was removed and the residue was purified via column chromatography ($SiO_2$, 10:1, $CH_2Cl_2$:methanol) to afford a white amorphous solid (81%). $^1$H NMR (500 MHz, DMSO-d$_6$) δ 10.68 (s, 1H, NH), 8.45 (s, 1H), 8.07 (dd, J=7.4, 1.5 Hz, 1H), 8.05-7.99 (m, 1H), 7.87 (d, J=8.7 Hz, 2H), 7.64 (d, J=8.7 Hz, 2H), 7.62 (d, J=8.7 Hz, 2H), 7.53-7.46 (m, 2H), 7.07 (d, J=8.8 Hz, 2H), 4.68-4.46 (m, 1H), 3.06-2.96 (m, 2H), 2.85-2.74 (m, 2H), 2.54 (s, 3H), 2.17-2.03 (m, 2H), 1.91-1.78 (m, 2H). $^{13}$C NMR (126 MHz, DMSO) δ 160.23, 156.09, 140.44, 140.04, 139.12, 137.50, 135.17, 132.39, 127.47, 126.34, 125.89, 125.39, 125.04, 122.83, 122.71, 120.58, 116.33, 69.70, 50.70, 43.47, 28.36. HRMS (ESI+) m/z: [M+H$^+$] calcd for $C_{27}H_{27}N_2O_2S$ 443.1793. found 443.1791.

5'-((3'-isopentyl-4'-((1-methylpiperidin-4-yl)oxy)-[1,1'-biphenyl]-4-yl)carbamoyl)-2'-methoxy-[1,1'-biphenyl]-3-yl acetate (51)

$^1$H NMR (500 MHz, chloroform-d) δ 7.86 (dd, J=8.5, 2.4 Hz, 1H), 7.79 (s, 1H), 7.76 (d, J=2.4 Hz, 1H), 7.62 (d, J=8.5 Hz, 2H), 7.48 (d, J=8.5 Hz, 2H), 7.32-7.30 (m, 1H), 7.28 (d, J=8.1 Hz, 2H), 7.06 (dt, J=7.8, 1.2 Hz, 1H), 7.02 (dd, J=2.6, 1.5 Hz, 1H), 6.99 (d, J=8.6 Hz, 1H), 6.86 (ddd, J=8.3, 2.6, 1.0 Hz, 1H), 6.80 (d, J=8.4 Hz, 1H), 4.41 (m, 1H), 3.82 (s, 3H), 3.79 (s, 3H), 2.71 (t, J=10.1 Hz, 2H), 2.63-2.56 (m, 2H), 2.55 (m, 2H), 2.37 (s, 3H), 2.14-2.04 (m, 2H), 1.93 (m, 2H), 1.57 (m, 1H), 1.48-1.40 (m, 2H), 0.90 (s, 3H), 0.89 (s, 3H). $^{13}$C NMR (126 MHz, CDCl$_3$) δ 165.07, 159.33, 154.26, 154.21, 138.84, 137.05, 136.78, 132.92, 132.80, 130.71, 129.54, 129.17, 128.75, 128.41, 127.22, 127.15, 125.03, 121.99, 120.40, 115.32, 112.97, 112.70, 111.08, 69.58, 55.87, 55.35, 51.95, 45.71, 39.64, 29.99, 28.68, 28.25, 22.71.

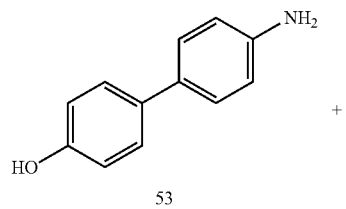

solvent was removed and the residue purified via column chromatography (SiO$_2$, 10:1, DCM:methanol) to afford 54 as a off-white amorphous solid (62%). $^1$H NMR (500 MHz, DMSO-d$_6$) δ 9.50 (s, 1H, NH), 8.02 (dd, J=8.6, 2.4 Hz, 1H), 7.98 (d, J=2.4 Hz, 1H), 7.82 (d, J=8.7 Hz, 2H), 7.56 (d, J=8.7 Hz, 2H), 7.49 (d, J=8.6 Hz, 2H), 7.37 (t, J=7.9 Hz, 1H), 7.25 (d, J=8.7 Hz, 1H), 7.15-7.07 (m, 2H), 6.95 (ddd, J=8.3, 2.6, 1.0 Hz, 1H), 6.84 (d, J=8.6 Hz, 2H), 3.86 (s, 3H), 3.80 (s, 3H). $^{13}$C NMR (126 MHz, DMSO) δ 164.61, 158.93, 158.66, 156.75, 138.82, 137.79, 135.24, 130.51, 129.79, 129.19, 129.11, 129.06, 127.29, 126.91, 125.89, 121.74, 120.63, 115.64, 115.16, 112.53, 111.39, 55.83, 55.07. HRMS (ESI$^+$) m/z [M+Na$^+$] calcd for C$_{27}$H$_{23}$NO$_4$Na 448.1525. found 448.1522.

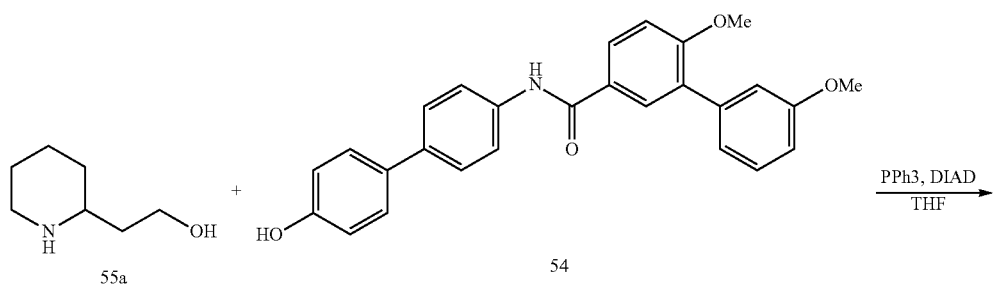

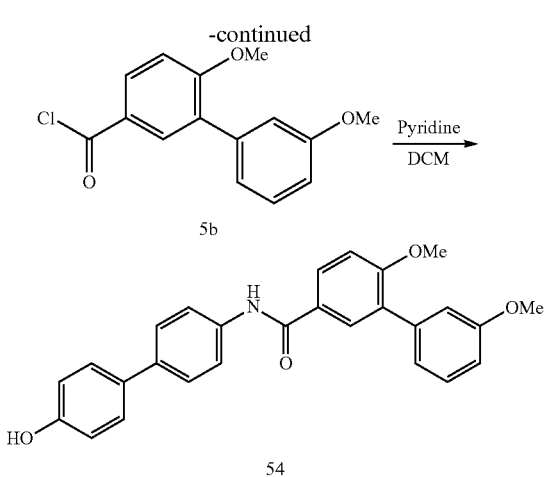

N-(4'-hydroxy-[1,1'-biphenyl]-4-yl)-3',6-dimethoxy-[1,1'-biphenyl]-3-carboxamide (54)

A solution of acid chloride (5b, 0.27 mmol), in anhydrous dichloromethane (2 mL) was added to a solution of the aniline (53, 0.18 mmol) and anhydrous pyridine (0.94 mmol) in anhydrous dichloromethane (5 mL). After 12 h, the 3',6-dimethoxy-N-(4'-(2-(piperidin-2-yl)ethoxy)-[1,1'-biphenyl]-4-yl)-[1,1'-biphenyl]-3-carboxamide (56a)

Diisopropylazodicarboxylate (9.36 mmol) was added to a solution of phenol (54, 4.18 mmol), alcohol 55a (480 mg, 4.18 mmol) and triphenylphosphine (2.46 g, 9.36 mmol) in anhydrous THF (50 mL). After 2 h, the solvent was removed and the residue purified via column chromatography (SiO$_2$, 10:1, DCM:methanol) to afford desired product 56a as a colorless amorphous solid (1.02 g, 75%). $^1$H NMR (400 MHz, Methanol-d$_4$) δ 7.83 (dd, J=8.6, 2.4 Hz, 1H), 7.79 (d, J=2.4 Hz, 1H), 7.60 (d, J=8.7 Hz, 2H), 7.42 (d, J=6.4 Hz, 2H), 7.40 (d, J=6.4 Hz, 2H), 7.23 (t, J=7.9 Hz, 1H), 7.04-7.01 (m, 1H), 6.99 (dd, J=2.7, 1.6 Hz, 1H), 6.97 (d, J=8.7 Hz, 1H), 6.85 (d, J=8.8 Hz, 2H), 6.80 (ddd, J=8.2, 2.6, 1.0 Hz, 1H), 4.06-4.01 (m, 2H), 3.30 (m, 1H), 3.18 (m, 1H), 2.79 (m, 1H), 2.16 (d, J=13.0 Hz, 1H), 1.95 (m, 2H), 1.87-1.72 (m, 2H), 1.65 (m, 1H), 1.46 (m, 2H). $^{13}$C NMR (126 MHz, CDCl$_3$+CH3OH) δ 166.26, 159.37, 159.28, 157.69, 139.00, 137.20, 136.63, 133.80, 130.53, 130.00, 129.16, 128.65, 127.93, 127.05, 127.03, 122.10, 121.01, 115.37, 114.77, 112.87, 111.02, 63.60, 55.83, 55.35, 54.84, 44.98, 33.04, 28.55, 22.28, 22.24.

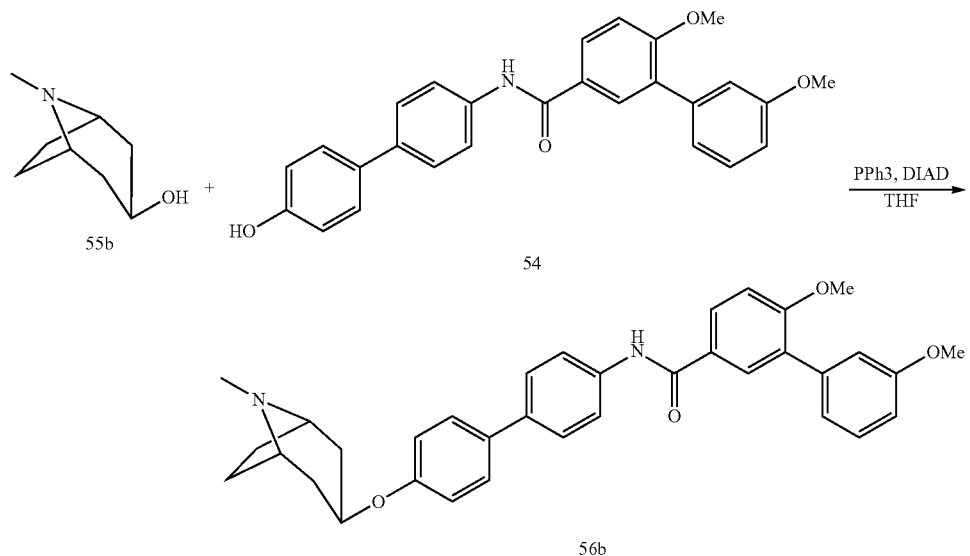

3',6-dimethoxy-N-(4'-(((1R,3s,5S)-8-methyl-8-azabicyclo[3.2.1]octan-3-yl)oxy)-[1,1'-biphenyl]-4-yl)-[1,1'-biphenyl]-3-carboxamide (56b)

Diisopropylazodicarboxylate (9.36 mmol) was added to a solution of phenol (54, 4.18 mmol), alcohol 55b (4.18 mmol) and triphenylphosphine (2.46 g, 9.36 mmol) in anhydrous THF (50 mL). After 2 h, the solvent was removed and the residue purified via column chromatography (SiO$_2$, 10:1, DCM:methanol) to afford desired product 56b as a colorless amorphous solid (71%). $^1$H NMR (500 MHz, DMSO-d$_6$) δ 7.94 (dd, J=8.6, 2.4 Hz, 1H), 7.84 (m, 2H), 7.70 (d, J=8.6 Hz, 2H), 7.55 (d, J=8.6 Hz, 2H), 7.50 (d, J=8.7 Hz, 2H), 7.38 (t, J=7.9 Hz, 1H), 7.14 (dt, J=7.6, 0.9 Hz, 1H), 7.11 (dd, J=2.6, 1.6 Hz, 1H), 7.08 (d, J=8.7 Hz, 1H), 6.96 (d, J=8.8 Hz, 2H), 4.65-4.47 (m, 1H), 3.90 (s, 3H), 3.87 (s, 3H), 3.48 (m, 2H), 2.54 (s, 3H), 2.24-2.18 (m, 2H), 2.12-2.03 (m, 4H), 1.80 (m, 2H). $^{13}$C NMR (126 MHz, DMSO) δ 165.27, 159.56, 159.55, 157.08, 139.03, 137.11, 136.96, 133.79, 130.94, 129.74, 129.39, 128.61, 128.13, 127.44, 127.32, 122.19, 120.64, 116.66, 115.53, 113.18, 111.30, 69.49, 60.85, 56.08, 55.56, 37.99, 35.39, 26.77.

N-(4'-(3-(dimethylamino)propoxy)-[1,1'-biphenyl]-4-yl)-3',6-dimethoxy-[1,1'-biphenyl]-3-carboxamide (56c)

Diisopropylazodicarboxylate (9.36 mmol) was added to a solution of phenol (54, 4.18 mmol), alcohol 55c (4.18 mmol) and triphenylphosphine (2.46 g, 9.36 mmol) in anhydrous THF (50 mL). After 2 h, the solvent was removed and the residue purified via column chromatography (SiO$_2$, 10:1, DCM:methanol) to afford desired product 56c as a colorless amorphous solid (68%). $^1$H NMR (500 MHz, Chloroform-d) δ 7.96 (dd, J=8.6, 2.4 Hz, 1H), 7.87-7.79 (m, 2H), 7.72 (d, J=8.6 Hz, 2H), 7.58 (d, J=8.6 Hz, 2H), 7.55 (d, J=8.7 Hz, 2H), 7.40 (t, J=7.9 Hz, 1H), 7.21-7.05 (m, 3H), 7.00-6.84 (m, 3H), 4.14 (t, J=5.7 Hz, 2H), 3.92 (s, 3H), 3.88 (s, 3H), 3.17 (m, 2H), 2.81 (s, 6H), 2.34 (m, 2H). $^{13}$C NMR (126 MHz, CDCl$_3$) δ 165.04, 163.26, 162.16, 159.35, 138.96, 137.17, 136.20, 131.01, 130.75, 129.51, 129.18, 128.40, 127.99, 127.25, 127.10, 121.98, 120.43, 115.33, 114.67, 112.97, 111.10, 71.86, 56.21, 55.88, 55.35, 43.70, 23.62.

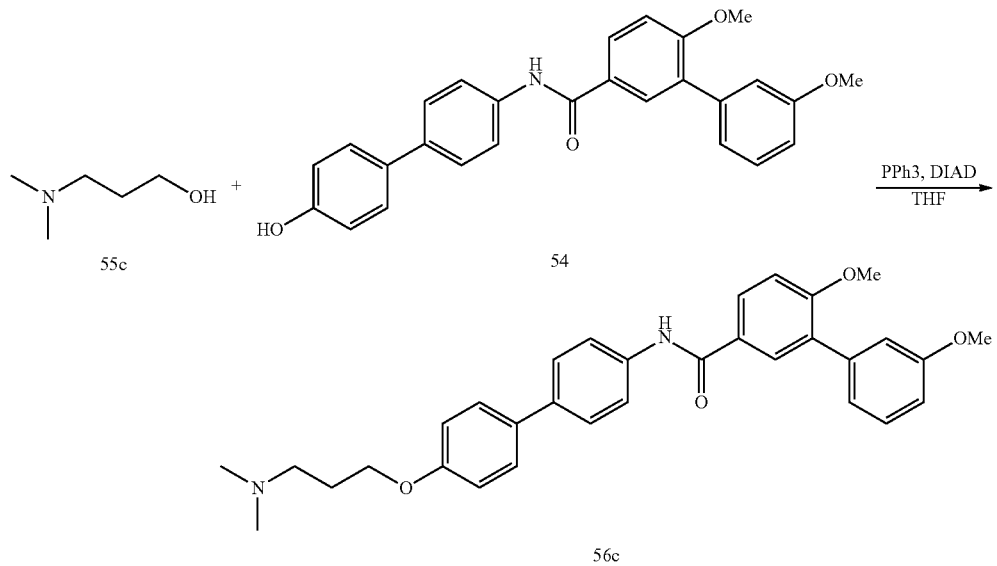

3',6-dimethoxy-N-(4'-(2-(1-methylpyrrolidin-2-yl)ethoxy)-[1,1'-biphenyl]-4-yl)-[1,1'-biphenyl]-3-carboxamide (56d)

¹H NMR (400 MHz, chloroform-d) δ 8.10 (s, 1H, NH), 7.95 (dd, J=8.6, 2.4 Hz, 1H), 7.86 (d, J=2.3 Hz, 1H), 7.73 (d, J=8.6 Hz, 2H), 7.54 (d, J=8.6 Hz, 2H), 7.51 (d, J=8.7 Hz, 2H), 7.36 (t, J=7.9 Hz, 1H), 7.17-7.09 (m, 2H), 7.06 (d, J=8.7 Hz, 1H), 6.97-6.87 (m, 3H), 4.18-4.10 (m, 1H), 4.02 (m, 1H), 3.45 (m, 1H), 2.82 (s, 1H), 2.55 (s, 3H), 2.54-2.46 (m, 1H), 2.40-2.29 (m, 1H), 2.20-2.13 (m, 1H), 2.08-1.96 (m, 2H), 1.92-1.82 (m, 1H), 1.82-1.69 (m, 1H).

4'-hydroxy-[1,1'-biphenyl]-4-carboxylic acid

[1,1'-Bis(diphenylphosphino)ferrocene]dichloropalladium(II) (20 mg, 0.02 mmol) and potassium carbonate solution (2M, 100 μL) were added to a solution of 4-iodobenzoic acid (248 mg, 1.0 mmol) and 4-hydroxyphenylboronic acid (276 mg, 2.0 mmol) in dioxane (15 mL). The mixture was stirred at 110° C. for 12 hours before concentrated to dryness. The brown residue was purified via column chromatography (SiO₂, 10:1, CH₂Cl₂:methanol) to afford desired product as a brown amorphous solid (152 mg, 71%). ¹H NMR (400 MHz, Chloroform-d) δ 7.93 (d, J=8.4 Hz, 2H), 7.48 (d, J=8.6 Hz, 2H), 7.37 (d, J=8.7 Hz, 2H), 6.78 (d, J=8.6 Hz, 2H). HRMS (ESI⁺) m/z [M+Na⁺] calcd for C₁₃H₁₀O₃Na 237.0528. found 237.0531.

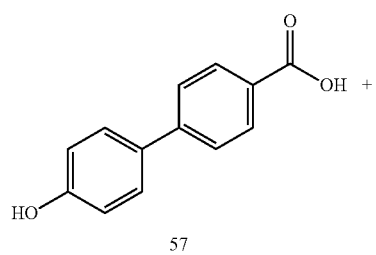

N-(3',6-dimethoxy-[1,1'-biphenyl]-3-yl)-4'-hydroxy-[1,1'-biphenyl]-4-carboxamide (59)

1-Ethyl-3-(3-dimethylaminopropyl)carbodiimide hydrochloride (169 mg, 0.88 mmol) and pyridine (100 mg, 1.43 mmol) were added to a solution of acid (120 mg, 0.56 mmol) and amine (100 mg, 0.44 mmol) in dry DCM (3 mL). The resulting mixture was stirred at room temperature overnight before concentrated to dryness. The black residue was purified was purified via column chromatography (SiO₂, 10:1, dichloromethane:acetone) to afford desired product as a brown amorphous solid (162 mg, 87%). ¹H NMR (400 MHz, chloroform-d) δ 8.48 (d, J=4.0 Hz, 2H), 7.88 (d, J=8.0 Hz, 1H), 7.70-7.62 (m, 3H), 7.58 (d, J=8.3 Hz, 1H), 7.51-7.47 (m, 1H), 7.46-7.39 (m, 1H), 7.33-7.28 (m, 2H), 7.06 (t, J=2.7 Hz, 1H), 6.95 (dd, J=8.8, 3.8 Hz, 1H), 6.91-6.78 (m, 2H), 3.79 (s, 3H), 3.76 (s, 3H). HRMS (ESI⁺) m/z [M+Na+] calcd for C₂₇H₂₃NO₄Na 448.1525. found 448.1528.

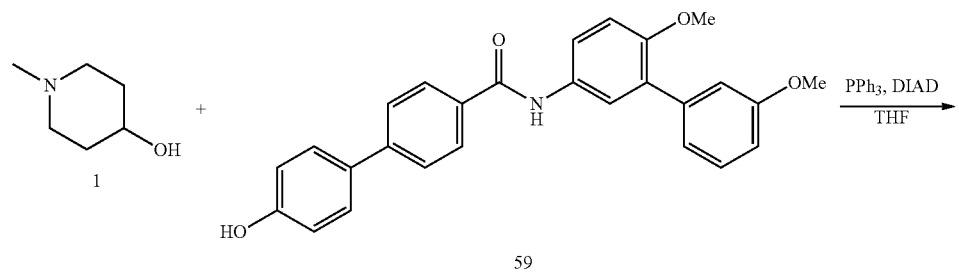

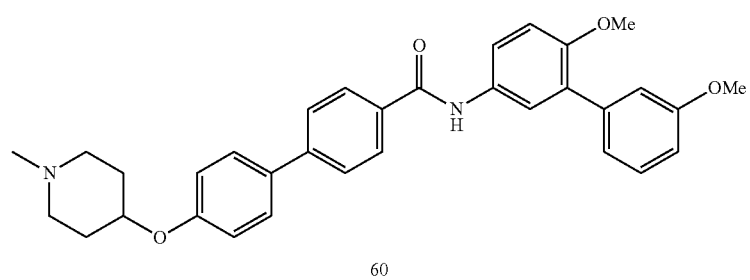

2'-methoxy-5'-(4'-((1-methylpiperidin-4-yl)oxy)-[1,1'-biphenyl]-4-ylcarboxamido)-[1,1'-biphenyl]-3-yl acetate (60)

Diisopropylazodicarboxylate (84 mg, 0.41 mmol) was added to a solution of phenol 59 (0.90 mg, 0.21 mmol), N-methyl-4-hydroxy-piperidine (24 mg, 0.21 mmol) and triphenylphosphine (108 mg, 0.41 mmol) in anhydrous THF (5 mL). After 2 h, the solvent was removed and the residue purified via column chromatography (SiO$_2$, 10:1, CH$_2$Cl$_2$: methanol) to afford desired product as a colorless amorphous solid (72 g, 65%). $^1$H NMR (500 MHz, chloroform-d) δ 7.96 (s, 1H), 7.86 (d, J=8.3 Hz, 2H), 7.65 (dd, J=8.8, 2.8 Hz, 1H), 7.55 (d, J=8.3 Hz, 2H), 7.47 (d, J=8.7 Hz, 1H), 7.43 (d, J=2.7 Hz, 1H), 7.27-7.21 (m, 2H), 7.06-7.01 (m, 2H), 6.93-6.87 (m, 3H), 6.80 (dd, J=8.4, 2.6 Hz, 1H), 4.38 (m, 1H), 3.75 (s, 3H), 3.73 (s, 3H), 2.75 (m, 2H), 2.48 (m, 2H), 2.36 (s, 3H), 2.17-2.01 (m, 2H), 1.88 (m, 2H). $^{13}$C NMR (126 MHz, CDCl$_3$) δ 165.42, 159.21, 157.29, 153.50, 143.93, 139.26, 132.95, 132.64, 131.18, 130.89, 129.00, 128.41, 127.63, 126.78, 123.51, 122.02, 121.20, 116.34, 115.22, 112.78, 111.78, 70.97, 55.96, 55.29, 51.88, 45.59, 29.82. HRMS (ESI$^+$) m/z [M+H$^+$] calcd for C$_{33}$H$_{35}$N$_2$O$_4$ 523.2597. found 523.2601.

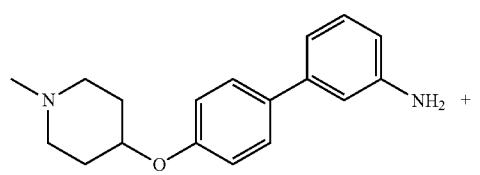

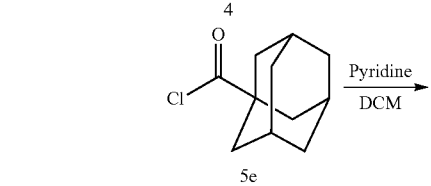

N-(4'-((1-methylpiperidin-4-yl)oxy)-[1,1'-biphenyl]-3-yl)adamantane-1-carboxamide (61a)

A solution of acid chloride (5e, 0.27 mmol), in anhydrous dichloromethane (2 mL) was added to a solution of the aniline (4, 0.18 mmol) and anhydrous pyridine (0.94 mmol) in anhydrous dichloromethane (5 mL). After 12 h, the solvent was removed and the residue purified via column chromatography (SiO$_2$, 10:1, DCM:methanol) to afford a white amorphous solid (63%). $^1$H NMR (500 MHz, chloroform-d) δ 7.78 (s, 1H), 7.45 (d, J=8.7 Hz, 2H), 7.36-7.31 (m, 2H), 7.28 (t, J=7.8 Hz, 1H), 7.22-7.19 (m, 1H), 6.87 (d, J=8.7 Hz, 2H), 4.39 (m, 1H), 2.79 (dd, J=12.2, 9.0 Hz, 2H), 2.59-2.44 (m, 2H), 2.39 (s, 3H), 2.15-2.06 (m, 2H), 2.04 (s, 3H), 1.91 (d, J=2.9 Hz, 6H), 1.90 (m, 2H), 1.79-1.59 (m, 6H). $^{13}$C NMR (126 MHz, CDCl$_3$) δ 176.21, 156.67, 141.49, 138.47, 133.71, 129.26, 128.37, 122.43, 118.38, 118.22, 116.18, 70.32, 51.80, 45.50, 41.55, 39.30, 36.43, 29.64, 28.14. HRMS (ESI) m/z: [M+H$^+$] calcd for C$_{29}$H$_{37}$N$_2$O$_2$ 445.2855. found 445.2856.

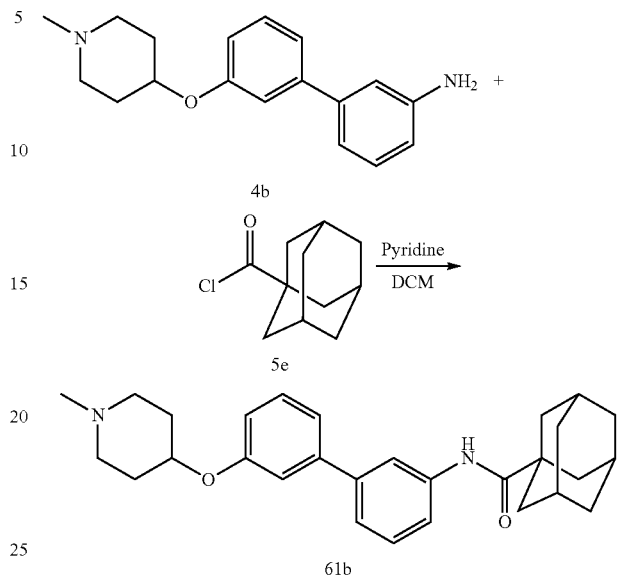

N-(3'-((1-methylpiperidin-4-yl)oxy)-[1,1'-biphenyl]-3-yl)adamantane-1-carboxamide (61b)

A solution of acid chloride (5e, 0.27 mmol), in anhydrous dichloromethane (2 mL) was added to a solution of the aniline (4b, 0.18 mmol) and anhydrous pyridine (0.94 mmol) in anhydrous dichloromethane (5 mL). After 12 h, the solvent was removed and the residue purified via column chromatography (SiO$_2$, 10:1, DCM:methanol) to afford a white amorphous solid (68%). $^1$H NMR (500 MHz, chloroform-d) δ 7.76 (s, 1H, NH), 7.40 (d, J=2.2 Hz, 1H), 7.34 (s, 1H), 7.32-7.26 (m, 1H), 7.23 (dd, J=7.8, 4.0 Hz, 2H), 7.11 (d, J=7.7 Hz, 1H), 7.07 (s, 1H), 6.80 (d, J=7.8 Hz, 1H), 4.40 (s, 1H), 2.76 (m, 2H), 2.47 (m, 2H), 2.36 (s, 3H), 2.13-1.99 (m, 5H), 1.95-1.81 (m, 8H), 1.77-1.59 (m, 6H). $^{13}$C NMR (126 MHz, CDCl$_3$) δ 176.42, 157.60, 142.65, 141.97, 138.65, 129.99, 129.47, 123.09, 120.29, 119.13, 118.96, 115.57, 114.77, 70.87, 52.13, 45.83, 41.74, 39.48, 36.61, 28.31. HRMS (ESI$^+$) m/z: [M+H$^+$] calcd for C$_{29}$H$_{37}$N$_2$O$_2$ 445.2855. found 445.2852.

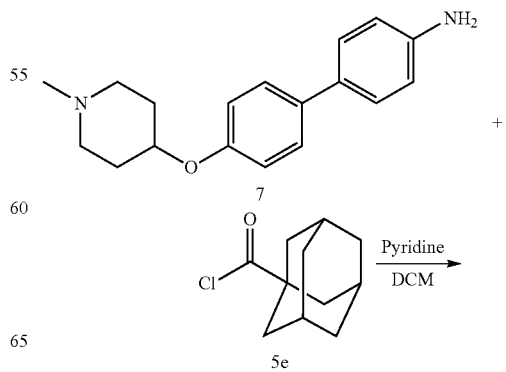

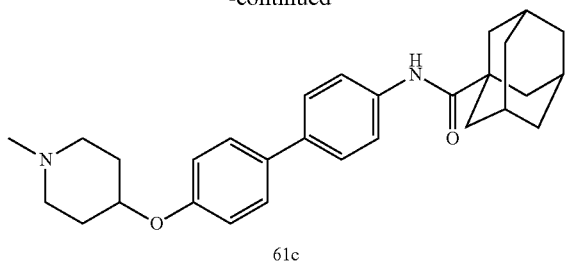

N-(4'-((1-methylpiperidin-4-yl)oxy)-[1,1'-biphenyl]-4-yl)adamantane-1-carboxamide (61c)

A solution of acid chloride (5e, 0.27 mmol), in anhydrous dichloromethane (2 mL) was added to a solution of the aniline (7, 0.18 mmol) and anhydrous pyridine (0.94 mmol) in anhydrous dichloromethane (5 mL). After 12 h, the solvent was removed and the residue purified via column chromatography (SiO$_2$, 10:1, DCM:methanol) to afford a white amorphous solid (66%). $^1$H NMR (500 MHz, DMSO-d$_6$) δ 9.19 (s, 1H, NH), 7.73 (d, J=8.7 Hz, 2H), 7.58 (d, J=8.8 Hz, 2H), 7.54 (d, J=8.7 Hz, 2H), 7.05 (d, J=8.8 Hz, 2H), 4.58 (m, 1H), 3.06 (m, 2H), 2.91-2.73 (m, 2H), 2.56 (s, 3H), 2.18-2.07 (m, 2H), 2.02 (dd, J=6.0, 3.1 Hz, 3H), 1.92 (d, J=2.9 Hz, 6H), 1.85 (m, 2H), 1.71 (t, J=3.1 Hz, 6H). $^{13}$C NMR (126 MHz, DMSO) δ 175.90, 155.90, 138.26, 134.29, 132.59, 127.34, 125.98, 120.44, 116.33, 69.36, 54.89, 50.80, 43.45, 40.90, 35.98, 28.40, 27.65. HRMS (ESI$^+$) m/z: [M+H$^+$] calcd for C$_{29}$H$_{37}$N$_2$O$_2$ 445.2855. found 445.2855.

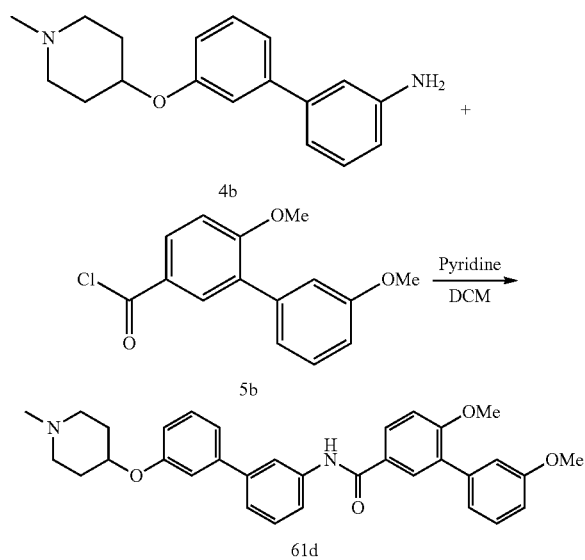

3',6-dimethoxy-N-(3'-((1-methylpiperidin-4-yl)oxy)-[1,1'-biphenyl]-3-yl)-[1,1'-biphenyl]-3-carboxamide (61d)

A solution of acid chloride (5b, 0.27 mmol), in anhydrous dichloromethane (2 mL) was added to a solution of the aniline (4b, 0.18 mmol) and anhydrous triethylamine (0.94 mmol) in anhydrous dichloromethane (5 mL). After 12 h, the solvent was removed and the residue purified via column chromatography (SiO2, 10:1, DCM:methanol) to afford a white amorphous solid (62%). $^1$H NMR (500 MHz, Chloroform-d) δ 8.54 (s, 1H, NH), 7.98 (s, 1H), 7.89-7.81 (m, 2H), 7.77 (s, 1H), 7.65-7.53 (m, 1H), 7.34 (t, J=7.8 Hz, 1H), 7.30-7.22 (m, 2H), 7.13 (dd, J=7.7, 1.7 Hz, 1H), 7.08 (d, J=2.5 Hz, 1H), 7.08-6.92 (m, 3H), 6.83 (m, 2H), 4.41 (m, 1H), 3.81 (s, 3H), 3.77 (s, 3H), 2.77 (m, 2H), 2.57-2.47 (m, 2H), 2.37 (s, 3H), 2.08 (m, 2H), 1.90 (m, 2H). $^{13}$C NMR (126 MHz, CDCl$_3$) δ 165.47, 159.57, 159.51, 157.58, 150.01, 142.61, 142.01, 138.99, 130.87, 130.08, 129.79, 129.63, 129.36, 128.65, 127.21, 123.32, 122.16, 120.32, 119.43, 119.14, 115.52, 115.42, 114.94, 113.13, 111.27, 70.53, 56.05, 55.53, 51.96, 45.72, 29.91. HRMS (ESI$^+$) m/z: [M+H$^+$] calcd for C$_{33}$H$_{35}$N$_2$O$_4$ 523.2597. found 523.2593.

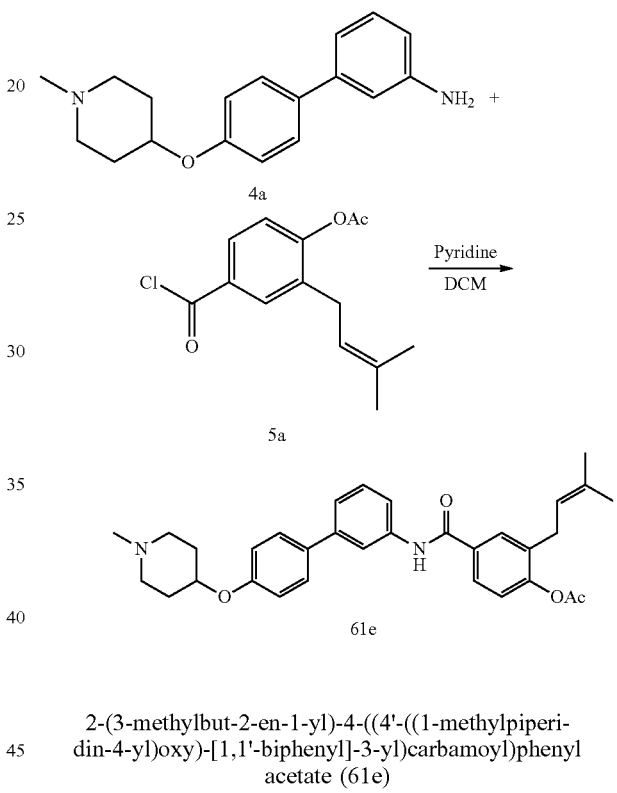

2-(3-methylbut-2-en-1-yl)-4-((4'-((1-methylpiperidin-4-yl)oxy)-[1,1'-biphenyl]-3-yl)carbamoyl)phenyl acetate (61e)

A solution of acid chloride 5a (75 mg, 0.27 mmol) in anhydrous dichloromethane (1 mL) was added to a solution of the aniline 4a (50 mg, 0.18 mmol) and anhydrous pyridine (0.13 mL, 0.94 mmol) in anhydrous dichloromethane (1 mL). The resulting solution was allowed to stir at room temperature for 12 h. After 12 h, the solvent was removed and the residue was purified by column chromatography (SiO$_2$, 10:1, CH$_2$Cl$_2$:methanol) to afford product as a white amorphous solid (48 mg, 59%). $^1$H NMR (500 MHz, Chloroform-d) δ 8.39 (d, J=2.9 Hz, 1H, NH), 7.94 (t, J=2.0 Hz, 1H), 7.79 (d, J=2.3 Hz, 1H), 7.72 (dd, J=8.4, 2.3 Hz, 1H), 7.59-7.57 (m, 1H), 7.51 (d, J=8.6 Hz, 2H), 7.37 (t, J=7.9 Hz, 1H), 7.33-7.29 (m, 1H), 7.07 (d, J=8.3 Hz, 1H), 6.92 (d, J=8.7 Hz, 2H), 5.30-5.06 (m, 1H), 4.54-4.25 (m, 1H), 3.26 (d, J=7.3 Hz, 2H), 2.84 (ddd, J=12.3, 8.9, 3.5 Hz, 2H), 2.62 (d, J=8.1 Hz, 2H), 2.44 (s, 3H), 2.32 (s, 3H), 2.13 (m, 2H), 1.94 (m, 2H), 1.71 (s, 3H), 1.68 (s, 3H). $^{13}$C NMR (126 MHz, CDCl$_3$) δ 169.29, 165.64, 156.77, 151.67, 141.58, 138.73, 134.50, 134.01, 133.76, 133.00, 129.75, 129.49, 128.47, 125.97, 122.89, 122.72, 120.97, 118.85, 118.79, 116.33, 70.11, 51.69, 45.36, 29.51, 29.02, 25.88, 21.04, 18.05. HRMS (ESI⁺) m/z: [M+H⁺] calcd for $C_{32}H_{37}N_2O_4$ 513.2753. found, 513.2752.

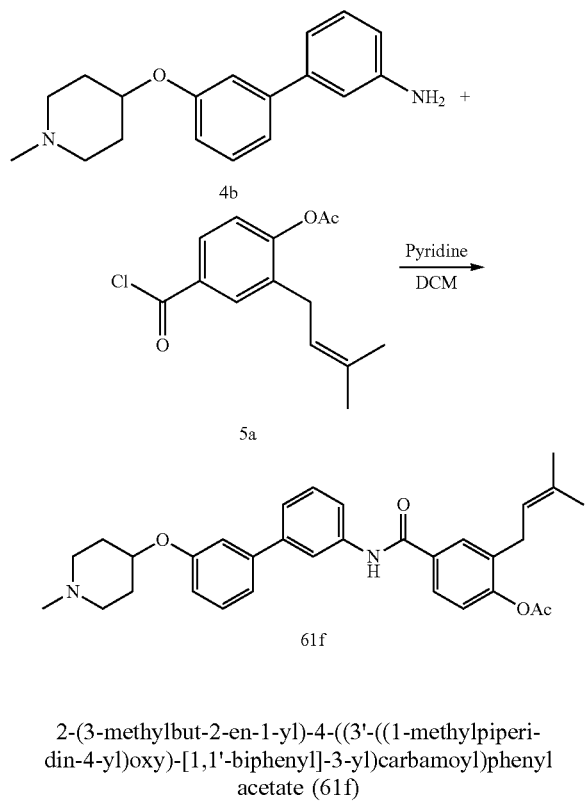

2-(3-methylbut-2-en-1-yl)-4-((3'-((1-methylpiperidin-4-yl)oxy)-[1,1'-biphenyl]-3-yl)carbamoyl)phenyl acetate (61f)

A solution of acid chloride (5a, 0.27 mmol), in anhydrous dichloromethane (2 mL) was added to a solution of the aniline (4b, 0.18 mmol) and anhydrous triethylamine (0.94 mmol) in anhydrous dichloromethane (5 mL). After 12 h, the solvent was removed and the residue purified via column chromatography (SiO₂, 10:1, DCM:methanol) to afford a white amorphous solid (46 mg, 72%). ¹H NMR (500 MHz, chloroform-d) δ 8.33 (s, 1H, NH), 7.85 (s, 1H), 7.71 (s, 1H), 7.66-7.61 (m, 1H), 7.61-7.56 (m, 1H), 7.31 (t, J=7.8 Hz, 1H), 7.25-7.15 (m, 2H), 7.12-7.09 (m, 1H), 7.06 (d, J=2.2 Hz, 1H), 6.98 (d, J=8.3 Hz, 1H), 6.82-6.75 (m, 1H), 5.10 (m, 1H), 4.41-4.32 (m, 1H), 3.17 (d, J=7.3 Hz, 2H), 2.74 (m, 2H), 2.46 (m, 2H), 2.32 (s, 3H), 2.24 (s, 3H), 2.01 (m, 2H), 1.90-1.77 (m, 2H), 1.63 (s, 3H), 1.60 (s, 3H). ¹³C NMR (126 MHz, CDCl₃) δ 169.13, 165.52, 157.39, 151.55, 149.71, 142.36, 141.71, 138.60, 134.37, 133.87, 132.81, 129.89, 129.37, 125.82, 123.20, 122.59, 120.82, 120.05, 119.41, 119.08, 115.13, 114.78, 70.49, 51.85, 45.45, 29.71, 28.88, 25.85, 20.93, 17.94. HRMS (ESI⁺) m/z: [M+H⁺] calcd for $C_{32}H_{37}N_2O_4$ 513.2753. found 513.2758.

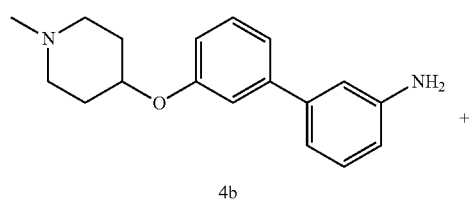

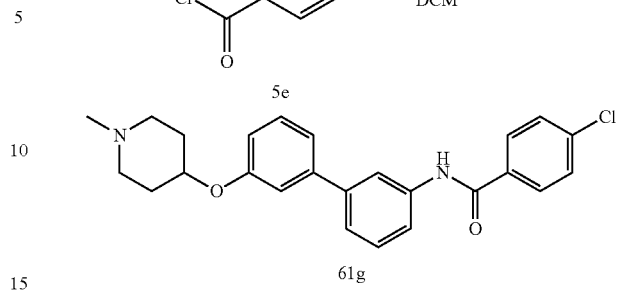

4-chloro-N-(3'-((1-methylpiperidin-4-yl)oxy)-[1,1'-biphenyl]-3-yl)benzamide (61g)

A solution of acid chloride (5e, 0.27 mmol), in anhydrous dichloromethane (2 mL) was added to a solution of the aniline (4b, 0.18 mmol) and anhydrous pyridine (0.94 mmol) in anhydrous dichloromethane (5 mL). After 12 h, the solvent was removed and the residue purified via column chromatography (SiO₂, 10:1, DCM:methanol) to afford a white amorphous solid (56%). ¹H NMR (500 MHz, chloroform-d) δ 8.40 (s, 1H, NH), 7.86 (s, 1H), 7.80 (d, J=8.5 Hz, 2H), 7.64-7.54 (m, 1H), 7.39-7.29 (m, 3H), 7.30-7.20 (m, 2H), 7.14-7.07 (m, 1H), 7.05 (s, 1H), 6.81-6.73 (m, 1H), 4.39 (dd, J=5.2, 2.8 Hz, 1H), 2.80 (m, 2H), 2.62-2.51 (m, 2H), 2.14-2.03 (m, 2H), 1.89 (m, 2H). ¹³C NMR (126 MHz, CDCl₃) δ 165.17, 157.43, 149.94, 142.51, 141.88, 138.54, 133.32, 130.14, 129.62, 129.13, 128.91, 123.60, 120.33, 119.80, 119.46, 115.30, 114.90, 70.06, 51.69, 45.35, 29.45. HRMS (ESI) m/z: [M+H⁺] calcd for $C_{25}H_{26}ClN_2O_2$ 421.1683. found 421.1686.

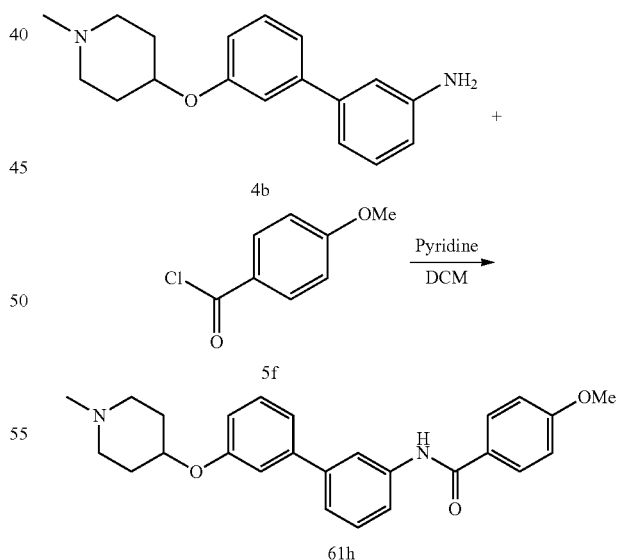

4-methoxy-N-(3'-((1-methylpiperidin-4-yl)oxy)-[1,1'-biphenyl]-3-yl)benzamide (61h)

A solution of acid chloride (5f, 0.27 mmol), in anhydrous dichloromethane (2 mL) was added to a solution of the aniline (4b, 0.18 mmol) and anhydrous pyridine (0.94 mmol) in anhydrous dichloromethane (5 mL). After 12 h, the solvent was removed and the residue purified via column chromatography (SiO$_2$, 10:1, DCM:methanol) to afford a white amorphous solid (66%). $^1$H NMR (500 MHz, chloroform-d) δ 7.94-7.88 (s, 1H), 7.85 (d, J=8.8 Hz, 2H), 7.55 (dd, J=8.2, 2.5 Hz, 1H), 7.36 (t, J=7.9 Hz, 1H), 7.32-7.27 (m, 2H), 7.23-7.18 (m, 1H), 7.13 (s, 1H), 6.93 (d, J=8.9 Hz, 2H), 6.83 (dd, J=8.4, 3.1 Hz, 1H), 4.63 (m, 1H), 3.82 (s, 3H), 3.11 (s, 3H), 2.68 (s, 3H), 2.39-2.22 (m, 2H), 2.16-1.98 (m, 2H). $^{13}$C NMR (126 MHz, CDCl$_3$+CH$_3$OH) δ166.36, 162.61, 156.79, 142.82, 141.45, 138.87, 130.17, 129.41, 129.30, 123.08, 120.69, 119.78, 119.42, 115.11, 114.74, 113.94, 67.09, 55.52, 50.62, 44.05, 27.72. HRMS (ESI$^+$) m/z: [M+H] calcd for C$_{26}$H$_{29}$N$_2$O$_3$ 417.2178; found 417.2172.

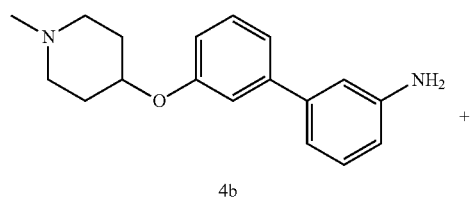

4b

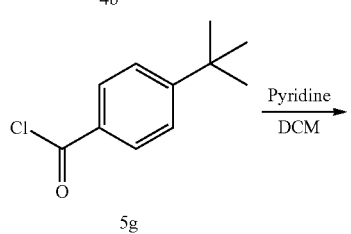

5g

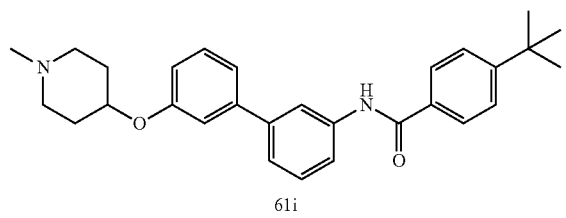

61i 4-(tert-butyl)-N-(3'-((1-methylpiperidin-4-yl)oxy)-[1,1'-biphenyl]-3-yl)benzamide (61i)

A solution of acid chloride (5g, 0.27 mmol), in anhydrous dichloromethane (2 mL) was added to a solution of the aniline (4b, 0.18 mmol) and anhydrous pyridine (0.94 mmol) in anhydrous dichloromethane (5 mL). After 12 h, the solvent was removed and the residue purified via column chromatography (SiO$_2$, 10:1, DCM:methanol) to afford a white amorphous solid (69%). H NMR (500 MHz, chloroform-d) δ 8.03 (s, 1H), 7.92 (s, 1H), 7.82 (d, J=8.5 Hz, 2H), 7.59-7.58 (m, 1H), 7.47 (d, J=8.4 Hz, 2H), 7.39 (t, J=7.8 Hz, 1H), 7.33-7.28 (m, 2H), 7.19-7.16 (m, 1H), 7.12 (dd, J=2.5, 1.6 Hz, 1H), 6.85 (dd, J=8.4, 2.6 Hz, 1H), 4.48 (m, 1H), 2.87 (m, 2H), 2.67 (m, 2H), 2.46 (s, 3H), 2.25-2.00 (m, 2H), 2.03-1.91 (m, 2H), 1.32 (s, 9H). $^{13}$C NMR (126 MHz, CDCl$_3$) δ 165.78, 157.25, 155.58, 142.49, 141.80, 138.56, 131.92, 129.94, 129.44, 126.94, 125.79, 123.19, 120.26, 119.24, 118.97, 115.27, 114.66, 69.67, 51.47, 45.21, 35.03, 31.17, 29.26. HRMS (ESI$^+$) m/z: [M+H$^+$] calcd for C$_{29}$H$_{35}$N$_2$O$_2$: 443.2699. found 443.2695.

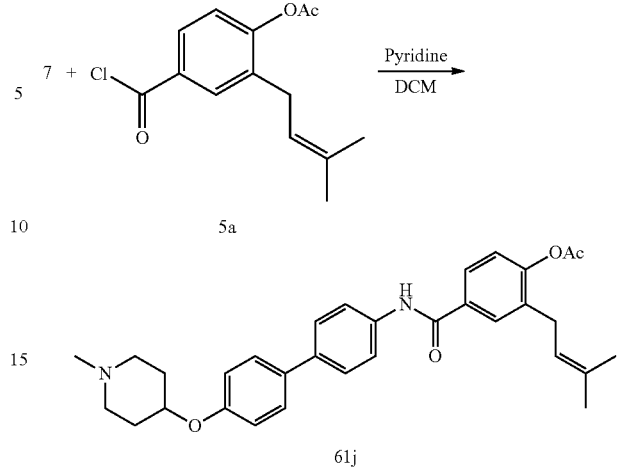

2-(3-methylbut-2-en-1-yl)-4-((4'-((1-methylpiperidin-4-yl)oxy)-[1,1'-biphenyl]-4-yl)carbamoyl)phenyl acetate (61j)

A solution of acid chloride (5a, 0.27 mmol), in anhydrous dichloromethane (2 mL) was added to a solution of the aniline (7, 0.18 mmol) and anhydrous pyridine (0.94 mmol) in anhydrous dichloromethane (5 mL). After 12 h, the solvent was removed and the residue purified via column chromatography (SiO$_2$, 10:1, DCM:methanol) to afford 61j as a white amorphous solid (65%). $^1$H NMR (500 MHz, chloroform-d) δ 7.81 (d, J=2.3 Hz, 1H), 7.76 (dd, J=8.3, 2.4 Hz, 1H), 7.72 (d, J=8.6 Hz, 2H), 7.54-7.49 (m, 4H), 7.10 (d, J=8.4 Hz, 1H), 6.97 (d, J=8.7 Hz, 2H), 5.20 (m, 1H), 4.56 (m, 1H), 3.28 (d, J=7.2 Hz, 2H), 3.03 (m, 2H), 2.95-2.84 (m, 2H), 2.60 (s, 3H), 2.32 (s, 3H), 2.19 (m, 2H), 2.09-2.00 (m, 2H), 1.72 (s, 3H), 1.70 (s, 3H). $^{13}$C NMR (126 MHz, CDCl$_3$+CH3OH) δ 169.75, 166.51, 155.99, 151.39, 137.20, 136.62, 134.11, 133.92, 133.68, 132.94, 129.75, 127.98, 126.91, 126.14, 122.38, 121.09, 120.89, 116.27, 68.57, 50.89, 44.31, 28.86, 28.40, 25.48, 20.64, 17.63. HRMS (ESI) m/z: [M+H$^+$] calcd for C$_{32}$H$_{37}$N$_2$O$_4$ 513.2753. found 513.2756.

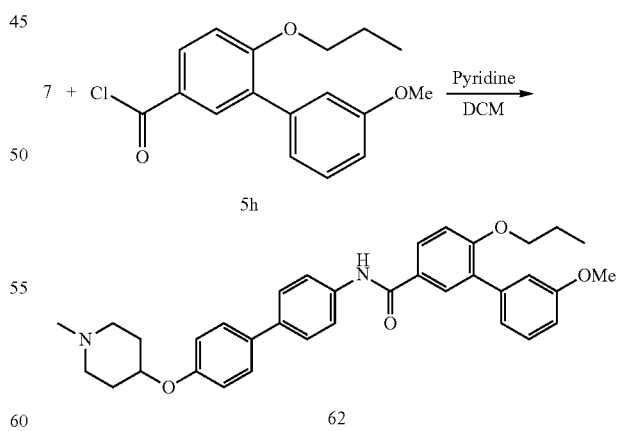

3'-methoxy-N-(4'-((1-methylpiperidin-4-yl)oxy)-[1,1'-biphenyl]-4-yl)-6-propoxy-[1,1'-biphenyl]-3-carboxamide (62)

A solution of acid chloride (5h, 0.27 mmol), in anhydrous dichloromethane (2 mL) was added to a solution of the aniline (7, 0.18 mmol) and anhydrous pyridine (0.94 mmol) in anhydrous dichloromethane (5 mL). After 12 h, the solvent was removed and the residue purified via column chromatography (SiO$_2$, 10:1, DCM:methanol) to afford a white amorphous solid (73%). $^1$H NMR (500 MHz, chloroform-d) δ 8.04 (s, 1H), 7.91 (dd, J=8.6, 2.4 Hz, 1H), 7.87 (d, J=2.4 Hz, 1H), 7.72 (d, J=8.6 Hz, 2H), 7.54 (d, J=8.6 Hz, 2H), 7.51 (d, J=8.7 Hz, 2H), 7.34 (t, J=7.9 Hz, 1H), 7.18-7.12 (m, 2H), 7.03 (d, J=8.6 Hz, 1H), 6.96 (d, J=8.7 Hz, 2H), 6.92 (ddd, J=8.2, 2.5, 1.0 Hz, 1H), 4.50 (m, 1H), 4.01 (t, J=6.5 Hz, 2H), 3.85 (s, 3H), 2.93 (dd, J=12.8, 9.7 Hz, 2H), 2.74 (m, 2H), 2.52 (s, 3H), 2.34-2.17 (m, 2H), 2.09-1.96 (m, 2H), 1.86-1.69 (m, 2H), 1.00 (t, J=7.4 Hz, 3H). $^{13}$C NMR (126 MHz, CDCl$_3$) δ 165.45, 159.41, 159.10, 156.41, 139.14, 137.28, 136.71, 133.92, 130.84, 129.85, 129.16, 128.56, 128.22, 127.35, 127.02, 122.25, 120.75, 116.45, 115.27, 113.30, 112.14, 70.33, 69.82, 55.49, 51.55, 45.29, 29.26, 22.63, 10.86. HRMS (ESI$^+$) m/z [M+H$^+$] calcd for C$_{35}$H$_{39}$N$_2$O$_4$ 551.2910. found 551.2913.

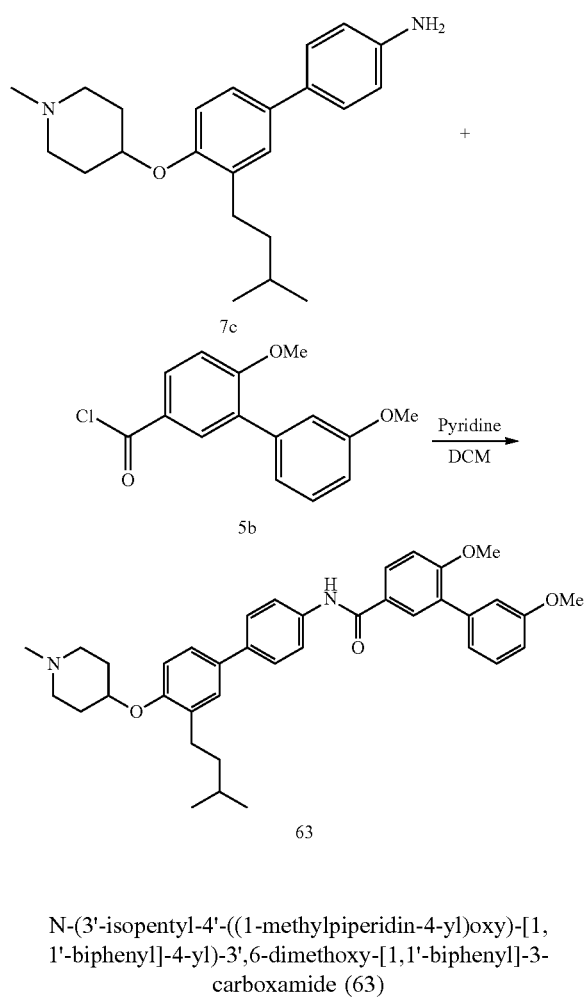

N-(3'-isopentyl-4'-((1-methylpiperidin-4-yl)oxy)-[1,1'-biphenyl]-4-yl)-3',6-dimethoxy-[1,1'-biphenyl]-3-carboxamide (63)

A solution of acid chloride (5a, 0.27 mmol), in anhydrous dichloromethane (2 mL) was added to a solution of the aniline (7c, 0.18 mmol) and anhydrous pyridine (0.94 mmol) in anhydrous dichloromethane (5 mL). After 12 h, the solvent was removed and the residue purified via column chromatography (SiO$_2$, 10:1, DCM:methanol) to afford a white amorphous solid (73%). $^1$H NMR (500 MHz, chloroform-d) δ 7.86 (dd, J=8.5, 2.4 Hz, 1H), 7.79 (s, 1H), 7.76 (d, J=2.4 Hz, 1H), 7.62 (d, J=8.5 Hz, 2H), 7.48 (d, J=8.5 Hz, 2H), 7.32-7.30 (m, 1H), 7.28 (d, J=8.1 Hz, 2H), 7.06 (dt, J=7.8, 1.2 Hz, 1H), 7.02 (dd, J=2.6, 1.5 Hz, 1H), 6.99 (d, J=8.6 Hz, 1H), 6.86 (ddd, J=8.3, 2.6, 1.0 Hz, 1H), 6.80 (d, J=8.4 Hz, 1H), 4.41 (m, 1H), 3.82 (s, 3H), 3.79 (s, 3H), 2.71 (t, J=10.1 Hz, 2H), 2.63-2.56 (m, 2H), 2.55 (m, 2H), 2.37 (s, 3H), 2.14-2.04 (m, 2H), 1.93 (m, 2H), 1.57 (m, 1H), 1.48-1.40 (m, 2H), 0.90 (s, 3H), 0.89 (s, 3H). $^{13}$C NMR (126 MHz, CDCl$_3$) δ 165.07, 159.33, 154.26, 154.21, 138.84, 137.05, 136.78, 132.92, 132.80, 130.71, 129.54, 129.17, 128.75, 128.41, 127.22, 127.15, 125.03, 121.99, 120.40, 115.32, 112.97, 112.70, 111.08, 69.58, 55.87, 55.35, 51.95, 45.71, 39.64, 29.99, 28.68, 28.25, 22.71.

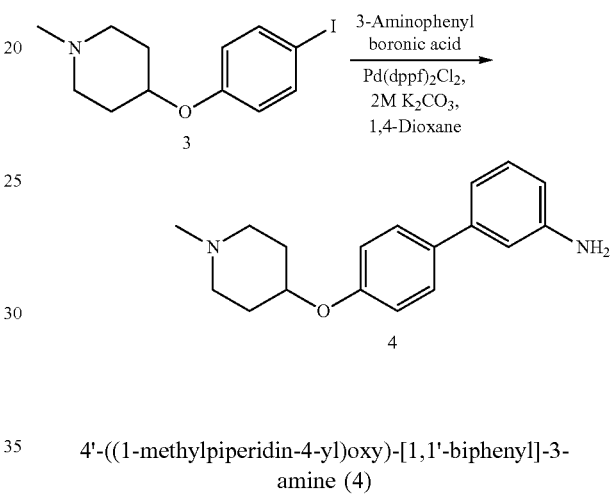

4'-((1-methylpiperidin-4-yl)oxy)-[1,1'-biphenyl]-3-amine (4)

[1,1'-Bis(diphenylphosphino) ferrocene]dichloropalladium(II) (57 mg, 0.08 mmol) and potassium carbonate solution (2M, 100 µL) were added to a solution of iodide (250 mg, 0.79 mmol) and boronic acid (216 mg, 1.58 mmol) in dioxane (15 mL). The mixture was stirred at 110° C. for 12 hours before concentrated to dryness. The brown residue was purified via column chromatography (SiO$_2$, 10:1, DCM:methanol) to afford desired product 4 as a brown amorphous solid (149 mg, 67%). $^1$H NMR (500 MHz, chloroform-d) δ 7.50 (d, J=8.7 Hz, 2H), 7.22 (t, J=7.8 Hz, 1H), 6.99-6.92 (m, 3H), 6.88 (s, 1H), 6.66 (dd, J=7.9, 2.3 Hz, 1H), 4.45-4.34 (m, 1H), 3.74 (s, 2H), 2.79 (ddd, J=11.8, 7.8, 3.8 Hz, 2H), 2.48-2.42 (m, 2H), 2.39 (s, 3H), 2.11 (ddt, J=11.5, 7.3, 3.6 Hz, 2H), 1.94 (ddt, J=14.0, 7.9, 3.7 Hz, 2H). $^{13}$C NMR (126 MHz, CDCl$_3$) δ 156.77, 146.69, 141.94, 134.13, 129.65, 128.16, 117.28, 116.15, 113.60, 113.49, 71.45, 52.37, 45.96, 30.42. HRMS (ESI+) m/z: [M+H$^+$] calcd for C$_{18}$H$_{23}$N$_2$O 283.1810. found, 283.1808.

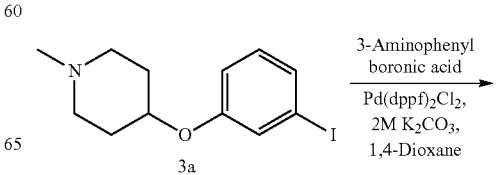

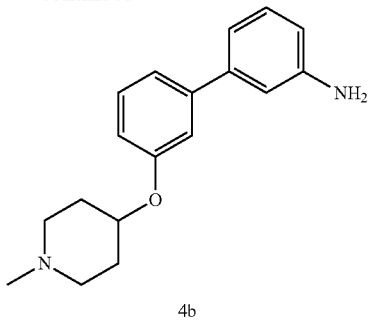

3'-((1-methylpiperidin-4-yl)oxy)-[1,1'-biphenyl]-3-amine (4b)

[1,1'-Bis(diphenylphosphino)ferrocene]dichloropalladium(II) (57 mg, 0.08 mmol) and potassium carbonate solution (2M, 100 μL) were added to a solution of iodide (250 mg, 0.79 mmol) and boronic acid (216 mg, 1.58 mmol) in dioxane (15 mL). The mixture was stirred at 110° C. for 12 hours before concentrated to dryness. The brown residue was purified via column chromatography (SiO$_2$, 10:1, DCM: methanol) to afford desired product 4 as a brown amorphous solid (72%). $^1$H NMR (500 MHz, chloroform-d) δ 7.19 (t, J=7.9 Hz, 1H), 7.09 (t, J=7.8 Hz, 1H), 7.03 (m, 2H, NH$_2$), 6.98-6.96 (m, 1H), 6.86-6.83 (m, 1H), 6.80 (t, J=2.0 Hz, 1H), 6.77-6.73 (m, 1H), 6.68-6.64 (m, 1H), 6.59 (dd, J=8.1, 2.3 Hz, 1H), 4.36 (m, 1H), 2.66 (m, 2H), 2.37 (m, 2H), 2.25 (s, 3H), 1.92 (s, 2H), 1.80 (m, 2H). $^{13}$C NMR (126 MHz, CDCl$_3$+CH$_3$OH) δ 157.29, 146.62, 143.06, 142.03, 129.70, 129.59, 119.98, 117.78, 115.03, 114.74, 114.64, 114.14, 72.15, 54.63, 45.46, 29.85. HRMS (ESI$^+$) m/z: [M+H$^+$] calcd for C$_{18}$H$_{23}$N$_2$O 283.1810. found, 283.18108.

All of the methods disclosed and claimed herein can be made and executed without undue experimentation in light of the present disclosure. While the methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references to the extent that they provide exemplary procedural or other details supplementary to those set forth herein, are specifically incorporated herein by reference.

Burlison, et al., *J. Am. Chem. Soc.*, 128:15529, 2006.
Burlison, et al., *J. Org. Chem.*, 73:2130, 2008.
Conde, et al., *Biochem. Cell Biol.*, 87:845-851, 2009.
Donnelly, et al., *J. Org. Chem.*, 73:8901, 2008.
Donnelly, et al., *Med. Chem. Commun.*, 1:165, 2010.
Eskew, et al., *BMC Cancer*, 11:468, 2011.
Hanahan and Weinberg, *Cell*, 144:646-674, 2011.
*Handbook of Pharmaceutical Salts: Properties, and Use,* Stahl and Wermuth Eds.), Verlag Helvetica Chimica Acta, 2002.
*March's Advanced Organic Chemistry: Reactions, Mechanisms, and Structure,* 2007.
Marcu, et al., *J. Biol. Chem.*, 275:37181, 2000.
Marcu, et al., *J. Natl. Cancer Inst.*, 92:242-248, 2000.
Neckers and Workman, *Clin. Cancer Res.*, 1:64-76, 2012.
Shelton, et al., *Mol. Pharmacol.*, 76:1314-1322, 2009.
Taipale, et al., *Nat. Rev. Mol. Cell. Biol.*, 11:515-528, 2010.
Tran, et al., *BMC Cancer*, 10:276, 2010.
Whitesell, et al., *Curr. Mol. Med.*, 12:11108-1124, 2012.
Yu, et al., *J. Am. Chem. Soc.*, 127:12778, 2005.
Zhao and Blagg, *ACS Med. Chem. Lett.*, 1:311, 2010.
Zhao, et al., *J. Med. Chem.*, 2011.
Zhao, et al., *Bioorg. Med. Chem. Lett.*, 21:2659-2664, 2011.
Zhao, et al., *ACS Med. Chem. Lett.*, 3:327-331, 2012.
Zhao, et al., *ACS Med. Chem. Lett.*, 4:57-62, 2013.

What is claimed is:

1. A compound selected from formulas I, II, III, or IV, wherein
the formulas are further defined as:

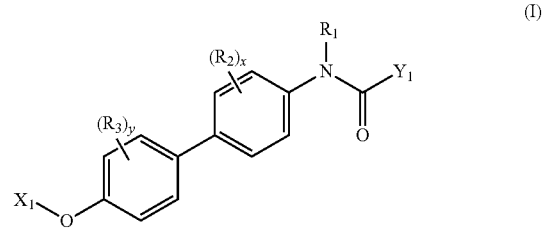

(I)

wherein:
X$_1$ is heterocycloalkyl$_{(C\le12)}$ or a substituted version thereof;
Y$_1$ is cycloalkyl$_{(C\le18)}$, aryl$_{(C\le24)}$, heteroaryl$_{(C\le24)}$, -arenediyl$_{(C\le18)}$-alkyl$_{(C\le8)}$, -arenediyl$_{(C\le18)}$-alkenyl$_{(C\le8)}$, -arenediyl$_{(C\le18)}$-alkoxy$_{(C\le8)}$, or a substituted version of any of these groups;
R$_1$ is hydrogen, alkyl$_{(C\le6)}$, or substituted alkyl$_{(C\le6)}$;
each R$_2$ and R$_3$ are each independently selected from hydrogen, amino, cyano, halo, hydroxy, mercapto, nitro, sulfato, sulfamido, alkyl$_{(C\le12)}$, substituted alkyl$_{(C\le12)}$, alkoxy$_{(C\le12)}$, substituted alkoxy$_{(C\le12)}$, acyl$_{(C\le12)}$, substituted acyl$_{(C\le12)}$, acyloxy$_{(C\le12)}$, substituted acyloxy$_{(C\le12)}$, amido$_{(C\le12)}$, or substituted amido$_{(C\le12)}$; and
x and y are each independently selected from 0, 1, 2, 3, or 4;

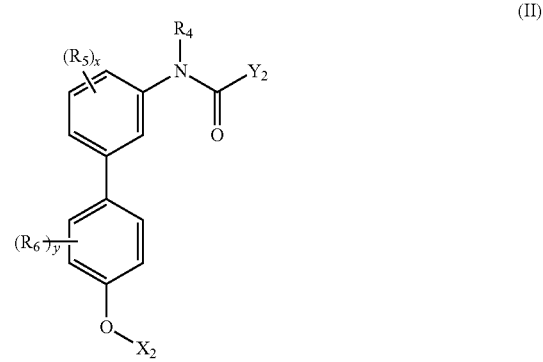

(II)

wherein:
X$_2$ is heterocycloalkyl$_{(C\leq12)}$ or a substituted version thereof;
Y$_2$ is cycloalkyl$_{(C\leq18)}$, aryl$_{(C\leq24)}$, heteroaryl$_{(C\leq24)}$, -arenediyl$_{(C\leq18)}$-alkyl$_{(C\leq8)}$, -arenediyl$_{(C\leq18)}$-alkenyl$_{(C\leq8)}$, -arenediyl$_{(C\leq18)}$-alkoxy$_{(C\leq8)}$, or a substituted version of any of these groups;
R$_4$ is hydrogen, alkyl$_{(C\leq6)}$, or substituted alkyl$_{(C\leq6)}$;
each R$_5$ and R$_6$ are each independently selected from hydrogen, amino, cyano, halo, hydroxy, mercapto, nitro, sulfato, sulfamido, alkyl$_{(C\leq12)}$, substituted alkyl$_{(C\leq12)}$, alkoxy$_{(C\leq12)}$, substituted alkoxy$_{(C\leq12)}$, acyl$_{(C\leq12)}$, substituted acyl$_{(C\leq12)}$, acyloxy$_{(C\leq12)}$, substituted acyloxy$_{(C\leq12)}$, amido$_{(C\leq12)}$, or substituted amido$_{(C\leq12)}$; and
x and y are each independently selected from 0, 1, 2, 3, or 4;

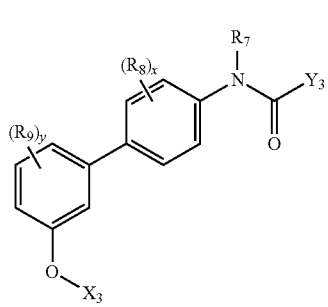

(III)

wherein:
X$_3$ is heterocycloalkyl$_{(C\leq12)}$ or a substituted version thereof;
Y$_3$ is cycloalkyl$_{(C\leq18)}$, aryl$_{(C\leq24)}$, heteroaryl$_{(C\leq24)}$, -arenediyl$_{(C\leq18)}$-alkyl$_{(C\leq8)}$, -arenediyl$_{(C\leq18)}$-alkenyl$_{(C\leq8)}$, -arenediyl$_{(C\leq18)}$-alkoxy$_{(C\leq8)}$, or a substituted version of any of these groups;
R$_7$ is hydrogen, alkyl$_{(C\leq6)}$, or substituted alkyl$_{(C\leq6)}$;
each R$_8$ and R$_9$ are each independently selected from hydrogen, amino, cyano, halo, hydroxy, mercapto, nitro, sulfato, sulfamido, alkyl$_{(C\leq12)}$, substituted alkyl$_{(C\leq12)}$, alkoxy$_{(C\leq12)}$, substituted alkoxy$_{(C\leq12)}$, acyl$_{(C\leq12)}$, substituted acyl$_{(C\leq12)}$, acyloxy$_{(C\leq12)}$, substituted acyloxy$_{(C\leq12)}$, amido$_{(C\leq12)}$, or substituted amido$_{(C\leq12)}$; and
x and y are each independently selected from 0, 1, 2, 3, or 4;

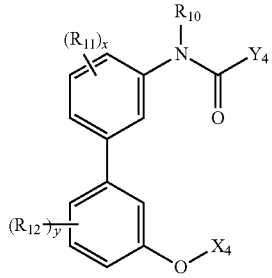

(IV)

wherein:
X$_4$ is heterocycloalkyl$_{(C\leq12)}$ or a substituted version thereof;
Y$_4$ is cycloalkyl$_{(C\leq18)}$, aryl$_{(C\leq24)}$, heteroaryl$_{(C\leq24)}$, -arenediyl$_{(C\leq18)}$-alkyl$_{(C\leq8)}$, -arenediyl$_{(C\leq18)}$-alkenyl$_{(C\leq8)}$, -arenediyl$_{(C\leq18)}$-alkoxy$_{(C\leq8)}$, or a substituted version of any of these groups;
R$_{10}$ is hydrogen, alkyl$_{(C\leq6)}$, or substituted alkyl$_{(C\leq6)}$;
each R$_{11}$ and R$_{12}$ are each independently selected from hydrogen, amino, cyano, halo, hydroxy, mercapto, nitro, sulfato, sulfamido, alkyl$_{(C\leq12)}$, substituted alkyl$_{(C\leq12)}$, alkoxy$_{(C\leq12)}$, substituted alkoxy$_{(C\leq12)}$, acyl$_{(C\leq12)}$, substituted acyl$_{(C\leq12)}$, acyloxy$_{(C\leq12)}$, substituted acyloxy$_{(C\leq12)}$, amido$_{(C\leq12)}$, or substituted amido$_{(C\leq12)}$; and
x and y are each independently selected from 0, 1, 2, 3, or 4;
or a pharmaceutically acceptable salt thereof.

2. The compound of claim 1, wherein the compound is further defined as:

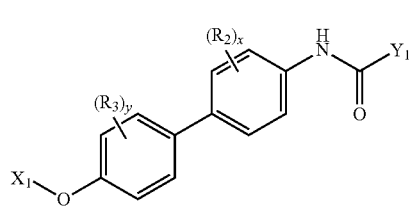

(VI)

wherein:
X$_1$ is heterocycloalkyl$_{(C\leq12)}$ or substituted heterocycloalkyl$_{(C\leq12)}$;
Y$_1$ is cycloalkyl$_{(C\leq18)}$, aryl$_{(C\leq24)}$, heteroaryl$_{(C\leq24)}$, -arenediyl$_{(C\leq18)}$-alkyl$_{(C\leq8)}$, -arenediyl$_{(C\leq18)}$-alkenyl$_{(C\leq8)}$, -arenediyl$_{(C\leq18)}$-alkoxy$_{(C\leq8)}$, or a substituted version of any of these groups;
each R$_2$ and R$_3$ are each independently selected from hydrogen, amino, cyano, halo, hydroxy, mercapto, nitro, sulfato, sulfamido, alkyl$_{(C\leq12)}$, substituted alkyl$_{(C\leq12)}$, alkoxy$_{(C\leq12)}$, substituted alkoxy$_{(C\leq12)}$, acyl$_{(C\leq12)}$, substituted acyl$_{(C\leq12)}$, acyloxy$_{(C\leq12)}$, substituted acyloxy$_{(C\leq12)}$, amido$_{(C\leq12)}$, or substituted amido$_{(C\leq12)}$; and
x and y are each independently selected from 1, 2, 3, or 4;
or a pharmaceutically acceptable salt thereof.

3. The compound of claim 1, wherein the compound is further defined as:

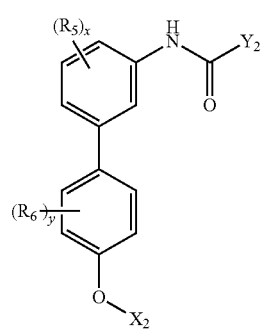

(VII)

wherein:
X$_2$ is heterocycloalkyl$_{(C\leq12)}$ or substituted heterocycloalkyl$_{(C\leq12)}$;

Y$_2$ is cycloalkyl$_{(C\leq18)}$, aryl$_{(C\leq24)}$, heteroaryl$_{(C\leq24)}$, -arenediyl$_{(C\leq18)}$-alkyl$_{(C\leq8)}$, -arenediyl$_{(C\leq18)}$-alkenyl$_{(C\leq8)}$, -arenediyl$_{(C\leq18)}$-alkoxy$_{(C\leq8)}$, or a substituted version of any of these groups;

each R$_5$ and R$_6$ are each independently selected from hydrogen, amino, cyano, halo, hydroxy, mercapto, nitro, sulfato, sulfamido, alkyl$_{(C\leq12)}$, substituted alkyl$_{(C\leq12)}$, alkoxy$_{(C\leq12)}$, substituted alkoxy$_{(C\leq12)}$, acyl$_{(C\leq12)}$, substituted acyl$_{(C\leq12)}$, acyloxy$_{(C\leq12)}$, substituted acyloxy$_{(C\leq12)}$, amido$_{(C\leq12)}$, or substituted amido$_{(C\leq12)}$; and x and y are each independently selected from 1, 2, 3, or 4;

or a pharmaceutically acceptable salt thereof.

4. The compound of claim 1, wherein the compound is further defined as:

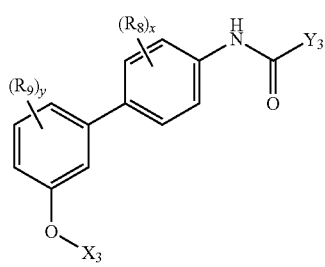

(VIII)

wherein:

X$_3$ is heterocycloalkyl$_{(C\leq12)}$ or substituted heterocycloalkyl$_{(C\leq12)}$;

Y$_3$ is cycloalkyl$_{(C\leq18)}$, aryl$_{(C\leq24)}$, heteroaryl$_{(C\leq24)}$, -arenediyl$_{(C\leq18)}$-alkyl$_{(C\leq8)}$, -arenediyl$_{(C\leq18)}$-alkenyl$_{(C\leq8)}$, -arenediyl$_{(C\leq18)}$-alkoxy$_{(C\leq8)}$, or a substituted version of any of these groups;

each R$_5$ and R$_9$ are each independently selected from hydrogen, amino, cyano, halo, hydroxy, mercapto, nitro, sulfato, sulfamido, alkyl$_{(C\leq12)}$, substituted alkyl$_{(C\leq12)}$, alkoxy$_{(C\leq12)}$, substituted alkoxy$_{(C\leq12)}$, acyl$_{(C\leq12)}$, substituted acyl$_{(C\leq12)}$, acyloxy$_{(C\leq12)}$, substituted acyloxy$_{(C\leq12)}$, amido$_{(C\leq12)}$, or substituted amido$_{(C\leq12)}$; and x and y are each independently selected from 1, 2, 3, or 4;

or a pharmaceutically acceptable salt thereof.

5. The compound of claim 1, wherein the compound is further defined as:

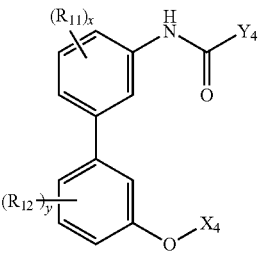

(IX)

wherein:

X$_4$ is heterocycloalkyl$_{(C\leq12)}$ or substituted heterocycloalkyl$_{(C\leq12)}$;

Y$_4$ is cycloalkyl$_{(C\leq18)}$, aryl$_{(C\leq24)}$, heteroaryl$_{(C\leq24)}$, -arenediyl$_{(C\leq18)}$-alkyl$_{(C\leq8)}$, -arenediyl$_{(C\leq18)}$-alkenyl$_{(C\leq8)}$, -arenediyl$_{(C\leq18)}$-alkoxy$_{(C\leq8)}$, or a substituted version of any of these groups;

each R$_{11}$ and R$_{12}$ are each independently selected from hydrogen, amino, cyano, halo, hydroxy, mercapto, nitro, sulfato, sulfamido, alkyl$_{(C\leq12)}$, substituted alkyl$_{(C\leq12)}$, alkoxy$_{(C\leq12)}$, substituted alkoxy$_{(C\leq12)}$, acyl$_{(C\leq12)}$, substituted acyl$_{(C\leq12)}$, acyloxy$_{(C\leq12)}$, substituted acyloxy$_{(C\leq12)}$, amido$_{(C\leq12)}$, or substituted amido$_{(C\leq12)}$; and x and y are each independently selected from 1, 2, 3, or 4;

or a pharmaceutically acceptable salt thereof.

6. The compound of claim 1, wherein X$_1$, X$_2$, X$_3$, or X$_4$ is heterocycloalkyl$_{(C\leq12)}$.

7. The compound of claim 6, wherein X$_1$, X$_2$, X$_3$, or X$_4$ is:

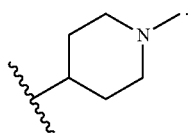

8. The compound of claim 1, wherein Y$_1$, Y$_2$, Y$_3$, or Y$_4$ is aryl$_{(C\leq18)}$ or substituted aryl$_{(C\leq18)}$.

9. The compound of claim 8, wherein Y$_1$, Y$_2$, Y$_3$, or Y$_4$ is aryl$_{(C\leq18)}$.

10. The compound of claim 8, wherein Y$_1$, Y$_2$, Y$_3$, or Y$_4$ is substituted aryl$_{(C\leq18)}$.

11. The compound of claim 1, wherein x is 1 or 2.

12. The compound of claim 1, wherein y is 1 or 2.

13. The compound of claim 1 further defined as:

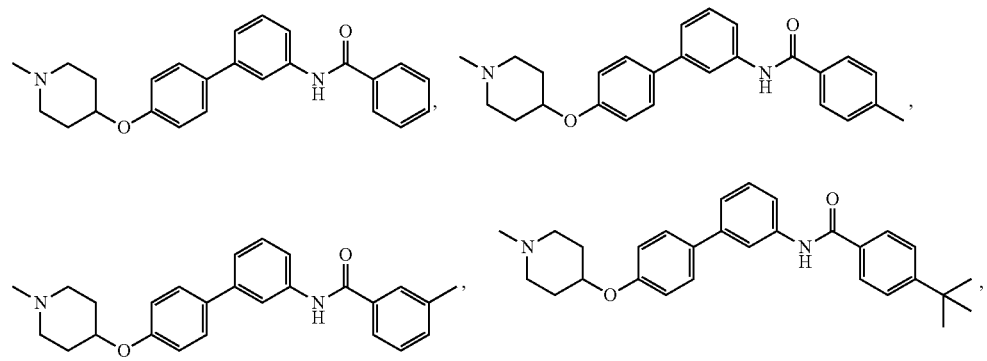

-continued
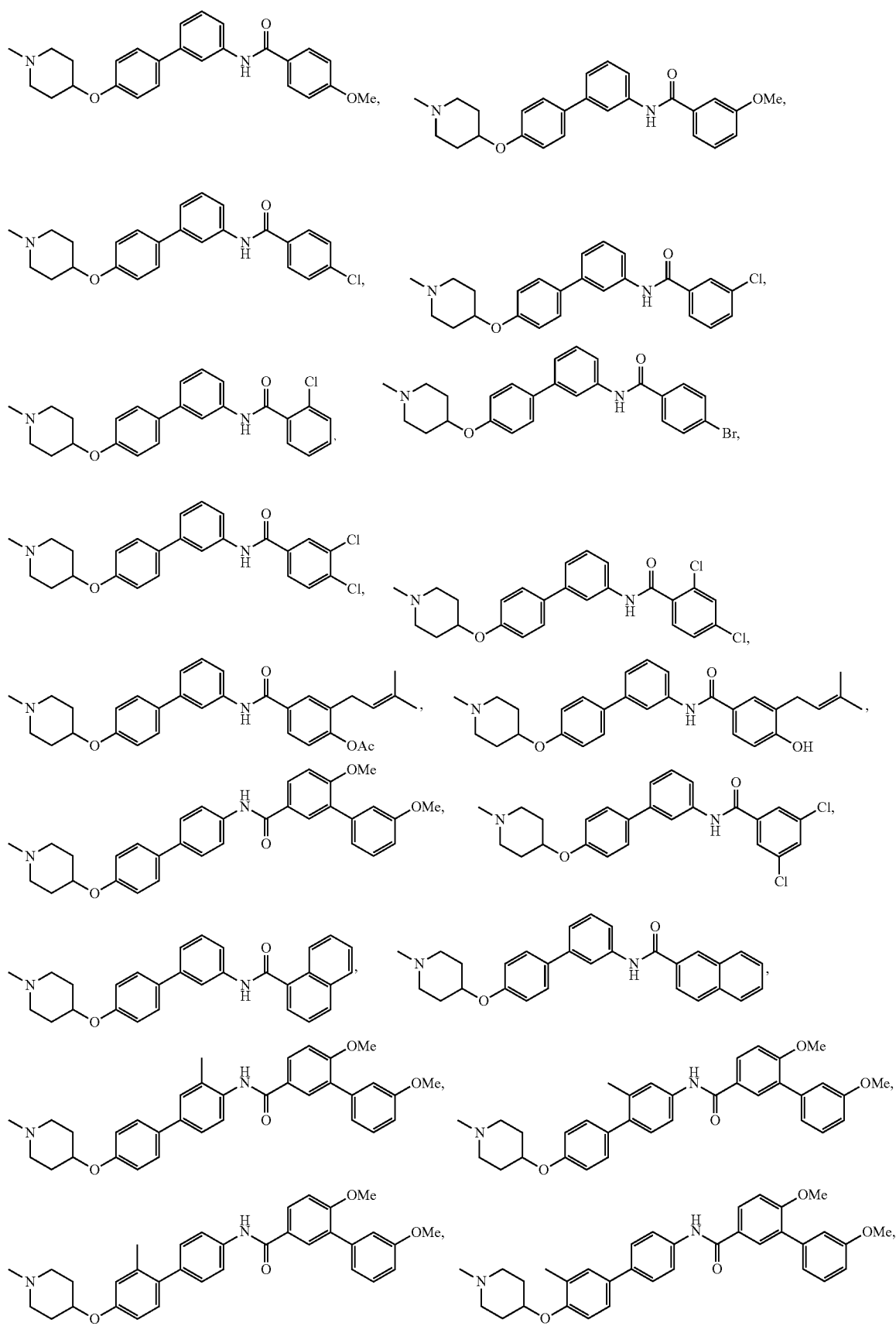

175 176
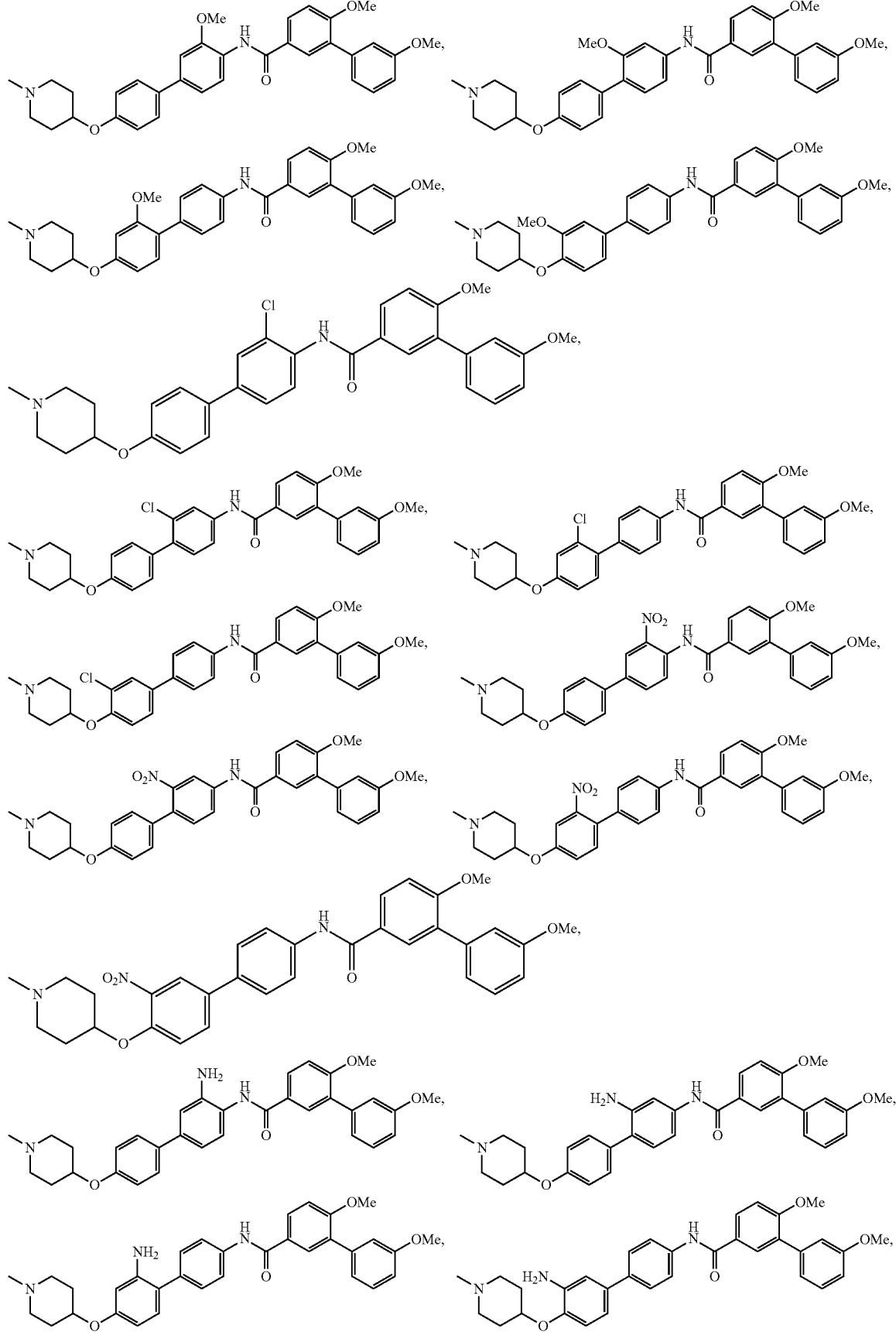

177 178
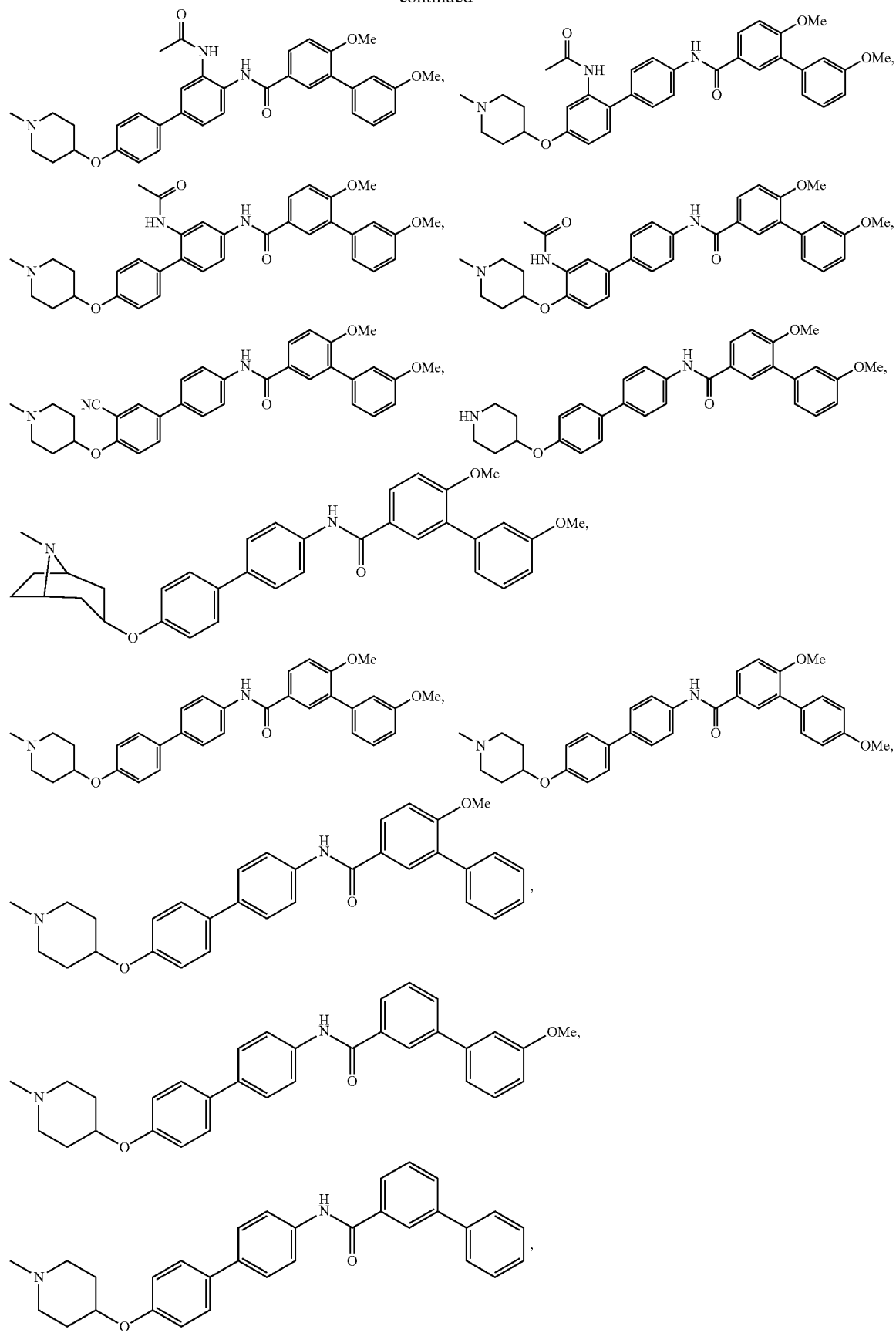
-continued

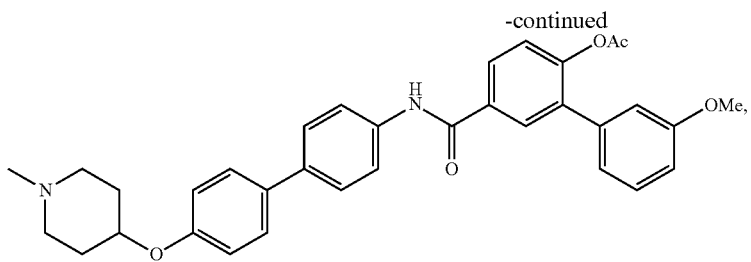
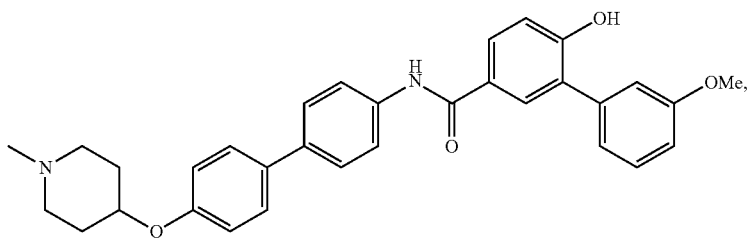
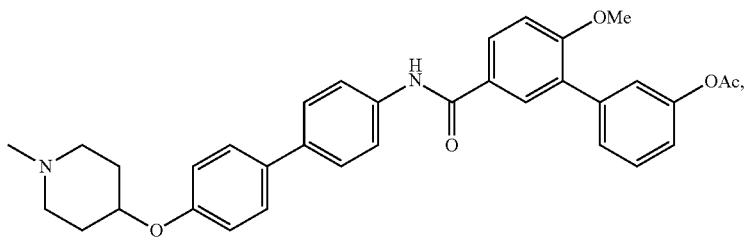
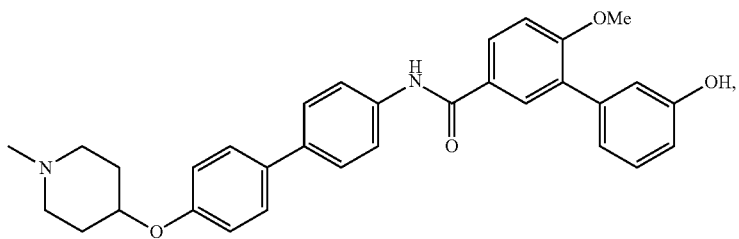
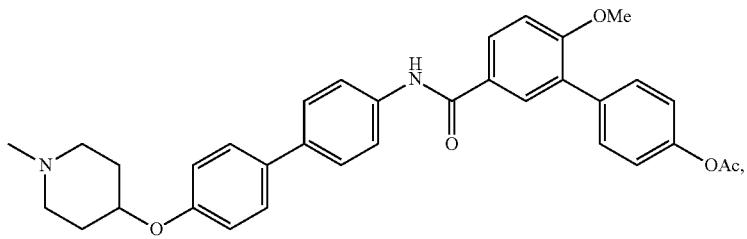
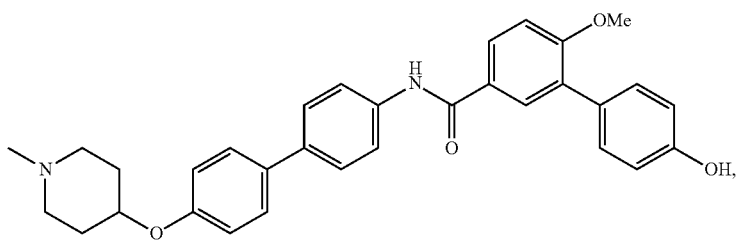
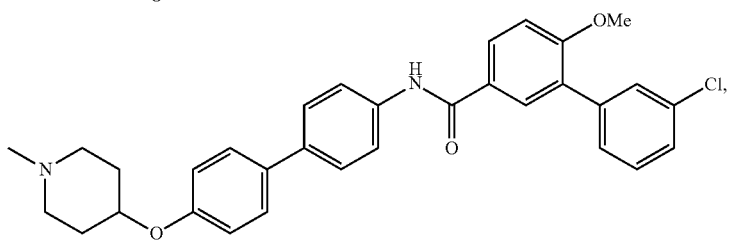

-continued
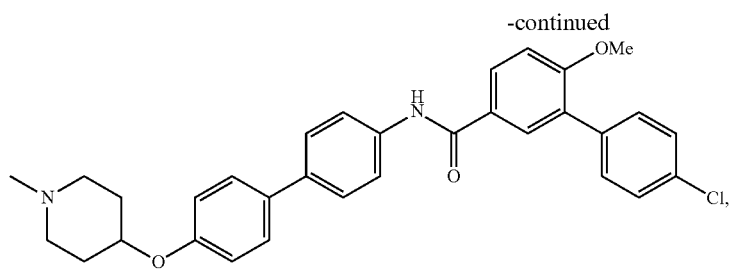
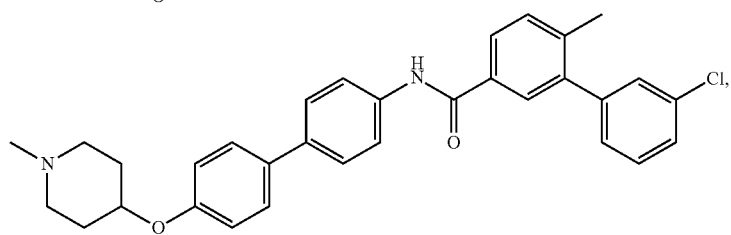
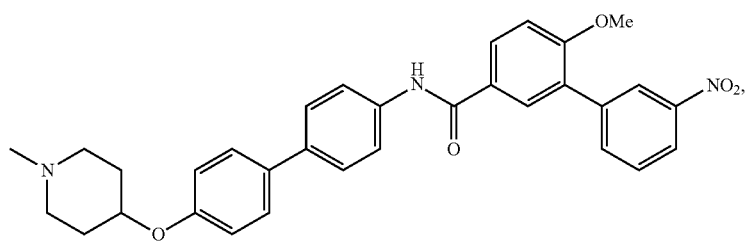
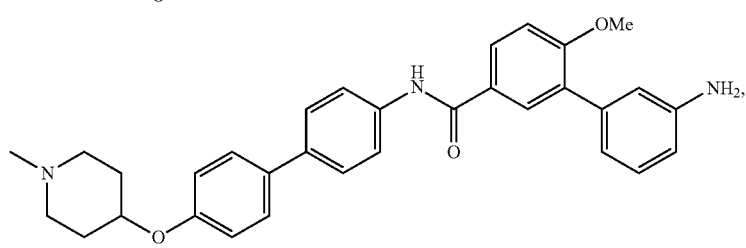
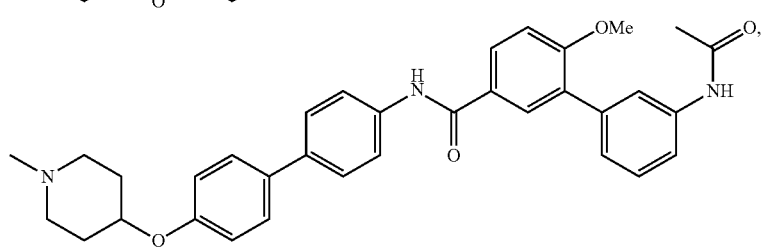
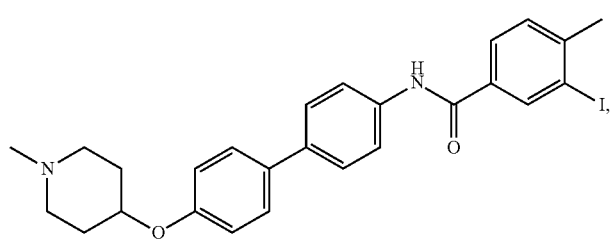
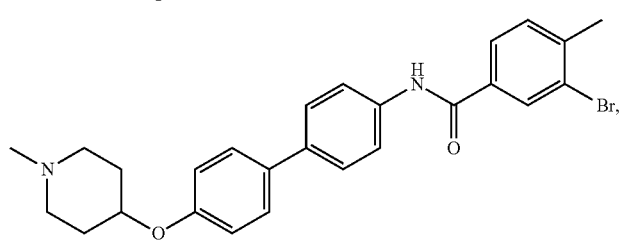

183 184
-continued
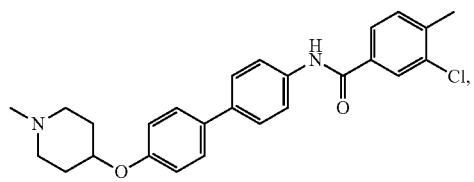
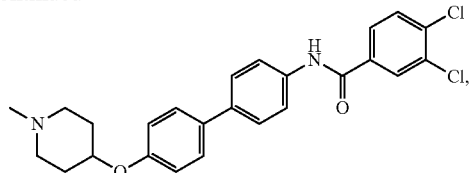
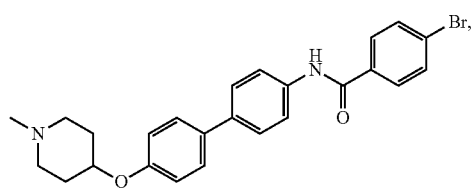
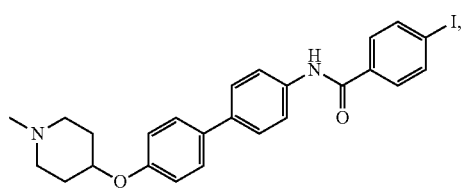
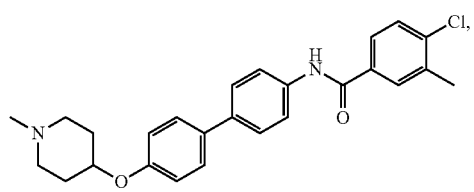
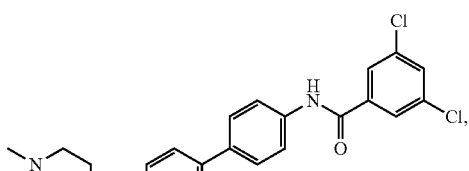
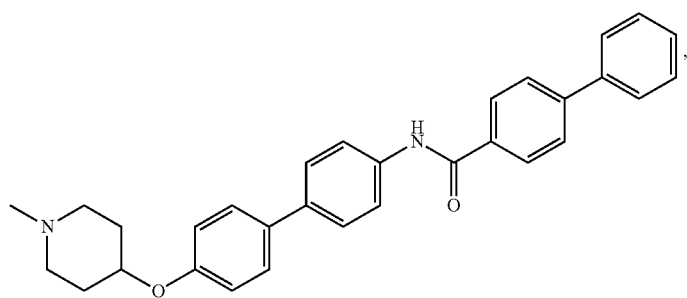
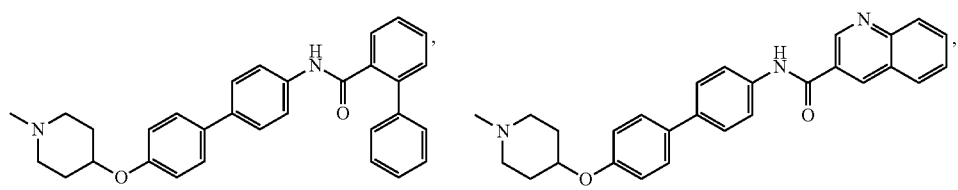
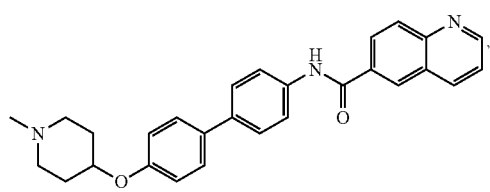
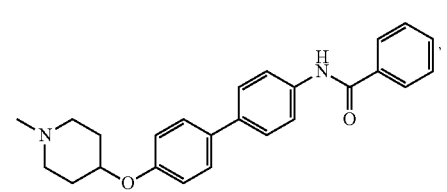
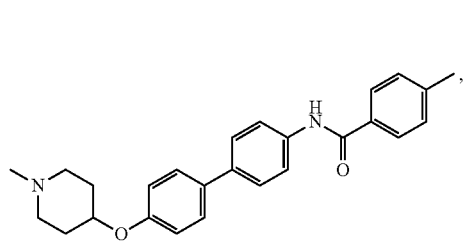
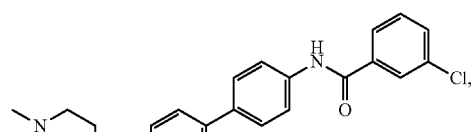

-continued
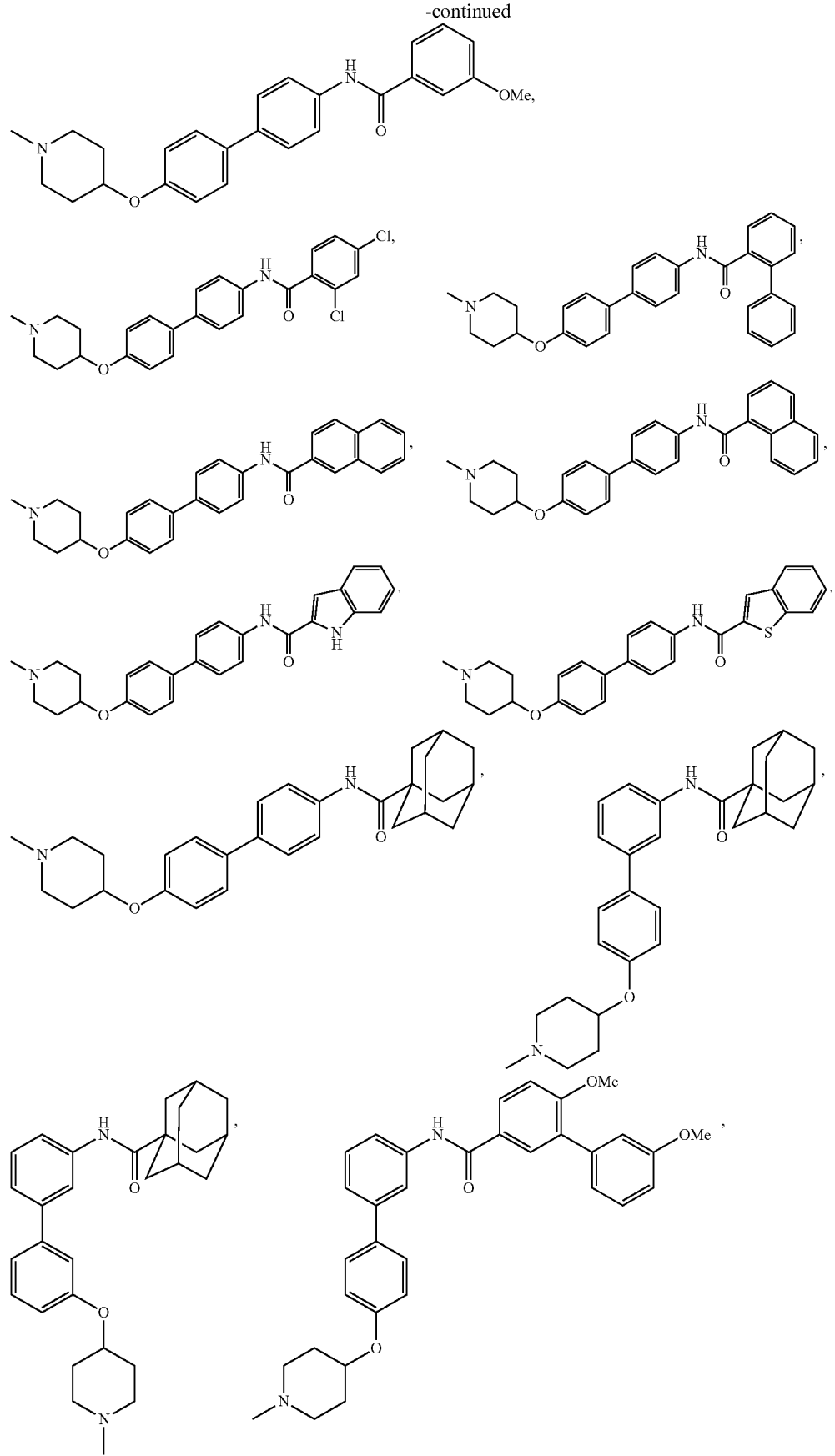

187
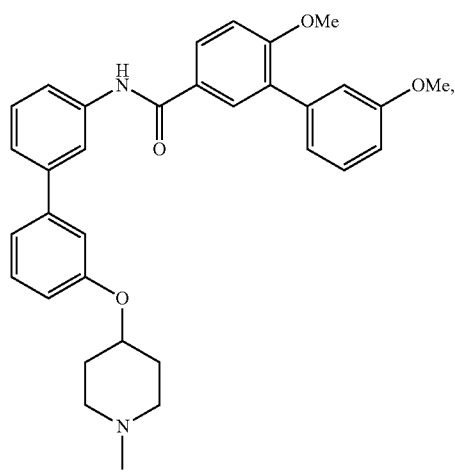
188
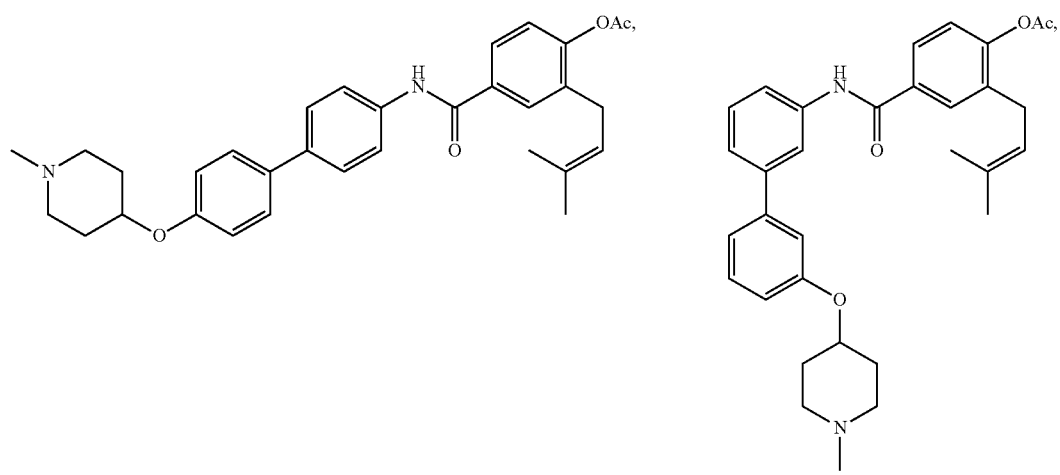
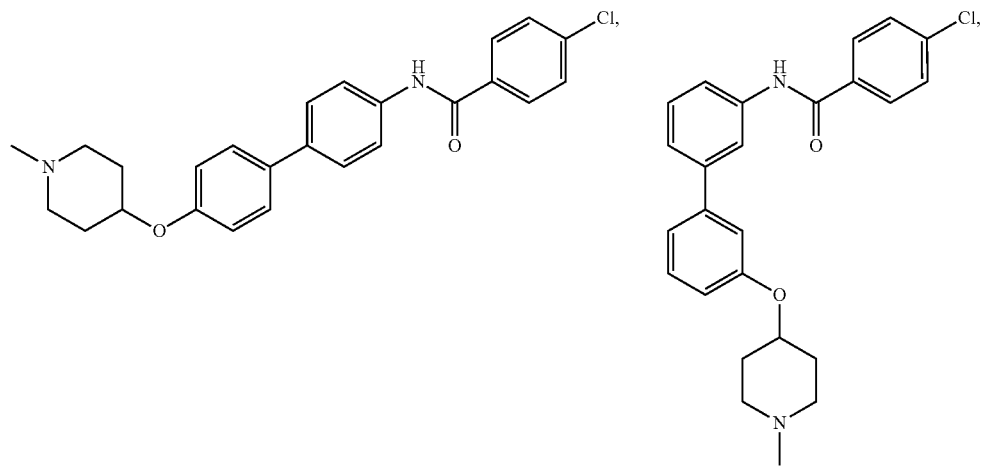

189 190
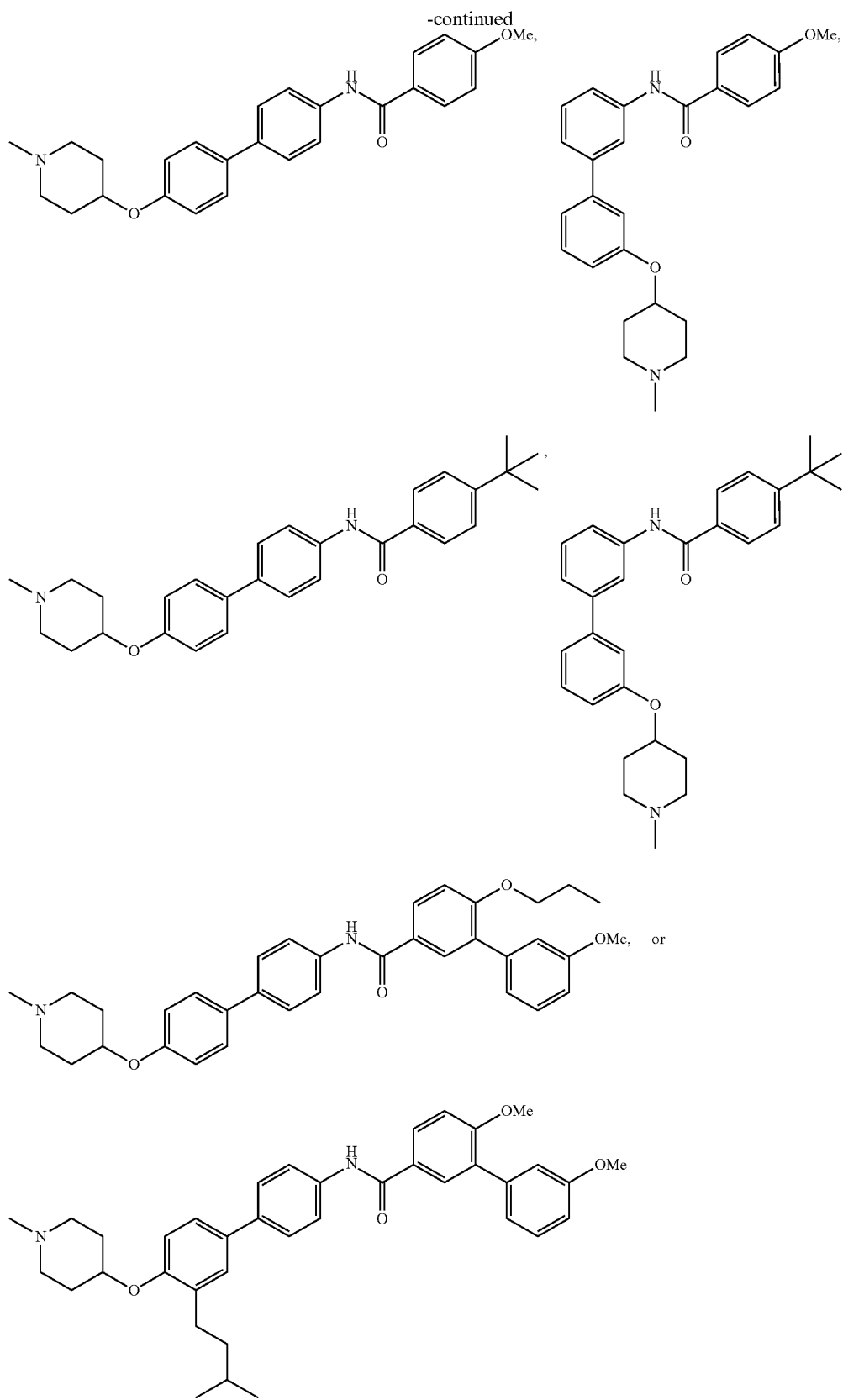
or a pharmaceutically acceptable salt of any of the above formulas.

14. A compound of the formula:
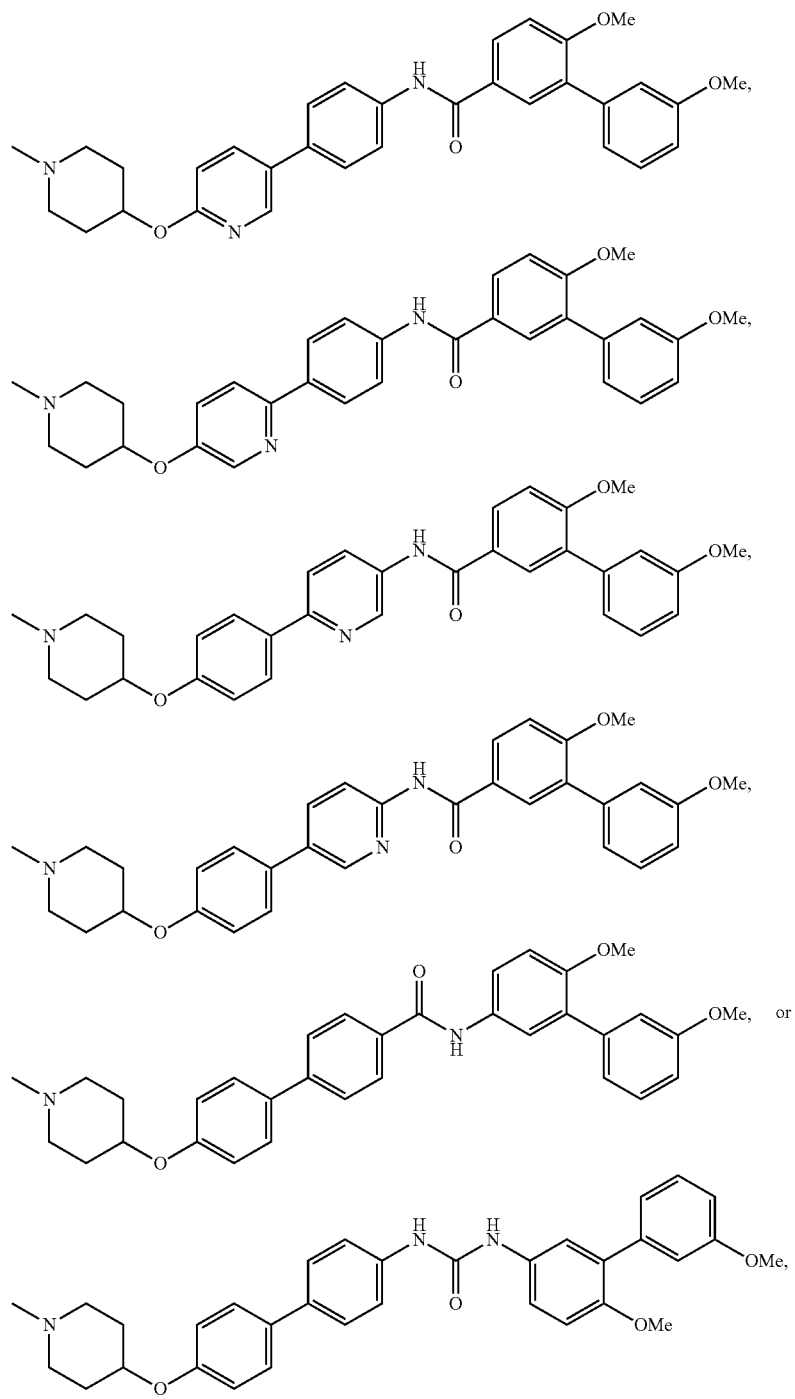
or a pharmaceutically acceptable salt of any of the above formulas.
15. A pharmaceutical composition comprising a compound of claim 1 and an excipient.
16. A method of treating a breast cancer comprising administering to a patient in need thereof a pharmaceutically acceptable amount of a compound of claim 1.
* * * * *

UNITED STATES PATENT AND TRADEMARK OFFICE
CERTIFICATE OF CORRECTION

PATENT NO. : 10,689,344 B2
APPLICATION NO. : 15/034957
DATED : June 23, 2020
INVENTOR(S) : Brian S. J. Blagg and Huiping Zhao Page 1 of 1

It is certified that error appears in the above-identified patent and that said Letters Patent is hereby corrected as shown below:

In the Specification

Column 1, Lines 10-13, delete the entire contents and insert --This invention was made with government support under CA120458 and CA167079 awarded by the National Institutes of Health. The government has certain rights in the invention.-- therefor.

Signed and Sealed this
Third Day of November, 2020

Andrei Iancu
*Director of the United States Patent and Trademark Office*